US008435978B2

(12) United States Patent
Oberboersch et al.

(10) Patent No.: US 8,435,978 B2
(45) Date of Patent: May 7, 2013

(54) SUBSTITUTED SULFONAMIDE COMPOUNDS

(75) Inventors: Stefan Oberboersch, Aachen (DE); Melanie Reich, Aachen (DE); Stefan Schunk, Aachen (DE); Sabine Hees, Aachen (DE); Ruth Jostock, Stolberg (DE); Michael Franz-Martin Engels, Turnhout (BE); Achim Kless, Aachen (DE); Thomas Christoph, Aachen (DE); Klaus Schiene, Duesseldorf (DE); Tieno Germann, Aachen (DE); Edward Bijsterveld, Nijmegen (NL)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/862,297

(22) Filed: Aug. 24, 2010

(65) Prior Publication Data

US 2010/0317644 A1 Dec. 16, 2010

Related U.S. Application Data

(63) Continuation of application No. 11/905,381, filed on Sep. 28, 2007, now abandoned.

(60) Provisional application No. 60/849,438, filed on Oct. 5, 2006.

(30) Foreign Application Priority Data

Sep. 29, 2006 (DE) .......................... 10 2006 046 743

(51) Int. Cl.
| | |
|---|---|
| *A61K 31/453* | (2006.01) |
| *A61K 31/496* | (2006.01) |
| *A61K 31/4709* | (2006.01) |
| *C07D 401/00* | (2006.01) |
| *C07D 401/14* | (2006.01) |
| *C07D 221/02* | (2006.01) |

(52) U.S. Cl.
USPC ........ 514/210.2; 514/312; 514/316; 514/320; 514/326; 546/186; 546/187; 546/201

(58) Field of Classification Search ........................ None
See application file for complete search history.

(56) References Cited

U.S. PATENT DOCUMENTS

| 7,256,186 B2 * | 8/2007 | Pissarntiski et al. ..... 514/210.01 |
| 8,106,055 B2 * | 1/2012 | Oberboersch et al. ... 514/253.01 |
| 8,124,624 B2 * | 2/2012 | Oberboersch et al. ........ 514/316 |
| 2004/0171614 A1 | 9/2004 | Pissarnitski et al. |
| 2005/0212663 A1 | 9/2005 | Matsumoto et al. |
| 2008/0306084 A1 | 12/2008 | Oberboersch et al. |
| 2009/0203672 A1 * | 8/2009 | Merla et al. .............. 514/217.05 |
| 2009/0264400 A1 * | 10/2009 | Oberboersch et al. ..... 514/210.2 |
| 2009/0275558 A1 * | 11/2009 | Reich et al. .............. 514/210.21 |
| 2009/0298812 A1 * | 12/2009 | Oberboersch et al. ... 514/217.04 |

FOREIGN PATENT DOCUMENTS

| WO | WO 2006/071775 A2 | 7/2006 |
| WO | WO 2007/101007 A2 | 9/2007 |
| WO | WO 2007101007 A2 * | 9/2007 |
| WO | WO 2008024692 A1 * | 2/2008 |

OTHER PUBLICATIONS

German Search Report dated Dec. 18, 2007 (Thirteen (13) pages).
International Search Report dated Dec. 12, 2007 (Six (6) pages).
João B. Calixto et al., "Kinin $B_1$ receptors: key G-protien-coupled receptors and their role in inflammatory and painful process", British Journal of Pharmacology, 2004, vol. 143 (7), pp. 803-818.
Bichoy H. Gabra et al., "The kinin system mediates hyperalgesia through the inducible bradykinin B1 receptor subtype: evidence in various experimental animal models of type 1 and type 2 diabetic neuropathy", Biol. Chem., vol. 387, pp. 127-143, Feb. 2006.
J. Fred Hess et al., "Generation and Characterization of a humanized bradykinin B1 receptor mouse", Biol. Chem., vol. 387, pp. 195-201, Feb. 2006.

* cited by examiner

*Primary Examiner* — Yong Chu
(74) *Attorney, Agent, or Firm* — Crowell & Moring LLP

(57) ABSTRACT

Substituted sulfonamide derivatives, a process for their preparation, pharmaceutical compositions containing these compounds, and to the use of substituted sulfonamide derivatives in the treatment or inhibition of pain and/or various disorders or disease states.

12 Claims, No Drawings

SUBSTITUTED SULFONAMIDE COMPOUNDS

CROSS REFERENCE TO RELATED APPLICATIONS

This application is a continuation of co-pending patent application Ser. No. 11/905,381, filed Sep. 28, 2007. Priority is claimed based on U.S. provisional patent application No. 60/849,438, filed Oct. 5, 2006, the entire disclosure of which is corporated herein by reference. Priority is also claimed based on Federal Republic of Germany patent application no. DE 10 2006 046 743.4, filed Sep. 29, 2006.

BACKGROUND OF THE INVENTION

The present invention relates to substituted sulfonamide derivatives, to a process for their preparation, to medicaments containing these compounds, and to the use of substituted sulfonamide derivatives in the preparation of pharmaceutical compositions and in treatment and/or inhibition of pain and/or various disease states.

Unlike the constitutive expression of the bradykinin 2 receptor (B2R), the bradykinin 1 receptor (B1R) is not expressed or is expressed only weakly in most tissues. However, the expression of B1R in various cells is inducible. For example, following inflammation reactions there is a rapid and pronounced induction of B1R in neuronal cells but also in various peripheral cells such as fibroblasts, endothelial cells, granulocytes, macrophages and lymphocytes. Accordingly, following inflammation reactions there is a switch from B2R to B1R dominance in the cells that are involved. The cytokines interleukin-1 (IL-1) and tumour necrosis factor alpha (TNFα) play a substantial part in this B1R up-regulation (Passos et al., J. Immunol. 2004, 172, 1839-1847). Following activation with specific ligands, B1R-expressing cells are then themselves able to secrete inflammation-promoting cytokines such as IL-6 and IL-8 (Hayashi et al., Eur. Respir. J. 2000, 16, 452-458). This results in the immigration of further inflammatory cells, for example neutrophilic granulocytes (Pesquero et al., PNAS 2000, 97, 8140-8145). By way of these mechanisms, the bradykinin B1R system can contribute to the chronification of diseases. This is proved by a large number of animal experiments (overviews in Leeb-Lundberg et al., Pharmacol. Rev. 2005, 57, 27-77 and Pesquero et al., Biol. Chem. 2006, 387, 119-126). In humans too, enhanced expression of B1R is found, for example in enterocytes and macrophages in the affected tissue of patients with inflammatory intestinal diseases (Stadnicki et al., Am. J. Physiol. Gastrointest. Liver Physiol. 2005, 289, G361-366) or on T-lymphocytes of patients with multiple sclerosis (Prat et al., Neurology, 1999; 53, 2087-2092), or activation of the bradykinin B2R-B1R system is found following infections with *Staphylococcus aureus* (Bengtson et al., Blood 2006, 108, 2055-2063). Infections with *Staphylococcus aureus* are responsible for symptoms ranging from superficial skin infections to septic shock.

Due to the described pathophysiological relationships there is a great therapeutic potential for the use of B1R antagonists in acute and, in particular, chronic inflammatory diseases. These include respiratory diseases (Asthma bronchiale, allergies, COPD/chronic-obstructive pulmonary disease, cystic fibrosis, etc.), inflammatory intestinal diseases (ulcerative colitis, CD/Crohn's disease, etc.), neurological diseases (multiple sclerosis, neurodegeneration, etc.), inflammations of the skin (atopic dermatitis, psoriasis, bacterial infections, etc.) and mucosa (Behcet's disease, pelvitis, prostatitis, etc.), rheumatic diseases (rheumatoid arthritis, osteoarthritis, etc.), septic shock and reperfusion syndrome (following heart attack, stroke).

Moreover, the bradykinin (receptor) system is also involved in regulating angiogenesis (potential as an angiogenesis inhibitor in cancer and macular degeneration of the eye), and B1R knockout mice are protected against the induction of excess weight as a result of a particularly high-fat diet (Pesquero et al., Biol. Chem. 2006, 387, 119-126). B1R antagonists are therefore suitable also for the treatment of obesity.

B1R antagonists are suitable in particular for the treatment of pain, in particular inflammatory pain and neuropathic pain (Calixto et al., Br. J. Pharmacol. 2004, 1-16), in particular diabetic neuropathy (Gabra et al., Biol. Chem. 2006, 387, 127-143). They are also suitable for the treatment of migraine.

When developing B1R modulators there is, however, the problem that the human and the rat B1R receptor are so very different from one another that many compounds that are good B1R modulators on the human receptor exhibit only poor affinity or no affinity for the rat receptor. This makes animal pharmacological studies considerably more difficult, because many studies are normally carried out on the rat. If there is no activity on the rat receptor, however, neither action nor side-effects can be studied on the rat. This has already resulted in the production of transgenic animals having human B1 receptors for animal pharmacological studies (Hess et al., Biol. Chem. 2006; 387(2): 195-201). However, it is more expensive to work with transgenic animals than with the unchanged animals. Nonetheless, because long-term toxicity studies on the rat form part of the standard studies that are carried out when developing medicaments, but such studies are meaningless where there is an absence of activity on the receptor, there is no important, established instrument for checking safety when developing such compounds. There is therefore a need for novel B1R modulators, B1R modulators that bind both to the rat receptor and to the human receptor offering particular advantages.

SUMMARY OF THE INVENTION

It is an object of the present invention to provide new pharmaceutically useful compounds.

A particular object of the invention is to provide compounds which a suitable for use in the treatment or inhibition of disorders or diseases which are at least in part related to the B1R-receptor.

Another object of the invention is to provide methods of treating or inhibiting disorders or disease states which are at least in part mediated by the B1R-receptor.

These and other objects are achieved in accordance with the present invention by providing substituted sulfonamide compounds corresponding to the formula I

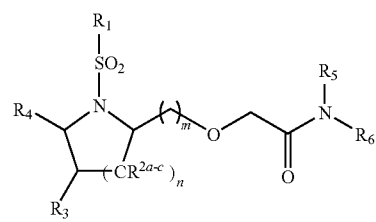

wherein n represents 0, 1, 2 or 3;

m represents 1 or 2;

$R^1$ represents aryl or heteroaryl;

$R^{2a-c}$, $R^3$ and $R^4$ represent H or, with an adjacent radical $R^{2a-c}$, $R^3$ or $R^4$, form a five- or six-membered ring which can be saturated or unsaturated and mono- or poly-substituted and which can contain hetero atoms from the group N and O, $R^5$ and $R^6$ together form a 4- to 8-membered ring which can be saturated or unsaturated but not aromatic, wherein the 4- to 8-membered ring can be fused to an aromatic, saturated or unsaturated 4- to 10-membered ring, and the 4- to 8-membered ring and/or the fused 4- to 10-membered ring is substituted by or fused to a basic radical and can be substituted by a further basic radical or radicals from the group $C_{1-6}$-alkyl, $C_{1-3}$-alkoxy, $C_{3-8}$-cycloalkyl, =O, aralkyl and aryl; or $R^5$ and $R^6$ together form a 4- to 8-membered ring which contains a further hetero atom from the group N and O and can be substituted by a basic or non-basic radical and, in the case where the basic or non-basic substituent is not bonded via the further hetero atom N to the 4- to 8-membered ring, that further hetero atom N can additionally be substituted by a $C_{1-6}$-alkyl group, an aryl or aralkyl group; or $R^5$ represents H, $C_{3-8}$-cycloalkyl, aryl or aralkyl and $R^6$ represents aryl or $C_{3-8}$-cycloalkyl; or $R^6$ represents an aryl radical linked via a $C_{1-3}$-alkyl chain, or $C_{3-8}$-cycloalkyl, wherein the aryl radical and the $C_{3-8}$-cycloalkyl ring can be fused to a 5- to 10-membered saturated or unsaturated ring optionally containing one or more hetero atoms, and the aryl or $C_{3-8}$-cycloalkyl ring is substituted by a basic radical or, where appropriate, the substitution with the basic radical takes place on the bridging $C_{1-3}$-alkyl chain, or $R^5$ represents H, $C_{3-8}$-cycloalkyl, aryl or aralkyl and $R^6$ represents $C_{4-8}$-hetero-cyclyl; or $R^6$ represents a $C_{4-8}$-heterocyclyl radical linked via a $C_{1-4}$-alkyl chain, wherein the heterocyclyl ring can be substituted on one or two ring members by a basic or non-basic radical, or $R^5$ and $R^6$, independently of one another, represent H, aralkyl or a branched or unbranched, optionally mono- or poly-substituted $C_{1-10}$-alkyl radical which contains from one to three nitrogen atoms, wherein $R^5$ and $R^6$ do not both represent H, or $R^5$ represents H, $C_{1-6}$-alkyl, $C_{3-8}$-cycloalkyl, aralkyl or aryl and $R^6$ represents a basic heteroaryl radical which is optionally linked via a $C_{1-4}$-alkyl group and can be mono- or poly-substituted, wherein the $C_{1-4}$-alkyl chain can be substituted by a basic radical;

wherein, unless indicated to the contrary, the above-mentioned radicals $C_{1-6}$-alkyl, $C_{1-3}$-alkoxy, aralkyl, aryl and heteroaryl can be unsubstituted or mono- or poly-substituted and the radical $C_{3-8}$-cycloalkyl can be unsubstituted or monosubstituted on one or more ring members, and wherein the compound may be in the form of the racemate; in the form of the enantiomers, diastereoisomers, mixtures of the enantiomers or diastereoisomers or in the form of an individual enantiomer or diastereoisomer; and/or in the form of a free base or a salt thereof with a physiologically acceptable acid.

Within the scope of this invention, the expressions "$C_{1-3}$-alkyl", $C_{1-6}$-alkyl" and "$C_{1-10}$-alkyl" denote acyclic saturated or unsaturated hydrocarbon radicals which can be branched- or straight-chained as well as unsubstituted or mono- or poly-substituted, having from 1 to 3 carbon atoms or from 1 to 6 carbon atoms or from 1 to 10 carbon atoms, respectively, that is to say $C_{1-3}$-alkanyls, $C_{2-3}$-alkenyls and $C_{2-3}$-alkynyls or $C_{1-6}$-alkanyls, $C_{2-6}$-alkenyls and $C_{2-6}$-alkynyls or $C_{1-10}$-alkanyls, $C_{2-10}$-alkenyls and $C_{2-10}$-alkynyls. Alkenyls have at least one C—C double bond and alkynyls have at least one C—C triple bond. Alkyl is advantageously selected from the group comprising methyl, ethyl, n-propyl, 2-propyl, n-butyl, isobutyl, sec-butyl, tert-butyl, n-pentyl, isopentyl, neopentyl, hexyl, heptanyl, octanyl, nonanyl, decyl, ethylenyl (vinyl), ethynyl, propenyl (—$CH_2CH=CH_2$, —$CH=CH—CH_3$, —$C(=CH_2)$—$CH_3$), propynyl (—CH—C≡CH, —C≡C—$CH_3$), butenyl, butynyl, pentenyl, pentynyl, hexenyl and hexynyl. Methyl, ethyl, n-propyl and isopropyl are particularly advantageous.

For the purposes of this invention, the term "cycloalkyl" or "$C_{3-8}$-cycloalkyl" denotes cyclic hydrocarbons having 3, 4, 5, 6, 7 or 8 carbon atoms, wherein the hydrocarbons can be saturated or unsaturated (but not aromatic), unsubstituted or monosubstituted on one or more ring members. $C_{3-8}$-Cycloalkyl is advantageously selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl.

Within the scope of this invention, the term "heterocyclyl" denotes mono- or poly-cyclic organic radicals in which at least one ring contains one hetero atom or 2, 3, 4 or 5 identical or different hetero atoms selected from the group consisting of N, O and S. Each heterocyclyl radical can be unsubstituted or monosubstituted on one or more ring members. Saturated and unsaturated heterocyclyl are understood as being in particular monocyclic 5- or 6-membered compounds having at least one hetero atom from the group N, O and S, wherein a further 5- or 6-membered, saturated, unsaturated or aromatic ring, which can likewise contain at least one hetero atom from the group N, O and S, can be fused to those compounds. Examples are the benzo- or pyridino-fused analogues of the above-mentioned monocyclic 5- or 6-membered compounds. A saturated or unsaturated heterocyclyl radical is preferably selected from the group comprising pyrrolidinyl, piperidinyl, piperazinyl, pyrazolinyl, morpholinyl, tetrahydropyranyl, dioxanyl, dioxolanyl, indolinyl, isoindolinyl, or

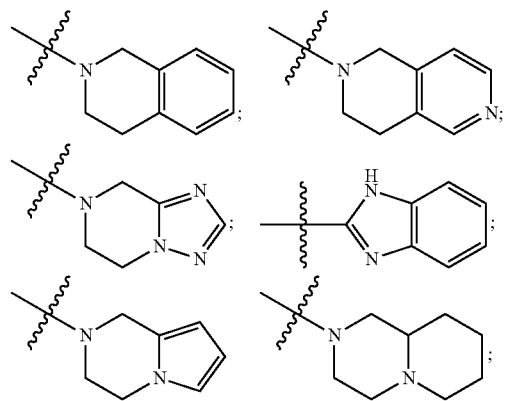

Unless indicated to the contrary, the substitution by a heterocyclyl radical can take place via any desired position of the heterocyclyl radical.

Within the scope of this invention, the term "aryl" denotes aromatic hydrocarbons, including phenyls and naphthyls. The aryl radicals can also be fused to further saturated, (partially) unsaturated or aromatic ring systems. Each aryl radical can be unsubstituted or mono- or poly-substituted, wherein the aryl substituents can be identical or different and can be located at any desired and possible position of the aryl. Aryl is advantageously selected from the group comprising phenyl, 1-naphthyl and 2-naphthyl, each of which can be unsubstituted or mono- or poly-substituted.

The term "heteroaryl" is synonymous with "aromatic heterocyclyl" and denotes a 5-, 6- or 7-membered cyclic aromatic radical containing at least one, optionally also 2, 3, 4 or 5, hetero atom(s), the hetero atoms being identical or different and the heterocycle being unsubstituted or mono- or poly-substituted; in the case of substitution on the heterocycle, the substituents can be identical or different and can be located at any desired and possible position of the heteroaryl. The heterocycle can also be part of a bi- or poly-cyclic system, which can then be more than 7-membered in total, preferably up to 14-membered. Preferred hetero atoms are nitrogen, oxygen and sulfur. It is preferred for the heteroaryl radical to be selected from the group comprising pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, it being possible for bonding to the compounds of the general structure I to take place via any desired and possible ring member of the heteroaryl radical. Pyridyl is particularly preferred.

The expression "aryl or heteroaryl bonded via $C_{1-3}$-alkyl" means, for the purposes of the present invention, that $C_{1-3}$-alkyl and aryl or heteroaryl have the meanings defined above and the aryl or heteroaryl radical is bonded to the compound of the general structure I via a $C_{1-3}$-alkyl group. Phenyl, benzyl and phenethyl are particularly advantageous within the scope of this invention.

The term "aralkyl" denotes an alkyl group substituted by an aryl group. The aralkyl group is preferably selected from the group consisting of benzyl, phenylethyl and phenylpropyl.

In connection with "alkyl" and "cycloalkyl", the term "substituted" within the scope of this invention is understood as meaning the substitution of a hydrogen radical by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl, polysubstituted radicals being understood as being those radicals that are polysubstituted, for example di- or tri-substituted, either on different atoms or on the same atom, for example trisubstituted on the same carbon atom, as in the case of $CF_3$ or —$CH_2CF_3$, or at different positions, as in the case of —CH(OH)—CH=CH—$CHCl_2$. Polysubstitution can be carried out with the same or with different substituents.

In connection with "saturated or unsaturated heterocyclyl", the term "substituted" is understood as meaning the substitution of a hydrogen radical on one or more ring members by F, Cl, Br, I, —CN, $NH_2$, NH—$C_{1-6}$-alkyl, $C_{1-6}$-alkyl, $N(C_{1-6}$-alkyl$)_2$, $N(C_{1-6}$-alkyl-OH$)_2$, pyrrolinyl, piperazinyl, morpholinyl, $NO_2$, SH, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl. The hydrogen bonded to a N hetero atom can be substituted in particular by a $C_{1-6}$-alkyl group.

In relation to "aryl" and "heteroaryl" or "aromatic heterocyclyl", "mono- or poly-substituted" within the scope of this invention means the substitution of one or more hydrogen atoms of the ring system one or more times, for example two, three or four times, by F, Cl, Br, I, CN, $NH_2$, NH—$C_{1-6}$-alkyl, $N(C_{1-6}$-alkyl$)_2$, $N(C_{1-6}$-alkyl-OH$)_2$, NHaryl, N(aryl$)_2$, $N(C_{1-6}$-alkyl)aryl, pyrrolinyl, piperazinyl, morpholinyl, $NO_2$, SH, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$,

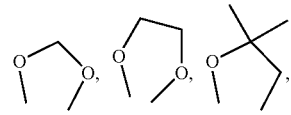

$C_{1-6}$-alkyl, pyrrolidinyl, imidazolyl, piperidinyl, morpholinyl, benzyloxy, phenoxy, phenyl, pyridyl, alkylaryl, in particular benzyl, thienyl or furyl; on one atom or optionally on different atoms, wherein a substituent can itself optionally be substituted. The polysubstitution is carried out with the same or with different substituents. Preferred substituents for "aryl" or "heteroaryl" are —F, —Cl, $CF_3$, $CH_3$ or $OCH_3$.

Within the scope of the present invention, the symbol

used in the formulae denotes a linking of a corresponding radical to the particular higher-order general structure. If this symbol is arranged in a cyclic or polycyclic, for example aromatic or fused aromatic, group in such a manner that a concrete linkage to a specific position is not identifiable, then this means that a linkage at any position of the cyclic or polycyclic group is to be included.

Within the scope of this invention, the expression "a salt formed with a physiologically acceptable acid" is understood as meaning salts of the active ingredient in question with inorganic or organic acids that are physiologically acceptable—in particular when used in humans and/or mammals. The hydrochloride is particularly preferred. Examples of physiologically acceptable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro-1$\lambda^6$-benzo[d]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. Citric acid and hydrochloric acid are particularly preferred.

Within the scope of this invention, a basic radical is understood as being a group that is able to react while taking up protons. In particular, it is understood as being a group that contains at least one protonisable nitrogen. A basic radical can in particular represent an optionally fused heterocycle containing at least one nitrogen atom as hetero atom, wherein the heterocycle can optionally be monosubstituted on one or more ring members by $C_{1-6}$-alkyl, O—$C_{1-6}$-alkyl, heterocyclyl, OH, F, Cl, Br, I, —CN, $NH_2$, NH($C_{1-6}$-alkyl), $N(C_{1-6}$-alkyl$)_2$, —NH(aryl), —$N(C_{1-3}$-alkyl)(aryl), wherein the aryl radicals bonded to these amino groups can be mono- or poly-substituted by F, Cl, Br, $CF_3$, CN, OH or OMe. Examples of such heterocycles referred to as basic radicals are piperidine, pyrrolidine, azepane, azetidine, azocane, pyrazine, pyridine, imidazole, imidazolidine, 1,2,4-triazole, diazepane, pyrimidine, imidazoline, piperazine, morpholine, quinazoline or quinoxaline. Further basic radicals within the scope of the invention are N(C$_{1-6}$-alkyl)$_2$, NHC$_{1-6}$-alkyl, a N(C$_{1-6}$-alkyl)$_2$-substituted aryl radical, in particular phenyl or naphthyl, an aryl or heteroaryl radical, in particular phenyl, naphthyl or pyridinyl, substituted by a 5- to 7-membered heterocyclyl containing at least one N hetero atom, in particular pyrrolidinyl, piperidinyl, 4-methylpiperidinyl or morpholinyl. All the above-mentioned basic radicals can be linked to the structure of the general formula I via a bridging —OH—, —NH—, —NH[(CH$_2$)$_p$—] group, —N(C$_{1-3}$-alkyl)[—(CH$_2$)$_p$—] group, —O—[(CH$_2$)$_p$—] group, —O—[—(CH$_2$)$_p$—O—] group, wherein in each case p=1, 2 or 3, or C$_{1-3}$-alkyl group. If the bridging chain contains a terminal O or N atom, then that atom can be bonded to the basic radical or to the structure to be bonded to the basic radical. The bridging —(CH$_2$)$_p$— groups or the C$_{1-3}$-alkyl chain can optionally be substituted by =O, F, Cl, Br, I, —CN, phenyl or pyridinyl. Further examples of basic radicals within the scope of the present invention are C$_{1-6}$-alkylN(C$_{1-6}$-alkyl)$_2$ or C$_{1-6}$-alkylNH(C$_{1-6}$-alkyl). If the basic radical is fused to the heterocycle formed from R$^5$ and R$^6$, it can represent a 6-membered, saturated, unsaturated or aromatic heterocycle containing at least one N hetero atom, preferably pyridine or thiazole. A basic radical is also understood as being in particular a pyridyl, pyrrolyl, imidazolyl, pyrimidinyl or pyrazinyl radical, each of which can be linked via a C$_{1-3}$-alkyl chain. Further examples of basic radicals are groups having the structure shown below:

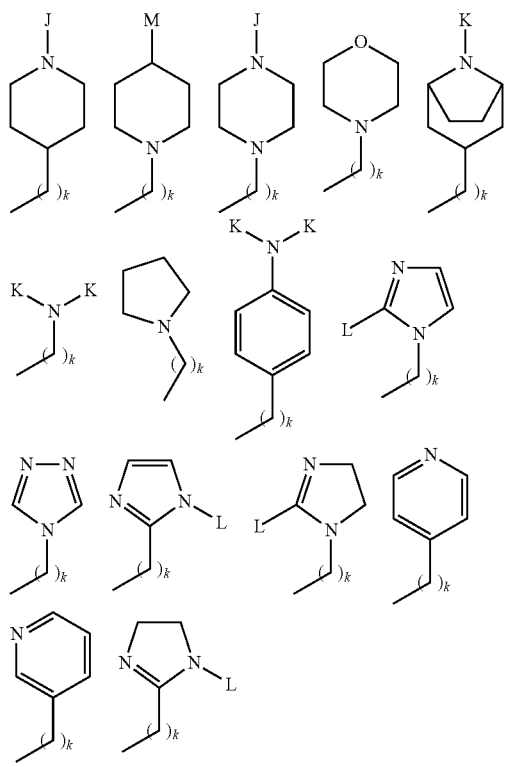

wherein
k represents 0, 1 or 2,
L represents H or C$_{1-6}$-alkyl,
K represents C$_{1-6}$-alkyl,
M represents C$_{1-6}$-alkyl or N(CH$_3$)$_2$, and
J represents 2-, 3- or 4-pyridyl, phenyl, piperidyl or C$_{1-6}$-alkyl.

Further examples and/or preferred forms of basic radicals will become apparent from the following descriptions of the preferred substances according to the invention.

A non-basic radical is understood as being a group that does not possess basic properties. In particular, it is understood as being a group that does not carry a protonatable nitrogen. Examples of such non-basic radicals are —CN, C$_{1-6}$-alkyl, optionally substituted by methoxy or C$_{1-3}$-alkoxy; or aryl, heteroaryl, 3- to 7-membered heterocycles containing at least one oxygen or sulfur atom, in particular tetrahydropyran or thiophene, each unsubstituted or mono- or polysubstituted. Further examples are unsubstituted C$_{3-8}$-cycloalkyl or C$_{3-8}$-cycloalkyl monosubstituted on one or more ring members. The above-mentioned non-basic groups can be linked to the structure of the general formula I via a —O—, —O—[(CH$_2$)$_q$—] or —[(CH$_2$)$_q$—]—O group, —O—[—(CH$_2$)$_q$—O—] group or a bridging C$_{1-3}$-alkyl group, wherein the —(CH$_2$)$_q$— chain or the alkyl chain can each be substituted by =O and q=1, 2 or 3. The substituents of the non-basic groups aryl, heteroaryl, 3- to 7-membered heterocycle and C$_{3-8}$-cycloalkyl are preferably selected from F, Cl, Br, I, CN, NO$_2$, aralkyl, SH, alkyl, OH, O—C$_{1-6}$-alkyl, O—C$_{1-6}$-alkyl-OH, C(=O)C$_{1-6}$-alkyl, CO$_2$H, CH$_2$SO$_2$-phenyl, CO$_2$—C$_{1-6}$-alkyl, OCF$_3$, CF$_3$,

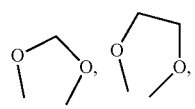

C$_{1-6}$alkyl.

Preference is given to radicals from the group aryl, heteroaryl, C$_{3-8}$-cycloalkyl, each unsubstituted or substituted as described above, which can be linked to the structure of the general formula I via a C$_{1-3}$-alkyl chain, wherein the alkyl chain can be substituted by =O. Preference is further given to C$_{1-6}$-alkyl, optionally substituted by methoxy; C$_{1-3}$-alkoxy.

In a preferred embodiment of the invention, C$_{4-8}$-heterocyclyl in connection with R$^6$ represents a saturated or unsaturated, 4- to 8-membered cyclic radical which can contain 1, 2, 3, 4 or 5 identical or different hetero atoms in the ring system, wherein the hetero atoms are preferably selected from the group N, O and S and wherein both the bond of the heterocyclyl radical to the general basic structure of formula I and the optional substitution with the basic or non-basic groups can be present at any desired ring member. The C$_{4-8}$-heterocyclyl radical is preferably selected from the group consisting of piperidinyl, 2,6-dimethylpiperidinyl, piperazinyl, morpholinyl, pyrrolidinyl, tetrahydropyranyl and tetrahydrofuranyl.

In another preferred embodiment of the invention, a basic heteroaryl radical in connection with R$^6$ represents a 5- to 10-membered, fused or non-fused hetero-atom-containing radical which contains at least one nitrogen atom as hetero atom and wherein both the bond of the heteroaryl radical to the general basic structure of formula I, or the bond of the heteroaryl radical to the bridging C$_{1-4}$-alkyl group, and the optional substitution can be present at any desired ring member of the heteroaryl radical. The basic heteroaryl is preferably pyrrolyl, pyrazolyl, imidazolyl, pyridinyl, pyrazinyl, pyridazinyl, pyrimidinyl, indolyl, indazolyl, benzoimidazolyl and quinolinyl, quinoxalinyl, quinazolinyl.

In another preferred embodiment of the invention, a 5- to 10-membered, aromatic or unsaturated ring fused to an aryl group and optionally containing one or more hetero atoms represents, in connection with R$^6$, a ring selected from the group:

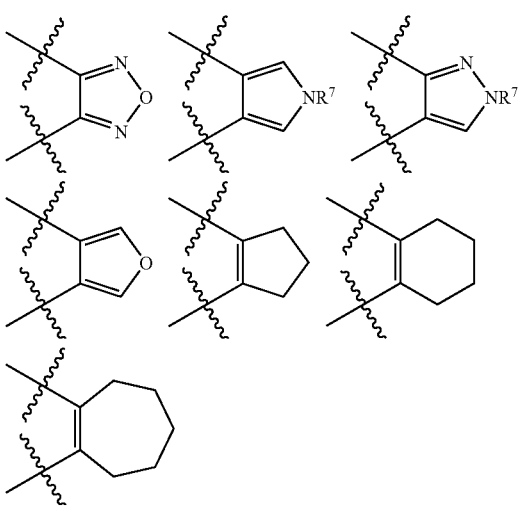

wherein $R^7$ represents H or $C_{1-6}$-alkyl.

In a further preferred embodiment of the invention, a 5- to 10-membered, saturated or unsaturated ring fused to a $C_{3-8}$-cycloalkyl ring and optionally containing one or more hetero atoms represents, in connection with $R^6$, a ring selected from the group: phenyl, pyridinyl, cyclopentane, cyclohexane and cycloheptane.

In a further preferred variant of the present invention, an aromatic, unsaturated or saturated 4- to 10-membered ring fused to the 4- to 8-membered ring formed by $R^5$ and $R^6$ represents a ring selected from the group consisting of $C_{4-10}$-cycloalkane, $C_{4-10}$-cycloalkene and $C_{6-10}$-aromatic compounds and 6-membered heteroaromatic compounds.

Preference is given within the scope of this invention to substituted sulfonamide derivatives of the general formula I wherein $R^1$ represents phenyl or benzothiophenyl, especially phenyl, unsubstituted or mono- or poly-substituted by $C_{1-3}$-alkoxy, $C_{1-6}$-alkyl, Cl, F, I, $CF_3$, $OCF_3$, OH, SH, aryl or heteroaryl, each unsubstituted or mono- or poly-substituted.

In a preferred embodiment of the invention, $R^1$ in the substituted sulfonamide derivatives according to the invention represents phenyl, naphthyl, indolyl, benzofuranyl, benzothiophenyl, benzoxazolyl, benzoxadiazolyl, pyrrolyl, furanyl, thiophenyl, pyridinyl, pyridazinyl, pyrimidinyl, pyrazinyl, imidazothiazolyl, carbazolyl, dibenzofuranyl and dibenzothiophenyl, preferably phenyl, naphthyl, benzothiophenyl, benzoxadiazolyl, thiophenyl, pyridinyl, imidazothiazolyl and dibenzofuranyl, particularly preferably phenyl, naphthyl and benzothiophenyl, wherein all those radicals can be unsubstituted or mono- or poly-substituted, preferably by $C_{1-3}$-alkoxy, $C_{1-6}$-alkyl, Br, Cl, F, I, $CF_3$, $OCF_3$, OH, SH, aryl or heteroaryl, each unsubstituted or mono- or poly-substituted.

In a further preferred form of the substituted sulfonamide derivatives according to the invention, $R^1$ represents phenyl or naphthyl, especially phenyl, optionally mono- or poly-substituted by methyl, methoxy, $CF_3$, Cl, Br and/or F.

Particular preference is further given to substituted sulfonamide derivatives wherein $R^1$ represents phenyl substituted in the 4-position by aryl or heteroaryl and in the 2-, 3-, 5- and/or 6-position position by methyl, methoxy, Cl or F, preferably in the 2- and 6-position by methyl.

Most particular preference is given to substituted sulfonamide derivatives wherein $R^1$ represents 2,6-dimethyl-4-methoxyphenyl, 2,6-dichloro-4-trifluoromethylphenyl, 2,6-dimethyl-4-bromophenyl, 2,6-dichloro-4-bromophenyl, 2,4,6-trichlorophenyl, 2,4-dichlorophenyl, 2,6-dichlorophenyl, 2,3-dichlorophenyl.

Preference is given also to substituted sulfonamide derivatives of the general formula I wherein n represents 2, $R^4$ and $R^{2b}$ represent H and $R^3$ and $R^{2a}$ together form a six-membered aromatic ring, or wherein n represents 1 and $R^{2a}$ represents H and $R^4$ and $R^3$ together form a six-membered aromatic ring.

In a further preferred form of the substituted sulfonamide derivatives according to the invention, $R^{2a-c}$, $R^3$ and $R^4$ represent H or, with an adjacent radical $R^{2a-c}$, $R^3$ or $R^4$, form an aromatic ring, preferably a benzene group, which is optionally mono- or poly-substituted, preferably by methyl, methoxy, $CF_3$, Cl, Br and/or F. Particular preference is given to substituted sulfonamide derivatives wherein $R^{2a-c}$, $R^3$ and $R^4$ represent H.

In a further form according to the invention of the substituted sulfonamide derivatives, n in the group $(CR^{2a-c})_n$ represents 1 or 2, preferably 2.

In a further preferred form of the substituted sulfonamide derivatives, m in the general formula I is 1.

In further preferred embodiments of the present invention:
a) the group $NR^5R^6$ in the general formula I forms a cyclic group according to formula a1, a2, a3 or a4

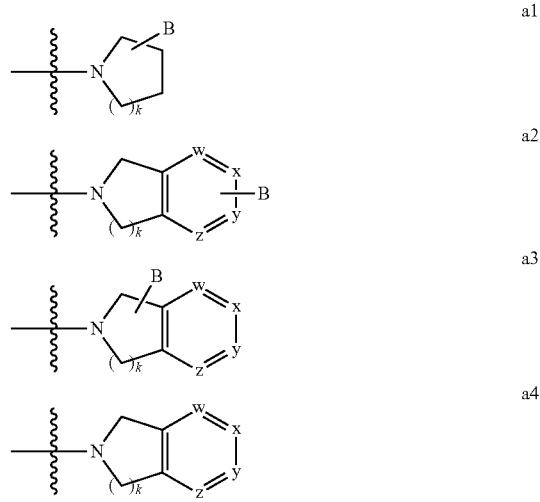

wherein
k=0, 1, 2 or 3, preferably 1 or 2, and
w, x, y and z, independently of one another, represent CH or N, with the proviso that not more than two of the groups w, x, y and z simultaneously represent N and that, in the cyclic group according to formula a4, at least one group from w, x, y and z represents N. In formulas a1, a2 and a3, w, x, y and z are preferably all CH or one of w, x, y and z is N and all the others are CH.

In formulas a1, a2 and a3, B represents a basic radical, preferably selected from the group consisting of $-NR^8R^9$, wherein $R^8$ and $R^9$, independently of one another, can represent H or $C_{1-6}$-alkyl, and a radical having the general formula aa1

In the radical aa1, a, b and c, independently of one another, can be 0 or 1, with the proviso that when b is equal to 0, a and c are not simultaneously 1; and
the bridging $C_{1-3}$-alkyl can be monosubstituted by =O.

$R^{10}$ represents a 4- to 10-membered, aromatic, unsaturated or saturated, mono- or poly-cyclic heterocyclyl group which can contain 1, 2, 3 or 4 N hetero atoms and optionally O and/or S as further hetero atoms, wherein the heterocyclyl group is unsubstituted or monosubstituted on one or more ring members. $R^{10}$ can further represent an aryl group substituted by at least one group or a 5- or 6-membered, monocyclic N-containing aromatic, saturated or unsaturated heterocycle containing 1 or 2 N hetero atoms, wherein $R^{11}$ and $R^{12}$, independently of one another, represent H or $C_{1-6}$-alkyl, and the aryl group can optionally carry further substituents.

$R^{10}$ can further represent a group of the general formula aa2:

(aa2)

wherein
d is 1, 2 or 3,
$R^{13}$ can be H or $C_{1-3}$-alkyl, $R^{14}$, for each chain member d independently, can be H or an optionally substituted aryl or N-heteroaryl group, preferably phenyl, naphthyl or pyridinyl, wherein $R^{14}$ can be H only once within the alkyl chain defined by d, and $R^{15}$ is a 5- to 7-membered, saturated or unsaturated heterocyclyl group which is optionally mono-substituted on one or more ring members, contains 1 or 2 N hetero atoms and can contain O or S as further hetero atoms, preferably morpholinyl, piperidinyl or 4-methylpiperazinyl.

In preferred embodiments of the invention, the cyclic group formed by the group $NR^5R^6$ is selected from the group consisting of

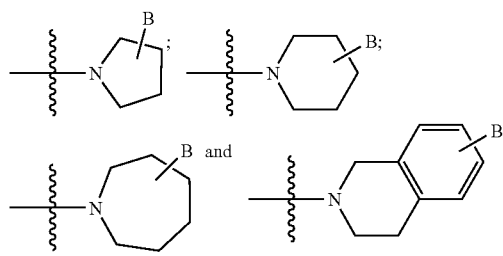

particular preference being given to piperidine substituted in the 4-position by the basic radical B,
and the basic radical B is selected from the group comprising: $-N(C_{1-6}$-alkyl), preferably $-N(CH_3)_2$; a radical having the general formula (aa1), wherein $R^{10}$ is selected from the group comprising:

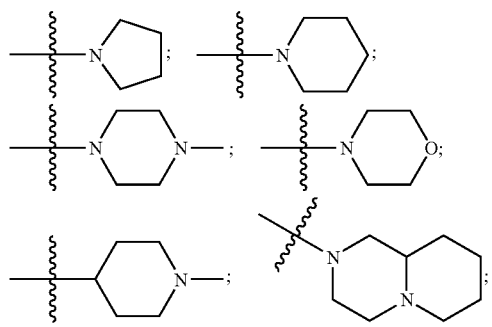

-continued

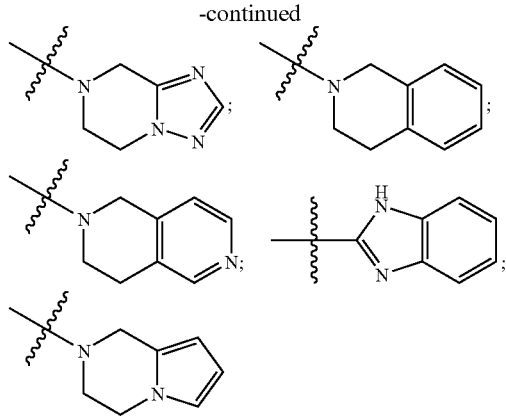

wherein those radicals can be unsubstituted or monosubstituted on one or more ring members, preferably by $C_{1-6}$-alkyl, especially methyl or ethyl, F, Cl or Br; or $R^{10}$ represents

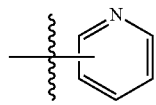

which can be unsubstituted or mono- or poly-substituted, preferably by $C_{1-5}$-alkyl, especially methyl or ethyl, F, Cl, Br, $C_{1-6}$-alkoxy, especially methoxy, or phenyl; or
$R^{10}$ represents phenyl substituted by $-N(C_{1-3}$-alkyl)$_2$, preferably dimethylamino or diethylamino, or
phenyl substituted by pyrrolidinyl, imidazolidinyl, dihydroimidazolyl, wherein the linkage can take place at any of the ring members of the phenyl and of the substituent, or
$R^{10}$ represents a group of the general formula (aa2), d=1 or 2, $R^{13}$ represents H or methyl,
$R^{14}$ represents phenyl or pyridinyl, and $R^{15}$ represents morpholinyl or 4-methylpiperazinyl.

In further embodiments according to the invention, the cyclic group formed by the group $NR^5R^6$ is

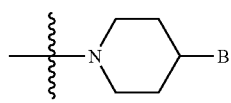

and the basic radical B is a group having the general formula (aa1) wherein i) a=b=c=0, ii) a=c=0 and b=1, iii) a=b=0 and c=1 or iv) a=b=1 and c=0; or the basic radical B is a group having the general formula (aa2) wherein d=1 or 2, preferably 2, and $R^{14}$ is pyridinyl, preferably 3-pyridinyl, and $R^{15}$ is morpholinyl.

In further preferred embodiments of the invention,
b) the group $NR^5R^6$ in the general formula I is a cyclic group according to one of the general formulae b1 and b2:

(b1)

-continued

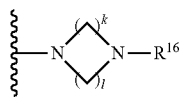 (b2)

wherein
k=1 or 2, preferably 2,
l=1, 2 or 3, preferably 2,
Z can be $NR^{17}$ or O, and $R^{17}$ is H or $C_{1-6}$-alkyl, and
$R^{16}$ represents H or a group of the general formula bb1:

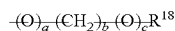 (bb1)

wherein
a and c, independently of one another, are 0 or 1,
b=0, 1, 2 or 3, with the proviso that when b=0, a and c are not simultaneously 1, and wherein in the alkyl chain defined by b, a $CH_2$ chain member can be replaced by C(=O), $R^{18}$ is selected from the group consisting of unsubstituted or mono- or poly-substituted aryl or heteroaryl, wherein the heteroaryl contains at least one N hetero atom, preferably 1, 2 or 3 N hetero atoms, and can contain O and S as further hetero atoms; saturated or unsaturated 5- to 7-membered heterocyclyl, wherein the heterocyclyl contains at least one hetero atom selected from the group N, O and S, preferably 1 or 2 N hetero atoms, and can optionally be monosubstituted or monosubstituted on a plurality of ring members; $C_{1-6}$-alkyl, optionally mono- or poly-substituted; $C_{3-8}$-cycloalkyl, optionally monosubstituted or monosubstituted on a plurality of ring members; and, apart from the cases where i) c=1 or ii) b=c=0 and a=1, $R^{18}$ can also be selected from the group consisting of —CN and $NR^{19}R^{20}$, wherein $R^{19}$ and $R^{20}$, independently of one another, can be H or $C_{1-6}$-alkyl but do not simultaneously represent H.

In preferred embodiments of the present invention, the cyclic group formed by the group $NR^5R^6$ is selected from the group consisting of:

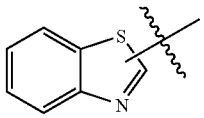

wherein $R^{16}$ represents a group of the general formula bb1 and in the formula bb1 (i) a=0, b=1, 2 or 3 and c=0 or (ii) a=0, b=1, 2 or 3 and c=0. In formula bb1, $R^{18}$ is preferably selected from the group consisting of:

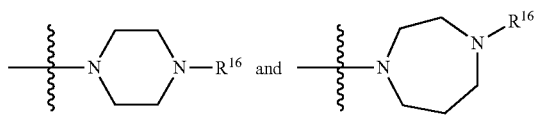

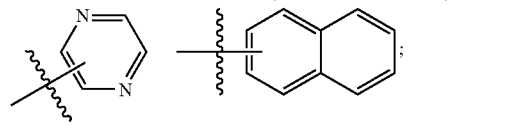

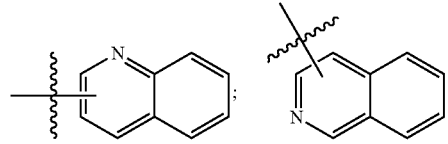

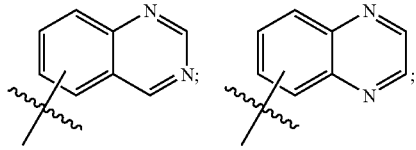

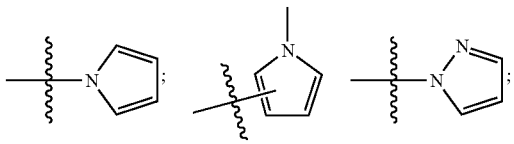

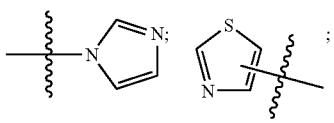

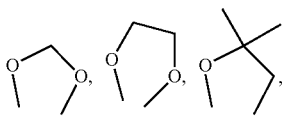

wherein those groups can be unsubstituted or mono- or poly-substituted, preferably by $C_{1-3}$-alkyl, especially methyl and/or ethyl; $C_{1-3}$-alkoxy, especially methoxy; F, Cl, Br, I; —CN; $CF_3$; $N(C_{1-3}$-alkyl$)_2$, $NH(C_{1-3}$-alkyl), $N(C_{1-3}$-alkyl)(aryl), especially $N(C_{1-3}$-alkyl)(phenyl or phenethyl), wherein phenyl or phenethyl can be mono- or poly-substituted; benzyl or

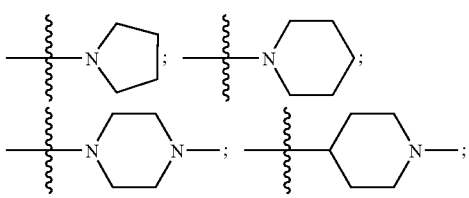

and wherein all those substituents can likewise be mono- or poly-substituted, preferably by F, Cl, Br, —CN, —$CF_3$, $C_{1-3}$-alkyl; pyrrolidinyl, piperidinyl, 4-methylpiperidinyl or morpholinyl.

$R^{18}$ can further represent a heterocyclyl selected from the group consisting of:

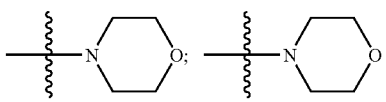

wherein those heterocyclyl groups can be monosubstituted on one or more ring members.

Alternatively, $R^{18}$ can represent cyclopentyl, cyclohexyl, optionally monosubstituted on one or more ring members, or $C_{1-3}$-alkyl, optionally mono- or poly-substituted.

In further preferred embodiments of the invention, the cyclic group formed by the group $NR^5R^6$ is

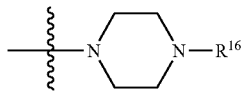

and $R^{16}$ represents a group according to formula bb1 shown above, wherein a=c=0 and b=0, 1 or 2, and $R^{18}$ is selected from

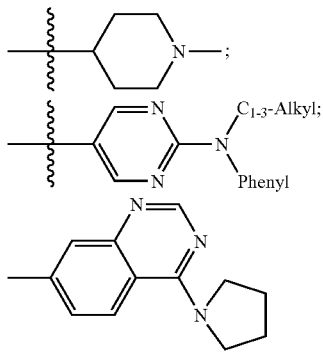

wherein the phenyl group can be substituted, preferably monosubstituted by F, Cl or Br, especially F, preferably in the 4-position.

In further preferred forms of the compounds according to the invention:

c) in the group $NR^5R^6$ from the general formula I, $R^5$ is selected from the group consisting of H and $C_{1-6}$-alkyl, optionally mono- or poly-substituted, and $R^6$ is selected from groups of the general formulae c1 and c2 shown below:

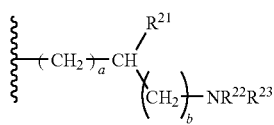 (c1)

wherein in formula c1:
a=0, 1 or 2;
b=0, 1, 2 or 3;
$R^{21}$ is an unsubstituted or substituted aryl group, preferably phenyl or naphthyl, both substituted or unsubstituted,
$R^{22}$ and $R^{23}$, independently of one another, represent —H or $C_{1-6}$-alkyl, or the group —$NR^{22}R^{23}$ together represents a 5-, 6- or 7-membered, saturated or unsaturated heterocycle which contains at least one N hetero atom and can optionally be monosubstituted or monosubstituted on a plurality of ring members;

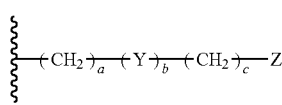 (c2)

wherein in formula c2:
a=0, 1, 2 or 3;
b=0 or 1, with the proviso that when b=0 also c=0;
c=0, 1, 2 or 3,
Y represents aryl or heteroaryl, preferably N-hetero-atom-containing 5- or 6-membered heteroaryl, optionally substituted; $C_{3-8}$-cycloalkyl, preferably $C_{5-6}$-cycloalkyl; and
Z represents a saturated, unsaturated or aromatic, optionally substituted heterocyclyl group which contains at least one N hetero atom and can contain O and/or S as further hetero atoms; or Z represents a group $NR^{24}R^{25}$, wherein $R^{24}$ and $R^{25}$, independently of one another, represent H, or —C(=O)—(CH$_2$)$_d$—$NR^{26}R^{27}$, wherein d=1 or 2 and $R^{26}$ and $R^{27}$, independently of one another, represent H or $C_{1-6}$-alkyl, or $NR^{26}R^{27}$ forms a 5-, 6- or 7-membered, preferably saturated heterocycle.

In further preferred forms of the substances according to the invention, $R^5$ in the group $NR^5R^6$ from the general formula I is selected from the group consisting of H and methyl, ethyl, propyl and isopropyl, optionally mono- or poly-substituted. $R^6$ is a group according to the general formula c1 shown above, wherein:
$R^{21}$ is a phenyl or naphthyl group which can be mono- or poly-substituted and is preferably unsubstituted or substituted by F, Cl, Br, I, CN, $C_{1-3}$-alkyl, preferably methyl or ethyl;
$R^{22}$ and $R^{23}$, independently of one another, represent methyl, ethyl or propyl or isopropyl, or the group $NR^{22}R^{23}$ together represents a N-heterocycle selected from the group consisting of:

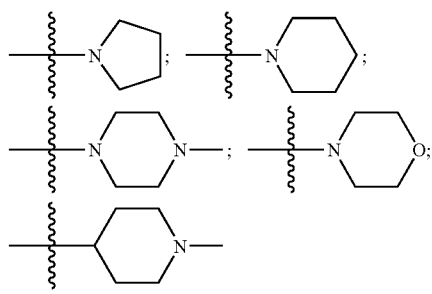

wherein those N-heterocycles can be unsubstituted or monosubstituted on one or more ring members, or
$R^6$ represents a group of the general formula c2 shown above, wherein
Y represents phenyl, naphthyl, benzooxadiazole, cyclopentyl, cyclohexyl or cycloheptyl, all optionally monosubstituted on one or more ring members, and
Z is selected from the group consisting of:
$N(C_{1-3}$-alkyl$)_2$;

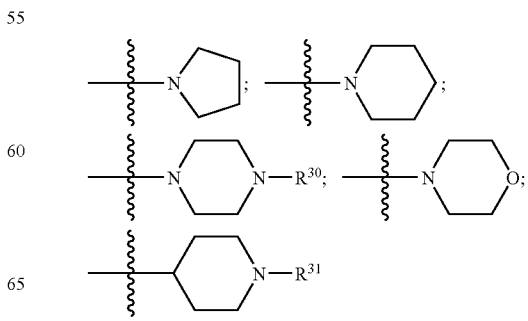

-continued

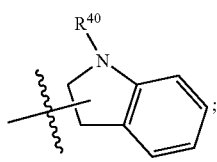

wherein those radicals can be monosubstituted on one or more ring members, and $R^{30}$, $R^{31}$ and $R_{40}$ can represent H, methyl, ethyl, propyl or isopropyl, optionally mono- or poly-substituted, or Z is selected from the group consisting of:

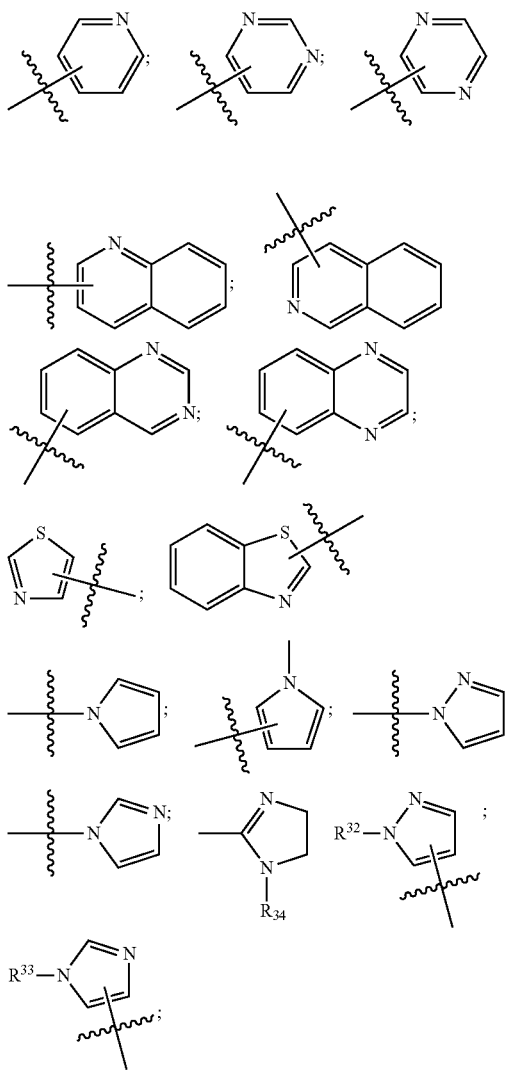

wherein $R^{32}$, $R^{33}$ and $R^{34}$ are selected from H, methyl, ethyl, propyl and isopropyl, optionally mono- or poly-substituted, and the N-heterocycles can optionally be monosubstituted on one or more ring members; or Z is a group $NR^{24}R^{25}$ wherein $R^{24}$ and $R^{25}$, independently of one another, represent methyl, ethyl, propyl or isopropyl, or Z represents a group —C(=O)—$(CH_2)_d$—$NR^{26}R^{27}$ wherein d is 1 or 2 and $NR^{26}R^{27}$ together forms a heterocycle selected from

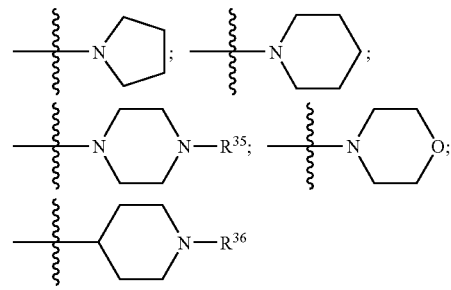

wherein the ring members of those radicals can be monosubstituted on one or more ring members, and $R^{35}$ and $R^{36}$ can represent methyl, ethyl, propyl or isopropyl, optionally mono- or poly-substituted.

In further preferred embodiments of the invention, in the group $NR^5R^6$ from the general formula I, $R^5$ is selected from the group consisting of H, methyl, ethyl, propyl and isopropyl, preferably methyl, and $R^6$ represents a group according to the general formula c2 wherein a=1 or 2, b=1 and c=0, Y represents phenyl or cyclohexyl and Z represents pyrrolidinyl or dihydroimidazolyl.

In further preferred forms of the compounds according to the invention:

d) $R^5$ in the group $NR^5R^6$ from the general formula I is selected from the group consisting of H, $C_{1-6}$-alkyl, optionally mono- or poly-substituted, $C_{3-8}$-cycloalkyl, optionally monosubstituted on one or more ring members. $R^6$ is selected from groups of the general formula d1

$$\xi\!-\!(CH_2)_a\!-\!(J)_b\!-\!(CH_2)_c\!-\!K \qquad (d1)$$

wherein in formula d1:
a=0, 1, 2, 3 or 4;
b=0 or 1, with the proviso that when b=0 also c=0;
c=0, 1, 2 or 3;
J represents a 4- to 7-membered heterocycle which contains at least one N-hetero atom and is preferably saturated or unsaturated and which can optionally be monosubstituted on one or more ring members, and
K represents H or an optionally substituted aryl or heteroaryl group.

In further preferred forms of the compounds according to the invention, in the group $NR^5R^6$ from the general formula I, $R^5$ is selected from the group consisting of H and methyl, ethyl, propyl and isopropyl, optionally mono- or poly-substituted, and $R^6$ represents a group according to formula d1 shown above wherein J is selected from the group:

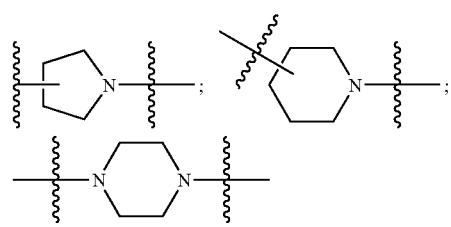

and K is selected from the group consisting of H, phenyl, naphthyl, pyridinyl, all optionally mono- or poly-substituted.

In further preferred forms of the compounds according to the invention:

e) in the group $NR^5R^6$ from the general formula I, $R^5$ and $R^6$ are selected, independently of one another, from the group consisting of H; $C_{1-6}$-alkyl; aralkyl; and $-(CH_2)_r-NR^{28}R^{29}$ wherein r=from 1 to 6 and wherein $R^{28}$ and $R^{29}$ are selected, independently of one another, from the group consisting of H and $C_{1-3}$-alkyl.

In further preferred embodiments according to the invention, in the group $NR^5R^6$ from the general formula I:

$R^5$ is selected from the group consisting of H, $-(CH_2)_r-NR^{28}R^{29}$ wherein r=from 1 to 3 and wherein $R^{28}$ and $R^{29}$ can be $C_{1-3}$-alkyl, and $R^6$ is $-(CH_2)_r-NR^{28}R^{29}$ wherein r=from 1 to 3 and wherein $R^{28}$ and $R^{29}$ can be $C_{1-3}$-alkyl, or $R^6$ represents a $C_{1-3}$-alkyl group substituted by a $N(C_{1-3}$-alkyl)(aryl) group, wherein the aryl group can be substituted and aryl preferably represents phenyl or naphthyl.

In further preferred forms of the compounds according to the invention:

f) in the group $NR^5R^6$ from the general formula I, $R^5$ is selected from the group consisting of H, $C_{1-6}$-alkyl, aryl and aralkyl, and $R^6$ is a group of the type $-(C_{1-4}$-alkyl$)_s$-X wherein s=0 or 1 and wherein the group X is a heteroaryl group which contains at least one N hetero atom and is optionally mono- or poly-substituted, and wherein in the $C_{1-4}$-alkyl group a hydrogen atom can be replaced by a 5- or 6-membered, saturated heterocyclyl group which contains at least one N hetero atom and can contain, in addition to N, also O and/or S as hetero atom.

In further preferred embodiments according to the invention, in the group $NR^5R^6$ from the general formula I:

$R^5$ represents H, methyl, ethyl, propyl, isopropyl, phenyl or benzyl; and $R^6$ represents a group of the $(C_{1-3}$-alkyl$)_s$-X type, wherein s=0 or 1 and wherein the $C_{1-3}$-alkyl group can be substituted by a pyrrolidinyl, piperidinyl, piperazinyl or morpholinyl group and the radical X is selected from the group consisting of:

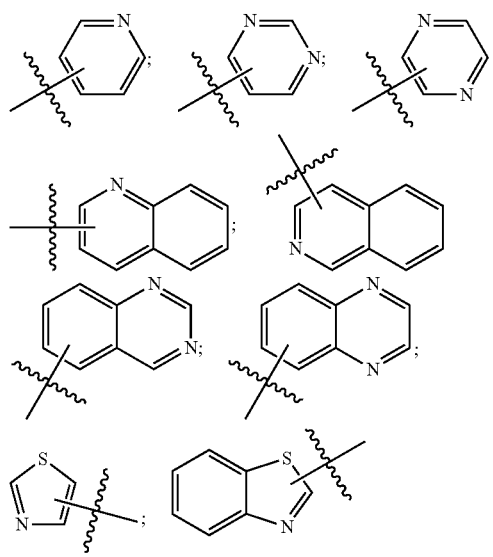

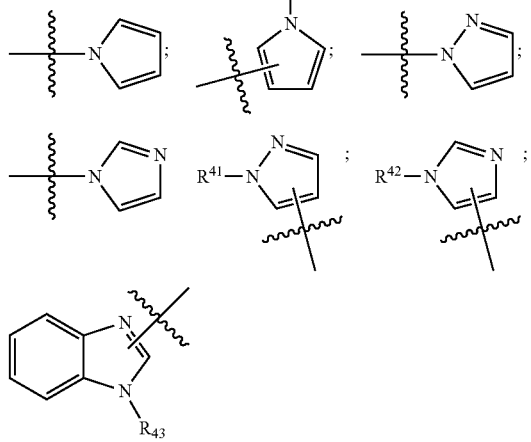

wherein $R^{41}$, $R^{42}$ and $R^{43}$ are selected from H, methyl, ethyl, propyl and isopropyl, optionally mono- or poly-substituted, and the N-heteroaryls can optionally be mono- or poly-substituted.

In further preferred embodiments according to the invention, in general formula I:

n represents 0, 1, 2 or 3;

m represents 1 or 2;

$R^1$ represents aryl or heteroaryl, unsubstituted or mono- or poly-substituted;

$R^{2a-c}$, $R^3$ and $R^4$ represent H or, with an adjacent radical $R^{2a-c}$, $R^3$ or $R^4$, form a five- or six-membered ring which can be saturated or unsaturated and mono- or poly-substituted and which can contain hetero atoms from the group N and O, $R^5$ and $R^6$ together form a 4- to 8-membered ring which can be saturated or unsaturated but not aromatic, is substituted by or fused to a basic radical and can be substituted by a further basic radical or radicals from the group $C_{1-6}$-alkyl, $C_{1-3}$-alkoxy, $C_{3-8}$-cycloalkyl and optionally substituted phenyl; or $R^5$ and $R^6$ together form a 4- to 8-membered ring which contains a further hetero atom from the group N and O and can be substituted by a basic or non-basic radical, or $R^5$ represents H or $C_{1-5}$-alkyl and $R^6$ represents aryl or $C_{3-8}$-cycloalkyl; or an aryl radical linked via a $C_{1-3}$-alkyl chain, wherein the aryl or $C_{3-8}$-cycloalkyl ring is substituted by a basic radical or, where appropriate, the basic substitution takes place on the bridging $C_{1-3}$-alkyl chain, or $R^5$ represents H or $C_{1-5}$-alkyl and $R^6$ represents $C_{4-8}$-heterocyclyl; or a $C_{4-8}$-heterocyclyl radical linked via a $C_{1-3}$-alkyl chain, wherein the heterocyclyl ring is substituted by a basic radical or a non-basic radical, or $R^5$ and $R^6$, independently of one another, represent H or a branched or unbranched alkyl radical which contains from one to three nitrogen atoms, wherein $R^5$ and $R^6$ do not both represent H, in the form of the racemate; in the form of the enantiomers, diastereoisomers, mixtures of the enantiomers or diastereoisomers or in the form of an individual enantiomer or diastereoisomer; in the form of bases and/or salts of physiologically acceptable acids, wherein preferably a substituted aryl or heteroaryl radical is substituted by F, Cl, Br, I, CN, $NH_2$, $NH$—$C_{1-6}$-alkyl, $NH$—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$-alkyl-OH, $CO_2H$, $CH_2SO_2$-phenyl, $CO_2$—$C_{1-6}$-alkyl, $OCF_3$, $CF_3$,

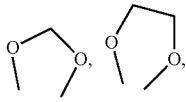

$C_{1-6}$-alkyl, phenoxy, phenyl, pyridyl, thienyl or furyl, a substituted cycloalkyl radical or alkyl radical is substituted by F, Cl, Br, I, —CN, $NH_2$, $NH$—$C_{1-6}$-alkyl, $NH$—$C_{1-6}$-alkyl-OH, $C_{1-6}$alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl, a basic radical preferably denotes piperidine, pyrrolidine, azepane, azetidine, azocane, pyridine, imidazole, imidazolidine, 1,2,4-triazole, diazepane, pyrimidine, imidazoline, piperazine, $N(C_{1-6}$-alkyl$)_2$, $NHC_{1-6}$-alkyl, an aryl radical substituted by $N(C_{1-6}$-alkyl$)_2$; wherein these radicals can all be linked to the structure of the general formula I via a $C_{1-3}$-alkyl group, the $C_{1-3}$-alkyl chain is optionally substituted by =O and the remaining radicals can themselves be substituted by $C_{1-6}$-alkyl; $C_{1-6}$-alkylN($C_{1-6}$-alkyl$)_2$ or $C_{1-6}$-alkylNH($C_{1-6}$-alkyl), and a non-basic radical preferably denotes aryl, heteroaryl, each unsubstituted or mono- or poly-substituted by F, Cl, Br, I, CN, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CH_2SO_2$-phenyl, $CO_2$—$C_{1-6}$-alkyl, $OCF_3$, $CF_3$,

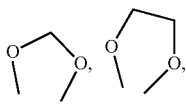

$C_{1-6}$-alkyl;

which can be linked to the structure of the general formula I via a $C_{1-3}$-alkyl chain, wherein the alkyl chain can be substituted by =O; $C_{1-6}$-alkyl optionally substituted by methoxy or $C_{1-3}$-alkoxy; or $C_{3-8}$-cycloalkyl.

Within the scope of this invention, preference is further given to substituted sulfonamide derivatives of the general formula I wherein $R^5$ and $R^6$ together form a 4- to 8-membered ring which can be saturated or unsaturated but not aromatic and is substituted by a basic radical selected from the group consisting of

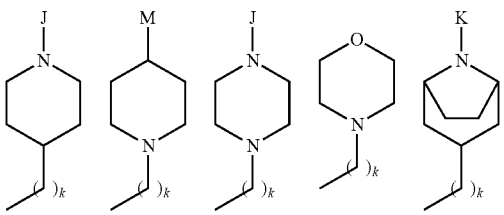

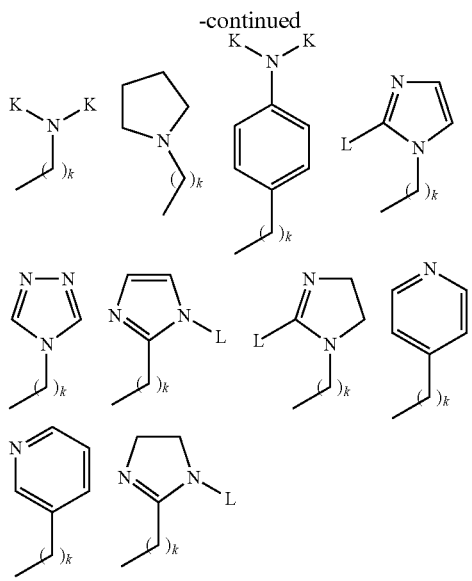

wherein
  k represents 0, 1 or 2,
  L represents H or $C_{1-6}$-alkyl,
  K represents $C_{1-6}$-alkyl,
  M represents $C_{1-6}$-alkyl or $N(CH_3)_2$,
  J represents 2-, 3- or 4-pyridyl, phenyl, piperidyl or $C_{1-6}$-alkyl.

Particular preference is given to substituted sulfonamide derivatives wherein the group

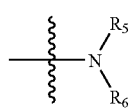

represents piperidine, pyrrolidine or azepane, substituted by optionally $C_{1-3}$-alkyl-linked piperidine, pyrrolidine, azepane, piperazine or diazepane, unsubstituted or monosubstituted by methyl or ethyl, with the proviso that the linkage takes place between two carbon atoms or between a carbon atom and a nitrogen atom but not between two nitrogen atoms;

in particular a radical selected from the group consisting of:

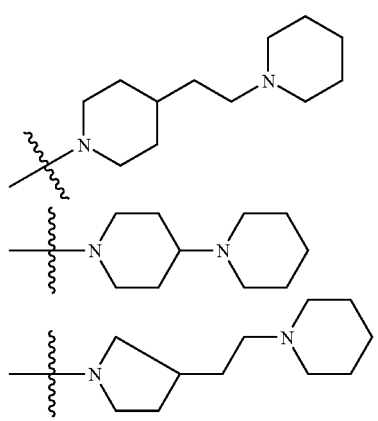

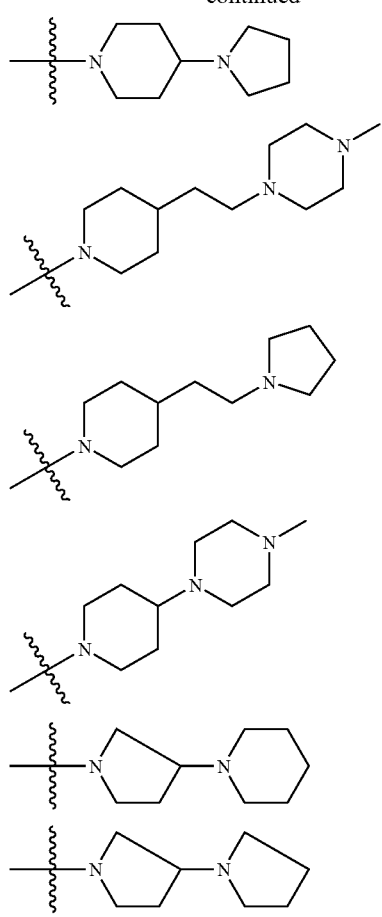

Preference is given also to substituted sulfonamide derivatives of the general formula I wherein $R^5$ and $R^6$ together form a 4- to 8-membered ring which contains a further hetero atom from the group N and O and can be substituted by a basic radical from the group

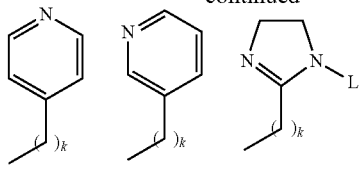

wherein
k represents 0, 1 or 2,
L represents H or $C_{1-6}$-alkyl,
K represents $C_{1-6}$-alkyl,
M represents $C_{1-6}$-alkyl or $N(CH_3)_2$,
J represents 2-, 3- or 4-pyridyl, phenyl, piperidyl or $C_{1-6}$-alkyl,
or by a non-basic radical from the group aryl, heteroaryl, each unsubstituted or mono- or poly-substituted by F, Cl, Br, I, $CF_3$, $OCH_3$, $C_{1-6}$-alkyl, $C_{1-6}$-cycloalkyl, unsubstituted or monosubstituted by F, Cl, Br, I, $CF_3$, $OCH_3$, $C_{1-6}$-alkyl; which can be linked to the structure of the general formula I via a $C_{1-3}$-alkyl chain, wherein the alkyl chain can be substituted by =O; $C_{1-6}$-alkyl or $C_{1-3}$-alkoxy.

Particular preference is given to substituted sulfonamide derivatives wherein the group

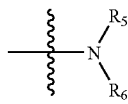

represents piperazine or diazepane, substituted by optionally $C_{1-3}$-alkyl-linked phenyl, unsubstituted or mono- or poly-substituted by

methyl, methoxy, F, Cl, Br, $CF_3$ or CN; $(CH_2)_2OCH_3$; substituted by cyclohexyl or cyclopentyl optionally bonded via $C_{1-3}$-alkyl; pyrrolidine, piperazine, piperidine, unsubstituted or monosubstituted by methyl or ethyl, each linked via a $C_{1-3}$-alkyl group; or pyrrolidine, piperazine, piperidine, unsubstituted or monosubstituted by methyl or ethyl, with the proviso that the linkage takes place between two carbon atoms or between a carbon atom and a nitrogen atom but not between two nitrogen atoms; or by $(CH_2)_aN(CH_3)_2$ wherein a=2, 3;
in particular a radical selected from the group consisting of

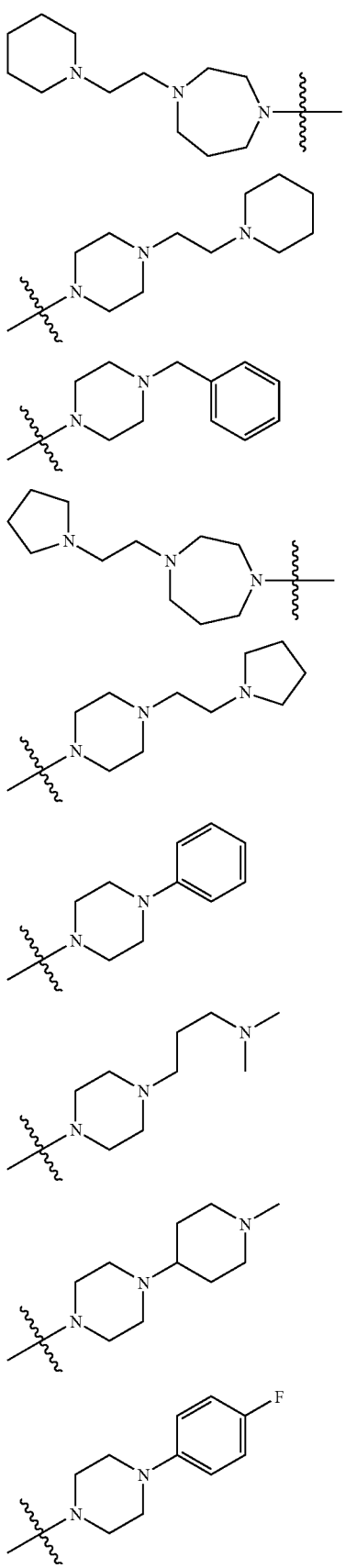
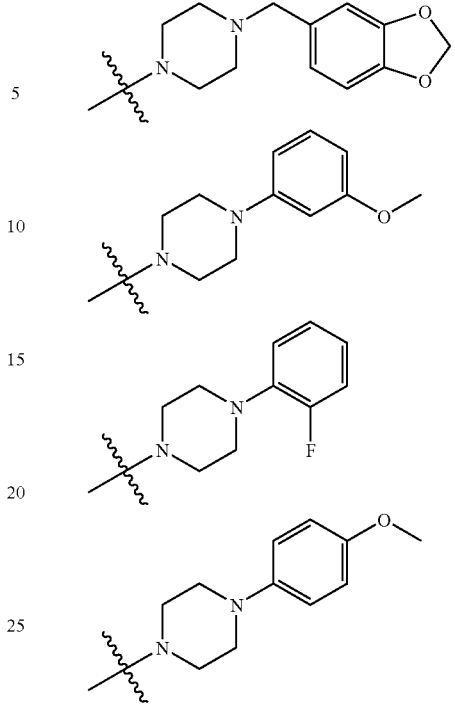
Preference is additionally given to substituted sulfonamide derivatives of the general formula I wherein $R^5$ represents H and $R^6$ represents aryl or $C_{3-8}$-cycloalkyl; or an aryl radical linked via a $C_{1-3}$-alkyl chain, wherein the aryl or $C_{3-8}$-cycloalkyl ring is substituted by at least one basic radical from the group
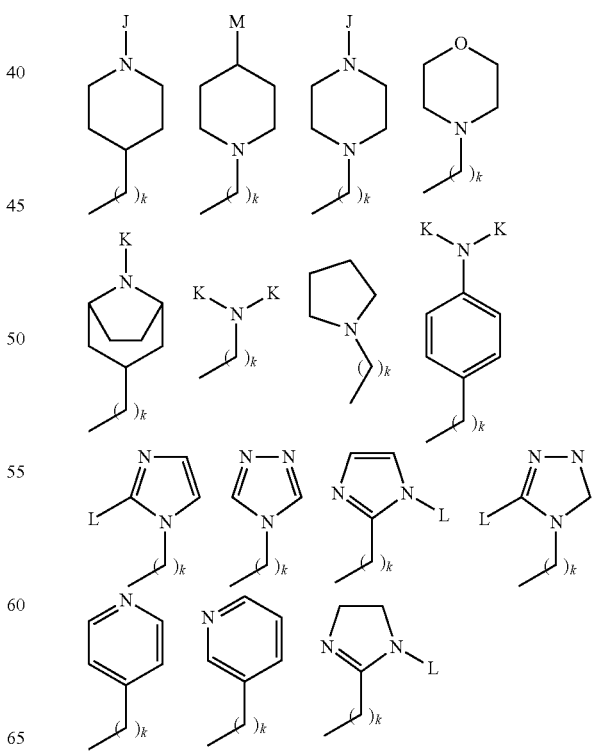

wherein
k represents 0, 1 or 2,
L represents H or $C_{1-6}$-alkyl,
K represents $C_{1-6}$-alkyl,
M represents $C_{1-6}$-alkyl or $N(CH_3)_2$,
J represents 2-, 3- or 4-pyridyl, phenyl, piperidyl or $C_{1-6}$-alkyl.

Particular preference is given to substituted sulfonamide derivatives of the general formula I wherein $R^5$ represents H or $CH_3$ and $R^6$ represents benzyl or phenethyl substituted by pyrrolidine, piperazine, morpholine or piperidine, wherein these radicals are themselves unsubstituted or monosubstituted by methyl or ethyl and are optionally linked via a $C_{1-3}$-alkyl chain, wherein the benzyl or phenethyl radical is optionally substituted by a further basic radical, in particular $R^6$ represents

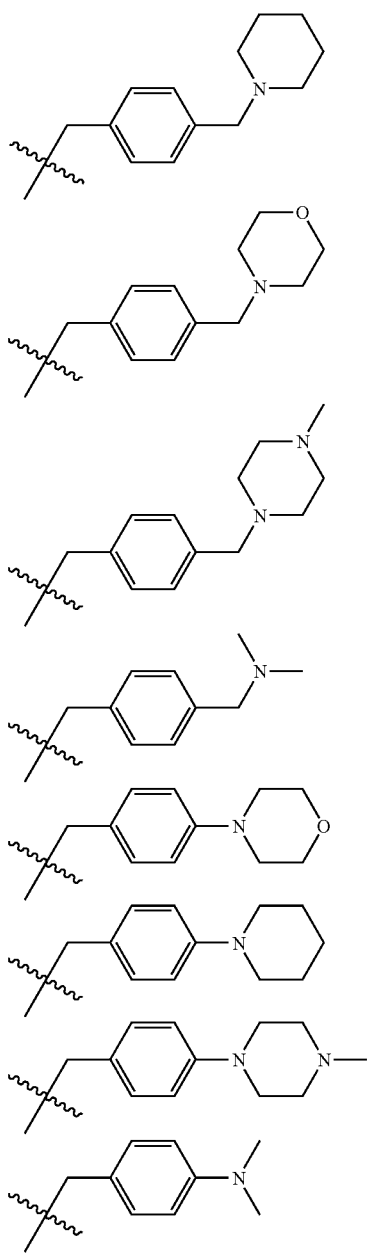

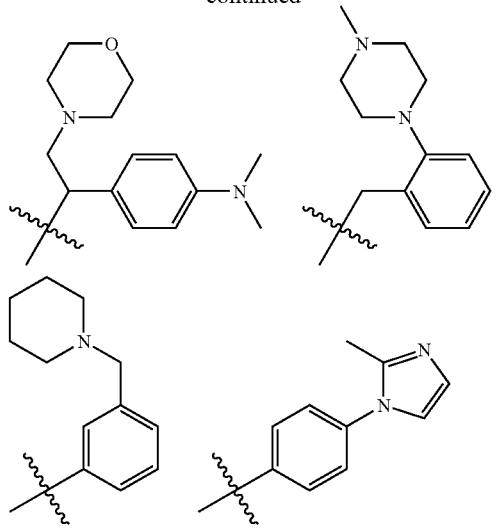

Preference is given also to substituted sulfonamide derivatives wherein $R^5$ represents H or $C_{1-5}$-alkyl and $R^6$ represents $C_{4-8}$-heterocyclyl, wherein the heterocyclyl radical is linked to the structure of the general formula I via a carbon atom; or $R^6$ represents a $C_{4-8}$-heterocyclyl radical linked via a $C_{1-3}$-alkyl chain, wherein the heterocyclyl ring is substituted by a basic radical from the group

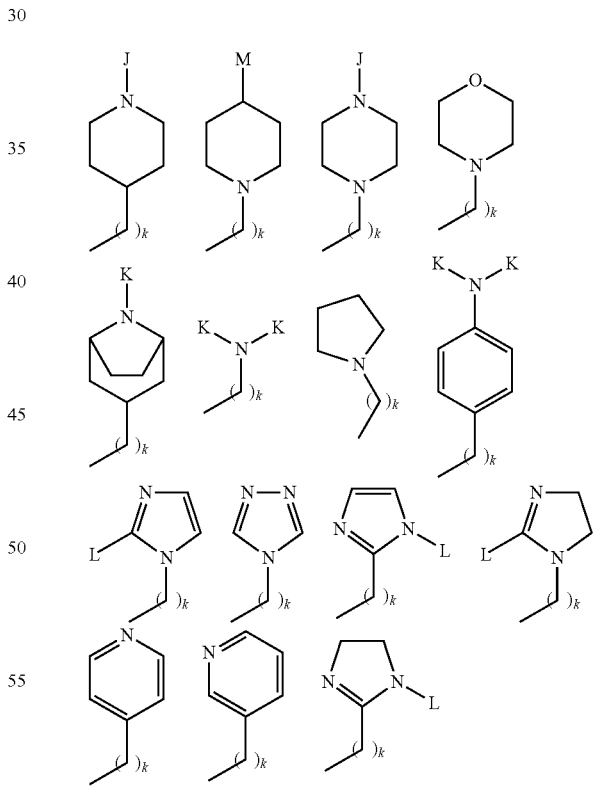

wherein
k represents 0, 1 or 2,
L represents H or $C_{1-6}$-alkyl,
K represents $C_{1-6}$-alkyl,
M represents $C_{1-6}$-alkyl or $N(CH_3)_2$, and
J represents 2-, 3- or 4-pyridyl, phenyl, piperidyl or $C_{1-6}$-alkyl, or by a non-basic radical from the group aryl, heteroaryl, each unsubstituted or mono- or poly-substituted by F, Cl, Br, I, $CF_3$, $OCH_3$, $C_{3-8}$-cycloalkyl, unsubstituted or mono- or poly-substituted by F, Cl, Br, I, $CF_3$, $OCH_3$, $C_{1-6}$-alkyl; which can be linked to the structure of the general formula I via a $C_{1-3}$-alkyl chain, wherein the alkyl chain can be substituted by =O; $C_{1-6}$-alkyl or $C_{1-3}$-alkoxy.

Particular preference is given to substituted sulfonamide derivatives wherein $R^5$ represents H, methyl or ethyl and $R^6$ represents piperidine, pyrrolidine, azepane; piperidine, pyrrolidine, azepane, diazepane or piperazine linked via a $C_{1-3}$-alkyl chain; each substituted by phenyl, pyrrolidine, piperazine, morpholine or piperidine linked via a $C_{1-3}$-alkyl chain and unsubstituted or monosubstituted by methyl or ethyl.

Very particular preference is given to substituted sulfonamide derivatives wherein the group

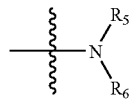

represents

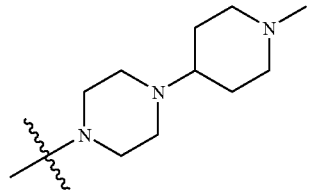 [SMILES: *N1CCN(C2CCN(C)CC2)CC1]

Very particular preference is given to substituted sulfonamide compounds selected from the group consisting of 1   2-[1-(4-methoxy-2,6-dimethyl-phenylsulfonyl)-pyrrolidin-2-ylmethoxy]-N-(4-piperidin-1-ylmethyl-benzyl)-acetamide
2   2-[1-(4-methoxy-2,6-dimethyl-phenylsulfonyl)-piperidin-2-ylmethoxy]-N-(4-piperidin-1-ylmethyl-benzyl)-acetamide
3   2-[1-(4-methoxy-2,6-dimethyl-phenylsulfonyl)-piperidin-2-ylmethoxy]-N-[4-(4-methyl-piperazin-1-yl)-benzyl]-acetamide
4   N-(4-piperidin-1-ylmethyl-benzyl)-2-[1-(2,4,6-trichloro-phenylsulfonyl)-piperidin-2-ylmethoxy]-acetamide
5   1-[4-(1-methyl-piperidin-4-yl)-piperazin-1-yl]-2-[2-(2,4,6-trimethyl-phenylsulfonyl)-1,2,3,4-tetrahydro-isoquinolin-3-ylmethoxy]-ethanone
6   1-(4-benzyl-[1,4]diazepan-1-yl)-2-[1-(naphthyl-1-sulfonyl)-piperidin-2-ylmethoxy]-ethanone
7   2-[1-(4-methoxy-2,6-dimethyl-phenylsulfonyl)-piperidin-2-ylmethoxy]-N-[4-(4-methyl-piperazin-1-ylmethyl)-benzyl]-acetamide
8   2-[1-(4-methoxy-2,6-dimethyl-phenylsulfonyl)-piperidin-2-ylmethoxy]-1-[4-(1-methyl-piperidin-4-yl)-piperazin-1-yl]-ethanone
9   1-(1,4'-bipiperidin-1'-yl)-2-((2-(2,4-dichlorophenylsulfonyl)-1,2,3,4-tetrahydro-isoquinolin-3-yl)methoxy)ethanone
10  N-(4-piperidin-1-ylmethyl-benzyl)-2-[1-(2,4,6-trichloro-phenylsulfonyl)-pyrrolidin-2-ylmethoxy]-acetamide
11  N-(4-dimethylaminomethyl-benzyl)-2-[1-(4-methoxy-2,6-dimethyl-phenylsulfonyl)-piperidin-2-ylmethoxy]-acetamide
12  N-(1-benzyl-piperidin-3-ylmethyl)-2-[1-(2,4,6-trimethyl-phenylsulfonyl)-piperidin-2-ylmethoxy]-acetamide
13  N-[4-(4-methyl-piperazin-1-yl)-benzyl]-2-[1-(2,4,6-trichloro-phenylsulfonyl)-piperidin-2-ylmethoxy]-acetamide
14  2-[1-(4-methoxy-2,6-dimethyl-phenylsulfonyl)-piperidin-2-ylmethoxy]-N-(4-piperidin-1-yl-benzyl)-acetamide
15  N-[4-(4-methyl-piperazin-1-ylmethyl)-benzyl]-2-[1-(2,4,6-trichloro-phenylsulfonyl)-piperidin-2-ylmethoxy]-acetamide
16  N-(1-benzyl-piperidin-3-ylmethyl)-2-[1-(3,4-dichloro-phenylsulfonyl)-2,3-dihydro-1H-indol-2-ylmethoxy]-acetamide
17  2-((2-(2,4-dichlorophenylsulfonyl)-1,2,3,4-tetrahydroisoquinolin-3-yl)methoxy)-1-(4-pyrrolidin-1-yl)piperidin-1-yl)ethanone
18  2-[1-(4-methoxy-2,6-dimethyl-phenylsulfonyl)-pyrrolidin-2-ylmethoxy]-N-[4-(4-methyl-piperazin-1-yl)-benzyl]-acetamide
19  2-((1-(mesitylsulfonyl)piperidin-2-yl)methoxy)-1-(4-(pyrrolidin-1-yl)piperidin-1-yl)-ethanone
20  2-((1-(3,4-dichlorophenylsulfonyl)piperidin-2-yl)methoxy)-1-(4-(2-(piperidin-1-yl)-ethyl)piperidin-1-yl)ethanone
21  2-[1-(4-methoxy-2,6-dimethyl-phenylsulfonyl)-piperidin-2-ylmethoxy]-N-(4-morpholin-4-yl-benzyl)-acetamide
22  1-[4-(1-methyl-piperidin-4-yl)-piperazin-1-yl]-2-[1-(3-trifluoromethyl-phenylsulfonyl)-piperidin-2-ylmethoxy]-ethanone
23  2-((1-(naphthalen-1-ylsulfonyl)piperidin-2-yl)methoxy)-1-(4-(pyrrolidin-1-yl)piperidin-1-yl)ethanone
24  2-[1-(4-methoxy-2,6-dimethyl-phenylsulfonyl)-piperidin-2-ylmethoxy]-N-(4-morpholin-4-ylmethyl-benzyl)-acetamide
25  1-[4-(3-dimethylamino-propyl)-piperazin-1-yl]-2-[2-(2,4,6-trimethyl-phenylsulfonyl)-1,2,3,4-tetrahydro-isoquinolin-3-ylmethoxy]-ethanone
26  2-[1-(3,4-dichloro-phenylsulfonyl)-piperidin-2-ylmethoxy]-1-(4-pyrrolidin-1-yl-piperidin-1-yl)-ethanone
27  1-(2-piperidin-1-ylmethyl-pyrrolidin-1-yl)-2-[1-(2,4,6-trimethyl-phenylsulfonyl)-piperidin-2-ylmethoxy]-ethanone
28  2-[1-(3,4-dichloro-phenylsulfonyl)-piperidin-2-ylmethoxy]-1-[4-(4-methyl-piperazin-1-yl)-piperidin-1-yl]-ethanone
29  N-[4-(4-methyl-piperazin-1-yl)-benzyl]-2-[1-(2,4,6-trichloro-phenylsulfonyl)-pyrrolidin-2-ylmethoxy]-acetamide
30  N-(4-morpholin-4-ylmethyl-benzyl)-2-[1-(2,4,6-trichloro-phenylsulfonyl)-piperidin-2-ylmethoxy]-acetamide
31  1-(4-benzyl-[1,4]diazepan-1-yl)-2-[1-(2,4,6-trimethyl-phenylsulfonyl)-piperidin-2-ylmethoxy]-ethanone
32  2-[1-(3,4-dichloro-phenylsulfonyl)-piperidin-2-ylmethoxy]-1-[4-(1-methyl-piperidin-4-yl)-piperazin-1-yl]-ethanone
33  N-[3-(4-methyl-piperazin-1-yl)-benzyl]-2-[2-(2,4,6-trimethyl-phenylsulfonyl)-1,2,3,4-tetrahydro-isoquinolin-3-ylmethoxy]-acetamide
34  N-(1-benzyl-piperidin-3-ylmethyl)-2-[1-(naphthyl-1-sulfonyl)-piperidin-2-ylmethoxy]-acetamide
35  N-(4-dimethylaminomethyl-benzyl)-2-[1-(4-methoxy-2,6-dimethyl-phenylsulfonyl)-pyrrolidin-2-ylmethoxy]-acetamide 36 2-((1-(3,4-dichlorophenylsulfonyl)pyrrolidin-2-yl)methoxy)-1-(4-(2-(piperidin-1-yl)-ethyl)piperidin-1-yl)ethanone
37 N-(4-dimethylaminomethyl-benzyl)-2-[1-(2,4,6-trichloro-phenylsulfonyl)-piperidin-2-ylmethoxy]-acetamide
38 2-((2-(3,4-dichlorophenylsulfonyl)-1,2,3,4-tetrahydroisoquinolin-3-yl)methoxy)-1-(4-(pyrrolidin-1-yl)piperidin-1-yl)ethanone
39 1-(4-benzo[1,3]dioxol-5-ylmethyl-piperazin-1-yl)-2-[1-(3,4-dichloro-phenylsulfonyl)-piperidin-2-ylmethoxy]-ethanone
40 2-[1-(4-methoxy-2,6-dimethyl-phenylsulfonyl)-pyrrolidin-2-ylmethoxy]-N-[4-(4-methyl-piperazin-1-ylmethyl)-benzyl]-acetamide
41 N-(1-benzyl-piperidin-3-ylmethyl)-2-[2-(2,4,6-trimethyl-phenylsulfonyl)-1,2,3,4-tetrahydro-isoquinolin-3-ylmethoxy]-acetamide
42 2-((1-(3,4-dichlorophenylsulfonyl)piperidin-2-yl)methoxy)-1-(4-(2-(piperidin-1-yl)-ethyl)piperazin-1-yl)ethanone
43 2-[2-(3,4-dichloro-phenylsulfonyl)-1,2,3,4-tetrahydro-isoquinolin-3-ylmethoxy]-N,N-bis-(2-diethylamino-ethyl)-acetamide
44 1-(4-benzo[1,3]dioxol-5-ylmethyl-piperazin-1-yl)-2-[1-(3,4-dichloro-phenylsulfonyl)-pyrrolidin-2-ylmethoxy]-ethanone
45 N-[4-(4-methyl-piperazin-1-ylmethyl)-benzyl]-2-[1-(2,4,6-trichloro-phenylsulfonyl)-pyrrolidin-2-ylmethoxy]-acetamide
46 2-[1-(3,4-dichloro-phenylsulfonyl)-piperidin-2-ylmethoxy]-1-[4-(2-methoxy-ethyl)-piperazin-1-yl]-ethanone
47 N-methyl-N-(2-morpholin-4-yl-1-phenyl-ethyl)-2-[1-(naphthyl-1-sulfonyl)-piperidin-2-ylmethoxy]-acetamide
46 N,N-bis-(2-diethylamino-ethyl)-2-[2-(2,4,6-trimethyl-phenylsulfonyl)-1,2,3,4-tetra-hydro-isoquinolin-3-ylmethoxy]-acetamide
49 N-(4-morpholin-4-ylmethyl-benzyl)-2-[1-(2,4,6-trichloro-phenylsulfonyl)-pyrrolidin-2-ylmethoxy]-acetamide
50 N-(3-morpholin-4-yl-benzyl)-2-[2-(2,4,6-trimethyl-phenylsulfonyl)-1,2,3,4-tetrahydro-isoquinolin-3-ylmethoxy]-acetamide
51 2-[2-(2,4-dichloro-phenylsulfonyl)-1,2,3,4-tetrahydro-isoquinolin-3-ylmethoxy]-1-(2-piperidin-1-ylmethyl-pyrrolidin-1-yl)-ethanone
52 2-((1-(4-methoxyphenylsulfonyl)piperidin-2-yl)methoxy)-1-(4-(2-(piperidin-1-yl)-ethyl)piperidin-1-yl)ethanone
53 2-[1-(3,4-dichloro-phenylsulfonyl)-piperidin-2-ylmethoxy]-1-[4-(3-methoxy-phenyl)-piperazin-1-yl]-ethanone
54 1-(4-cyclohexylmethyl-piperazin-1-yl)-2-[1-(3,4-dichloro-phenylsulfonyl)-pyrrolidin-2-ylmethoxy]-ethanone
55 2-[1-(4-methoxy-2,6-dimethyl-phenylsulfonyl)-pyrrolidin-2-ylmethoxy]-N-(4-morpholin-4-ylmethyl-benzyl)-acetamide
56 2-[1-(3,4-dichloro-phenylsulfonyl)-piperidin-2-ylmethoxy]-1-(4-phenyl-piperazin-1-yl)-ethanone
57 1-(4-benzyl-piperidin-1-yl)-2-[1-(3,4-dichloro-phenylsulfonyl)-piperidin-2-ylmethoxy]-ethanone
58 1-[4-(3-dimethylamino-propyl)-piperazin-1-yl]-2-[1-(3-trifluoromethyl-phenylsulfonyl)-piperidin-2-ylmethoxy]-ethanone
59 2-[1-(3,4-dichloro-phenylsulfonyl)-piperidin-2-ylmethoxy]-1-[4-(4-fluoro-phenyl)-piperazin-1-yl]-ethanone
60 2-[1-(4-methoxy-2,6-dimethyl-phenylsulfonyl)-pyrrolidin-2-ylmethoxy]-N-(4-piperidin-1-yl-benzyl)-acetamide
61 N-(4-morpholin-4-ylmethyl-benzyl)-2-[1-(naphthyl-1-sulfonyl)-piperidin-2-ylmethoxy]-acetamide
62 2-[1-(3,4-dichloro-phenylsulfonyl)-pyrrolidin-2-ylmethoxy]-1-[4-(1-methyl-piperidin-4-yl)-piperazin-1-yl]-ethanone
63 1-[2-(4-dimethylamino-phenyl)-azepan-1-yl]-2-[1-(naphthyl-1-sulfonyl)-piperidin-2-ylmethoxy]-ethanone
64 2-[1-(naphthyl-1-sulfonyl)-piperidin-2-ylmethoxy]-1-(2-piperidin-1-ylmethyl-pyrrolidin-1-yl)-ethanone
65 2-((2-(2,4-dichlorophenylsulfonyl)-1,2,3,4-tetrahydroisoquinolin-3-yl)methoxy)-1-(4-morpholinopiperidin-1-yl)ethanone
66 1-(3-dimethylamino-pyrrolidin-1-yl)-2-[1-(naphthyl-1-sulfonyl)-piperidin-2-yletoxy]-ethanone
67 1-(4-benzyl-[1,4]diazepan-1-yl)-2-[2-(2,4,6-trimethyl-phenylsulfonyl)-1,2,3,4-tetrahydro-isoquinolin-3-ylmethoxy]-ethanone
68 1-(4-cyclohexylmethyl-piperazin-1-yl)-2-[1-(3,4-dichloro-phenylsulfonyl)-piperidin-2-ylmethoxy]-ethanone
69 2-((2-(4-methoxyphenylsulfonyl)-1,2,3,4-tetrahydroisoquinolin-3-yl)methoxy)-1-(4-(2-piperidin-1-yl)ethyl)piperidin-1-yl)ethanone
70 N-(1-benzyl-piperidin-3-ylmethyl)-2-[1-(3,4-dichloro-phenylsulfonyl)-piperidin-2-yl-methoxy]-acetamide
71 N-(4-piperidin-1-yl-benzyl)-2-[1-(2,4,6-trichloro-phenylsulfonyl)-pyrrolidin-2-yl-methoxy]-acetamide
72 2-((1-(3,4-dichlorophenylsulfonyl)pyrrolidin-2-yl)methoxy)-1-(4-(2-(piperidin-1-yl)-ethyl)piperazin-1-yl)ethanone
73 N-(4-dimethylaminomethyl-benzyl)-2-[1-(2,4,6-trichloro-phenylsulfonyl)-pyrrolidin-2-ylmethoxy]-acetamide
74 N-(4-piperidin-1-yl-benzyl)-2-[1-(2,4,6-trichloro-phenylsulfonyl)-piperidin-2-yl-methoxy]-acetamide
75 N-[2-(4-methyl-piperazin-1-yl)-benzyl]-2-[2-(2,4,6-trimethyl-phenylsulfonyl)-1,2,3,4-tetrahydro-isoquinolin-3-ylmethoxy]-acetamide
76 N-(3-piperidin-1-ylmethyl-phenyl)-2-[1-(2,4,6-trimethyl-phenylsulfonyl)-piperidin-2-ylmethoxy]-acetamide
77 1-[4-(3-methoxy-phenyl)-piperazin-1-yl]-2-[1-(2,4,6-trimethyl-phenylsulfonyl)-piperidin-2-ylmethoxy]-ethanone
78 N-(1-benzyl-pyrrolidin-3-yl)-2-[2-(2,4-dichloro-phenylsulfonyl)-1,2,3,4-tetrahydro-isoquinolin-3-ylmethoxy]-N-methyl-acetamide
79 1-(4-benzyl-[1,4]diazepan-1-yl)-2-[2-(2,4-dichloro-phenylsulfonyl)-1,2,3,4-tetra-hydro-isoquinolin-3-ylmethoxy]-ethanone
80 N-[2-(4-methyl-piperazin-1-yl)-benzyl]-2-[1-(2,4,6-trimethyl-phenylsulfonyl)-piperidin-2-ylmethoxy]-acetamide
81 2-[1-(3,4-dichloro-phenylsulfonyl)-2,3-dihydro-1H-indol-2-ylmethoxy]-N-(4-pyrrolidin-1-ylmethyl-benzyl)-acetamide
82 2-[2-(3,4-dichloro-phenylsulfonyl)-1,2,3,4-tetrahydro-isoquinolin-3-ylmethoxy]-1-(2-piperidin-1-ylmethyl-pyrrolidin-1-yl)-ethanone
83 N-(4-pyrrolidin-1-ylmethyl-benzyl)-2-[2-(2,4,6-trimethyl-phenylsulfonyl)-1,2,3,4-tetrahydro-isoquinolin-3-ylmethoxy]-acetamide

| # | Name |
|---|---|
| 84 | 2-[1-(3,4-dichloro-phenylsulfonyl)-piperidin-2-yl-methoxy]-1-[4-(4-methoxy-phenyl)-piperazin-1-yl]-ethanone |
| 85 | 2-[1-(3,4-dichloro-phenylsulfonyl)-piperidin-2-yl-methoxy]-1-[4-(3-dimethylamino-propyl)-piperazin-1-yl]-ethanone |
| 86 | 2-[1-(3,4-dichloro-phenylsulfonyl)-piperidin-2-yl-methoxy]-1-[4-(2-fluoro-phenyl)-piperazin-1-yl]-ethanone |
| 87 | N-[4-(2-methyl-imidazol-1-yl)-phenyl]-2-[1-(2,4,6-trimethyl-phenylsulfonyl)-piperidin-2-ylmethoxy]-acetamide |
| 88 | 2-[1-(3,4-dichloro-phenylsulfonyl)-pyrrolidin-2-yl-methoxy]-1-[4-(3-dimethylamino-propyl)-piperazin-1-yl]-ethanone |
| 89 | 2-[1-(3,4-dichloro-phenylsulfonyl)-pyrrolidin-2-yl-methoxy]-1-(4-phenyl-piperazin-1-yl)-ethanone |
| 90 | 2-(2-(1-(4-methoxyphenylsulfonyl)piperidin-2-yl)ethoxy)-1-(4-(2-(piperidin-1-yl)-ethyl)piperidin-1-yl)ethanone |
| 91 | 2-(2-(1-(4-methoxyphenylsulfonyl)piperidin-2-yl)ethoxy)-1-(4-phenethylpiperazin-1-yl)ethanone |
| 92 | 3-((4-(2-((1-(4-methoxy-2,6-dimethylphenylsulfonyl)piperidin-2-yl)methoxy)acetyl)-piperazin-1-yl)methyl)benzonitrile hydrochloride |
| 93 | 3-((4-(2-((1-(4-methoxy-2,6-dimethylphenylsulfonyl)pyrrolidin-2-yl)methoxy)acetyl)-piperazin-1-yl)methyl)benzonitrile hydrochloride |
| 94 | 2-((1-(4-methoxy-2,6-dimethylphenylsulfonyl)piperidin-2-yl)methoxy)-1-(4-(2-(pyrrolidin-1-yl)ethyl)piperidin-1-yl)ethanone hydrochloride |
| 95 | 2-((1-(4-methoxy-2,6-dimethylphenylsulfonyl)pyrrolidin-2-yl)methoxy)-1-(4-(2-(pyrrolidin-1-yl)ethyl)piperidin-1-yl)ethanone |
| 96 | 1-(3,4-dihydro-2,6-naphthyridin-2(1H)-yl)-2-((1-(4-methoxy-2,6-dimethylphenyl-sulfonyl)piperidin-2-yl)methoxy)ethanone hydrochloride |
| 97 | 2-((1-(4-methoxy-2,6-dimethylphenylsulfonyl)piperidin-2-yl)methoxy)-1-(4-(1-methylpiperidin-4-yl)piperazin-1-yl)ethanone dihydrochloride |
| 98 | 1-(4-(dihydro-1H-pyrido[1,2-a]pyrazin-2(6H,7H,8H,9H,9aH)-yl)piperidin-1-yl)-2-((1-(4-methoxy-2,6-dimethylphenylsulfonyl)piperidin-2-yl)methoxy)ethanone |
| 99 | 1-(4-dihydro-1H-pyrido[1,2-a]pyrazin-2(6H,7H,8H,9H,9aH)-yl)piperidin-1-yl)-2-((1-(4-methoxy-2,6-dimethylphenylsulfonyl)piperidin-2-yl)methoxy)ethanone dihydrochloride |
| 100 | 1-(4-(3,4-dihydro-2,6-naphthyridin-2(1H)-yl)piperidin-1-yl)-2-((1-(4-methoxy-2,6-dimethylphenylsulfonyl)piperidin-2-yl)methoxy)ethanone |
| 101 | tert-butyl 4-(2-((1-(4-methoxy-2,6-dimethylphenylsulfonyl)piperidin-2-yl)methoxy)acetyl)piperazin-1-carboxylate |
| 102 | 2-((1-(4-methoxy-2,6-dimethylphenylsulfonyl)piperidin-2-yl)methoxy)-1-(piperazin-1-yl)ethanone hydrochloride |
| 103 | 2-((1-(4-methoxy-2,6-dimethylphenylsulfonyl)piperidin-2-yl)methoxy)-1-(4-(3-(pyridin-4-yl)-1,2,4-oxadiazol-5-yl)piperidin-1-yl)ethanone |
| 104 | 2-((1-(4-methoxy-2,6-dimethylphenylsulfonyl)piperidin-2-yl)methoxy)-1-(4-(tetrahydro-2H-pyran-4-yl)piperazin-1-yl)ethanone |
| 105 | 2-((1-(4-methoxy-2,6-dimethylphenylsulfonyl)piperidin-2-yl)methoxy)-1-(4-(4-methylcyclohexyl)piperazin-1-yl)ethanone |
| 106 | 2-((1-(4-methoxy-2,6-dimethylphenylsulfonyl)piperidin-2-yl)methoxy)-1-(4-((1-methylpiperidin-4-yl)methyl)piperazin-1-yl)ethanone dihydrochloride |
| 107 | 2-((1-(mesitylsulfonyl)piperidin-2-yl)methoxy)-1-(4-(1-methylpiperidin-4-yl)piperazin-1-yl)ethanone |
| 108 | 2-((1-(2,6-dichloro-4-(trifluoromethyl)phenylsulfonyl)piperidin-2-yl)methoxy)-1-(4-(1-methylpiperidin-4-yl)piperazin-1-yl)ethanone |
| 109 | 2-((1-(2-chloro-6-methylphenylsulfonyl)piperidin-2-yl)methoxy)-1-(4-(1-methylpiperidin-4-yl)piperazin-1-yl)ethanone |
| 110 | 1-(4-(1-methylpiperidin-4-yl)piperazin-1-yl)-2-((1-(naphthalen-1-ylsulfonyl)piperidin-2-yl)methoxy)ethanone |
| 111 | 1-(4-(1-methylpiperidin-4-yl)piperazin-1-yl)-2-((1-(naphthalen-2-ylsulfonyl)piperidin-2-yl)methoxy)ethanone |
| 112 | 2-((1-(4-methoxy-2,6-dimethylphenylsulfonyl)piperidin-2-yl)methoxy)-1-(4-(4-methylpiperazin-1-yl)piperidin-1-yl)ethanone hydrochloride |
| 113 | 2-((1-(4-methoxy-2,6-dimethylphenylsulfonyl)piperidin-2-yl)methoxy)-1-(4-(thieno[3,2-d]pyrimidin-4-yl)piperazin-1-yl)ethanone |
| 114 | 2-((1-(4-chloro-2,5-dimethylphenylsulfonyl)piperidin-2-yl)methoxy)-1-(4-(1-methylpiperidin-4-yl)piperazin-1-yl)ethanone dihydrochloride |
| 115 | 2-((1-(4-chloro-3-(trifluoromethyl)phenylsulfonyl)piperidin-2-yl)methoxy)-1-(4-(1-methylpiperidin-4-yl)piperazin-1-yl)ethanone |
| 116 | 1-(2-((1-(4-methoxy-2,6-dimethylphenylsulfonyl)piperidin-2-yl)methoxy)acetyl)piperidin-4-one |
| 117 | 1-(4-((1H-benzo[d]imidazol-2-yl)methyl)piperazin-1-yl)-2-((1-(4-methoxy-2,6-dimethylphenylsulfonyl)piperidin-2-yl)methoxy)ethanone |
| 118 | 1-(4-(1-methylpiperidin-4-yl)piperazin-1-yl)-2-((1-(2,4,6-trichlorophenylsulfonyl)piperidin-2-yl)methoxy)ethanone |
| 119 | 1-(4-(1-methylpiperidin-4-yl)piperazin-1-yl)-2-((1-(2,4,6-triisopropylphenylsulfonyl)piperidin-2-yl)methoxy)ethanone |
| 120 | 2-((1-(2,4-dichlorophenylsulfonyl)piperidin-2-yl)methoxy)-1-(4-(1-methylpiperidin-4-yl)piperazin-1-yl)ethanone |
| 121 | 2-((1-(3-bromophenylsulfonyl)piperidin-2-yl)methoxy)-1-(4-(1-methylpiperidin-4-yl)piperazin-1-yl)ethanone |
| 122 | 2-((1-(3-bromophenylsulfonyl)piperidin-2-yl)methoxy)-1-(4-(pyridin-4-yl)piperazin-1-yl)ethanone |
| 123 | 2-((1-(4-bromophenylsulfonyl)piperidin-2-yl)methoxy)-1-(4-(1-methylpiperidin-4-yl)piperazin-1-yl)ethanone |
| 124 | 2-((1-(3-bromophenylsulfonyl)piperidin-2-yl)methoxy)-1-(4-(2-(pyrrolidin-1-yl)ethyl)piperidin-1-yl)ethanone |
| 125 | 2-((1-(4-bromophenylsulfonyl)piperidin-2-yl)methoxy)-1-(4-(2-(pyrrolidin-1-yl)ethyl)piperidin-1-yl)ethanone |
| 126 | 2-((1-(4-bromophenylsulfonyl)piperidin-2-yl)methoxy)-1-(4-(pyridin-4-yl)piperazin-1-yl)ethanone |
| 127 | (S)-2-((2-(4-methoxy-2,6-dimethylphenylsulfonyl)-1,2,3,4-tetrahydroisoquinolin-3-yl)methoxy)-1-(4-(1-methylpiperidin-4-yl)piperazin-1-yl)ethanone |
| 128 | 2-((1-(5-chloro-1,3-dimethyl-1H-pyrazol-4-ylsulfonyl)piperidin-2-yl)methoxy)-1-(4-(1-methylpiperidin-4-yl)piperazin-1-yl)ethanone |
| 129 | 2-((1-(6-chloroimidazo[2,1-b]thiazol-5-ylsulfonyl)piperidin-2-yl)methoxy)-1-(4-(1-methylpiperidin-4-yl)piperazin-1-yl)ethanone |

130 1-(4-fluoro-1,4'-bipiperidin-1'-yl)-2-((1-(4-methoxy-2,6-dimethylphenylsulfonyl)piperidin-2-yl)methoxy)ethanone
131 1-(4-(1-methylpiperidin-4-yl)piperazin-1-yl)-2-((1-(3-(o-tolyloxy)phenylsulfonyl)piperidin-2-yl)methoxy)ethanone
133 (S)-2-((2-(2,4-dichlorophenylsulfonyl)-1,2,3,4-tetrahydroisoquinolin-3-yl)methoxy)-1-(4-(1-methylpiperidin-4-yl)piperazin-1-yl)ethanone
134 2-((1-(4-methoxy-2,6-dimethylphenylsulfonyl)piperidin-2-yl)methoxy)-1-(4-(4-(trifluoromethyl)cyclohexyl)piperazin-1-yl)ethanone
135 (S)-2-((1-(4-methoxy-2,6-dimethylphenylsulfonyl)azetidin-2-yl)methoxy)-1-(4-(1-methylpiperidin-4-yl)piperazin-1-yl)ethanone
136 2-((1-(4-methoxy-2,6-dimethylphenylsulfonyl)piperidin-2-yl)methoxy)-1-(4-(2-morpholin-2-(pyridin-3-yl)ethylamino)piperidin-1-yl)ethanone
137 2-((1-(benzo[b]thiophen-3-ylsulfonyl)piperidin-2-yl)methoxy)-1-(4-(1-methylpiperidin-4-yl)piperazin-1-yl)ethanone
138 2-((1-(2-chloro-4-(trifluoromethyl)phenylsulfonyl)piperidin-2-yl)methoxy)-1-(4-(1-methylpiperidin-4-yl)piperazin-1-yl)ethanone
139 2-((1-(2-chlorophenylsulfonyl)piperidin-2-yl)methoxy)-1-(4-(1-methylpiperidin-4-yl)piperazin-1-yl)ethanone dihydrochloride
140 (R)-2-((1-(4-methoxy-2,3,6-trimethylphenylsulfonyl)pyrrolidin-2-yl)methoxy)-1-(4-(1-methylpiperidin-4-yl)piperazin-1-yl)ethanone dihydrochloride
141 2-((1-(2,6-dichlorophenylsulfonyl)piperidin-2-yl)methoxy)-1-(4-(1-methylpiperidin-4-yl)piperazin-1-yl)ethanone dihydrochloride
142 (S)-2-((2-(4-methoxyphenylsulfonyl)-1,2,3,4-tetrahydroisoquinolin-3-yl)methoxy)-1-(4-(1-methylpiperidin-4-yl)piperazin-1-yl)ethanone
143 2-((1-(4-methoxy-2,6-dimethylphenylsulfonyl)piperidin-2-yl)methoxy)-N-(2-(1-(pyridin-4-yl)piperidin-4-yl)ethyl)acetamide
144 1-(4-(5,6-dihydroimidazo[1,2-a]pyrazin-7(8H)-yl)piperidin-1-yl)-2-((1-(4-methoxy-2,6-dimethylphenylsulfonyl)piperidin-2-yl)methoxy)ethanone
145 1-(4-(5,6-dihydro-[1,2,4]triazolo[1,5-a]pyrazin-7(8H)-yl)piperidin-1-yl)-2-((1-(4-methoxy-2,6-dimethylphenylsulfonyl)piperidin-2-yl)methoxy)ethanone
146 2-((1-(4-methoxy-2,6-dimethylphenylsulfonyl)piperidin-2-yl)methoxy)-1-(4-(4-methylpiperazin-1-carbonyl)piperidin-1-yl)ethanone
147 2-((1-(4-methoxy-2,6-dimethylphenylsulfonyl)piperidin-2-yl)methoxy)-1-(4-(pyridin-4-yl)piperazin-1-yl)ethanone
148 2-((1-(4-bromo-2,6-dimethylphenylsulfonyl)piperidin-2-yl)methoxy)-1-(4-(1-methylpiperidin-4-yl)piperazin-1-yl)ethanone
149 2-((1-(4-bromo-2,6-dimethylphenylsulfonyl)piperidin-2-yl)methoxy)-1-(4-(2-(pyrrolidin-1-yl)ethyl)piperidin-1-yl)ethanone
150 2-((1-(4-bromo-2,6-dimethylphenylsulfonyl)piperidin-2-yl)methoxy)-1-(4-(pyridin-4-yl)piperazin-1-yl)ethanone
151 2-((1-(5-chloro-3-methylbenzo[b]thiophen-2-ylsulfonyl)piperidin-2-yl)methoxy)-1-(4-(1-methylpiperidin-4-yl)piperazin-1-yl)ethanone dihydrochloride
152 (R)-2-((1-(2-chloro-6-methylphenylsulfonyl)pyrrolidin-2-yl)methoxy)-1-(4-(1-methylpiperidin-4-yl)piperazin-1-yl)ethanone dihydrochloride
153 2-((1-(2,5-bis(trifluoromethyl)phenylsulfonyl)piperidin-2-yl)methoxy)-1-(4-(1-methylpiperidin-4-yl)piperazin-1-yl)ethanone
154 2-((1-(7-chlorobenzo[c][1,2,5]oxadiazol-4-ylsulfonyl)piperidin-2-yl)methoxy)-1-(4-(1-methylpiperidin-4-yl)piperazin-1-yl)ethanone
155 2-((1-(4-methylnaphthalen-1-ylsulfonyl)piperidin-2-yl)methoxy)-1-(4-(1-methylpiperidin-4-yl)piperazin-1-yl)ethanone dihydrochloride
156 1-(4-(1-methylpiperidin-4-yl)piperazin-1-yl)-2-((1-(2,4,5-trichlorophenylsulfonyl)piperidin-2-yl)methoxy)ethanone dihydrochloride
157 2-((1-(2-methylnaphthalen-1-ylsulfonyl)piperidin-2-yl)methoxy)-1-(4-(1-methylpiperidin-4-yl)piperazin-1-yl)ethanone dihydrochloride
158 2-((1-(5-(dimethylamino)naphthalen-1-ylsulfonyl)piperidin-2-yl)methoxy)-1-(4-(1-methylpiperidin-4-yl)piperazin-1-yl)ethanone dihydrochloride
159 1-(4-(1-methylpiperidin-4-yl)piperazin-1-yl)-2-((1-(o-tolylsulfonyl)piperidin-2-yl)methoxy)ethanone dihydrochloride
160 2-((1-(4-bromo-2,6-dichlorophenylsulfonyl)piperidin-2-yl)methoxy)-1-(4-(1-methylpiperidin-4-yl)piperazin-1-yl)ethanone dihydrochloride
161 (S)-2-((1-(2-chloro-6-methylphenylsulfonyl)pyrrolidin-2-yl)methoxy)-1-(4-(2-(pyrrolidin-1-yl)ethyl)piperidin-1-yl)ethanone hydrochloride
162 (S)-2-((1-(2-chloro-6-methylphenylsulfonyl)pyrrolidin-2-yl)methoxy)-1-(4-(1-methylpiperidin-4-yl)piperazin-1-yl)ethanone dihydrochloride
163 (S)-2-((1-(2-chloro-6-methylphenylsulfonyl)pyrrolidin-2-yl)methoxy)-1-(4-((1-methylpiperidin-4-yl)methyl)piperazin-1-yl)ethanone dihydrochloride
164 2-(2-(1-(4-methoxy-2,6-dimethylphenylsulfonyl)piperidin-2-yl)ethoxy)-1-(4-(1-methylpiperidin-4-yl)piperazin-1-yl)ethanone
165 2-((1-(4-methoxy-2,6-dimethylphenylsulfonyl)piperidin-2-yl)methoxy)-1-(4-(pyridin-3-yloxy)piperidin-1-yl)ethanone
166 2-((1-(4-methoxy-2,6-dimethylphenylsulfonyl)piperidin-2-yl)methoxy)-1-(4-(quinoxalin-6-ylmethyl)piperazin-1-yl)ethanone
167 (S)-2-((1-(4-methoxy-2,6-dimethylphenylsulfonyl)piperidin-2-yl)methoxy)-1-(4-(1-methylpiperidin-4-yl)piperazin-1-yl)ethanone
168 2-((1-(4-methoxy-2,6-dimethylphenylsulfonyl)piperidin-2-yl)methoxy)-1-(4-(4-(pyrrolidin-1-yl)quinazolin-7-yl)piperazin-1-yl)ethanone
169 2-((1-(4-fluoro-2,6-dimethylphenylsulfonyl)piperidin-2-yl)methoxy)-1-(4-(1-methylpiperidin-4-yl)piperazin-1-yl)ethanone dihydrochloride
170 2-((1-(2,5-dichlorothiophen-3-ylsulfonyl)piperidin-2-yl)methoxy)-1-(4-(1-methylpiperidin-4-yl)piperazin-1-yl)ethanone dihydrochloride
171 2-((1-(benzo[b]thiophen-2-ylsulfonyl)piperidin-2-yl)methoxy)-1-(4-(1-methylpiperidin-4-yl)piperazin-1-yl)ethanone
172 2-((1-(2,5-dimethylthiophen-3-ylsulfonyl)piperidin-2-yl)methoxy)-1-(4-(1-methylpiperidin-4-yl)piperazin-1-yl)ethanone
173 2-((1-(2,3-dichlorophenylsulfonyl)piperidin-2-yl)methoxy)-1-(4-(1-methylpiperidin-4-yl)piperazin-1-yl)ethanone dihydrochloride
174 2-((1-(4-methoxynaphthalen-1-ylsulfonyl)piperidin-2-yl)methoxy)-1-(4-(1-methylpiperidin-4-yl)piperazin-1-yl)ethanone dihydrochloride 175 1-(4-(1-methylpiperidin-4-yl)piperazin-1-yl)-2-((1-(quinolin-8-ylsulfonyl)piperidin-2-yl)methoxy)ethanone dihydrochloride
176 2-((1-(isoquinolin-5-ylsulfonyl)piperidin-2-yl)methoxy)-1-(4-(1-methylpiperidin-4-yl)piperazin-1-yl)ethanone dihydrochloride
177 (R)-2-((1-(4-methoxy-2,6-dimethylphenylsulfonyl)piperidin-2-yl)methoxy)-1-(4-(1-methylpiperidin-4-yl)piperazin-1-yl)ethanone dihydrochloride
178 1-(4-(1-methylpiperidin-4-yl)piperazin-1-yl)-2-((2-(naphthalen-2-ylsulfonyl)-1,2,3,4-tetrahydroisoquinolin-3-yl)methoxy)ethanone dihydrochloride
179 1-(4-(1-methylpiperidin-4-yl)piperazin-1-yl)-2-((1-(5,6,7,8-tetrahydronaphthalen-2-ylsulfonyl)piperidin-2-yl)methoxy)ethanone dihydrochloride
180 (S)-2-((1-(4-methoxy-2,6-diimethylphenylsulfonyl)pyrrolidin-2-yl)methoxy)-1-(4-(1-methylpiperidin-4-yl)piperazin-1-yl)ethanone
181 (S)-2-((1-(4-methoxy-2,6-dimethylphenylsulfonyl)pyrrolidin-2-yl)methoxy)-1-(4-((1-methylpiperidin-4-yl)methyl)piperazin-1-yl)ethanone
182 (S)-2-((2-(4-methoxyphenylsulfonyl)-1,2,3,4-tetrahydroisoquinolin-3-yl)methoxy)-1-(4-(2-(pyrrolidin-1-yl)ethyl)piperidin-1-yl)ethanone
183 (S)-2-((2-(2,4-dichlorophenylsulfonyl)-1,2,3,4-tetrahydroisoquinolin-3-yl)methoxy)-1-(4-(2-(pyrrolidin-1-yl)ethyl)piperidin-1-yl)ethanone
184 (S)-2-((2-(2,4-dichlorophenylsulfonyl)-1,2,3,4-tetrahydroisoquinolin-3-yl)methoxy)-1-(4-((1-methylpiperidin-4-yl)methyl)piperazin-1-yl)ethanone
185 (S)-2-((2-(4-methoxy-2,6-dimethylphenylsulfonyl)-1,2,3,4-tetrahydroisoquinolin-3-yl)methoxy)-1-(4-((1-methylpiperidin-4-yl)methyl)piperazin-1-yl)ethanone
186 (S)-2-((1-(4-methoxy-2,6-dimethylphenylsulfonyl)piperidin-2-yl)methoxy)-1-(4-(pyridin-4-yloxy)piperidin-1-yl)ethanone hydrochloride
187 (S)-2-((2-(4-methoxy-2,6-dimethylphenylsulfonyl)-1,2,3,4-tetrahydroisoquinolin-3-yl)methoxy)-1-(4-(2-(pyrrolidin-1-yl)ethyl)piperidin-1-yl)ethanone
188 2-((1-(4-methoxy-2,6-dimethylphenylsulfonyl)piperidin-2-yl)methoxy)-1-(4-((pyridin-4-yloxy)methyl)piperidin-1-yl)ethanone
189 (S)-2-((2-(4-methoxyphenylsulfonyl)-1,2,3,4-tetrahydroisoquinolin-3-yl)methoxy)-1-(4-((1-methylpiperidin-4-yl)methyl)piperazin-1-yl)ethanone dihydrochloride
190 (S)-2-((1-(4-methoxy-2,6-dimethylphenylsulfonyl)pyrrolidin-2-yl)methoxy)-1-(4-(2-(pyrrolidin-1-yl)ethyl)piperidin-1-yl)ethanone hydrochloride
191 2-((1-(2-chloronaphthalen-1-ylsulfonyl)piperidin-2-yl)methoxy)-1-(4-(1-methylpiperidin-4-yl)piperazin-1-yl)ethanone dihydrochloride
192 2-((1-(4-methoxy-2,6-dimethylphenylsulfonyl)pyrrolidin-2-yl)methoxy)-1-(4-(1-methylpiperidin-4-yl)piperazin-1-yl)ethanone
193 N-(4-(4,5-dihydro-1H-imidazol-2-yl)benzyl)-2-((1-(4-methoxy-2,6-dimethylphenylsulfonyl)piperidin-2-yl)methoxy)-N-methylacetamide hydrochloride
194 2-((1-(4-methoxy-2,6-dimethylphenylsulfonyl)piperidin-2-yl)methoxy)-N-methyl-N-(2-(4-(pyrrolidin-1-yl)cyclohexyl)ethyl)acetamide
195 2-((1-(4-methoxy-2,6-dimethylphenylsulfonyl)piperidin-2-yl)methoxy)-N-(3-(pyrazin-2-yloxy)benzyl)acetamide
196 2-((1-(4-methoxy-2,6-dimethylphenylsulfonyl)piperidin-2-yl)methoxy)-N-(4-(pyrazin-2-yloxy)benzyl)acetamide
197 1-(4-((5-chloro-2-phenyl-1H-imidazol-4-yl)methyl)piperazin-1-yl)-2-((1-(4-methoxy-2,6-dimethylphenylsulfonyl)piperidin-2-yl)methoxy)ethanone
198 1-(4-((1,5-dimethyl-1H-pyrazol-4-yl)methyl)piperazin-1-yl)-2-((1-(4-methoxy-2,6-dimethylphenylsulfonyl)piperidin-2-yl)methoxy)ethanone
199 1-(4-((2-(dimethylamino)pyrimidin-5-yl)methyl)piperazin-1-yl)-2-((1-(4-methoxy-2,6-dimethylphenylsulfonyl)piperidin-2-yl)methoxy)ethanone
200 1-(4-(6-fluoro-3,4-dihydroisoquinolin-2(1H)-yl)piperidin-1-yl)-2-((1-(4-methoxy-2,6-dimethylphenylsulfonyl)piperidin-2-yl)methoxy)ethanone
201 2-((1-(4-methoxy-2,6-dimethylphenylsulfonyl)piperidin-2-yl)methoxy)-1-(4-(pyridin-4-yl)piperidin-1-yl)ethanone
202 2-((1-(4-methoxy-2,6-dimethylphenylsulfonyl)-1,2,3,4-tetrahydroquinolin-2-yl)methoxy)-1-(4-(1-methylpiperidin-4-yl)piperazin-1-yl)ethanone
203 1-(4-(1-methylpiperidin-4-yl)piperazin-1-yl)-2-((1-(naphthalen-2-ylsulfonyl)-1,2,3,4-tetrahydroquinolin-2-yl)methoxy)ethanone
204 2-((1-(4-methoxyphenylsulfonyl)-1,2,3,4-tetrahydroquinolin-2-yl)methoxy)-1-(4-(1-methylpiperidin-4-yl)piperazin-1-yl)ethanone
205 2-((1-(4-methoxy-2,6-dimethylphenylsulfonyl)piperidin-2-yl)methoxy)-N-(2-(pyrazin-2-yloxy)benzyl)acetamide
206 2-((1-(4-methoxy-2,6-dimethylphenylsulfonyl)piperidin-2-yl)methoxy)-1-(1H-pyrrol[3,4-c]pyridin-2(3H)-yl)ethanone
207 2-((1-(4-methoxy-2,6-dimethylphenylsulfonyl)piperidin-2-yl)methoxy)-1-(2-(pyridin-3-yl)morpholin)ethanone
208 2-((1-(4-methoxy-2,6-dimethylphenylsulfonyl)piperidin-2-yl)methoxy)-1-(3-(pyridin-3-ylmethyl)pyrrolidin-1-yl)ethanone
209 N-(2-(4-(dimethylamino)cyclohexyl)ethyl)-2-((1-(4-methoxy-2,6-dimethylphenylsulfonyl)piperidin-2-yl)methoxy)-N-methylacetamide
210 2-((1-(6-methoxynaphthalen-2-ylsulfonyl)piperidin-2-yl)methoxy)-1-(4-(1-methylpiperidin-4-yl)piperazin-1-yl)ethanone
211 1-(4-(3,4-dihydropyrrolo[1,2-a]pyrazin-2(1H)-yl)piperidin-1-yl)-2-((1-(4-methoxy-2,6-dimethylphenylsulfonyl)piperidin-2-yl)methoxy)ethanone
212 2-((1-(4-methoxy-2,6-dimethylphenylsulfonyl)piperidin-2-yl)methoxy)-1-(4-(2-(1-methylpiperidin-4-yl)ethyl)piperazin-1-yl)ethanone
213 2-((1-(3,4-dichlorophenylsulfonyl)-1,2,3,4-tetrahydroquinolin-2-yl)methoxy)-N-(2-(4-(dimethylamino)cyclohexyl)ethyl)-N-methylacetamide
214 1-(4-((2-((4-fluorophenyl)(methyl)amino)pyrimidin-5-yl)methyl)piperazin-1-yl)-2-((1-(4-methoxy-2,6-dimethylphenylsulfonyl)piperidin-2-yl)methoxy)ethanone
215 2-((1-(4-methoxy-2,6-dimethylphenylsulfonyl)piperidin-2-yl)methoxy)-1-(6-(4-methylpiperazin-1-yl)-3,4-dihydroisoquinolin-2(1H)-yl)ethanone
216 2-((1-(3,4-dichlorophenylsulfonyl)-1,2,3,4-tetrahydroquinolin-2-yl)methoxy)-N-methyl-N-(2-(4-(pyrrolidin-1-yl)cyclohexyl)ethyl)acetamide
217 2-((1-(4-methoxy-2,6-dimethylphenylsulfonyl)piperidin-2-yl)methoxy)-1-(4-(pyridin-3-yl)piperidin-1-yl)ethanone
218 N—((S)-1-benzylpyrrolidin-3-yl)-N-methyl-2-((1-(2-(trifluoromethyl)phenylsulfonyl)piperidin-2-yl)methoxy)acetamide 219 2-((1-(4-methoxyphenylsulfonyl)piperidin-2-yl)methoxy)-1-(4-(3-methylbenzyl)piperazin-1-yl)ethanone
220 2-((1-(4-methoxyphenylsulfonyl)piperidin-2-yl)methoxy)-1-(4-(4-phenethylthiazol-2-yl)piperazin-1-yl)ethanone
221 2-(2-(1-(4-methoxyphenylsulfonyl)piperidin-2-yl)ethoxy)-1-(4-(2-(piperidin-1-yl)ethyl)piperazin-1-yl)ethanone
222 2-((1-(mesitylsulfonyl)piperidin-2-yl)methoxy)-1-(4-(5-methyl-1H-benzo[d]imidazol-2-yl)piperidin-1-yl)ethanone
223 1-(2-((4,6-dimethylpyridin-2-yl)methyl)piperidin-1-yl)-2-((2-(mesitylsulfonyl)-1,2,3,4-tetrahydroisoquinolin-3-yl)methoxy)ethanone
224 1-(2-(5-bromopyridin-3-yl)piperidin-1-yl)-2-((1-(3-(trifluoromethyl)phenylsulfonyl)piperidin-2-yl)methoxy)ethanone
225 1-(1,4'-bipiperidin-1'-yl)-2-((1-(mesitylsulfonyl)piperidin-2-yl)methoxy)ethanone
226 2-((1-(mesitylsulfonyl)piperidin-2-yl)methoxy)-1-(2-(pyridin-2-ylmethyl)pyrrolidin-1-yl)ethanone
227 2-((1-(mesitylsulfonyl)piperidin-2-yl)methoxy)-1-(2-(6-methoxypyridin-3-yl)piperidin-1-yl)ethanone
228 1-(2-((5-ethylpyridin-2-yl)methyl)piperidin-1-yl)-2-((1-(mesitylsulfonyl)piperidin-2-yl)methoxy)ethanone
229 2-((1-(mesitylsulfonyl)piperidin-2-yl)methoxy)-1-(2-((3-methylpyridin-2-yl)methyl)piperidin-1-yl)ethanone
230 1-(4-(4-methylpiperazin-1-yl)piperidin-1-yl)-2-((1-(naphthen-1-ylsulfonyl)piperidin-2-yl)methoxy)ethanone
231 2-((1-(mesitylsulfonyl)piperidin-2-yl)methoxy)-1-(4-(4-methylpiperazin-1-yl)piperidin-1-yl)ethanone
232 2-((1-(mesitylsulfonyl)piperidin-2-yl)methoxy)-1-(4-((1-methylpiperidin-4-yl)methyl)piperazin-1-yl)ethanone
233 2-((2-(2,4-dichlorophenylsulfonyl)-1,2,3,4-tetrahydroisoquinolin-3-yl)methoxy)-1-(4-(4-methylpiperazin-1-yl)piperidin-1-yl)ethanone
234 1-(4-(4-benzylthiazol-2-yl)piperazin-1-yl)-2-((1-(mesitylsulfonyl)piperidin-2-yl)methoxy)ethanone
235 1-(1,4'-bipiperidin-1'-yl)-2-(1-(naphthen-1-ylsulfonyl)piperidin-2-yl)methoxy)ethanone
236 2-((1-(4-methoxy-2,6-dimethylphenylsulfonyl)piperidin-2-yl)methoxy)-1-(3-(pyridin-2-yl)pyrrolidin-1-yl)ethanone
237 2-((1-(4-methoxy-2,6-dimethylphenylsulfonyl)piperidin-2-yl)methoxy)-1-(3-(pyridin-3-yl)pyrrolidin-1-yl)ethanone
238 2-((1-(4-methoxy-2,6-dimethylphenylsulfonyl)piperidin-2-yl)methoxy)-1-(3-(pyridin-4-yl)pyrrolidin-1-yl)ethanone
239 2-((1-(4-methoxy-2,6-dimethylphenylsulfonyl)piperidin-2-yl)methoxy)-N-methyl-N-(2-(pyridin-4-yl)ethyl)acetamide
240 1-(2-((4,6-dimethylpyridin-2-yl)methyl)pyrrolidin-1-yl)-2-((1-(naphthen-1-ylsulfonyl)piperidin-2-yl)methoxy)ethanone
241 2-((1-(4-methoxy-2,6-dimethylphenylsulfonyl)piperidin-2-yl)methoxy)-N-methyl-N-(1-phenyl-2-(pyrrolidin-1-yl)ethyl)acetamide
242 2-((1-(4-methoxy-2,6-dimethylphenylsulfonyl)piperidin-2-yl)methoxy)-1-(4-methylpiperazin-1-yl)ethanone
243 N-(2-(1H-indol-3-yl)ethyl)-2-((1-(4-methoxy-2,6-dimethylphenylsulfonyl)piperidin-2-yl)methoxy)acetamide
244 2-((1-(4-methoxy-2,6-dimethylphenylsulfonyl)piperidin-2-yl)methoxy)-N-(2-methylquinolin-4-yl)acetamide
245 1-(4-(2-ethoxyethyl)piperazin-1-yl)-2-((2-(mesitylsulfonyl)-1,2,3,4-tetrahydroisoquinolin-3-yl)methoxy)ethanone
246 2-((2-(mesitylsulfonyl)-1,2,3,4-tetrahydroisoquinolin-3-yl)methoxy)-1-(4-(2-methoxyethyl)piperazin-1-yl)ethanone
247 2-((1-(4-methoxy-2,6-dimethylphenylsulfonyl)piperidin-2-yl)methoxy)-1-(2-(pyridin-2-yl)pyrrolidin-1-yl)ethanone
248 2-((1-(4-methoxy-2,6-dimethylphenylsulfonyl)piperidin-2-yl)methoxy)-N-(2-(4-methylpiperazin-1-yl)ethyl)acetamide
249 2-((1-(4-methoxy-2,6-dimethylphenylsulfonyl)piperidin-2-yl)methoxy)-N-(2-morpholin-2-(4-(trifluoromethyl)phenyl)ethyl)acetamide
250 N-(5-(dimethylamino)pentyl)-2-((1-(4-methoxy-2,6-dimethylphenylsulfonyl)piperidin-2-yl)methoxy)acetamide
251 N-(2-(2-chlorophenyl)-2-morpholinoethyl)-2-((1-(4-methoxy-2,6-dimethylphenylsulfonyl)piperidin-2-yl)methoxy)acetamide
252 2-((1-(4-methoxy-2,6-dimethylphenylsulfonyl)piperidin-2-yl)methoxy)-N-(2-(4-methoxyphenyl)-2-(pyrrolidin-1-yl)ethyl)acetamide 253 1-(4-(3,5-dimethoxyphenyl)piperazin-1-yl)-2-((1-(2,4,6-trichlorophenylsulfonyl)piperidin-2-yl)methoxy)ethanone
254 1-(4-(2-(diisopropylamino)ethyl)piperazin-1-yl)-2-((1-(2,4,6-trichlorophenylsulfonyl)piperidin-2-yl)methoxy)ethanone
255 N-(1-benzylpiperidin-4-yl)-N-cyclopropyl-2-((1-(2,4,6-trichlorophenylsulfonyl)piperidin-2-yl)methoxy)acetamide
256 N-(2-morpholino-2-(pyridin-3-yl)ethyl)-2-((1-(2,4,6-trichlorophenylsulfonyl)piperidin-2-yl)methoxy)acetamide
257 N-(1-ethyl-1H-pyrazol-5-yl)-2-((1-(4-methoxy-2,6-dimethylphenylsulfonyl)piperidin-2-yl)methoxy)acetamide
258 N-(isoquinolin-5-yl)-2-(1-(4-methoxy-2,6-dimethylphenylsulfonyl)piperidin-2-yl)methoxy)acetamide
259 N-(2-(dimethylamino)ethyl)-2-((1-(4-methoxy-2,6-dimethylphenylsulfonyl)piperidin-2-yl)methoxy)acetamide
260 N-(3-(2,6-dimethylpiperidin-1-yl)propyl)-2-((1-(4-methoxy-2,6-dimethylphenylsulfonyl)piperidin-2-yl)methoxy)acetamide
261 N-(2-(dimethylamino)-1-phenylethyl)-2-((1-(4-methoxy-2,6-dimethylphenylsulfonyl)piperidin-2-yl)methoxy)acetamide
262 2-((1-(4-methoxy-2,6-dimethylphenylsulfonyl)piperidin-2-yl)methoxy)-N-(1-phenyl-2-(pyrrolidin-1-yl)ethyl)acetamide
263 2-((1-(4-methoxy-2,6-dimethylphenylsulfonyl)piperidin-2-yl)methoxy)-N-(2-(4-methylpiperazin-1-yl)-1-phenylethyl)acetamide
264 N-(3-morpholinophenyl)-2-((2-(phenylsulfonyl)-1,2,3,4-tetrahydroisoquinolin-3-yl)methoxy)acetamide
265 2-((2-(2,4-dichlorophenylsulfonyl)-1,2,3,4-tetrahydroisoquinolin-3-yl)methoxy)-N-(3-morpholinophenyl)acetamide
266 2-((1-(3,4-dichlorophenylsulfonyl)piperidin-2-yl)methoxy)-1-(2-(piperidin-1-ylmethyl)morpholino)ethanone
267 2-((1-(4-methoxy-2,6-dimethylphenylsulfonyl)pyrrolidin-2-yl)methoxy)-1-(4-(4-methylpiperazin-1-yl)piperidin-1-yl)ethanone
268 2-((1-(4-methoxy-2,6-dimethylphenylsulfonyl)pyrrolidin-2-yl)methoxy)-1-(4-(2-(piperidin-1-yl)ethyl)piperidin-1-yl)ethanone 269  1-(4-(2-(2,5-dimethyl-1H-pyrrol-1-yl)ethyl)piperazin-1-yl)-2-((1-(4-methoxy-2,6-dimethylphenylsulfonyl)pyrrolidin-2-yl)methoxy)ethanone
270  1-(4-(2-(diisopropylamino)ethyl)piperazin-1-yl)-2-((1-(4-methoxy-2,6-dimethylphenylsulfonyl)pyrrolidin-2-yl)methoxy)ethanone
271  2-((1-(4-methoxy-2,6-dimethylphenylsulfonyl)pyrrolidin-2-yl)methoxy)-1-(2-(pyridin-2-yl)pyrrolidin-1-yl)ethanone
272  2-((1-(4-methoxy-2,6-dimethylphenylsulfonyl)pyrrolidin-2-yl)methoxy)-1-(3-(pyridin-3-yl)pyrrolidin-1-yl)ethanone
273  2-((1-(4-methoxy-2,6-dimethylphenylsulfonyl)pyrrolidin-2-yl)methoxy)-1-(3-(pyridin-4-yl)pyrrolidin-1-yl)ethanone
274  2-((1-(4-methoxy-2,6-dimethylphenylsulfonyl)pyrrolidin-2-yl)methoxy)-1-(4-(pyridin-4-yl)piperazin-1-yl)ethanone
275  2-((2-(4-methoxy-2,3,6-trimethylphenylsulfonyl)-1,2,3,4-tetrahydroisoquinolin-3-yl)methoxy)-1-(4-(4-methylpiperazin-1-yl)piperidin-1-yl)ethanone
276  2-((2-(4-methoxy-2,3,6-trimethylphenylsulfonyl)-1,2,3,4-tetrahydroisoquinolin-3-yl)methoxy)-1-(4-(2-(piperidin-1-yl)ethyl)piperidin-1-yl)ethanone
277  2-((2-(4-methoxy-2,3,6-trimethylphenylsulfonyl)-1,2,3,4-tetrahydroisoquinolin-3-yl)methoxy)-1-(2-((6-methylpyridin-2-yl)methyl)piperidin-1-yl)ethanone
278  2-((1-(2,6-dichlorophenylsulfonyl)piperidin-2-yl)methoxy)-1-(4-(4-methylpiperazin-1-yl)piperidin-1-yl)ethanone
279  2-((1-(2,6-dichlorophenylsulfonyl)piperidin-2-yl)methoxy)-1-(4-(2-(piperidin-1-yl)ethyl)piperidin-1-yl)ethanone
280  2-((1-(2,6-dichlorophenylsulfonyl)piperidin-2-yl)methoxy)-1-(4-(2-(2,5-dimethyl-1H-pyrrol-1-yl)ethyl)piperazin-1-yl)ethanone
281  2-((1-(2,6-dichlorophenylsulfonyl)piperidin-2-yl)methoxy)-1-(4-(2-(diisopropylamino)ethyl)piperazin-1-yl)ethanone
282  2-((1-(2,6-dichlorophenylsulfonyl)piperidin-2-yl)methoxy)-1-(3-(pyridin-4-yl)pyrrolidin-1-yl)ethanone
283  2-((1-(2,6-dichlorophenylsulfonyl)piperidin-2-yl)methoxy)-1-(4-(pyridin-4-yl)piperazin-1-yl)ethanone
284  2-((1-(2,6-dichlorophenylsulfonyl)piperidin-2-yl)methoxy)-1-(2-((6-methylpyridin-2-yl)methyl)piperidin-1-yl)ethanone
285  2-((1-(2,6-dichlorophenylsulfonyl)pyrrolidin-2-yl)methoxy)-1-(4-(4-methylpiperazin-1-yl)piperidin-1-yl)ethanone
286  2-((1-(2,6-dichlorophenylsulfonyl)pyrrolidin-2-yl)methoxy)-1-(4-(2-(piperidin-1-yl)ethyl)piperidin-1-yl)ethanone
287  2-((1-(2,6-dichlorophenylsulfonyl)pyrrolidin-2-yl)methoxy)-1-(4-(2-(2,5-dimethyl-1H-pyrrol-1-yl)ethyl)piperazin-1-yl)ethanone
288  2-((1-(4-methoxy-2,6-dimethylphenylsulfonyl)piperidin-2-yl)methoxy)-1-(4-(3-methoxyphenyl)piperazin-1-yl)ethanone
289  1-(4-(4-fluorophenyl)piperazin-1-yl)-2-((1-(4-methoxy-2,6-dimethylphenylsulfonyl)piperidin-2-yl)methoxy)ethanone
290  2-((1-(4-methoxy-2,6-dimethylphenylsulfonyl)piperidin-2-yl)methoxy)-1-(4-(4-methoxyphenyl)piperazin-1-yl)ethanone
291  1-(4-isopropylpiperazin-1-yl)-2-((1-(4-methoxy-2,6-dimethylphenylsulfonyl)piperidin-2-yl)methoxy)ethanone
292  2-((2-(mesitylsulfonyl)-1,2,3,4-tetrahydroisoquinolin-3-yl)methoxy)-1-(4-(4-methylpiperazin-1-yl)piperidin-1-yl)ethanone
293  2-((1-(3,4-dichlorophenylsulfonyl)piperidin-2-yl)methoxy)-N-(3-(pyrrolidin-1-ylmethyl)phenyl)acetamide
294  N-(4-(dimethylamino)butyl)-2-((1-(2,4,6-trichlorophenylsulfonyl)pyrrolidin-2-yl)methoxy)acetamide
295  1-(4-ethylpiperazin-1-yl)-2-((1-(2,4,6-trichlorophenylsulfonyl)pyrrolidin-2-yl)methoxy)ethanone
296  1-(4-(pyrrolidin-1-yl)piperidin-1-yl)-2-((1-(2,4,6-trichlorophenylsulfonyl)pyrrolidin-2-yl)methoxy)ethanone
297  1-(4-morpholinopiperidin-1-yl)-2-((1-(2,4,6-trichlorophenylsulfonyl)pyrrolidin-2-yl)methoxy)ethanone
298  1-(1,4'-bipiperidin-1-yl)-2-((1-(2,4,6-trichlorophenylsulfonyl)pyrrolidin-2-yl)methoxy)ethanone
299  2-((1-(4-methoxy-2,6-dimethylphenylsulfonyl)pyrrolidin-2-yl)methoxy)-N-(4-(pyrrolidin-1-ylmethyl)benzyl)acetamide
300  N-((1-benzylpiperidin-3-yl)methyl)-2-((1-(4-methoxy-2,6-dimethylphenylsulfonyl)pyrrolidin-2-yl)methoxy)acetamide
301  2-((1-(4-methoxy-2,6-dimethylphenylsulfonyl)pyrrolidin-2-yl)methoxy)-N-(4-(4-methylpiperazin-1-yl)phenyl)acetamide
302  2-((1-(4-methoxy-2,6-dimethylphenylsulfonyl)pyrrolidin-2-yl)methoxy)-N-(4-(4-methylpiperazin-1-yl)benzyl)acetamide
303  N—((S)-1-benzylpyrrolidin-3-yl)-2-((1-(4-methoxy-2,6-dimethylphenylsulfonyl)pyrrolidin-2-yl)methoxy)-N-methylacetamide
304  2-((1-(4-methoxy-2,6-dimethylphenylsulfonyl)pyrrolidin-2-yl)methoxy)-N-methyl-N-(2-morpholino-1-phenylethyl)acetamide
305  2-((1-(4-methoxy-2,6-dimethylphenylsulfonyl)pyrrolidin-2-yl)methoxy)-1-(4-(pyridin-2-yl)piperazin-1-yl)ethanone
306  2-((1-(4-methoxy-2,6-dimethylphenylsulfonyl)pyrrolidin-2-yl)methoxy)-1-(4-(3-methoxyphenyl)piperazin-1-yl)ethanone
307  1-(4-(4-fluorophenyl)piperazin-1-yl)-2-((1-(4-methoxy-2,6-dimethylphenylsulfonyl)pyrrolidin-2-yl)methoxy)ethanone
308  2-((1-(4-methoxy-2,6-dimethylphenylsulfonyl)pyrrolidin-2-yl)methoxy)-1-(4-(4-methoxyphenyl)piperazin-1-yl)ethanone
309  2-((1-(4-methoxy-2,6-dimethylphenylsulfonyl)pyrrolidin-2-yl)methoxy)-1-(4-(pyrimidin-2-yl)piperazin-1-yl)ethanone
310  2-((1-(4-methoxy-2,6-dimethylphenylsulfonyl)pyrrolidin-2-yl)methoxy)-1-(4-phenethylpiperazin-1-yl)ethanone
311  1-(4-(5-chloro-2-methylphenyl)piperazin-1-yl)-2-((1-(4-methoxy-2,6-dimethylphenylsulfonyl)pyrrolidin-2-yl)methoxy)ethanone
312  2-(4-(2-((1-(4-methoxy-2,6-dimethylphenylsulfonyl)pyrrolidin-2-yl)methoxy)acetyl)piperazin-1-yl)nicotinonitrile
313  2-((1-(2,6-dichlorophenylsulfonyl)piperidin-2-yl)methoxy)-N-(4-(pyrrolidin-1-ylmethyl)benzyl)acetamide
314  N-((1-benzylpiperidin-3-yl)methyl)-2-((1-(2,6-dichlorophenylsulfonyl)piperidin-2-yl)methoxy)acetamide
315  N—((S)-1-benzylpyrrolidin-3-yl)-2-((1-(2,6-dichlorophenylsulfonyl)piperidin-2-yl)methoxy)-N-methylacetamide
316  2-((1-(2,6-dichlorophenylsulfonyl)piperidin-2-yl)methoxy)-1-(4-(pyridin-2-yl)piperazin-1-yl)ethanone 317 2-((1-(2,6-dichlorophenylsulfonyl)piperidin-2-yl)methoxy)-1-(4-(3-methoxyphenyl)piperazin-1-yl)ethanone
318 2-((1-(2,6-dichlorophenylsulfonyl)piperidin-2-yl)methoxy)-1-(4-(4-fluorophenyl)piperazin-1-yl)ethanone
319 2-((1-(2,6-dichlorophenylsulfonyl)piperidin-2-yl)methoxy)-1-(4-(4-methoxyphenyl)piperazin-1-yl)ethanone
320 2-((1-(2,6-dichlorophenylsulfonyl)piperidin-2-yl)methoxy)-1-(4-phenethylpiperazin-1-yl)ethanone
321 1-(4-(5-chloro-2-methylphenyl)piperazin-1-yl)-2-((1-(2,6-dichlorophenylsulfonyl)piperidin-2-yl)methoxy)ethanone
322 2-((1-(2,6-dichlorophenylsulfonyl)pyrrolidin-2-yl)methoxy)-N-(4-(pyrrolidin-1-ylmethyl)benzyl)acetamide
323 N-((1-benzylpiperidin-3-yl)methyl)-2-((1-(2,6-dichlorophenylsulfonyl)pyrrolidin-2-yl)methoxy)acetamide
324 2-((1-(2,6-dichlorophenylsulfonyl)pyrrolidin-2-yl)methoxy)-1-(4-(3-methoxyphenyl)piperazin-1-yl)ethanone
325 2-((1-(2,6-dichlorophenylsulfonyl)pyrrolidin-2-yl)methoxy)-1-(4-(4-methoxyphenyl)piperazin-1-yl)ethanone
326 2-((1-(2,6-dichlorophenylsulfonyl)pyrrolidin-2-yl)methoxy)-1-(4-phenethylpiperazin-1-yl)ethanone
327 N-((1-benzylpiperidin-3-yl)methyl)-2-((1-(2,4,6-trichlorophenylsulfonyl)pyrrolidin-2-yl)methoxy)acetamide
328 1-(4-(4-methoxyphenyl)piperazin-1-yl)-2-((1-(2,4,6-trichlorophenylsulfonyl)pyrrolidin-2-yl)methoxy)ethanone
329 1-(4-phenethylpiperazin-1-yl)-2-((1-(2,4,6-trichlorophenylsulfonyl)pyrrolidin-2-yl)methoxy)ethanone
330 1-(4-(4-methylpiperazin-1-yl)piperidin-1-yl)-2-((1-(2,4,6-trichlorophenylsulfonyl)pyrrolidin-2-yl)methoxy)ethanone
331 1-(4-(2-(piperidin-1-yl)ethyl)piperidin-1-yl)-2-((1-(2,4,6-trichlorophenylsulfonyl)pyrrolidin-2-yl)methoxy)ethanone
332 1-(4-(2-(2,5-dimethyl-1H-pyrrol-1-yl)ethyl)piperazin-1-yl)-2-((1-(2,4,6-trichlorophenylsulfonyl)pyrrolidin-2-yl)methoxy)ethanone
333 1-(4-(2-(diisopropylamino)ethyl)piperazin-1-yl)-2-((1-(2,4,6-trichlorophenylsulfonyl)pyrrolidin-2-yl)methoxy)ethanone
334 N-(1-benzylpiperidin-4-yl)-N-cyclopropyl-2-((1-(2,4,6-trichlorophenylsulfonyl)pyrrolidin-2-yl)methoxy)acetamide
335 1-(4-(pyridin-4-yl)piperazin-1-yl)-2-((1-(2,4,6-trichlorophenylsulfonyl)pyrrolidin-2-yl)methoxy)ethanone
336 1-(1,4'-bipiperidin-1'-yl)-2-((1-(2,6-dichlorophenylsulfonyl)piperidin-2-yl)methoxy)ethanone
337 1-(1,4'-bipiperidin-1'-yl)-2-((1-(2,6-dichlorophenylsulfonyl)pyrrolidin-2-yl)methoxy)ethanone
338 N-(2-(piperidin-1-yl)ethyl)-2-((1-(2,4,6-trichlorophenylsulfonyl)pyrrolidin-2-yl)methoxy)acetamide
339 N-(2-(pyrrolidin-1-yl)ethyl)-2-((1-(2,4,6-trichlorophenylsulfonyl)pyrrolidin-2-yl)methoxy)acetamide
340 1-(4-(3,5-dimethoxyphenyl)piperazin-1-yl)-2-((1-(4-methoxy-2,6-dimethylphenylsulfonyl)piperidin-2-yl)methoxy)ethanone
341 1-(4-(2-(diisopropylamino)ethyl)piperazin-1-yl)-2-((1-(4-methoxy-2,6-dimethylphenylsulfonyl)piperidin-2-yl)methoxy)ethanone
342 N-(1-benzylpiperidin-4-yl)-N-cyclopropyl-2-((1-(4-methoxy-2,6-dimethylphenylsulfonyl)piperidin-2-yl)methoxy)acetamide
343 2-((1-(4-methoxy-2,6-dimethylphenylsulfonyl)piperidin-2-yl)methoxy)-N-(2-(pyrrolidin-1-yl)ethyl)acetamide
344 2-((1-(4-methoxy-2,6-dimethylphenylsulfonyl)piperidin-2-yl)methoxy)-N-(3-morpholinopropyl)acetamide
345 2-((1-(4-methoxy-2,6-dimethylphenylsulfonyl)piperidin-2-yl)methoxy)-N-(pyridin-3-ylmethyl)acetamide
346 1-(4-(3-chlorophenyl)piperazin-1-yl)-2-((1-(4-methoxy-2,6-dimethylphenylsulfonyl)pyrrolidin-2-yl)methoxy)ethanone
347 1-(4-(3,4-dimethylphenyl)piperazin-1-yl)-2-((1-(4-methoxy-2,6-dimethylphenylsulfonyl)pyrrolidin-2-yl)methoxy)ethanone
348 1-(4-(3,4-dichlorophenyl)piperazin-1-yl)-2-((1-(4-methoxy-2,6-dimethylphenylsulfonyl)pyrrolidin-2-yl)methoxy)ethanone
349 1-(4-(3,4-dichlorobenzyl)piperazin-1-yl)-2-((1-(4-methoxy-2,6-dimethylphenylsulfonyl)pyrrolidin-2-yl)methoxy)ethanone
350 1-(4-(4-bromobenzyl)piperazin-1-yl)-2-((1-(4-methoxy-2,6-dimethylphenylsulfonyl)pyrrolidin-2-yl)methoxy)ethanone
351 2-((1-(4-methoxy-2,6-dimethylphenylsulfonyl)pyrrolidin-2-yl)methoxy)-1-(4-(2,4,6-trimethylbenzyl)piperazin-1-yl)ethanone
352 1-(4-(4-chlorobenzyl)piperazin-1-yl)-2-((1-(4-methoxy-2,6-dimethylphenylsulfonyl)pyrrolidin-2-yl)methoxy)ethanone
353 2-((1-(4-methoxy-2,6-dimethylphenylsulfonyl)pyrrolidin-2-yl)methoxy)-1-(4-(4-methylbenzyl)piperazin-1-yl)ethanone
354 1-(4-(3-chlorophenyl)piperazin-1-yl)-2-((1-(2,6-dichlorophenylsulfonyl)pyrrolidin-2-yl)methoxy)ethanone
355 2-((1-(2,6-dichlorophenylsulfonyl)pyrrolidin-2-yl)methoxy)-1-(4-(3,4-dimethylphenyl)piperazin-1-yl)ethanone
356 1-(4-(3,4-dichlorophenyl)piperazin-1-yl)-2-((1-(2,6-dichlorophenylsulfonyl)pyrrolidin-2-yl)methoxy)ethanone
357 1-(4-(3,4-dichlorobenzyl)piperazin-1-yl)-2-((1-(2,6-dichlorophenylsulfonyl)pyrrolidin-2-yl)methoxy)ethanone
358 1-(4-(4-bromobenzyl)piperazin-1-yl)-2-((1-(2,6-dichlorophenylsulfonyl)pyrrolidin-2-yl)methoxy)ethanone
359 1-(4-(4-chlorobenzyl)piperazin-1-yl)-2-((1-(2,6-dichlorophenylsulfonyl)pyrrolidin-2-yl)methoxy)ethanone
360 2-((1-(2,6-dichlorophenylsulfonyl)pyrrolidin-2-yl)methoxy)-1-(4-(4-methylbenzyl)piperazin-1-yl)ethanone
361 N-benzyl-N-(2-(dimethylamino)ethyl)-2-((1-(4-methoxy-2,6-dimethylphenylsulfonyl)piperidin-2-yl)methoxy)acetamide
362 1-(4-benzyl-1,4-diazepan-1-yl)-2-((1-(4-methoxy-2,6-dimethylphenylsulfonyl)piperidin-2-yl)methoxy)ethanone
363 1-((R)-3-(dimethylamino)pyrrolidin-1-yl)-2-((1-(4-methoxy-2,6-dimethylphenylsulfonyl)piperidin-2-yl)methoxy)ethanone
364 N—((S)-1-benzylpyrrolidin-3-yl)-2-((1-(4-methoxy-2,6-dimethylphenylsulfonyl)piperidin-2-yl)methoxy)-N-methylacetamide
365 N-(1-benzylpyrrolidin-3-yl)-2-((1-(4-methoxy-2,6-dimethylphenylsulfonyl)piperidin-2-yl)methoxy)acetamide
366 N-(3-(1H-imidazol-1-yl)propyl)-2-((1-(4-methoxy-2,6-dimethylphenylsulfonyl)piperidin-2-yl)methoxy)acetamide
367 N-(4-(dimethylamino)benzyl)-N-isopropyl-2-((1-(4-methoxy-2,6-dimethylphenylsulfonyl)piperidin-2-yl)methoxy)acetamide 368 2-((1-(4-methoxy-2,6-dimethylphenylsulfonyl)piperidin-2-yl)methoxy)-N-methyl-N-(2-morpholino-1-phenylethyl)acetamide
369 2-((1-(4-methoxy-2,6-dimethylphenylsulfonyl)piperidin-2-yl)methoxy)-1-(4-(pyridin-2-yl)piperazin-1-yl)ethanone
370 N-(isoquinolin-1-yl)-2-((1-(4-methoxy-2,6-dimethylphenylsulfonyl)piperidin-2-yl)methoxy)acetamide
371 2-((1-(4-methoxy-2,6-dimethylphenylsulfonyl)piperidin-2-yl)methoxy)-N-(1-methyl-1H-benzo[d]imidazol-2-yl)acetamide
372 2-((1-(4-methoxy-2,6-dimethylphenylsulfonyl)piperidin-2-yl)methoxy)-N-(pyrimidin-4-yl)acetamide
373 2-((1-(4-methoxy-2,6-dimethylphenylsulfonyl)piperidin-2-yl)methoxy)-1-(4-phenethylpiperazin-1-yl)ethanone
374 2-((1-(4-methoxy-2,6-dimethylphenylsulfonyl)piperidin-2-yl)methoxy)-1-((S)-2-(pyrrolidin-1-ylmethyl)pyrrolidin-1-yl)ethanone
375 2-((1-(4-methoxy-2,6-dimethylphenylsulfonyl)piperidin-2-yl)methoxy)-1-(4-methyl-1,4-diazepan-1-yl)ethanone
376 1-(4-(3-chloro-5-(trifluoromethyl)pyridin-2-yl)piperazin-1-yl)-2-((1-(4-methoxy-2,6-dimethylphenylsulfonyl)piperidin-2-yl)methoxy)ethanone
377 N-benzyl-N-(2-(dimethylamino)ethyl)-2-(1-(4-methoxy-2,6-dimethylphenylsulfonyl)piperidin-2-yl)methoxy)acetamide
378 1-(4-(3,4-dichlorophenyl)piperazin-1-yl)-2-((1-(4-methoxy-2,6-dimethylphenylsulfonyl)piperidin-2-yl)methoxy)ethanone
379 N-(2-(dimethylamino)ethyl)-2-((1-(4-methoxy-2,6-dimethylphenylsulfonyl)piperidin-2-yl)methoxy)-N-methylacetamide
380 N-(2-(diethylamino)ethyl)-N-ethyl-2-((1-(4-methoxy-2,6-dimethylphenylsulfonyl)piperidin-2-yl)methoxy)acetamide
381 1-(4-(3,4-dichlorobenzyl)piperazin-1-yl)-2-((1-(4-methoxy-2,6-dimethylphenylsulfonyl)piperidin-2-yl)methoxy)ethanone
382 1-(4-(4-bromobenzyl)piperazin-1-yl)-2-((1-(4-methoxy-2,6-dimethylphenylsulfonyl)piperidin-2-yl)methoxy)ethanone
383 2-((1-(4-methoxy-2,6-dimethylphenylsulfonyl)piperidin-2-yl)methoxy)-1-(4-(2,4,6-trimethylbenzyl)piperazin-1-yl)ethanone
384 1-(4-(4-chlorobenzyl)piperazin-1-yl)-2-((1-(4-methoxy-2,6-dimethylphenylsulfonyl)piperidin-2-yl)methoxy)ethanone
385 2-((1-(4-methoxy-2,6-dimethylphenylsulfonyl)piperidin-2-yl)methoxy)-1-(4-(4-methylbenzyl)piperazin-1-yl)ethanone
386 2-((1-(4-methoxy-2,6-dimethylphenylsulfonyl)piperidin-2-yl)methoxy)-1-(4-(4-methoxybenzyl)piperazin-1-yl)ethanone
387 1-(4-(2-fluorobenzyl)piperazin-1-yl)-2-((1-(4-methoxy-2,6-dimethylphenylsulfonyl)piperidin-2-yl)methoxy)ethanone
388 2-((1-(4-methoxy-2,6-dimethylphenylsulfonyl)piperidin-2-yl)methoxy)-1-(4-methyl-2-phenylpiperazin-1-yl)ethanone
389 1-(3-(pyridin-3-yl)pyrrolidin-1-yl)-2-(1-(2,4,6-trichlorophenylsulfonyl)piperidin-2-yl)methoxy)ethanone
390 1-(3-(pyridin-4-yl)pyrrolidin-1-yl)-2-((1-(2,4,6-trichlorophenylsulfonyl)piperidin-2-yl)methoxy)ethanone
391 N-methyl-N-(2-(pyridin-4-yl)ethyl)-2-((1-(2,4,6-trichlorophenylsulfonyl)piperidin-2-yl)methoxy)acetamide
392 N-methyl-N-(1-phenyl-2-(pyrrolidin-1-yl)ethyl)-2-((1-(2,4,6-trichlorophenylsulfonyl)piperidin-2-yl)methoxy)acetamide
393 1-(4-methylpiperazin-1-yl)-2-((1-(2,4,6-trichlorophenylsulfonyl)piperidin-2-yl)methoxy)ethanone
394 N-(pyridin-4-ylmethyl)-2-((1-(2,4,6-trichlorophenylsulfonyl)piperidin-2-yl)methoxy)acetamide
395 2-((1-(4-methoxy-2,6-dimethylphenylsulfonyl)piperidin-2-yl)methoxy)-N-(2-morpholinopyridin-3-yl)acetamide
396 2-((1-(4-methoxy-2,6-dimethylphenylsulfonyl)piperidin-2-yl)methoxy)-N-(6-morpholinopyridin-3-yl)acetamide
397 2-((1-(4-methoxy-2,6-dimethylphenylsulfonyl)piperidin-2-yl)methoxy)-1-(4-(5-methyl-1H-benzo[d]imidazol-2-yl)piperidin-1-yl)ethanone
398 1-(2-(4-(dimethylamino)phenyl)pyrrolidin-1-yl)-2-((1-(4-methoxy-2,6-dimethylphenylsulfonyl)piperidin-2-yl)methoxy)ethanone
399 2-((1-(4-methoxy-2,6-dimethylphenylsulfonyl)piperidin-2-yl)methoxy)-1-(2-(piperidin-1-ylmethyl)pyrrolidin-1-yl)ethanone
400 1-(2-(4-(dimethylamino)phenyl)azepan-1-yl)-2-((1-(4-methoxy-2,6-dimethylphenylsulfonyl)piperidin-2-yl)methoxy)ethanone
401 N-(2-(4-benzylpiperazin-1-yl)ethyl)-2-((1-(4-methoxy-2,6-dimethylphenylsulfonyl)piperidin-2-yl)methoxy)acetamide
402 2-((1-(4-methoxy-2,6-dimethylphenylsulfonyl)piperidin-2-yl)methoxy)-1-(4-(4-phenylthiazol-2-yl)piperazin-1-yl)ethanone
403 2-((1-(2,6-dichlorophenylsulfonyl)piperidin-2-yl)methoxy)-1-(4-(3,4-dimethylphenyl)piperazin-1-yl)ethanone
404 1-(4-(3,4-dichlorophenyl)piperazin-1-yl)-2-((1-(2,6-dichlorophenylsulfonyl)piperidin-2-yl)methoxy)ethanone
405 1-(4-(3,4-dichlorobenzyl)piperazin-1-yl)-2-((1-(2,6-dichlorophenylsulfonyl)piperidin-2-yl)methoxy)ethanone
406 1-(4-(4-bromobenzyl)piperazin-1-yl)-2-((1-(2,6-dichlorophenylsulfonyl)piperidin-2-yl)methoxy)ethanone
407 1-(4-(4-chlorobenzyl)piperazin-1-yl)-2-((1-(2,6-dichlorophenylsulfonyl)piperidin-2-yl)methoxy)ethanone
408 2-((1-(2,6-dichlorophenylsulfonyl)piperidin-2-yl)methoxy)-1-(4-(4-methylbenzyl)piperazin-1-yl)ethanone
409 2-((1-(4-methoxy-2,6-dimethylphenylsulfonyl)piperidin-2-yl)methoxy)-N-(4-(pyrrolidin-1-yl)phenyl)acetamide
410 3-(4-(2-((1-(4-methoxy-2,6-dimethylphenylsulfonyl)piperidin-2-yl)methoxy)acetyl)piperazin-1-yl)propanenitrile
411 N-(3-(4-benzylpiperazin-1-yl)propyl)-2-((1-(4-methoxy-2,6-dimethylphenylsulfonyl)piperidin-2-yl)methoxy)acetamide
412 N-(3-(4-ethylpiperazin-1-yl)propyl)-2-((1-(4-methoxy-2,6-dimethylphenylsulfonyl)piperidin-2-yl)methoxy)acetamide
413 2-((1-(4-methoxy-2,6-dimethylphenylsulfonyl)piperidin-2-yl)methoxy)-N-(3-(piperidin-1-yl)propyl)acetamide
414 N-((1-benzylpyrrolidin-3-yl)methyl)-2-((1-(4-methoxy-2,6-dimethylphenylsulfonyl)piperidin-2-yl)methoxy)acetamide
415 N-((1-benzylpiperidin-3-yl)methyl)-2-((1-(4-methoxy-2,6-dimethylphenylsulfonyl)piperidin-2-yl)methoxy)acetamide 416  2-((1-(4-methoxy-2,6-dimethylphenylsulfonyl)piperidin-2-yl)methoxy)-N-(2-(5-methyl-1H-pyrazol-1-yl)ethyl)acetamide
417  2-((1-(4-methoxy-2,6-dimethylphenylsulfonyl)piperidin-2-yl)methoxy)-N-(4-(2-(1-methyl-1H-benzo[d]imidazol-2-yl)ethyl)phenyl)acetamide
418  2-((1-(4-methoxy-2,6-dimethylphenylsulfonyl)piperidin-2-yl)methoxy)-N-(3-(piperidin-1-ylmethyl)phenyl)acetamide
419  2-((1-(4-methoxy-2,6-dimethylphenylsulfonyl)piperidin-2-yl)methoxy)-N-(4-(piperidin-1-ylmethyl)phenyl)acetamide
420  N-(4-((1H-imidazol-1-yl)methyl)phenyl)-2-((1-(4-methoxy-2,6-dimethylphenylsulfonyl)piperidin-2-yl)methoxy)acetamide
421  2-((1-(4-methoxy-2,6-dimethylphenylsulfonyl)piperidin-2-yl)methoxy)-N-(4-((4-methylpiperidin-1-yl)methyl)phenyl)acetamide
422  N-((1-benzylpiperidin-3-yl)methyl)-2-((1-(4-methoxyphenylsulfonyl)indolin-2-yl)methoxy)acetamide
423  2-((1-(4-methoxyphenylsulfonyl)indolin-2-yl)methoxy)-N-(3-(piperidin-1-ylmethyl)phenyl)acetamide
424  N-(3-(ethyl(phenyl)amino)propyl)-2-((1-(4-methoxy-2,6-dimethylphenylsulfonyl)piperidin-2-yl)methoxy)acetamide
425  2-((1-(4-methoxy-2,6-dimethylphenylsulfonyl)piperidin-2-yl)methoxy)-N-(2-(pyrazin-2-yl)ethyl)acetamide
426  N-(1-(1H-pyrazol-1-yl)propan-2-yl)-2-((1-(4-methoxy-2,6-dimethylphenylsulfonyl)piperidin-2-yl)methoxy)acetamide
427  2-((1-(4-methoxy-2,6-dimethylphenylsulfonyl)piperidin-2-yl)methoxy)-N-(4-(2-methyl-1H-imidazol-1-yl)phenyl)acetamide
428  2-((1-(4-methoxy-2,6-dimethylphenylsulfonyl)piperidin-2-yl)methoxy)-N-(2-(piperidin-1-yl)benzyl)acetamide
429  2-((1-(4-methoxy-2,6-dimethylphenylsulfonyl)piperidin-2-yl)methoxy)-N-(3-(piperidin-1-yl)phenyl)acetamide
430  2-((1-(4-methoxy-2,6-dimethylphenylsulfonyl)piperidin-2-yl)methoxy)-N-(3-(piperidin-1-yl)benzyl)acetamide
431  2-((1-(4-methoxy-2,6-dimethylphenylsulfonyl)piperidin-2-yl)methoxy)-N-(2-(4-methylpiperazin-1-yl)phenyl)acetamide
432  2-((1-(4-methoxy-2,6-dimethylphenylsulfonyl)piperidin-2-yl)methoxy)-N-(2-(4-methylpiperazin-1-yl)benzyl)acetamide
433  2-((1-(4-methoxy-2,6-dimethylphenylsulfonyl)piperidin-2-yl)methoxy)-N-(3-(4-methylpiperazin-1-yl)benzyl)acetamide
434  2-((1-(4-methoxy-2,6-dimethylphenylsulfonyl)piperidin-2-yl)methoxy)-N-(4-(4-methylpiperazin-1-yl)benzyl)acetamide
435  2-((1-(4-methoxy-2,6-dimethylphenylsulfonyl)piperidin-2-yl)methoxy)-N-(2-morpholinobenzyl)acetamide
436  2-((1-(4-methoxy-2,6-dimethylphenylsulfonyl)piperidin-2-yl)methoxy)-N-(3-morpholinophenyl)acetamide
437  2-((1-(4-methoxy-2,6-dimethylphenylsulfonyl)piperidin-2-yl)methoxy)-N-(3-morpholinobenzyl)acetamide
438  2-((1-(4-methoxy-2,6-dimethylphenylsulfonyl)piperidin-2-yl)methoxy)-N-(4-morpholinophenyl)acetamide
439  2-((1-(4-methoxy-2,6-dimethylphenylsulfonyl)piperidin-2-yl)methoxy)-N-(4-morpholinobenzyl)acetamide
440  2-((1-(2,6-dichlorophenylsulfonyl)piperidin-2-yl)methoxy)-N-(2-(piperidin-1-yl)ethyl)acetamide
441  2-((1-(2,6-dichlorophenylsulfonyl)piperidin-2-yl)methoxy)-N-(4-(dimethylamino)butyl)acetamide
442  2-((1-(2,6-dichlorophenylsulfonyl)piperidin-2-yl)methoxy)-1-(4-(2-fluorophenyl)piperazin-1-yl)ethanone
443  2-((1-(2,6-dichlorophenylsulfonyl)piperidin-2-yl)methoxy)-1-(4-(pyrrolidin-1-yl)piperidin-1-yl)ethanone
444  1-(4-(2-fluorobenzyl)piperazin-1-yl)-2-((1-(4-methoxy-2,6-dimethylphenylsulfonyl)pyrrolidin-2-yl)methoxy)ethanone
445  2-((1-(4-methoxy-2,6-dimethylphenylsulfonyl)pyrrolidin-2-yl)methoxy)-1-(4-methyl-2-phenylpiperazin-1-yl)ethanone
446  2-((1-(4-methoxy-2,6-dimethylphenylsulfonyl)pyrrolidin-2-yl)methoxy)-N-methyl-N-(2-(4-methylpiperazin-1-yl)-1-phenylethyl)acetamide
447  2-((1-(4-methoxy-2,6-dimethylphenylsulfonyl)pyrrolidin-2-yl)methoxy)-1-(2-(pyridin-2-ylmethyl)pyrrolidin-1-yl)ethanone
448  2-((1-(4-methoxy-2,6-dimethylphenylsulfonyl)pyrrolidin-2-yl)methoxy)-1-(2-((6-methylpyridin-2-yl)methyl)pyrrolidin-1-yl)ethanone
449  2-((1-(4-methoxy-2,6-dimethylphenylsulfonyl)pyrrolidin-2-yl)methoxy)-1-(2-(pyridin-2-ylmethyl)piperidin-1-yl)ethanone
450  2-((1-(4-methoxy-2,6-dimethylphenylsulfonyl)pyrrolidin-2-yl)methoxy)-N-methyl-N-(1-phenyl-2-(pyrrolidin-1-yl)ethyl)acetamide
451  2-((1-(2,6-dichlorophenylsulfonyl)pyrrolidin-2-yl)methoxy)-1-(4-(4-methoxybenzyl)piperazin-1-yl)ethanone
452  2-((1-(2,6-dichlorophenylsulfonyl)pyrrolidin-2-yl)methoxy)-1-(4-(2-(dimethylamino)ethyl)piperazin-1-yl)ethanone
453  2-((1-(2,6-dichlorophenylsulfonyl)pyrrolidin-2-yl)methoxy)-1-(2-(pyridin-4-ylmethyl)piperidin-1-yl)ethanone
454  2-((1-(2,6-dichlorophenylsulfonyl)piperidin-2-yl)methoxy)-1-(4-(2-fluorobenzyl)piperazin-1-yl)ethanone
455  2-((1-(2,6-dichlorophenylsulfonyl)piperidin-2-yl)methoxy)-1-(4-methyl-2-phenylpiperazin-1-yl)ethanone
456  2-((1-(2,6-dichlorophenylsulfonyl)piperidin-2-yl)methoxy)-1-(2-(pyridin-2-ylmethyl)pyrrolidin-1-yl)ethanone
457  2-((1-(2,6-dichlorophenylsulfonyl)piperidin-2-yl)methoxy)-1-(2-((4,6-dimethylpyridin-2-yl)methyl)pyrrolidin-1-yl)ethanone
458  2-((1-(2,6-dichlorophenylsulfonyl)piperidin-2-yl)methoxy)-1-(2-((6-methylpyridin-2-yl)methyl)pyrrolidin-1-yl)ethanone
459  N-(2-(pyrrolidin-1-yl)ethyl)-2-((1-(2,4,6-trichlorophenylsulfonyl)piperidin-2-yl)methoxy)acetamide
460  1-(4-benzylpiperazin-1-yl)-2-((1-(4-methoxy-2,6-dimethylphenylsulfonyl)pyrrolidin-2-yl)methoxy)ethanone
461  2-((1-(4-methoxy-2,6-dimethylphenylsulfonyl)pyrrolidin-2-yl)methoxy)-1-(4-phenylpiperazin-1-yl)ethanone
462  1-(4-(benzo[d][1,3]dioxol-5-ylmethyl)piperazin-1-yl)-2-((1-(4-methoxy-2,6-dimethylphenylsulfonyl)pyrrolidin-2-yl)methoxy)ethanone
463  N-benzyl-2-((1-(4-methoxy-2,6-dimethylphenylsulfonyl)pyrrolidin-2-yl)methoxy)-N-(4-methylpyridin-2-yl)acetamide
464  N-benzyl-2-((1-(4-methoxy-2,6-dimethylphenylsulfonyl)pyrrolidin-2-yl)methoxy)-N-(6-methylpyridin-2-yl)acetamide
465  2-((1-(4-methoxy-2,6-dimethylphenylsulfonyl)pyrrolidin-2-yl)methoxy)-1-(4-(3-(trifluoromethyl)phenyl)piperazin-1-yl)ethanone
466  N-ethyl-2-((1-(4-methoxy-2,6-dimethylphenylsulfonyl)pyrrolidin-2-yl)methoxy)-N-(pyridin-4-ylmethyl)acetamide
467  2-((1-(4-methoxy-2,6-dimethylphenylsulfonyl)pyrrolidin-2-yl)methoxy)-1-(4-methyl-1,4-diazepan-1-yl)ethanone
468  2-((1-(4-methoxy-2,6-dimethylphenylsulfonyl)pyrrolidin-2-yl)methoxy)-1-(4-(5-(trifluoromethyl)pyridin-2-yl)piperazin-1-yl)ethanone 469 1-(4-(3-chloro-5-(trifluoromethyl)pyridin-2-yl)piperazin-1-yl)-2-((1-(4-methoxy-2,6-dimethylphenylsulfonyl)pyrrolidin-2-yl)methoxy)ethanone
470 2-((1-(4-methoxy-2,6-dimethylphenylsulfonyl)pyrrolidin-2-yl)methoxy)-N-(4-(2-(1-methyl-1H-benzo[d]imidazol-2-yl)ethyl)phenyl)acetamide
471 2-((1-(4-methoxy-2,6-dimethylphenylsulfonyl)pyrrolidin-2-yl)methoxy)-N-(3-(piperidin-1-ylmethyl)phenyl)acetamide
472 N-(4-(2-(1H-benzo[d]imidazol-2-yl)ethyl)phenyl)-2-((1-(4-methoxy-2,6-dimethylphenylsulfonyl)pyrrolidin-2-yl)methoxy)acetamide
473 2-((1-(4-methoxy-2,6-dimethylphenylsulfonyl)pyrrolidin-2-yl)methoxy)-N-(2-(4-methylpiperazin-1-yl)benzyl)acetamide
474 2-((1-(4-methoxy-2,6-dimethylphenylsulfonyl)pyrrolidin-2-yl)methoxy)-1-(4-(5-methyl-1H-benzo[d]imidazol-2-yl)piperidin-1-yl)ethanone
475 1-(2-(4-(dimethylamino)phenyl)azepan-1-yl)-2-((1-(4-methoxy-2,6-dimethylphenylsulfonyl)pyrrolidin-2-yl)methoxy)ethanone
476 1-((R)-3-(dimethylamino)pyrrolidin-1-yl)-2-((1-(4-methoxy-2,6-dimethylphenylsulfonyl)pyrrolidin-2-yl)methoxy)ethanone
477 N-(1-benzylpiperidin-4-yl)-2-((1-(4-methoxy-2,6-dimethylphenylsulfonyl)pyrrolidin-2-yl)methoxy)acetamide
478 1-(4-benzylpiperazin-1-yl)-2-((1-(2,5-dichlorothiophen-3-ylsulfonyl)pyrrolidin-2-yl)methoxy)ethanone
479 2-((2-(4-Methoxy-2,3,6-trimethylphenylsulfonyl)-1,2,3,4-tetrahydroisoquinolin-3-yl)methoxy)-1-(4-phenylpiperazin-1-yl)ethanone
480 1-(4-benzylpiperazin-1-yl)-2-((1-(2,6-dichlorophenylsulfonyl)piperidin-2-yl)methoxy)ethanone
481 2-((1-(2,6-dichlorophenylsulfonyl)piperidin-2-yl)methoxy)-1-(4-(3-(trifluoromethyl)phenyl)piperazin-1-yl)ethanone
482 2-((1-(2,6-dichlorophenylsulfonyl)piperidin-2-yl)methoxy)-N-ethyl-N-(pyridin-4-ylmethyl)acetamide
483 2-((1-(2,6-dichlorophenylsulfonyl)piperidin-2-yl)methoxy)-1-(4-methyl-1,4-diazepan-1-yl)ethanone
484 2-((1-(2,6-dichlorophenylsulfonyl)piperidin-2-yl)methoxy)-1-(4-(5-(trifluoromethyl)pyridin-2-yl)piperazin-1-yl)ethanone
485 1-(4-(3-chloro-5-(trifluoromethyl)pyridin-2-yl)piperazin-1-yl)-2-((1-(2,6-dichlorophenylsulfonyl)piperidin-2-yl)methoxy)ethanone
486 N-benzyl-2-((1-(2,6-dichlorophenylsulfonyl)piperidin-2-yl)methoxy)-N-(pyridin-2-yl)acetamide
487 2-((1-(2,6-dichlorophenylsulfonyl)piperidin-2-yl)methoxy)-1-(4-(5-methyl-1H-benzo[d]imidazol-2-yl)piperidin-1-yl)ethanone
488 N-(1-benzylpiperidin-4-yl)-2-((1-(2,6-dichlorophenylsulfonyl)piperidin-2-yl)methoxy)acetamide
489 N-benzyl-2-((1-(2,6-dichlorophenylsulfonyl)piperidin-2-yl)methoxy)-N-(2-(dimethylamino)ethyl)acetamide
490 1-(2-((5-ethylpyridin-2-yl)methyl)pyrrolidin-1-yl)-2-((1-(4-methoxy-2,6-dimethylphenylsulfonyl)pyrrolidin-2-yl)methoxy)ethanone
491 2-((1-(4-methoxy-2,6-dimethylphenylsulfonyl)pyrrolidin-2-yl)methoxy)-1-(4-(2-methoxyphenyl)piperazin-1-yl)ethanone
492 1-(4-(cyclohexylmethyl)piperazin-1-yl)-2-((1-(4-methoxy-2,6-dimethylphenylsulfonyl)pyrrolidin-2-yl)methoxy)ethanone
493 N-(3-chloro-4-morpholinophenyl)-2-((1-(4-methoxy-2,6-dimethylphenylsulfonyl)pyrrolidin-2-yl)methoxy)acetamide
494 2-((1-(4-methoxy-2,6-dimethylphenylsulfonyl)pyrrolidin-2-yl)methoxy)-N-(1-methyl-1H-benzo[d]imidazol-5-yl)acetamide
495 N-(2-(dimethylamino)-2-(4-(trifluoromethyl)phenyl)ethyl)-2-((1-(4-methoxy-2,6-dimethylphenylsulfonyl)pyrrolidin-2-yl)methoxy)acetamide
496 2-((1-(4-methoxy-2,6-dimethylphenylsulfonyl)pyrrolidin-2-yl)methoxy)-N-(2-(pyrrolidin-1-yl)-2-(4-(trifluoromethyl)phenyl)ethyl)acetamide
497 2-((1-(2,6-dichlorophenylsulfonyl)piperidin-2-yl)methoxy)-1-(2-(pyridin-3-yl)pyrrolidin-1-yl)ethanone
498 2-((1-(2,6-dichlorophenylsulfonyl)piperidin-2-yl)methoxy)-1-(4-(2-methoxyphenyl)piperazin-1-yl)ethanone
499 1-(4-(cyclohexylmethyl)piperazin-1-yl)-2-((1-(2,6-dichlorophenylsulfonyl)piperidin-2-yl)methoxy)ethanone
500 2-((1-(4-methoxy-2,6-dimethylphenylsulfonyl)pyrrolidin-2-yl)methoxy)-N-(2-morpholino-1-phenylethyl)acetamide
501 2-((1-(4-methoxy-2,6-dimethylphenylsulfonyl)pyrrolidin-2-yl)methoxy)-N-(1-methyl-1H-indazol-6-yl)acetamide
502 N-(2-(2-chlorophenyl)-2-(pyrrolidin-1-yl)ethyl)-2-((1-(4-methoxy-2,6-dimethylphenylsulfonyl)pyrrolidin-2-yl)methoxy)acetamide
503 1-(4-(3,5-dimethoxyphenyl)piperazin-1-yl)-2-((1-(4-methoxy-2,6-dimethylphenylsulfonyl)pyrrolidin-2-yl)methoxy)ethanone
504 2-((1-(4-methoxy-2,6-dimethylphenylsulfonyl)pyrrolidin-2-yl)methoxy)-N-(1-methyl-1H-benzo[d]imidazol-2-yl)acetamide
505 2-((1-(4-methoxy-2,6-dimethylphenylsulfonyl)pyrrolidin-2-yl)methoxy)-N-(1-phenyl-2-(pyrrolidin-1-yl)ethyl)acetamide
506 3-(4-(2-((1-(2,6-dichlorophenylsulfonyl)piperidin-2-yl)methoxy)acetyl)piperazin-1-yl)propanenitrile
507 N-benzyl-2-((1-(4-methoxy-2,6-dimethylphenylsulfonyl)piperidin-2-yl)methoxy)-N-(4-methylpyridin-2-yl)acetamide
508 N-benzyl-2-((1-(4-methoxy-2,6-dimethylphenylsulfonyl)piperidin-2-yl)methoxy)-N-(6-methylpyridin-2-yl)acetamide
509 2-((1-(4-methoxy-2,6-dimethylphenylsulfonyl)piperidin-2-yl)methoxy)-1-(4-(3-(trifluoromethyl)phenyl)piperazin-1-yl)ethanone
510 N-ethyl-2-((1-(4-methoxy-2,6-dimethylphenylsulfonyl)piperidin-2-yl)methoxy)-N-(pyridin-4-ylmethyl)acetamide
511 1-(4-(3-chlorophenyl)piperazin-1-yl)-2-((1-(4-methoxy-2,6-dimethylphenylsulfonyl)piperidin-2-yl)methoxy)ethanone
512 1-(4-(3,4-dimethylphenyl)piperazin-1-yl)-2-((1-(4-methoxy-2,6-dimethylphenylsulfonyl)piperidin-2-yl)methoxy)ethanone
513 2-(4-(2-((1-(4-methoxy-2,6-dimethylphenylsulfonyl)piperidin-2-yl)methoxy)acetyl)piperazin-1-yl)nicotinonitrile
514 2-((1-(4-methoxy-2,6-dimethylphenylsulfonyl)piperidin-2-yl)methoxy)-1-(4-(5-(trifluoro methyl)pyridin-2-yl)piperazin-1-yl)ethanone
515 N-benzyl-2-((1-(2,5-dichlorothiophen-3-ylsulfonyl)piperidin-2-yl)methoxy)-N-(6-methylpyridin-2-yl)acetamide
516 1-(4-(2-fluorophenyl)piperazin-1-yl)-2-((1-(4-methoxy-2,6-dimethylphenylsulfonyl)pyrrolidin-2-yl)methoxy)ethanone 517 1-(4-ethylpiperazin-1-yl)-2-((1-(4-methoxy-2,6-dimethylphenylsulfonyl)pyrrolidin-2-yl)methoxy)ethanone
518 2-((1-(4-methoxy-2,6-dimethylphenylsulfonyl)pyrrolidin-2-yl)methoxy)-1-(4-(pyrrolidin-1-yl)piperidin-1-yl)ethanone
519 2-((1-(4-methoxy-2,6-dimethylphenylsulfonyl)pyrrolidin-2-yl)methoxy)-1-(4-morpholinopiperidin-1-yl)ethanone
520 1-(1,4'-bipiperidin-1'-yl)-2-((1-(4-methoxy-2,6-dimethylphenylsulfonyl)pyrrolidin-2-yl)methoxy)ethanone
521 N-(3-(4-benzylpiperazin-1-yl)propyl)-2-((1-(4-methoxy-2,6-dimethylphenylsulfonyl)pyrrolidin-2-yl)methoxy)acetamide
522 2-((1-(4-methoxy-2,6-dimethylphenylsulfonyl)pyrrolidin-2-yl)methoxy)-N-(3-(piperidin-1-yl)propyl)acetamide
523 2-((1-(4-methoxy-2,6-dimethylphenylsulfonyl)pyrrolidin-2-yl)methoxy)-N-(4-(pyrrolidin-1-yl)butyl)acetamide
524 2-((1-(4-methoxy-2,6-dimethylphenylsulfonyl)piperidin-2-yl)methoxy)-1-(4-(4-methylpiperazin-1-yl)piperidin-1-yl)ethanone
525 N-(3-(1H-benzo[d]imidazol-2-yl)propyl)-2-((1-(4-methoxy-2,6-dimethylphenylsulfonyl)piperidin-2-yl)methoxy)acetamide
526 1-(4-(benzo[d]thiazol-2-yl)piperazin-1-yl)-2-((1-(4-methoxy-2,6-dimethylphenylsulfonyl)piperidin-2-yl)methoxy)ethanone
527 2-((1-(2,6-dichlorophenylsulfonyl)piperidin-2-yl)methoxy)-N-(4-(2-methyl-1H-imidazol-1-yl)phenyl)acetamide
528 2-((1-(2,6-dichlorophenylsulfonyl)piperidin-2-yl)methoxy)-1-(2-(4-(dimethylamino)phenyl)pyrrolidin-1-yl)ethanone
529 1-(4-benzyl-1,4-diazepan-1-yl)-2-((1-(2,6-dichlorophenylsulfonyl)piperidin-2-yl)methoxy)ethanone
530 2-((1-(2,6-dichlorophenylsulfonyl)piperidin-2-yl)methoxy)-N-(4-(dimethylamino)benzyl)-N-isopropylacetamide
531 2-(4-(2-((1-(4-methoxy-2,6-dimethylphenylsulfonyl)pyrrolidin-2-yl)methoxy)acetyl)-1,4-diazepan-1-yl)nicotinonitrile
532 2-((1-(4-methoxy-2,6-dimethylphenylsulfonyl)piperidin-2-yl)methoxy)-N-methyl-N-(2-(piperidin-1-yl)ethyl)acetamide
533 2-((1-(4-methoxy-2,6-dimethylphenylsulfonyl)piperidin-2-yl)methoxy)-1-(4-(2-(piperidin-1-yl)ethyl)piperidin-1-yl)ethanone
534 2-((1-(4-methoxy-2,6-dimethylphenylsulfonyl)piperidin-2-yl)methoxy)-1-(2-(2-morpholinoethyl)piperidin-1-yl)ethanone
535 2-((1-(4-methoxy-2,6-dimethylphenylsulfonyl)piperidin-2-yl)methoxy)-N-(5-methyl-1H-pyrazol-3-yl)acetamide
536 2-((1-(4-methoxy-2,6-dimethylphenylsulfonyl)piperidin-2-yl)methoxy)-N-(5-phenyl-1H-pyrazol-3-yl)acetamide
537 N-(3-(4-chlorophenyl)-1H-pyrazol-5-yl)-2-((1-(4-methoxy-2,6-dimethylphenylsulfonyl)piperidin-2-yl)methoxy)acetamide
538 N-(4-(3,4-dimethoxyphenyl)-1H-pyrazol-5-yl)-2-((1-(4-methoxy-2,6-dimethylphenylsulfonyl)piperidin-2-yl)methoxy)acetamide
539 2-((1-(4-methoxy-2,6-dimethylphenylsulfonyl)piperidin-2-yl)methoxy)-N-(3-(thiophen-2-yl)-1H-pyrazol-5-yl)acetamide
540 2-((1-(4-methoxy-2,6-dimethylphenylsulfonyl)piperidin-2-yl)methoxy)-N-(5-(2-methoxyphenyl)-1H-pyrazol-3-yl)acetamide
541 2-((1-(4-methoxy-2,6-dimethylphenylsulfonyl)piperidin-2-yl)methoxy)-N-(5-(3-methoxyphenyl)-1H-pyrazol-3-yl)acetamide
542 N-(5-(3-fluorophenyl)-1H-pyrazol-3-yl)-2-((1-(4-methoxy-2,6-dimethylphenylsulfonyl)piperidin-2-yl)methoxy)acetamide
543 2-((1-(4-methoxy-2,6-dimethylphenylsulfonyl)piperidin-2-yl)methoxy)-N-(5-(4-methoxyphenyl)-1H-pyrazol-3-yl)acetamide
544 2-((1-(4-methoxy-2,6-dimethylphenylsulfonyl)piperidin-2-yl)methoxy)-N-(3-p-tolyl-1H-pyrazol-5-yl)acetamide
545 2-((1-(4-methoxy-2,6-dimethylphenylsulfonyl)piperidin-2-yl)methoxy)-N-(3-phenyl-1H-pyrazol-5-yl)acetamide
546 2-((1-(4-methoxy-2,6-dimethylphenylsulfonyl)piperidin-2-yl)methoxy)-N-(quinolin-2-yl)acetamide
547 2-((1-(4-methoxyphenylsulfonyl)indolin-2-yl)methoxy)-1-(4-(2-(piperidin-1-yl)ethyl)piperidin-1-yl)ethanone
548 1-(4-(2-(2,5-dimethyl-1H-pyrrol-1-yl)ethyl)piperazin-1-yl)-2-((1-(4-methoxyphenylsulfonyl)indolin-2-yl)methoxy)ethanone
549 2-((1-(2,6-dichlorophenylsulfonyl)piperidin-2-yl)methoxy)-N-(4-(morpholinomethyl)benzyl)acetamide
550 2-((1-(2,6-dichlorophenylsulfonyl)piperidin-2-yl)methoxy)-1-(4-(4-(trifluoromethyl)phenyl)piperazin-1-yl)ethanone
551 2-((1-(2,6-dichlorophenylsulfonyl)piperidin-2-yl)methoxy)-1-(4-(3,5-dichloropyridin-2-yl)piperazin-1-yl)ethanone
552 2-((1-(2,6-dichlorophenylsulfonyl)piperidin-2-yl)methoxy)-1-(4-(2-hydroxyethyl)piperazin-1-yl)ethanone
553 1-(4-(benzo[d]thiazol-2-yl)piperazin-1-yl)-2-((1-(2,6-dichlorophenylsulfonyl)piperidin-2-yl)methoxy)ethanone
554 1-(4-(6-chlorobenzo[d]thiazol-2-yl)piperazin-1-yl)-2-((1-(2,6-dichlorophenylsulfonyl)piperidin-2-yl)methoxy)ethanone
555 N-(4-(4-ethylpiperazin-1-yl)phenyl)-2-((1-(4-methoxyphenylsulfonyl)piperidin-2-yl)methoxy)acetamide
556 2-((1-(4-methoxyphenylsulfonyl)piperidin-2-yl)methoxy)-N-(7-morpholinobenzo[c][1,2,5]oxadiazol-4-yl)acetamide
557 2-((1-(4-methoxyphenylsulfonyl)piperidin-2-yl)methoxy)-N-(3-methyl-4-(2-(piperidin-1-yl)acetamideo)phenyl)acetamide
558 2-((1-(4-methoxyphenylsulfonyl)piperidin-2-yl)methoxy)-1-(4-(2-phenoxyethyl)piperazin-1-yl)ethanone
559 1-(4-(2-(2,5-dimethyl-1H-pyrrol-1-yl)ethyl)piperazin-1-yl)-2-((1-(4-methoxy-2,6-dimethylphenylsulfonyl)piperidin-2-yl)methoxy)ethanone
560 1-(4-(3-(dimethylamino)propyl)piperazin-1-yl)-2-((2-(4-methoxy-2,3,6-trimethylphenylsulfonyl)-1,2,3,4-tetrahydroisoquinolin-3-yl)methoxy)ethanone
561 N,N-bis(3-(dimethylamino)propyl)-2-((1-(4-methoxy-2,6-dimethylphenylsulfonyl)piperidin-2-yl)methoxy)acetamide
562 2-((2-(4-methoxy-2,3,6-trimethylphenylsulfonyl)-1,2,3,4-tetrahydroisoquinolin-3-yl)methoxy)-1-(4-(1-methylpiperidin-4-yl)piperazin-1-yl)ethanone
563 2-((2-(4-methoxy-2,3,6-trimethylphenylsulfonyl)-1,2,3,4-tetrahydroisoquinolin-3-yl)methoxy)-1-(4-((1-methylpiperidin-4-yl)methyl)piperazin-1-yl)ethanone 564 2-((1-(2,6-dichlorophenylsulfonyl)piperidin-2-yl)methoxy)-1-(4-(3-(dimethylamino)propyl)piperazin-1-yl)ethanone
565 2-((1-(2,6-dichlorophenylsulfonyl)piperidin-2-yl)methoxy)-1-(4-(1-methylpiperidin-4-yl)piperazin-1-yl)ethanone
566 2-((1-(2,6-dichlorophenylsulfonyl)pyrrolidin-2-yl)methoxy)-1-(4-(3-(dimethylamino)propyl)piperazin-1-yl)ethanone
567 2-((1-(2,6-dichlorophenylsulfonyl)pyrrolidin-2-yl)methoxy)-1-(4-(1-methylpiperidin-4-yl)piperazin-1-yl)ethanone
568 1-(4-benzylpiperazin-1-yl)-2-((1-(4-chloro-2,5-dimethylphenylsulfonyl)piperidin-2-yl)methoxy)ethanone
569 2-((1-(2,6-dichloro-4-(trifluoromethyl)phenylsulfonyl)pyrrolidin-2-yl)methoxy)-1-(4-(3-(dimethylamino)propyl)piperazin-1-yl)ethanone
570 2-((1-(2,6-dichloro-4-(trifluoromethyl)phenylsulfonyl)pyrrolidin-2-yl)methoxy)-1-(4-(1-methylpiperidin-4-yl)piperazin-1-yl)ethanone
571 1-(4-(1-methylpiperidin-4-yl)piperazin-1-yl)-2-((1-(2-(trifluoromethyl)phenylsulfonyl)piperidin-2-yl)methoxy)ethanone
572 2-((1-(benzo[b]thiophen-3-ylsulfonyl)piperidin-2-yl)methoxy)-1-(4-(4-methylpiperazin-1-yl)piperidin-1-yl)ethanone
573 2-((1-(benzo[b]thiophen-3-ylsulfonyl)piperidin-2-yl)methoxy)-1-(4-((1-methylpiperidin-4-yl)methyl)piperazin-1-yl)ethanone
574 N—((S)-1-benzylpyrrolidin-3-yl)-2-((1-(2,6-dichloro-4-(trifluoromethyl)phenylsulfonyl)piperidin-2-yl)methoxy)-N-methylacetamide
575 N-(4-(dimethylamino)benzyl)-2-((1-(2,4,6-trichlorophenylsulfonyl)pyrrolidin-2-yl)methoxy)acetamide
576 N-(4-(dimethylamino)benzyl)-2-((1-(4-methoxy-2,6-dimethylphenylsulfonyl)pyrrolidin-2-yl)methoxy)acetamide
577 N-(4-(dimethylamino)benzyl)-2-((1-(4-methoxy-2,6-dimethylphenylsulfonyl)piperidin-2-yl)methoxy)acetamide
578 N-(4-(dimethylamino)benzyl)-2-((1-(2,4,6-trichlorophenylsulfonyl)piperidin-2-yl)methoxy)acetamide
579 2-((1-(4-methoxy-2,6-dimethylphenylsulfonyl)pyrrolidin-2-yl)methoxy)-N-(4-morpholinobenzyl)acetamide
580 N-(4-morpholinobenzyl)-2-((1-(2,4,6-trichlorophenylsulfonyl)pyrrolidin-2-yl)methoxy)acetamide
581 N-(4-morpholinobenzyl)-2-((1-(2,4,6-trichlorophenylsulfonyl)piperidin-2-yl)methoxy)acetamide
in the form of the racemate; in the form of the enantiomers, diastereoisomers, mixtures of the enantiomers or diastereoisomers or in the form of an individual enantiomer or diastereoisomer; in the form of the bases and/or salts of physiologically acceptable acids.

The numbering of the individual forms of the substances according to the invention that is used above is retained in the explanations of the present invention that follow, in particular in the description of the examples.

The compounds according to the invention exhibit an antagonistic action on the human B1R receptor or the B1R receptor of the rat. In a preferred embodiment of the invention, the substances according to the invention exhibit an antagonistic action both on the human B1R receptor and on the B1R receptor of the rat.

Particular preference is given to compounds which exhibit at least 15%, 25%, 50%, 70%, 80% or 90% inhibition on the human B1R receptor and/or on the B1R receptor of the rat in the FLIPR assay at a concentration of 10 µM. Most particular preference is given to compounds which exhibit at least 70%, especially 80% and particularly preferably 90% inhibition on the human B1R receptor and on the B1R receptor of the rat.

The agonistic or antagonistic action of substances can be quantified on the bradykinin receptor 1 (B1R) of the species human and rat with ectopically expressing cell lines (CHO K1 cells) and with the aid of a $Ca^{2+}$-sensitive dye (Fluo-4) using a fluorescent imaging plate reader (FLIPR). The indication in % activation is based on the $Ca^{2+}$ signal after addition of Lys-Des-$Arg^9$-bradykinin (0.5 nM) or Des-$Arg^9$-bradykinin (100 nM). Antagonists result in a suppression of the $Ca^{2+}$ influx following administration of the agonist. The % inhibition in comparison with the maximum achievable inhibition is indicated.

The substances according to the invention are active, for example, on B1R, which is relevant in connection with various diseases, so that they are suitable as a pharmaceutical active ingredient in a medicament. The invention therefore further provides pharmaceutical compositions or medicaments comprising at least one substituted sulfonamide derivative according to the invention as well as, optionally, suitable additives and/or auxiliary substances and/or, optionally, further active ingredients.

In addition to comprising at least one substituted sulfonamide derivative according to the invention, the pharmaceutical compositions according to the invention optionally comprise suitable additives and/or auxiliary substances, that is to say carriers, fillers, solvents, diluents, colorings and/or binders, and can be administered as liquid pharmaceutical dosage forms in the form of injection solutions, drops or juices, as semi-solid pharmaceutical dosage forms in the form of granules, tablets, pellets, patches, capsules, plasters/spray-on plasters or aerosols. The choice of auxiliary substances etc. and the amounts thereof to be used depend on whether the medicament is to be administered orally, perorally, parenterally, intravenously, intraperitoneally, intradermally, intramuscularly, intranasally, buccally, rectally or locally, for example to the skin, the mucosa or to the eyes. Preparations suitable for oral administration are in the form of tablets, dragées, capsules, granules, drops, juices and syrups, and those suitable for parenteral and topical administration and administration by inhalation are solutions, suspensions, readily reconstitutable dry preparations and sprays. Substituted sulfonamide derivatives according to the invention in a depot, in dissolved form or in a plaster, optionally with the addition of agents promoting penetration through the skin, are suitable percutaneous forms of administration. Forms of preparation for oral or percutaneous administration can release the substituted sulfonamide derivatives according to the invention in a delayed manner. The substituted sulfonamide derivatives according to the invention can also be administered in parenteral long-term depot forms, such as, for example, implants or implanted pumps. In principle, other further active ingredients known to the person skilled in the art can be added to the medicaments according to the invention.

The amount of active ingredient to be administered to the patient varies depending on the weight of the patient, the manner of administration, the indication and the severity of the disease. Usually, from 0.00005 to 50 mg/kg, preferably from 0.01 to 5 mg/kg, of at least one substituted sulfonamide derivative according to the invention are administered.

In a preferred form of the pharmaceutical composition or medicament, a substituted sulfonamide derivative according to the invention that is present is in the form of a pure diastereoisomer and/or enantiomer, in the form of a racemate or in the form of a non-equimolar or equimolar mixture of the diastereoisomers and/or enantiomers.

B1R has been identified in particular in occurrences of pain. Accordingly, substituted sulfonamide derivatives according to the invention can be used in the treatment of pain, in particular of acute, visceral, neuropathic or chronic pain. The invention accordingly relates further to the use of a substituted sulfonamide derivative according to the invention in the treatment of pain, in particular of acute, visceral, neuropathic or chronic pain. The invention relates further to the use of a substituted sulfonamide derivative according to the invention in the treatment of diabetes, respiratory diseases, inflammatory intestinal diseases, neurological diseases, inflammations of the skin, rheumatic diseases, septic shock, reperfusion syndrome and obesity, and as an angiogenesis inhibitor.

In one of the above uses it can be preferred for a substituted sulfonamide derivative that is used to be in the form of a pure diastereoisomer and/or enantiomer, in the form of a racemate or in the form of a non-equimolar or equimolar mixture of the diastereoisomers and/or enantiomers.

The invention further provides a method of treating, in particular in one of the above-mentioned indications, a non-human mammal or a human requiring treatment for pain, in particular for chronic pain, by administering a therapeutically effective dose of a substituted sulfonamide derivative according to the invention or of a medicament according to the invention.

The invention further provides a process for the preparation of the substituted sulfonamide derivatives according to the invention as set out in the following description, examples and claims. The compounds according to the invention can be obtained according to the following synthesis scheme.

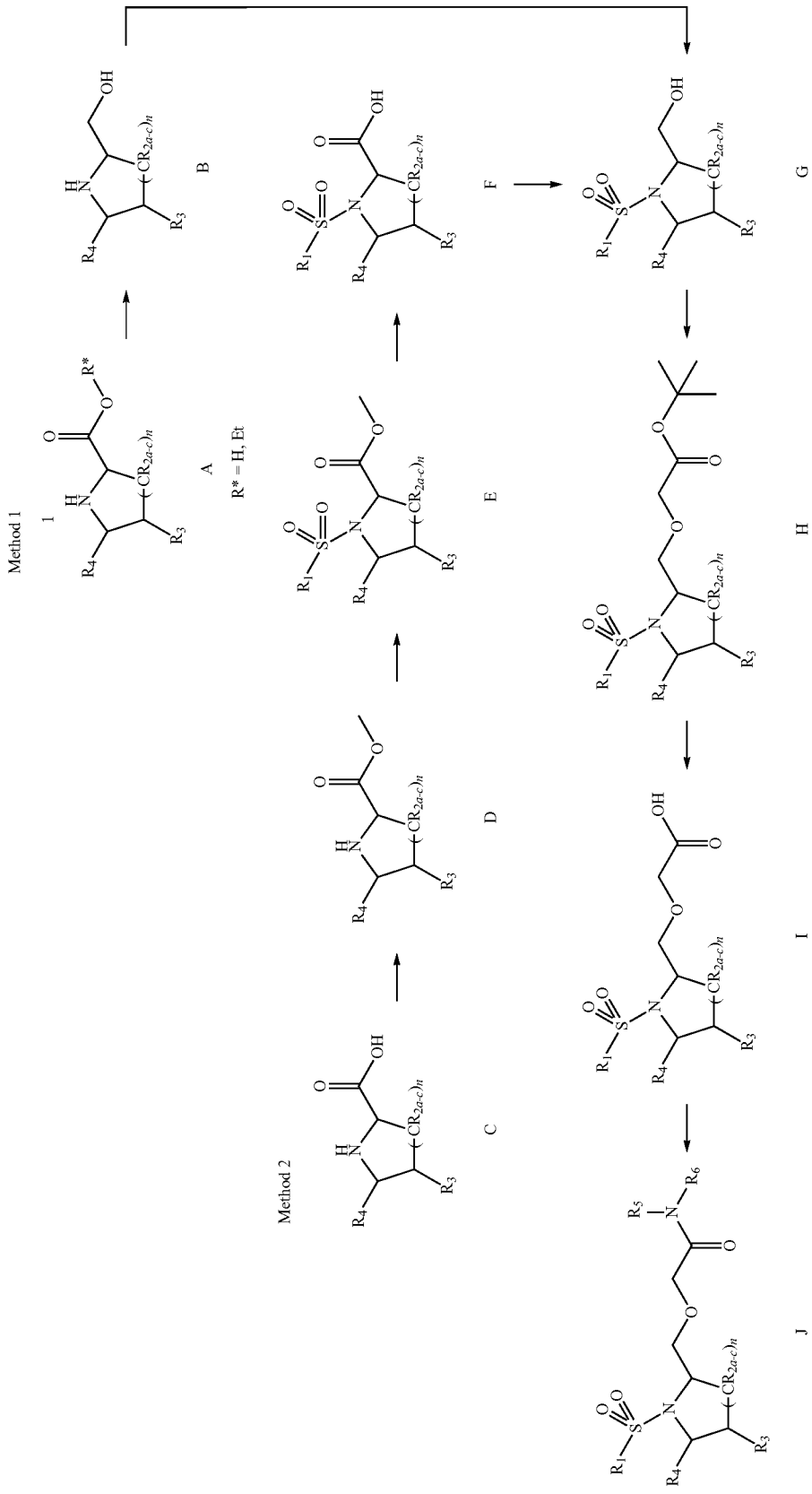

According to method 1, the racemic (R and S configuration) or enantiomerically pure (R or S configuration) amino acids/acid esters A are converted into an amino alcohol B by means of a reduction, using metal hydrides as reducing agents, such as, for example, $LiAlH_4$, $BH_3 \times DMS$, $BH_3 \times THF$ or $NaBH_4$, in an organic solvent, such as THF or diethyl ether, in a temperature range of from $-20°$ C. to $+100°$ C., preferably at from $0°$ C. to $+70°$ C. The amino alcohols B are converted into the sulfonylated amino alcohols G in a sulfonylation using sulfonyl chlorides, bromides or pentafluorophenolates $R_1SO_2X$ (X=Br, Cl or OPFP) in the presence of an organic or inorganic base, for example potassium carbonate, sodium hydrogen carbonate, diisopropylethylamine, triethylamine, pyridine, diethylamine or dimethylaminopyridine, or in the presence of tetra-n-butylammonium chloride and in an organic solvent, for example acetonitrile, dichloromethane or N,N-dimethylformamide, in a temperature range of from $0°$ C. to $+120°$ C. In method 2, the racemic (R and S configuration) or enantiomerically pure (R or S configuration) amino acids C are esterified to the amino esters D using water-removing reagents, for example inorganic acids such as $H_2SO_4$ or phosphorus oxides, or organic reagents, such as thionyl chloride, in organic solvents, such as THF, diethyl ether, methanol, ethanol or dichloromethane, in a temperature range of from $0°$ C. to the boiling temperature of the solvent in question, preferably at $40°$ C., and are then converted into the sulfonylated amino esters E in a sulfonylation using sulfonyl chlorides or bromides $RSO_2X$ (X=Br or Cl) in the presence of an organic or inorganic base, for example potassium carbonate, sodium hydrogen carbonate, diisopropylethylamine, pyridine, diethylamine or triethylamine, and in an organic solvent, for example acetonitrile or dichloromethane, in a temperature range of from $0°$ C. to $+25°$ C., which sulfonylated amino esters E, in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium hydrogen carbonate, potassium carbonate, in organic solvents, such as methanol, dioxane, dichloromethane, THF, diethyl ether or those solvents in the form of mixtures, in a temperature range of from $-20°$ C. to $+25°$ C., preferably at room temperature, yield the sulfonylated amino acids F. The sulfonylated amino alcohols G are then converted into the products of the general structure H in an alkylation reaction with halogenated ester derivatives using tetrabutyl-ammonium chloride or bromide or tetrabutylammonium hydrogen sulfate in a phase-transfer reaction using an organic solvent, such as toluene, benzene or xylene, and inorganic base, such as potassium hydroxide, sodium hydroxide, sodium carbonate, sodium hydrogen carbonate, potassium carbonate, or in the presence of an organic or inorganic base, conventional inorganic bases are metal alcoholates, such as sodium methanolate, sodium ethanolate, potassium tert-butoxide, lithium or sodium bases, such as lithium diisopropylamide, butyllithium, tert-butyllithium, sodium methoxide, or metal hydrides, such as potassium hydride, lithium hydride, sodium hydride; conventional organic bases are diisopropylethylamine, triethylamine, in an organic solvent, such as dichloromethane, THF or diethyl ether, in a temperature range of from $-20°$ C. to $+25°$ C., preferably at from $0°$ C. to $+25°$ C., which products of the general structure H, in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium hydrogen carbonate, potassium carbonate, in organic solvents, such as methanol, dioxane, dichloromethane, THF, diethyl ether or those solvents in the form of mixtures, in a temperature range of from $0°$ C. to $+25°$ C., yield the acid stages of the general formula I. The carboxylic acids I are converted into the end products of the general formula J in an amide formation using primary or secondary amines, in the presence of water-removing agents, such as sodium or magnesium sulfate, phosphorus oxide or reagents such as, for example, CDI, DCC, TBTU, EDCI or benzotriazol-1-yloxy-tris(dimethylamino)phosphonium hexafluorophosphate (BOP), also in the presence of HOAt or HOBt and of an organic base, for example DIPEA, pyridine or 4-methylmorpholine, in an organic solvent, such as THF, dichloromethane, diethyl ether, dioxane, DMF or acetonitrile, $0°$ C. to $+40°$ C., preferably at room temperature.

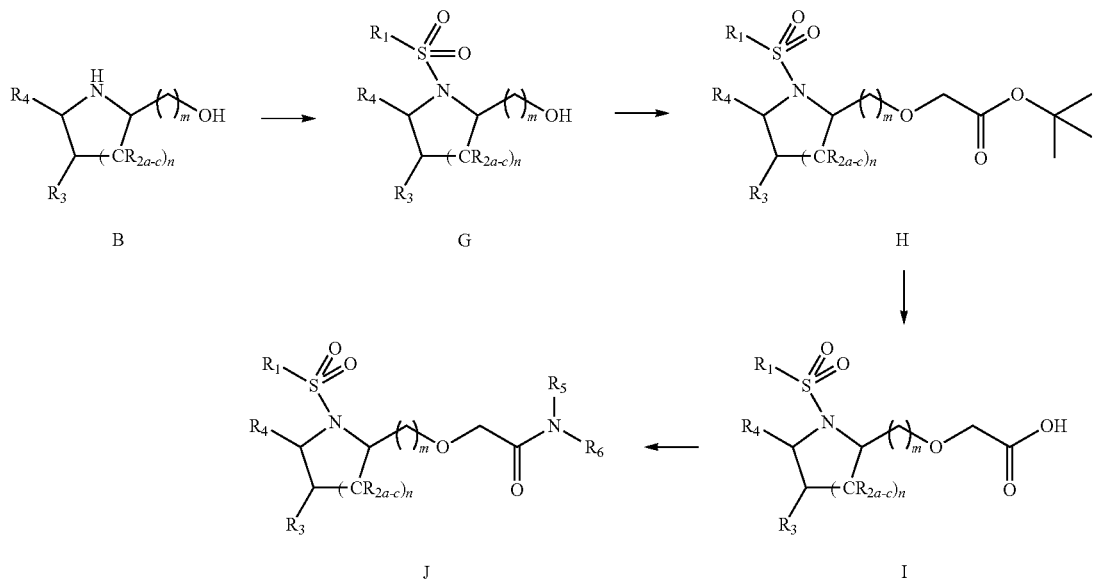

Commercially available amino alcohols are used as structural units B in the synthesis process and are converted into the end products of the general formula J in the manner described in methods 1 and 2.

Compounds corresponding to formula I in which m represents 2 can be prepared according to the same methods from starting materials of the general formula K

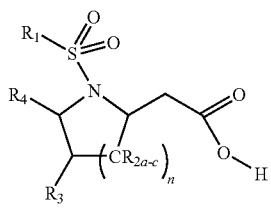

K

The synthesis preferably begins at the stage of the starting materials $G_a$.

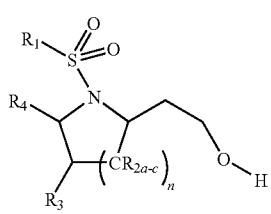

$G_a$

Process for the Preparation of Compounds of the General Formula $J_c$

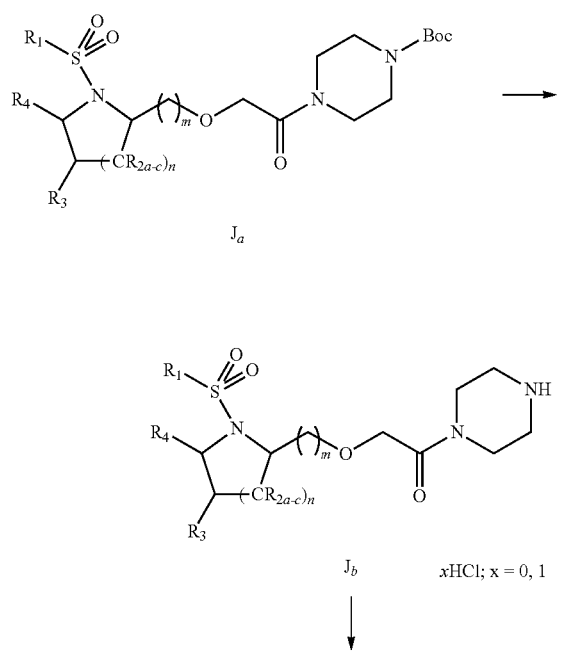

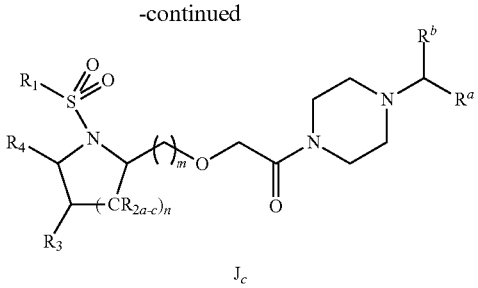

$J_c$

Compounds of the general formula $J_a$ can be prepared, as described in method 1 and 2, from commercially available amino alcohols which are used as the structural units B and are finally reacted, in the last step, in an amide formation, with tert-butyl piperazine-1-carboxylate and are converted into the products of the general structure $J_b$ under acid conditions, in the presence of, for example, trifluoroacetic acid, hydrogen chloride or chlorotrimethylsilane/water in an organic solvent, such as ethyl acetate, methanol, diethyl ether, methyl ethyl ketone or 1,4-dioxane or those solvents in the form of mixtures, in a temperature range of from 0° C. to +100° C., preferably at from +25° C. to +80° C. The amines or the corresponding hydrochlorides of the general formula $J_b$ can be converted into compounds of the general formula $J_c$ using aldehydes or ketones in a reductive amination, optionally in the presence of an organic base, such as triethylamine or diisopropylethylamine, and in the presence of a suitable reducing agent, for example sodium triacetoxyborohydride, sodium cyanoborohydride or sodium diacetoxyborohydride, or those or similar reducing agents in the form of polymer-bonded variants, optionally in the presence of acetic acid, in an organic solvent, for example tetrahydrofuran, dichloromethane, 1,2-dichloroethane or those solvents in the form of mixtures, in a temperature range of from –0° C. to +25° C.

Process for the Preparation of Compounds of the General Formula $J_e$

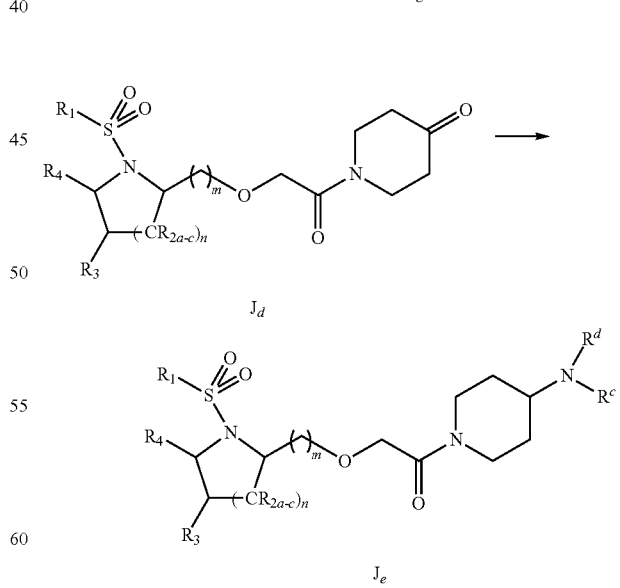

Compounds of the general formula $J_d$ can be prepared, as described in method 1 and 2, from commercially available amino alcohols which are used as structural units B and are finally reacted, in the last step, in an amide formation, with piperidin-4-one. The ketones of the general formula $J_d$ can be converted into compounds of the general formula $J_e$ using amines in a reductive amination, optionally in the presence of an organic base, such as triethylamine or diisopropylethylamine, and in the presence of a suitable reducing agent, for example sodium triacetoxyborohydride, sodium cyanoborohydride or sodium diacetoxy-borohydride, or those or similar reducing agents in the form of polymer-bonded variants, optionally in the presence of acetic acid, in an organic solvent, for example tetrahydrofuran, dichloromethane, 1,2-dichloroethane or those solvents in the form of mixtures, in a temperature range of from −0° C. to +25° C.

+110° C., preferably at from +25° C. to +90° C., yield the acid stages of the general formula $J_h$. The carboxylic acids $J_h$ can be converted into the products of the general formula $J_i$ in an amide formation using primary or secondary amines, in the presence of water-removing agents, such as sodium or magnesium sulfate, phosphorus oxide or reagents such as, for example, CDI, DCC, TBTU, EDCI or benzotriazol-1-yloxy-tris(dimethylamino)phosphonium hexafluorophosphate (BOP), also in the presence of HOAt or HOBt and an organic base, for example DIPEA, pyridine or 4-methylmorpholine, in an organic solvent, such as THF, dichloromethane, diethyl ether, dioxane, DMF or acetonitrile, at from 0° C. to +40° C., preferably at room temperature. The compounds J, can be deprotected in the presence of an inorganic or organic acid, such as HCl, trifluoroacetic acid or formic acid, in an organic solvent, such as THF, dichloro-methane, diethyl ether, diox- Process for the Preparation of Compounds of the General Formula $J_k$

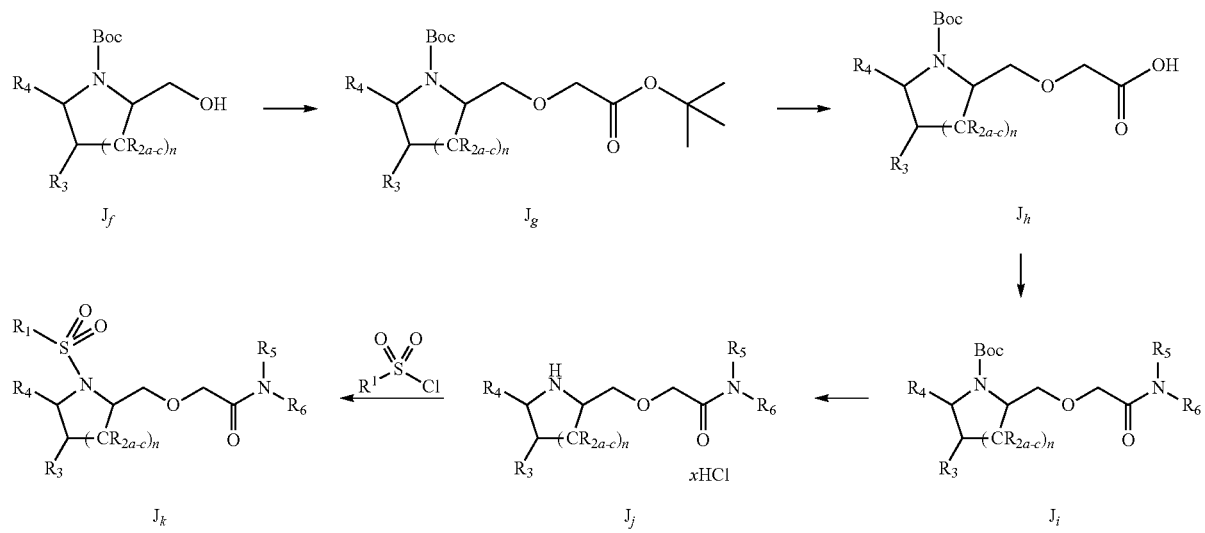

The commercially available, protected amino alcohols of the general formula $J_f$ can be converted into the products of the general structure $J_g$ in an alkylation reaction with halogenated ester derivatives using tetrabutylammonium chloride or bromide or tetra-butylammonium hydrogen sulfate in a phase-transfer reaction using an organic solvent, such as toluene, benzene or xylene, and an inorganic base, such as potassium hydroxide, sodium hydroxide, sodium carbonate, sodium hydrogen carbonate, potassium carbonate, or in the presence of an organic or inorganic base, conventional inorganic bases are metal alcoholates, such as sodium methanolate, sodium ethanolate, potassium tert-butoxide, lithium or sodium bases, such as lithium diisopropylamide, butyllithium, tert-butyllithium, sodium methoxide, or metal hydrides, such as potassium hydride, lithium hydride, sodium hydride; conventional organic bases are diisopropylethylamine, triethylamine, in an organic solvent, such as dichloromethane, THF or diethyl ether, in a temperature range of from −20° C. to +25° C., preferably at from 0° C. to +25° C., which products of the general structure $J_g$, in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium hydrogen carbonate, potassium carbonate, in organic solvents, such as methanol, dioxane, dichloromethane, THF, diethyl ether or those solvents in the form of mixtures, in a temperature range of from 0° C. to ane, MeOH or chloroform, at from 0° C. to +40° C., preferably at from +25 to +40° C., to form the products of the general formula $J_j$. The amines $J_j$ are converted into the sulfonamides $J_k$ in a sulfonylation using sulfonyl chlorides, bromides or pentafluorophenolates $R_1SO_2X$ (X=Br, Cl or OPFP) in the presence of an organic or inorganic base, for example potassium carbonate, sodium hydrogen carbonate, diiso-propylethylamine, triethylamine, pyridine, diethylamine, 1,8-diazabicyclo[5.4.0]-undec-7-ene (DBU) and/or dimethylaminopyridine, or in the presence of tetra-n-butylammonium chloride and in an organic solvent, for example acetonitrile, dichloromethane, THF or N,N-dimethylformamide, in a temperature range of from 0° C. to 120° C., preferably at from +25° C. to +70° C.

The separation of diastereoisomers and/or enantiomers is carried out according to methods known to the person skilled in the art, for example by recrystallization, chromatography or, in particular, HPLC chromatography or crystallization using an optionally chiral acid or base and with separation of the salts, or chiral HPLC chromatography (Fogassy et al., Optical resolution methods, Org. Biomol. Chem. 2006, 4, 3011-3030).

EXAMPLES

In the following examples the yields of the prepared compounds are not optimized, and all temperatures are uncorrected. The term "ether" means diethyl ether, "EE" means ethyl acetate, "DCM" means dichloromethane, "DMF" means dimethylformamide, "DME" means dimethoxyethane, "DMSO" means dimethyl sulfoxide and "THF" means tetrahydrofuran. The term "equivalents" means equivalent amounts, "m.p." means melting point or melting range, "decomp." means decomposition, "RT" means room temperature, "abs." means absolute (anhydrous), "rac." means racemic, "conc." means concentrated, "min." means minutes, "h" means hours, "d" means days, "vol. %" means percent by volume, "wt. %" means percent by weight, and "M" is the concentration in mol/l. The chemicals and solvents used were obtained commercially from the conventional suppliers (ABCR, Acros, Acocado, Aldrich, ApolloScientific, Bachem, Bionet, Chempur, Fluka, Lancaster, Maybridge, Merck, Sigma, TCi TygerScientific, etc.) or were synthesized. Silica gel 60 (0.040-0.063 mm) from E. Merck, Darmstadt was used as the stationary phase for the column chromatography. Thin-layer chromatographic investigations were carried out using precoated HPTLC plates, silica gel 60 F 254, from E. Merck, Darmstadt. The mixing ratios of eluants for chromatographic investigations are always given as volume/volume. Analysis was carried out by means of HPLC-MS, precursors were confirmed by NMR. Other abbreviations used in the examples include:

TBTU=O-(benzotriazol-1-yl)-N,N,N',N'-tetramethyluronium tetrafluoroborate,
CDI=1,1'-carbonyldiimidazole,
DCC=dicyclohexylcarbodiimide,
EDCI=1-ethyl-3-(3-dimethylaminopropyl)carbodiimide,
HOAt=1-hydroxy-7-azabenzotriazole,
DIPEA=N,N-diisopropylamine,
HOBt=1-hydroxybenzotriazole, and
PFP=pentafluorophenyl.

Preparation of the Acid Structural Units

Method 1

1. $LiAlH_4$ (100 ml, 1.0 M in diethyl ether) was added successively with stirring, at a temperature of from −10° C. to RT, under an inert gas atmosphere, to a suspension of the cyclic amino acid (100 mmol) in THF (150 ml). The reaction mixture was stirred for 16 h and thereby warmed to RT. It was then cooled to 0° C. again, and ethyl acetate (20 ml), water (8 ml), 15% aqueous NaOH (8 ml) and water (20 ml) were added, with stirring. After filtration, the residue was washed with diethyl ether. The solvent from the combined organic phases was removed in vacuo, and the product was used in the next step without being purified further.

2. $Et_3N$ (125 mmol) was added to a solution of the amino alcohol (100 mmol) in $CH_2Cl_2$ (200 ml), and the mixture was cooled to 0° C. using an ice-bath. The particular sulfonyl chloride (50 mmol), undiluted or in the form of a solution in $CH_2Cl_2$ (100 ml), was then added, and stirring was carried out for 3 h at RT. After addition of 0.5 M hydrochloric acid (100 ml), the organic phase was separated off, washed with water, dried over $Na_2SO_4$ and filtered, and the solvent was removed in vacuo. The crude product was used in the next step without being purified further or was purified by column chromatography.

3. $n-Bu_4NCl$ (10 mmol) was added to a solution of the product from step 2 (31 mmol) in toluene (200 ml); the mixture was cooled to 0° C., and first aqueous 35% NaOH (200 ml) and then bromoacetic acid tert-butyl ester (46 mmol) were added dropwise. The reaction mixture was stirred for 3 h and then washed with water until neutral and dried over $Na_2SO_4$, and the organic solvent was removed in vacuo. The crude product was used in the next step without being purified further or was purified by column chromatography.

4. The product from step 3 (30 mmol) was dissolved in $CH_2Cl_2$ (200 ml); TFA (30 ml) was added, and stirring was carried out for 2 h at RT. The solvent was largely removed in vacuo, and the crude product was purified by recrystallization or chromatography.

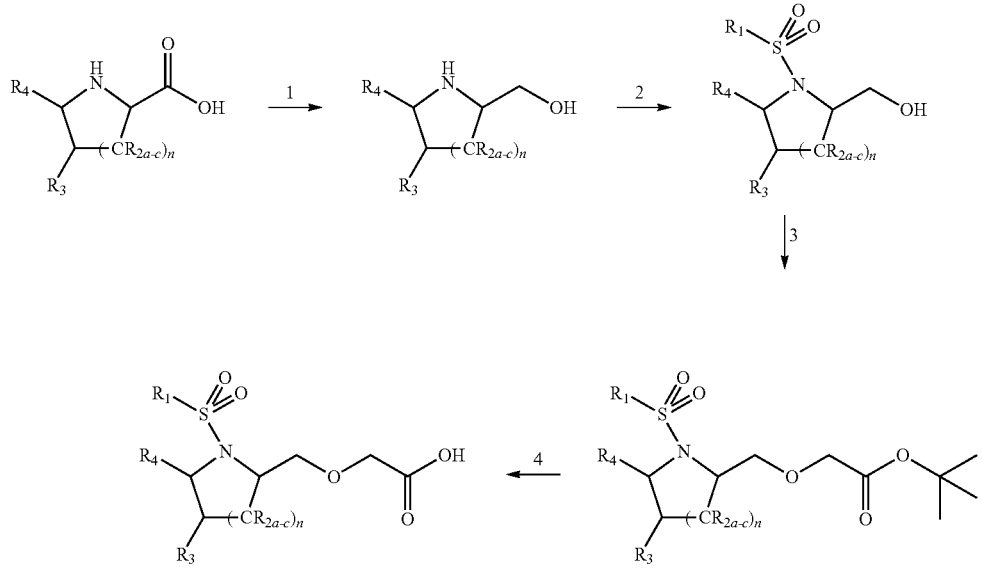

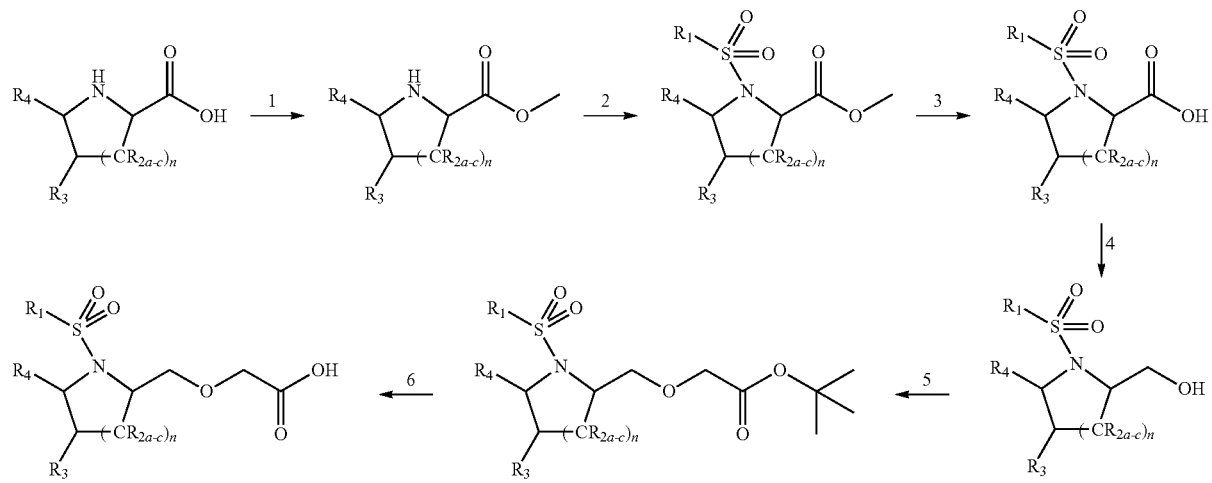

Method 2

1. A solution of the amino acid (153 mmol) in methanol (500 ml) was cooled to 0° C., and thionyl chloride (168 mmol, 12 ml) was added dropwise. After warming to RT, the reaction solution was heated overnight at 40° C. Removal of the solvent by distillation yielded the crude product, which was used in the next step without being purified further.
2. Pyridine (459 mmol) and a solution of the sulfonyl chloride (153 mmol) in $CH_2Cl_2$ (100 ml) were added to a solution of the methyl ester from step 1 (152 mmol) in $CH_2Cl_2$ (400 ml). The reaction solution was stirred overnight at RT. The solution was diluted with a small amount of $CH_2Cl_2$ and washed, in succession, with 0.5 M $KHSO_4$, saturated aqueous $NaHCO_3$ solution and saturated aqueous NaCl solution. The organic phase was separated off and dried over $Na_2SO_4$, the solvent was removed in vacuo, and the crude product was purified by means of column chromatography.
3. 4 M NaOH (153 ml, 610 mmol, 4.5 equivalents) was added, with stirring, to a solution of the product from step 2 (136 mmol) in a methanol/dioxane/4 M NaOH mixture in a ratio of 15/4/1 (1020 ml, 203 mmol NaOH, 1.5 equivalents), and stirring was carried out overnight at RT. The solvent was removed in vacuo. The residue was dissolved with ethyl acetate and washed with 0.5 M $KHSO_4$. The organic phase was washed with saturated aqueous NaCl solution, and the separated organic phase, after filtration, was dried over $Na_2SO_4$. After removal of the solvent in vacuo and washing with diethyl ether, the purified product from step 3 was obtained.
4. $BH_3 \times DMS$ (2.0 M in THF, 31.2 ml, 63 mmol) was slowly added dropwise at 0° C., with stirring, to a solution of the product from step 3 (31 mmol) in THF (250 ml). After stirring for 30 minutes at RT, the solution was allowed to warm slowly to RT overnight. Methanol was then added slowly until no more gas was liberated, and the solvent was reduced in vacuo. The crude product was filtered over silica and washed with $CH_2Cl_2$/methanol in a ratio of 9/1
5. n-$Bu_4$NCl (10 mmol, 2.9 g) was added to a solution of the product from step 4 (31 mmol) in toluene (175 ml), and the mixture was cooled to 0° C.; aqueous 35% NaOH (200 ml) was added first, and then bromoacetic acid tert-butyl ester (48 mmol, 7 ml) was added dropwise. The reaction mixture was stirred for 3 hours and then washed with water until neutral and dried over $Na_2SO_4$, and the organic solvent was removed in vacuo. The crude product was used in the next step without being purified further.
6. The product from step 5 (30 mmol) was dissolved in a mixture of MeOH/dioxane/4 M NaOH in a ratio of 15/4/1 (236 ml, 47 mmol NaOH); further NaOH (4 M, 35 ml, 141 mmol) was added, and stirring was carried out overnight at RT. The solvent was reduced in vacuo, and the residue was diluted with ethyl acetate and washed with 0.5 M $KHSO_4$. The organic phase was separated off, washed with saturated aqueous NaCl solution and dried over $Na_2SO_4$. After filtration, the solvent was removed in vacuo. The crude product was purified by coevaporation with diethyl ether and $CH_2Cl_2$.

Method 3

1. $K_2CO_3$ (148 mmol) and the sulfonyl chloride (82 mmol) were added at RT to a solution or suspension of the amino alcohol (74 mmol) in acetone (350 ml), and stirring was carried out overnight at 40-50° C. The reaction mixture was cooled to RT and filtered. The solvent of the filtrate was then removed in vacuo. The crude product was used in the next step without being purified further.
2. n-$Bu_4$NCl (10 mmol) was added to a solution of the product from step 1 (31 mmol) in toluene (200 ml); the mixture was cooled to 0° C., and first aqueous 35% NaOH (200 ml) and then bromoacetic acid tert-butyl ester (46 mmol) were added dropwise. The reaction mixture was stirred for 3 h and then washed with water until neutral and dried over $Na_2SO_4$, and the organic solvent was removed in vacuo. The crude product was used in the next step without being purified further or was purified by column chromatography.

Methods of Ester Cleavage a. 6 M NaOH (200 ml, 1200 mmol) was added to a solution of the tert-butyl ester (63 mmol) in THF (200 ml) and methanol (200 ml). The reaction mixture was stirred at RT. After 15 min. to 1 h, the organic solvent was removed, the residue was cooled to 0° C., and 6 M HCl (210 ml) was added. The aqueous phase was extracted with $CH_2Cl_2$ (200 ml) and ethyl acetate (200 ml). The combined organic phases were dried over $Na_2SO_4$. After filtration, the solvent was removed in vacuo and the residue was coevaporated twice with i-propyl ether.

b. Dioxane (30 ml) was added to a suspension of the tert-butyl ester (38 mmol) in 6 M NaOH (64 ml, 384 mmol) and methanol (64 ml) until a solution was obtained. The reaction solution was stirred at RT. After 15 min. to 3 h, the organic solvent was removed, the residue was cooled to 0° C., and 6 M HCl (200 ml) was added. The aqueous phase was extracted with $CH_2Cl_2$ (200 ml). The combined organic phases were dried over $Na_2SO_4$. After filtration, the solvent was removed in vacuo and the residue was coevaporated twice with i-propyl ether.

c) The tert-butyl ester (7 mmol) was stirred overnight at RT in 4 M HCl in dioxane (7 ml, 27 mmol). After removal of the solvent, the residue was coevaporated twice with i-propyl ether.

stirring was carried out overnight at RT. After removal of the solvent, the crude product was obtained, which was used in the next step without being purified further.

4. n-$Bu_4$NCl (8.8 mmol) was added to a solution of bromoacetic acid tent-butyl ester (40 mmol) in toluene (100 ml). The reaction mixture was cooled to 0° C., and 35% NaOH (150 ml) and then, dropwise, the alcohol (27 mmol) dissolved in toluene (50 ml) were added. After stirring for 1.5 h at RT, the organic phase was separated off and extracted with water (4×150 ml) and with saturated NaCl solution (150 ml). The organic phase was separated off and dried over $Na_2SO_4$; filtration was carried out, and then the solvent was removed in vacuo. The crude product was purified by column chromatography.

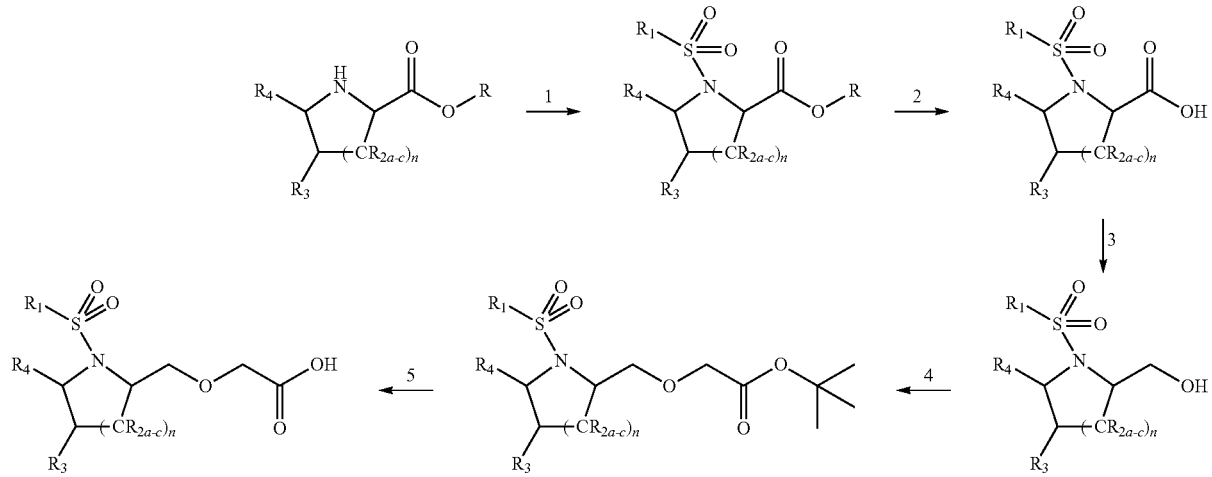

Preparation of 2-((1-(2,6-dichloro-4-(trifluoromethyl)phenylsulfonyl)piperidin-2-yl)-methoxy)acetic acid S24

1. $Et_3N$ (95 mmol) was added to a suspension of DL-piperidine-2-carboxylic acid ethyl ester (38 mmol) in $CH_2Cl_2$ (150 ml). The solution was cooled to 0° C., the sulfonyl chloride (42 mmol) in a solution of $CH_2Cl_2$ (30 ml) was slowly added dropwise, and stirring was carried out for 2 h at RT. The organic phase was extracted with 1 M HCl (250 ml) and $H_2O$ (250 ml). The organic phase was separated off and dried over $Na_2SO_4$. The solvent was removed in vacuo. The residue was coevaporated with i-propyl ether and the product was used in the next step without being purified further.

2. 4 M NaOH (113 mmol) was added at RT, with stirring, to a solution of the ester (38 mmol) in a solvent mixture of methanol/dioxane/4 M NaOH (15/4/1) (57 mmol NaOH), and stirring was carried out for 2 h. The organic solvent was removed in vacuo, and the residue was diluted with ethyl acetate (300 ml) and extracted with 1 M $KHSO_4$ (300 ml). The organic phase was washed with saturated NaCl solution (200 ml). The organic phase was separated off and dried over $Na_2SO_4$; filtration was carried out, and the solvent was removed in vacuo. The product was used in the next step without being purified further.

3. 2 M $BH_3$×DMS in THF (82 mmol) was added slowly at 0° C., with stirring, to a solution of the carboxylic acid (27 mmol) in THF (135 ml). After further cooling for 30 min., 5. The tert-butyl ester (16 mmol) was stirred overnight at RT in 4 M HCl in dioxane (70 ml, 27 mmol). After removal of the solvent, the crude product was purified by column chromatography.

Preparation of ((2-(1-(2,6-dichloro-4-(trifluoromethyl)phenylsulfonyl)pyrrolidin-2-yl)-methoxy)acetic acid S23

1. $Et_3N$ (181 mmol) was added to a suspension of DL-pyrrolidine-2-carboxylic acid methyl ester hydrochloride (36 mmol) in $CH_2Cl_2$ (180 ml). The solution was cooled to 0° C., the sulfonyl chloride (40 mmol) in a solution of $CH_2Cl_2$ (30 ml) was slowly added dropwise, and stirring was carried out for 2 h at RT. The organic phase was extracted with 1 M HCl (250 ml), $H_2O$ (250 ml). The organic phase was separated off and dried over $Na_2SO_4$. The solvent was removed in vacuo. The residue was coevaporated with i-propyl ether and the product was used in the next step without being purified further.

2. 4 M NaOH (108 mmol) was added at RT, with stirring, to a solution of the ester (36 mmol) in a solvent mixture of methanol/dioxane/4 M NaOH (15/4/1) (54 mmol NaOH), and stirring was carried out for 2 h. The organic solvent was removed in vacuo, and the residue was diluted with ethyl acetate (300 ml) and extracted with 1 M $KHSO_4$ (300 ml). The organic phase was washed with saturated NaCl solution (200 ml). The organic phase was separated off and dried over $Na_2SO_4$; filtration was carried out, and the solvent was removed in vacuo. The product was used in the next step without being purified further.

3. 2 M BH$_3$×DMS in THF (86 mmol) was slowly added at 0° C., with stirring, to a solution of the carboxylic acid (28 mmol) in THF (140 ml). After further cooling for 30 min., stirring was carried out overnight at RT. After removal of the solvent, the crude product was obtained, which was used in the next step without being purified further.

4. n-Bu$_4$NCl (9 mmol) was added to a solution of bromoacetic acid tert-butyl ester (42 mmol) in toluene (100 ml). The reaction mixture was cooled to 0° C., and 35% NaOH (150 ml) and then, dropwise, the alcohol (28 mmol) dissolved in toluene (50 ml) were added. After stirring for 1.5 h at RT, the organic phase was separated off and extracted with water (4×150 ml) and with saturated NaCl solution (150 ml). The organic phase was separated off and dried over Na$_2$SO$_4$; filtration was carried out, and then the solvent was removed in vacuo. The crude product was purified by column chromatography.

5. The tent-butyl ester (16 mmol) was stirred overnight at RT in 4 M HCl in dioxane (70 ml, 27 mmol). After removal of the solvent, the crude product was purified by column chromatography.

Preparation of 2-((1-(3,4-dichlorophenylsulfonyl)-1,2,3,4-tetrahydroquinolin-2-yl)-methoxy)acetic acid S35

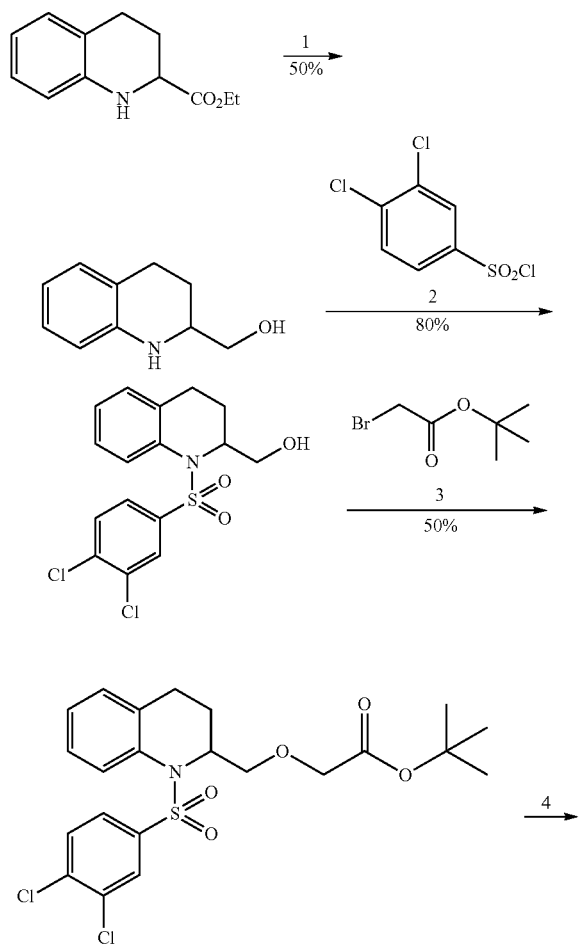

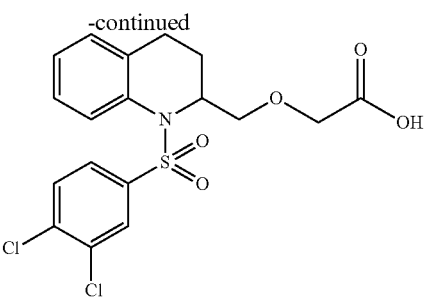

1. 1,2,3,4-tetrahydroquinolin-2-carboxylic acid ethyl ester (25 mmol) in THF (5 ml/mol) was added dropwise at 0° C. to a suspension of LAH (2 eq.) in THF (50 ml). The reaction mixture was stirred for 1 h at RT and then heated under reflux for 4 h. After addition of aqueous saturated Na$_2$SO$_4$ solution, filtration was carried out and the organic solvent was removed in vacuo. The product was purified by column chromatography (3:7 ethyl acetate/hexane). Yield: 50%.

2. Pyridine (5 eq.), DMAP (0.5 eq.) and 3,4-dichlorobenzenesulfonyl chloride (1.2 eq.) dissolved in CH$_2$Cl$_2$ (50 ml) were added to a suspension, cooled to 0° C., of the alcohol (16 mmol) in CH$_2$Cl$_2$ (5 ml/mmol). After stirring for 5 h at 0° C., CH$_2$Cl$_2$ was added and the mixture was washed with aqueous copper sulfate solution, water and saturated NaCl solution. After drying over sodium sulfate and filtration, the solvent was removed in vacuo. The product was purified by column chromatography (5:95 ethyl acetate/CH$_2$Cl$_2$). Yield: 80%.

3. A solution of the sulfonamide (16 mmol) dissolved in THF (100 ml) was added dropwise, with stirring, to a suspension, cooled to 0° C., of NaH (2 eq.) in THF (300 ml). After stirring for 45 min. at that temperature, a solution of bromoacetic acid tent-butyl ester (1.5 eq.) in THF (50 ml) was added. The reaction mixture was heated for 20 h at 50° C. It was then cooled to 0° C., ice was added, and extraction with ethyl acetate was carried out. The organic phase was washed with aqueous saturated NaCl solution and dried over Na$_2$SO$_4$. After filtration, the solvent was removed in vacuo. The product was purified by column chromatography (1:9 ethyl acetate/hexane). Yield: 50%.

4. TFA (13 eq.) was added at a temperature of 0° C., with stirring, to a solution of the tert-butyl ester (1 eq.) in CH$_2$Cl$_2$ (10 ml/mmol). After stirring for 3 h at 0° C., the solvent was removed in vacuo. The crude product was used without being worked up further.

Preparation of 4-methoxy-2,6-dimethoxybenzene-1-sulfonyl chloride

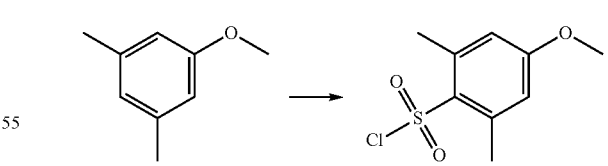

Chlorosulfonic acid (251 ml, 3763 mmol) in CH$_2$Cl$_2$ (250 ml) was added dropwise to a solution of 3,5-dimethylanisole (102.5 g, 753 mmol) in CH$_2$Cl$_2$ (1 l), cooled to 0° C. After 10 min., the reaction mixture was poured onto ice (1 l) and extracted with CH$_2$Cl$_2$ (1×250 ml). The organic phase was washed with water (1 l) and with aqueous saturated NaCl solution (1 l). After drying over Na$_2$SO$_4$ and filtration, the solvent was removed in vacuo. The product was purified by column chromatography (silica, heptane/CH$_2$Cl$_2$, 5:1). Yield: 63.5 g, 36%.

The following structural units were prepared according to these methods:
| Structural unit | Structure | Synthesis method |
|---|---|---|
| S1 | 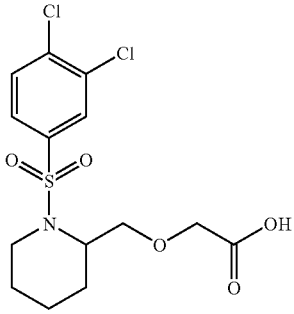 [SMILES: O=C(O)COCC1CCCCN1S(=O)(=O)c1ccc(Cl)c(Cl)c1] | 1 |
| S2 | 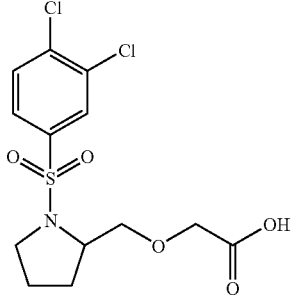 [SMILES: O=C(O)COCC1CCCN1S(=O)(=O)c1ccc(Cl)c(Cl)c1] | 1 |
| S3 | 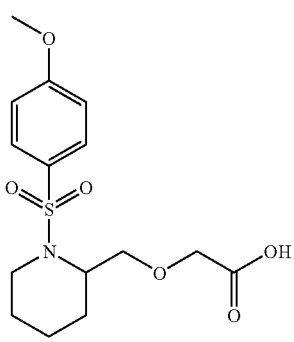 [SMILES: COc1ccc(S(=O)(=O)N2CCCCC2COCC(=O)O)cc1] | 1 |
| S4 | 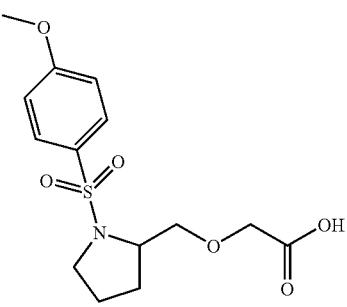 [SMILES: COc1ccc(S(=O)(=O)N2CCCC2COCC(=O)O)cc1] | 1 |

| Structural unit | Structure | Synthesis method |
|---|---|---|
| S5 | 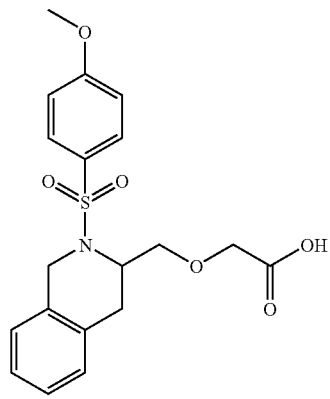 [SMILES: COc1ccc(S(=O)(=O)N2Cc3ccccc3CC2COCC(=O)O)cc1] | 1 |
| S6 | 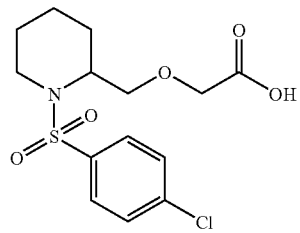 [SMILES: O=C(O)COCC1CCCCN1S(=O)(=O)c1ccc(Cl)cc1] | 1 |
| S7 | 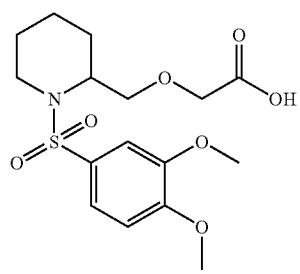 [SMILES: COc1ccc(S(=O)(=O)N2CCCCC2COCC(=O)O)cc1OC] | 1 |
| S8 | 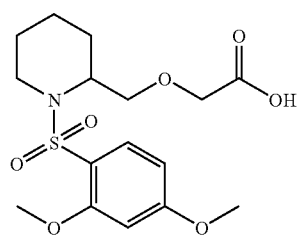 [SMILES: COc1ccc(S(=O)(=O)N2CCCCC2COCC(=O)O)c(OC)c1] | 1 |
| S9 | 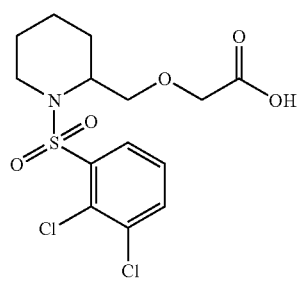 [SMILES: O=C(O)COCC1CCCCN1S(=O)(=O)c1cccc(Cl)c1Cl] | 1 |

-continued

| Structural unit | Structure | Synthesis method |
|---|---|---|
| S10 | 3-(trifluoromethyl)phenylsulfonyl piperidine-2-ylmethoxyacetic acid | 1 |
| S11 | 2,4,6-trimethylphenylsulfonyl piperidine-2-ylmethoxyacetic acid | 1 |
| S12 | (4-fluoro-3-methylpent-2-dien-2-yl)sulfonyl-N-methyl-benzyl-oxyacetic acid derivative | 1 |
| S13 | phenylsulfonyl-tetrahydroisoquinoline-3-ylmethoxyacetic acid | 1 |
| S14 | (3,4-dichloro-3-methylpent-2-dien-2-yl)sulfonyl-N-methyl-benzyl-oxyacetic acid derivative | 1 |

| Structural unit | Structure | Synthesis method |
|---|---|---|
| S15 | 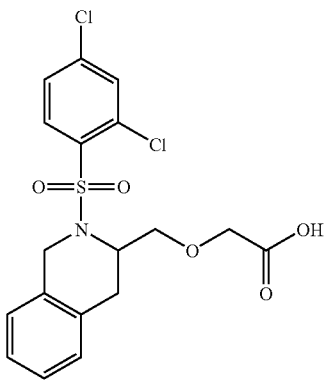 [SMILES: O=C(O)COCC1Cc2ccccc2CN1S(=O)(=O)c1ccc(Cl)cc1Cl] | 1 |
| S16 | 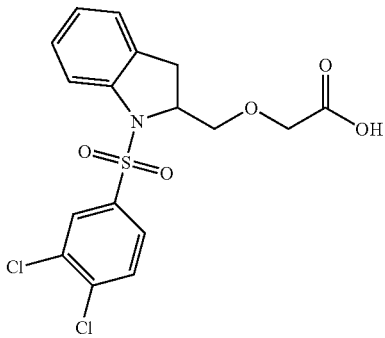 [SMILES: O=C(O)COCC1Cc2ccccc2N1S(=O)(=O)c1ccc(Cl)c(Cl)c1] | 2 |
| S17 | 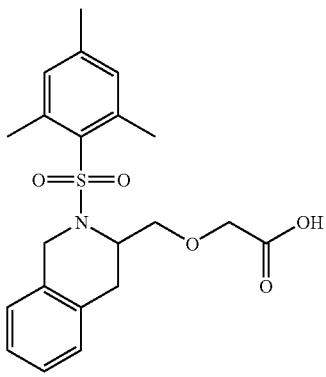 [SMILES: Cc1cc(C)c(S(=O)(=O)N2Cc3ccccc3CC2COCC(=O)O)c(C)c1] | 1 |
| S18 | 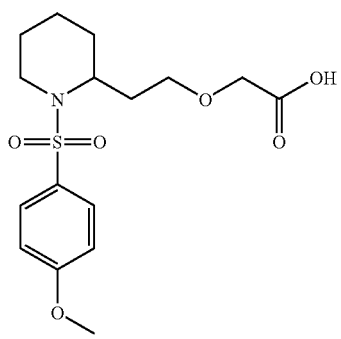 [SMILES: COc1ccc(S(=O)(=O)N2CCCCC2CCOCC(=O)O)cc1] | 1 |

-continued

| Structural unit | Structure | Synthesis method |
|---|---|---|
| S19 | 2,6-dichlorophenylsulfonyl-pyrrolidine-2-yl-methoxyacetic acid | 1b |
| S20 | 2,4,6-trichlorophenylsulfonyl-pyrrolidine-2-yl-methoxyacetic acid | 1c |
| S21 | 2,5-dichlorothiophene-3-sulfonyl-pyrrolidine-2-yl-methoxyacetic acid | 1c |
| S22 | 4-methoxyphenylsulfonyl-indoline-2-yl-methoxyacetic acid | 2 |
| S23 | 2,6-dichloro-4-trifluoromethylphenylsulfonyl-pyrrolidine-2-yl-methoxyacetic acid | — |
| S24 | 2,6-dichloro-4-trifluoromethylphenylsulfonyl-piperidine-2-yl-methoxyacetic acid | — |

-continued

| Structural unit | Structure | Synthesis method |
|---|---|---|
| S25 | 4-methoxy-2,6-dimethylphenylsulfonyl pyrrolidine-2-ylmethoxyacetic acid | 1b |
| S26 | 2,4,6-trichlorophenylsulfonyl piperidine-2-ylmethoxyacetic acid | 1c |
| S27 | 4-methoxy-2,6-dimethylphenylsulfonyl piperidine-2-ylmethoxyacetic acid | 3a |
| S28 | naphthalen-1-ylsulfonyl piperidine-2-ylmethoxyacetic acid | 1 |
| S29 | 2,5-dichlorothiophen-3-ylsulfonyl piperidine-2-ylmethoxyacetic acid | 3a |
| S30 | 4-methoxy-2,3,6-trimethylphenylsulfonyl tetrahydroisoquinoline-3-ylmethoxyacetic acid | 1 |

-continued
| Structural unit | Structure | Synthesis method |
|---|---|---|
| S31 | 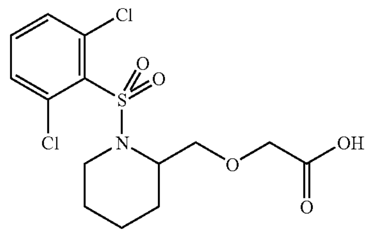 [SMILES: O=C(O)COCC1CCCCN1S(=O)(=O)c1c(Cl)cccc1Cl] | 3b |
| S32 | 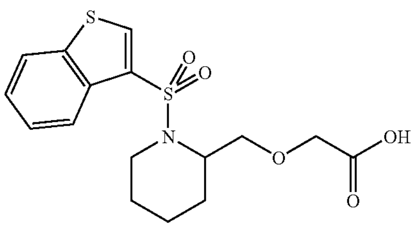 [SMILES: O=C(O)COCC1CCCCN1S(=O)(=O)c1csc2ccccc12] | 3a |
| S33 | 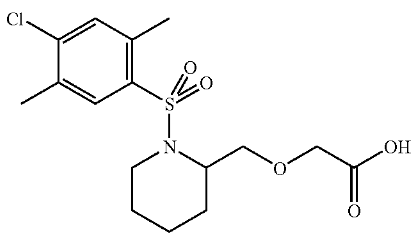 [SMILES: Cc1cc(S(=O)(=O)N2CCCCC2COCC(=O)O)c(C)cc1Cl] | 3a |
| S34 | 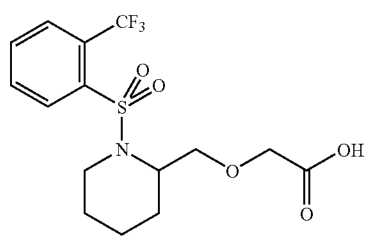 [SMILES: O=C(O)COCC1CCCCN1S(=O)(=O)c1ccccc1C(F)(F)F] | 3a |
| S35 | 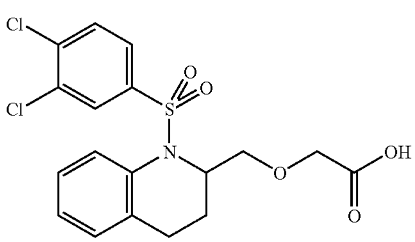 [SMILES: O=C(O)COCC1CCc2ccccc2N1S(=O)(=O)c1ccc(Cl)c(Cl)c1] | — |
S18 was prepared from structural unit
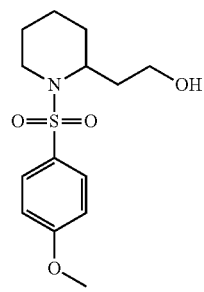
according to method 1.

The amines used were commercially available or were prepared according to methods known to the person skilled in the art or as described below. The following amine structural units were used for the syntheses:

Preparation of amine structural units A1-A4

Method 1

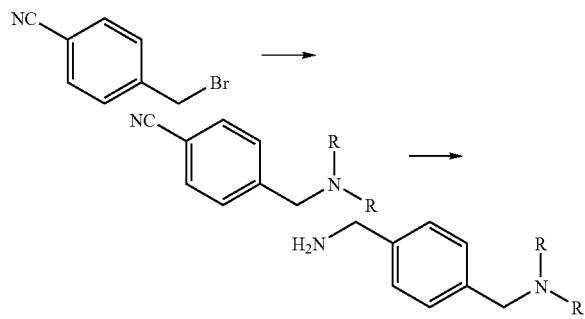

1. 4-bromomethylbenzonitrile (500 mg, 2.55 mmol), K$_2$CO$_3$ (388 mg, 2.8 mmol), amine (2.8 mmol) and DMF (6 ml) were stirred for 0.5 to 3 h at RT and then heated for 2 to 6 h at 80-90° C. The reaction mixture was cooled to RT, water (18 ml) was added, and stirring was carried out for 0.5 h at 0-5° C. The precipitates were filtered off, washed with cold water (2×10 ml) and dried in vacuo. The filtrates were extracted with ethyl acetate (3×15 ml) and dried over Na$_2$SO$_4$. The organic solvent was removed.
2. A solution of step 1 (1 mmol) dissolved in THF (5 ml) was added dropwise, under a nitrogen atmosphere, to a stirred suspension of LAH (4 mmol) in THF (5 ml). The reaction mixture was stirred at 25° C.; after 16 to 20 h, it was cooled with ice, and aqueous saturated Na$_2$SO$_4$ solution was added dropwise. After filtration and washing the residue with ethyl acetate (3×10 ml), the solvent was largely removed and HCl gas was introduced at 0-5° C. The precipitate was filtered off and washed with ether. The amine hydrochlorides were obtained in the form of products which were used without being worked up further.

Preparation of amine structural units A6, A8

Method 2

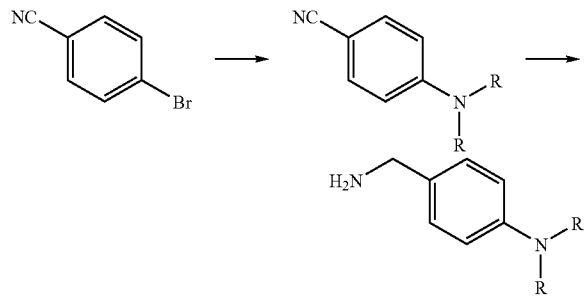

1. A reaction mixture of 4-benzonitrile (2 mmol), amine (3 mmol), K$_2$CO$_3$ (4 mmol), CuI (0.2 mmol) and L-proline (0.4 mmol) in DMSO (4 ml) was heated for 40 h at 80-90° C., with stirring. After addition of water, extraction with ethyl acetate was carried out. The organic phase was washed with aqueous saturated NaCl solution and dried over Na$_2$SO$_4$. After filtration and removal of the solvent, the residue was purified by column chromatography (30% ethyl acetate/CH$_2$Cl$_2$).
2. A solution of step 1 (1 mmol) dissolved in THF (5 ml) was added dropwise, under a nitrogen atmosphere, to a stirred suspension of LAH (4 mmol) in THF (5 ml). The reaction mixture was heated under reflux for 6 h and cooled with ice, and aqueous saturated Na$_2$SO$_4$ solution was added dropwise. After filtration, the residue was washed with a solvent mixture (ethyl acetate and 10% methanol, 3×10 ml). After removal of the solvent, the amines were obtained, which were used without being worked up further.

Preparation of 4-(aminomethyl)-N,N-dimethylaniline A5

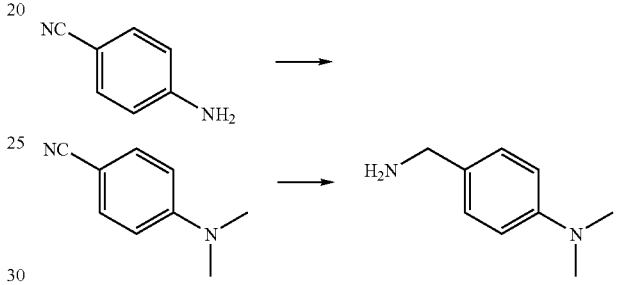

1. Me$_2$SO$_4$ (1.01 ml, 10.57 mmol) was added dropwise at 0° C. to a stirred suspension of 4-aminobenzonitrile (0.5 g, 4.23 mmol) in 10% aqueous Na$_2$CO$_3$ solution (18 ml). The reaction mixture was stirred for 1 h at 25° C. Further Me$_2$SO$_4$ (1.01 ml, 10.57 mmol) and 10% aqueous Na$_2$CO$_3$ solution (18 ml) were then added. After addition of water, extraction with ethyl acetate was carried out. The organic phase was separated off, washed with aqueous saturated NaCl solution and dried over Na$_2$SO$_4$. After filtration and removal of the solvent, the residue was purified by column chromatography (5% ethyl acetate/hexane).
2. A solution of step 1 (1 mmol) dissolved in THF (5 ml) was added dropwise, under a nitrogen atmosphere, to a stirred suspension of LAH (4 mmol) in THF (5 ml). The reaction mixture was heated under reflux for 6 h and cooled with ice, and aqueous saturated Na$_2$SO$_4$ solution was added dropwise. After filtration, the residue was washed with a solvent mixture (ethyl acetate and 10% methanol, 3×10 ml). The solvent was largely removed in vacuo and the amine was obtained in the form of the hydrochloride by introduction of HCl gas.

Preparation of (4-morpholinophenyl)methanamine A7

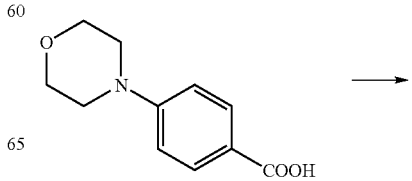

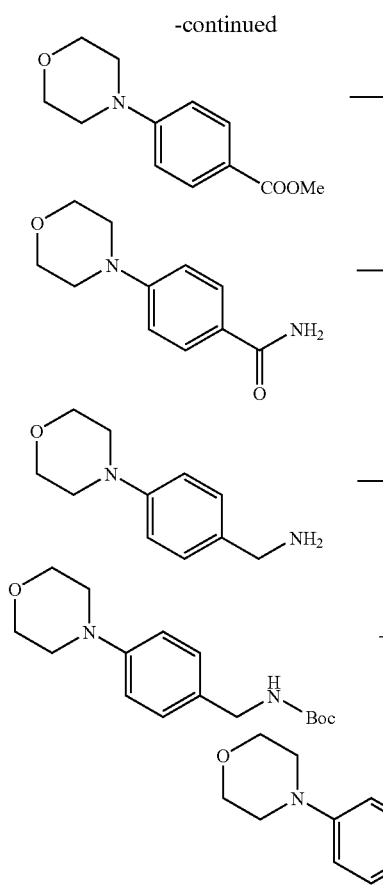

1. A reaction mixture of 4-morpholinebenzoic acid (0.5 g) and methanolic HCl solution (6 ml, 4%) was heated under reflux for 6 h, with stirring. After removal of the solvent in vacuo, water (10 ml) was added to the residue and the mixture was neutralized with aqueous saturated NaHCO$_3$ solution. The solution was extracted with ethyl acetate (3×20 ml). The organic phase was separated off and dried over Na$_2$SO$_4$. After filtration and removal of the solvent, the product was obtained, which was used in the next step without being worked up further.
2. A reaction mixture of product step 1 (4 g), NH$_3$ (25 ml) and methanol (20 ml) was heated for 4 d at 120° C. in an autoclave (pressure 50 kg/cm$^2$). After removal of the solvent in vacuo, the product was purified by column chromatography (50% ethyl acetate/hexane).
3. BH$_3$×DMS (1.86 ml, 19.4 mmol) was added at 0° C., with stirring, under a nitrogen atmosphere, to a solution of the amide from step 2 (1 g, 4.84 mmol) in THF (15 ml). The reaction mixture was heated under reflux for 18 h and cooled, and methanol was added. The solvent was removed in vacuo, and the residue was dissolved in ethyl acetate and washed with aqueous saturated NaCl solution. After filtration and drying over Na$_2$SO$_4$, the solvent was removed in vacuo and the product was used in the next step without being worked up further.
4. (Boc)$_2$O (0.82 ml, 3.83 mmol) was added to a solution of the amine from step 3 (0.67 g) dissolved in THF (12 ml), and stirring was carried out for 18 h. The solvent was then removed in vacuo and the product was purified by column chromatography (10% ethyl acetate/hexane).
5. A solution of HCl gas in ethyl acetate (4%) was added to the Boc-protected product from step 4 (280 mg), and stirring was carried out for 2 h at RT. The solvent was removed in vacuo and the residue was taken up in a small amount of ethyl acetate. After filtration and drying in vacuo, the product was obtained in the form of the amine hydrochloride.

Preparation of N,N-dimethyl-4-(2-(methylamino)ethyl)cyclohexanamine A9 and N-methyl-2-(4-(pyrrolidin-1-yl)cyclohexyl)ethanamine A10

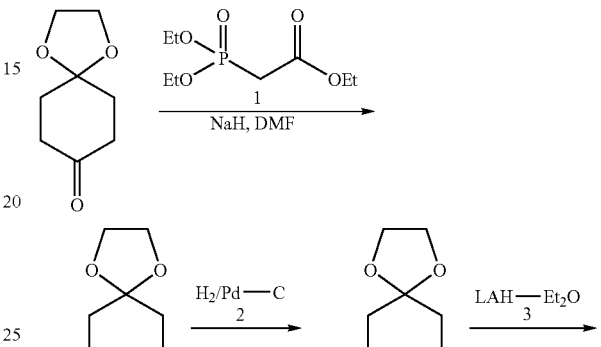

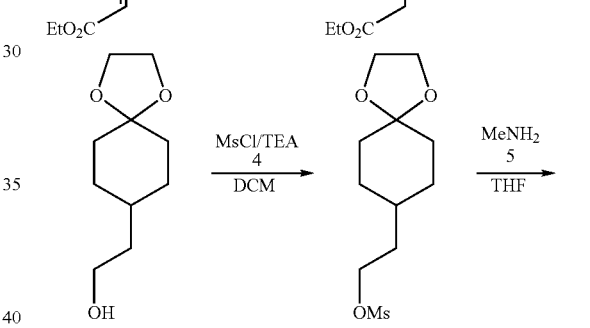

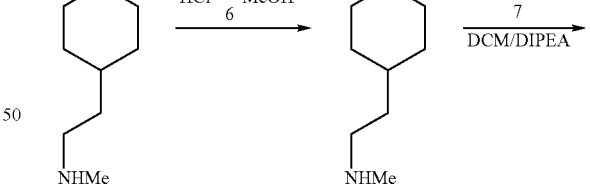

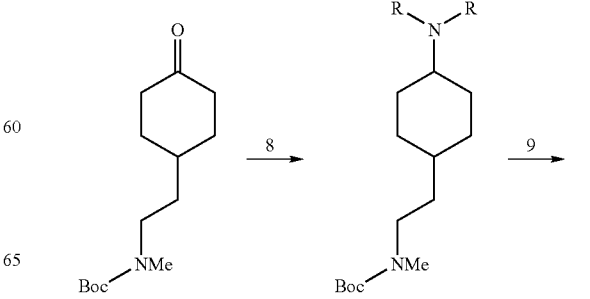

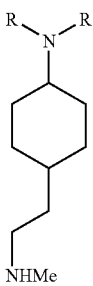

1. A solution of triethyl phosphonoacetate (11 mmol) in THF (50 ml) was added slowly to a suspension, cooled to 0° C., of NaH (10 mmol) in THF (50 ml), and the reaction mixture was stirred for 30 min. 1,4-Dioxa-spiro[4.5]decan-8-one (10 mmol) in THF (50 ml) was then added dropwise at 0° C., and stirring was carried out for 16 h. After addition of ice and aqueous saturated NaCl solution, the aqueous phase was washed with ethyl acetate and the organic phase with water and aqueous saturated NaCl solution. The combined organic phases were dried over $Na_2SO_4$ and, after filtration, the solvent was removed in vacuo. The product was purified by column chromatography (20% ethyl acetate/hexane). Yield: 90%.
2. A solution of the ester (10 mmol) in MeOH (30 ml) was hydrogenated with hydrogen for 16 h under argon with 10% Pd/C (50%). After filtration over Celite, the residue was washed with MeOH and the solvent of the combined organic phases was removed in vacuo. The product was used in the next step without being worked up further.
3. A solution of (1,4-dioxa-spiro[4.5]dec-8-yl)acetic acid ethyl ester (10 mmol) in THF (50 ml) was slowly added over a period of 30 min. to a suspension, cooled to 0° C., of LaH (10 mmol) in THF (30 ml). When the reaction of the ester was complete, the solution was cooled to 0° C., aqueous saturated $Na_2SO_4$ solution was added, and filtration over Celite was carried out. The solvent was removed in vacuo and the product was used in the next step without being worked up further.
4. Methanesulfonyl chloride (11 mmol) was added dropwise at 0° C., under nitrogen, to a solution of the alcohol (10 mmol) in $CH_2Cl_2$ (50 ml). The reaction mixture was stirred for a further 2 h and then diluted with $CH_2Cl_2$. After extraction with aqueous saturated NaCl solution, drying over $Na_2SO_4$ was carried out. After filtration and removal of the solvent, the crude product was obtained in a yield of 80%.
5. A 2 M solution of methylamine in $CH_2Cl_2$ (10 ml) was added to a solution of the Ms-protected alcohol (5 mmol) in THF (5 ml), and the reaction solution was heated for 16 h at 100° C. After removal of the solvent in vacuo, the crude product was used in the next step without being worked up further. Yield of crude product: 90%.
6. 6 N HCl (20 ml) was added at 0° C. to [2-(1,4-dioxa-spiro[4.5]dec-8-yl)-ethyl]methylamine (10 mmol), and stirring was carried out for 16 h at 25° C. The aqueous solution was extracted with ethyl acetate and then adjusted to pH 14 with 6N NaOH. The aqueous phase was extracted with $CH_2Cl_2$ and the organic phase was washed with water and aqueous saturated NaCl solution. The organic phase was dried over $Na_2SO_4$ and, after filtration, the solvent was removed. The crude product was used in the next step without being worked up further. Yield of crude product: 80%.
7. Diisopropylamine (37.5 mmol) and di-tert-arylbutyl dicarbonate (22.5 mmol) were added at 0° C. to a solution of 4-(2-methylamino-ethyl)-cyclohexanone (15 mmol) in $CH_2Cl_2$ (45 ml). The reaction mixture was stirred for 16 h at 25° C. After addition of $CH_2Cl_2$, extraction with water and aqueous saturated NaCl solution was carried out. The organic phase was separated off and dried over $Na_2SO_4$. After filtration, the solvent was removed in vacuo and the product was purified by column chromatography (5% methanol/$CH_2Cl_2$). Yield: 70%.
8. To a solution of the ketone (1 eq.) in methanol (10 ml/mmol) there were added the corresponding amine (1.5 eq.), sodium cyanoborohydride (2 eq.) and acetic acid (2 eq.). The reaction mixture was stirred for 16 h at 25° C. Ice was then added thereto, and the solvent was removed in vacuo. After addition of ethyl acetate, extraction was carried out first with aqueous saturated $Na_2CO_3$ solution and then with aqueous saturated NaCl solution. The organic phase was separated off, dried over $Na_2SO_4$ and filtered, and the solvent was removed in vacuo. The product was purified by column chromatography (3% methanol/$CH_2Cl_2$).
9. 20% TFA in $CH_2Cl_2$ (5 ml/mmol) was added at 0° C. to the Boc-protected precursor, and the reaction mixture was stirred for 3 h. The solvent was removed in vacuo and the amine was used in the form of the TFA salt in the further synthesis.

Amine Structural Units

| Structural unit | Structure | Synthesis method |
|---|---|---|
| A1 | 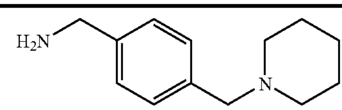 | 1 |
| A2 | 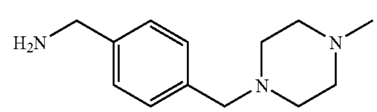 [SMILES: CN1CCN(Cc2ccc(CN)cc2)CC1] | 1 |
| A3 | 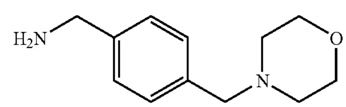 [SMILES: NCc1ccc(CN2CCOCC2)cc1] | 1 |
| A4 | 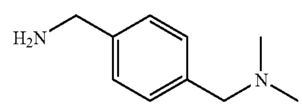 | 1 |
| A5 | 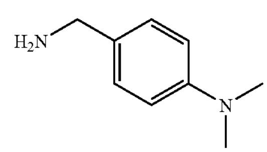 | — |
| A6 | 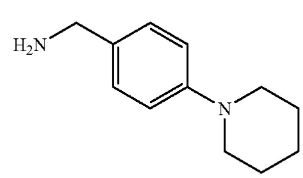 [SMILES: NCc1ccc(N2CCCCC2)cc1] | 2 |
| A7 | 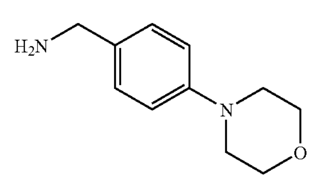 [SMILES: NCc1ccc(N2CCOCC2)cc1] | — |

| Structural unit | Structure | Synthesis method |
|---|---|---|
| A8 | H₂N–CH₂–C₆H₄–N(piperazine)–N–CH₃ | 2 |
| A9 | CH₃–NH–CH₂CH₂–cyclohexyl–N(CH₃)₂ | — |
| A10 | CH₃–NH–CH₂CH₂–cyclohexyl–N(pyrrolidine) | — |

Preparation of the Compounds of the Examples by Amide Formation in Parallel Synthesis

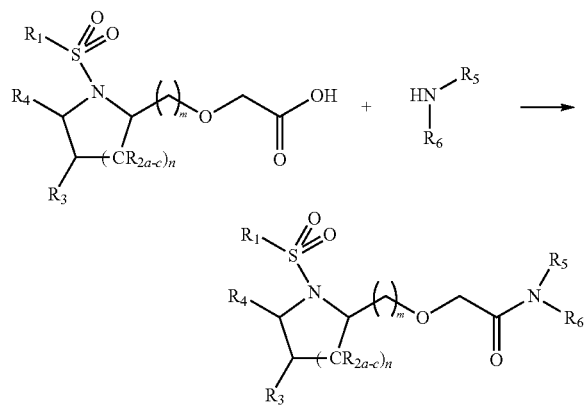

Parallel Synthesis Method 1

Acid solution (0.05 M in $CH_2Cl_2$, 2 ml) was added to 105 µmol of CDI solution (0.105 M in $CH_2Cl_2$, 1 ml), and the mixture was agitated for 1 h at RT. 100 µmol of the amine solution (0.1 M in $CH_2Cl_2$) were then added at RT, and the mixture was agitated for a further 12 h at RT. 3 ml of water were then added to the reaction mixture, agitation was carried out for 15 min., and the organic phase was separated off. After removal of the solvent by distillation, the crude products were analysed by LC-MS and purified by HPLC.

Parallel Synthesis Method 2

At RT, 100 µmol of acid solution (0.05 M in $CH_2Cl_2$, 2 ml) were placed in a vessel, and 105 µmol of CDI solution (0.105 M in $CH_2Cl_2$, 1 ml) were added. After stirring for 1 h at RT, 100 µmol of the corresponding amine (0.1 M in $CH_2Cl_2$) were pipetted into the reaction solution. The reaction solution was stirred for 16 h at RT. 3 ml of water were then added, and vortexing and thorough mixing were carried out for 30 min. The magnetic stirrer bar was filtered off, and the vessel was flushed with 1.5 ml of $CH_2Cl_2$.

The aqueous phase was removed and discarded. 3 ml of $H_2O$ and 0.5 ml of $CH_2Cl_2$ were added to the organic phase; vortexing was carried out, followed by intensive mixing for 15 min. After centrifugation, the aqueous phase was separated off and discarded. The organic phase was extracted in an analogous manner for a second time with 3 ml of saturated NaCl solution. The organic phase was then removed, introduced into a test glass and dried over a $MgSO_4$ cartridge. After removal of the solvent by distillation, the crude products were analysed by means of LC-MS and purified by HPLC.

Parallel Synthesis Method 3

The acids (50 mg, 1 eq.) were reacted with the amine (50-70 mg, 1.2 eq.) in $CH_2Cl_2$ (3 ml/mmol) using the coupling reagents EDCI (1.5 eq.), HOBt (1 eq.) and DIPEA (2 eq.). After removal of the solvent, the products were purified by column chromatography.

Parallel Synthesis Method 4

The acids (50 mg, 1 eq.) in $CH_2Cl_2$ (3 ml/mmol) were stirred for 15 min. at 25° C. with EDCI (1.5 eq.), HOBt (1 eq.) and DIPEA (1.5 eq.). DIPEA (4 eq.) was added at 0° C. to a solution of the amine-TFA salt (1.2 eq.) in $CH_2Cl_2$ (1 ml/mmol), and the whole was added to the solution of the acid. The reaction mixture was stirred for 16 h at 25° C. and then diluted with $CH_2Cl_2$. The organic phase was separated off, extracted with aqueous $NH_4Cl$ solution, $Na_2CO_3$ solution, NaCl solution and then dried over $Na_2SO_4$. After filtration and removal of the solvent, the products were purified by column chromatography.

The following compounds were prepared according to one of these methods of parallel synthesis.

| Example | Method | Mass |
|---|---|---|
| 1 | 1 | 543.28 |
| 2 | 1 | 557.29 |
| 3 | 1 | 558.29 |
| 4 | 1 | 601.13 |
| 5 | 2 | 568.31 |
| 6 | 1 | 535.25 |
| 7 | 1 | 572.30 |
| 9 | 2 | 579.17 |
| 10 | 1 | 587.12 |
| 11 | 1 | 517.26 |
| 12 | 1 | 541.30 |
| 13 | 1 | 602.13 |
| 14 | 1 | 543.28 |
| 15 | 1 | 616.14 |
| 16 | 2 | 601.16 |
| 17 | 1 | 565.16 |
| 18 | 1 | 544.27 |
| 19 | 1 | 491.28 |
| 20 | 1 | 559.20 |
| 21 | 1 | 545.26 |
| 22 | 2 | 546.25 |
| 23 | 2 | 499.25 |
| 24 | 1 | 559.27 |
| 25 | 2 | 556.31 |
| 26 | 1 | 517.16 |
| 27 | 2 | 505.30 |
| 28 | 1 | 546.18 |
| 29 | 1 | 588.11 |

| Example | Method | Mass |
|---|---|---|
| 30 | 1 | 603.11 |
| 31 | 2 | 527.28 |
| 32 | 1 | 546.18 |
| 33 | 2 | 590.29 |
| 34 | 1 | 549.27 |
| 35 | 1 | 503.25 |
| 36 | 1 | 545.19 |
| 37 | 1 | 561.10 |
| 38 | 1 | 565.16 |
| 39 | 1 | 583.13 |
| 40 | 1 | 558.29 |
| 41 | 2 | 589.30 |
| 42 | 1 | 560.20 |
| 43 | 1 | 626.25 |
| 44 | 1 | 569.12 |
| 45 | 1 | 602.13 |
| 46 | 1 | 507.14 |
| 47 | 1 | 565.26 |
| 48 | 2 | 600.37 |
| 49 | 1 | 589.10 |
| 50 | 2 | 577.26 |
| 51 | 1 | 579.17 |
| 52 | 1 | 521.29 |
| 53 | 1 | 555.14 |
| 54 | 1 | 531.17 |
| 55 | 1 | 545.26 |
| 56 | 1 | 525.13 |
| 57 | 1 | 538.15 |
| 58 | 2 | 534.25 |
| 59 | 1 | 543.12 |
| 60 | 1 | 529.26 |
| 61 | 1 | 551.25 |
| 62 | 1 | 532.17 |
| 63 | 1 | 563.28 |
| 64 | 1 | 513.27 |
| 65 | 2 | 581.15 |
| 66 | 1 | 459.22 |
| 67 | 2 | 575.28 |
| 68 | 1 | 545.19 |
| 69 | 1 | 569.29 |
| 70 | 1 | 567.17 |
| 71 | 1 | 573.10 |
| 72 | 1 | 546.18 |
| 73 | 1 | 547.09 |
| 74 | 1 | 587.12 |
| 75 | 2 | 590.29 |
| 76 | 1 | 527.28 |
| 77 | 2 | 529.26 |
| 78 | 1 | 601.16 |
| 79 | 1 | 601.16 |
| 80 | 1 | 542.29 |
| 81 | 2 | 587.14 |
| 82 | 1 | 579.17 |
| 83 | 2 | 575.28 |
| 84 | 1 | 555.14 |
| 85 | 1 | 534.18 |
| 86 | 1 | 543.12 |
| 87 | 1 | 510.23 |
| 88 | 1 | 520.17 |
| 89 | 1 | 511.11 |
| 90 | 2 | 535.30 |
| 91 | 2 | 529.26 |
| 194 | 4 | 563.3 |
| 209 | 4 | 537.3 |
| 213 | 4 | 595.2 |
| 216 | 4 | 621.2 |
| 218 | 2 | 553.2 |
| 219 | 1 | 515.3 |
| 220 | 1 | 598.2 |
| 221 | 1 | 536.3 |
| 222 | 2 | 552.3 |
| 223 | 2 | 589.3 |
| 224 | 2 | 603.1 |
| 225 | 2 | 505.3 |
| 226 | 2 | 499.3 |
| 227 | 2 | 529.3 |
| 228 | 2 | 541.3 |
| 229 | 2 | 527.3 |
| 230 | 2 | 528.3 |
| 231 | 2 | 520.3 |
| 232 | 2 | 534.3 |
| 233 | 2 | 594.2 |
| 234 | 2 | 596.3 |
| 235 | 2 | 513.3 |
| 236 | 2 | 501.2 |
| 237 | 2 | 501.2 |
| 238 | 2 | 501.2 |
| 239 | 2 | 489.2 |
| 240 | 2 | 535.3 |
| 241 | 2 | 557.3 |
| 242 | 2 | 453.2 |
| 243 | 2 | 513.2 |
| 244 | 2 | 511.2 |
| 245 | 2 | 543.3 |
| 246 | 2 | 529.3 |
| 247 | 2 | 501.2 |
| 248 | 2 | 496.3 |
| 249 | 2 | 627.3 |
| 250 | 2 | 483.3 |
| 251 | 2 | 593.2 |
| 252 | 2 | 573.3 |
| 253 | 2 | 619.1 |
| 254 | 2 | 610.2 |
| 255 | 2 | 627.2 |
| 256 | 2 | 604.1 |
| 257 | 2 | 463.2 |
| 258 | 2 | 496.2 |
| 259 | 2 | 440.2 |
| 260 | 2 | 522.3 |
| 261 | 2 | 516.3 |
| 262 | 2 | 542.3 |
| 263 | 2 | 571.3 |
| 264 | 2 | 521.2 |
| 265 | 2 | 589.1 |
| 266 | 1 | 547.2 |
| 267 | 2 | 522.3 |
| 268 | 2 | 535.3 |
| 269 | 2 | 546.3 |
| 270 | 2 | 552.3 |
| 271 | 2 | 487.2 |
| 272 | 2 | 487.2 |
| 273 | 2 | 487.2 |
| 274 | 2 | 502.2 |
| 275 | 2 | 598.3 |
| 276 | 2 | 611.3 |
| 277 | 2 | 605.3 |
| 278 | 2 | 546.2 |
| 279 | 2 | 559.2 |
| 280 | 2 | 570.2 |
| 281 | 2 | 576.2 |
| 282 | 2 | 511.1 |
| 283 | 2 | 526.1 |
| 284 | 2 | 553.2 |
| 285 | 2 | 532.2 |
| 286 | 2 | 545.2 |
| 287 | 2 | 556.2 |
| 288 | 2 | 545.3 |
| 289 | 2 | 533.2 |
| 290 | 2 | 545.3 |
| 291 | 2 | 481.3 |
| 292 | 2 | 568.3 |
| 293 | 1 | 539.1 |
| 294 | 2 | 613.3 |
| 295 | 2 | 497.1 |
| 296 | 2 | 537.1 |
| 297 | 2 | 553.1 |
| 298 | 2 | 551.1 |
| 299 | 2 | 529.3 |
| 300 | 2 | 543.3 |
| 301 | 2 | 530.3 |
| 302 | 2 | 544.3 |
| 303 | 2 | 529.3 |
| 304 | 2 | 559.3 |
| 305 | 2 | 502.2 |
| 306 | 2 | 531.2 |
| 307 | 2 | 519.2 |

-continued

| Example | Method | Mass |
|---|---|---|
| 308 | 2 | 531.2 |
| 309 | 2 | 503.2 |
| 310 | 2 | 529.3 |
| 311 | 2 | 549.2 |
| 312 | 2 | 527.2 |
| 313 | 2 | 553.2 |
| 314 | 2 | 567.2 |
| 315 | 2 | 553.2 |
| 316 | 2 | 526.1 |
| 317 | 2 | 555.1 |
| 318 | 2 | 543.1 |
| 319 | 2 | 555.1 |
| 320 | 2 | 553.2 |
| 321 | 2 | 573.1 |
| 322 | 2 | 539.1 |
| 323 | 2 | 553.2 |
| 324 | 2 | 541.1 |
| 325 | 2 | 541.1 |
| 326 | 2 | 539.1 |
| 327 | 2 | 587.1 |
| 328 | 2 | 575.1 |
| 329 | 2 | 573.1 |
| 330 | 2 | 566.1 |
| 331 | 2 | 579.2 |
| 332 | 2 | 590.1 |
| 333 | 2 | 596.2 |
| 334 | 2 | 613.1 |
| 335 | 2 | 546.1 |
| 336 | 2 | 531.2 |
| 337 | 2 | 517.2 |
| 338 | 2 | 511.1 |
| 339 | 2 | 497.1 |
| 340 | 2 | 575.3 |
| 341 | 2 | 566.4 |
| 342 | 2 | 583.3 |
| 343 | 2 | 467.3 |
| 344 | 2 | 497.3 |
| 345 | 2 | 461.2 |
| 346 | 2 | 535.2 |
| 347 | 2 | 529.3 |
| 348 | 2 | 569.2 |
| 349 | 2 | 583.2 |
| 350 | 2 | 593.2 |
| 351 | 2 | 557.3 |
| 352 | 2 | 549.2 |
| 353 | 2 | 529.3 |
| 354 | 2 | 545.1 |
| 355 | 2 | 539.1 |
| 356 | 2 | 579 |
| 357 | 2 | 593.1 |
| 358 | 2 | 603 |
| 359 | 2 | 559.1 |
| 360 | 2 | 539.1 |
| 361 | 2 | 531.3 |
| 362 | 2 | 543.3 |
| 363 | 2 | 467.3 |
| 364 | 2 | 543.3 |
| 365 | 2 | 529.3 |
| 366 | 2 | 478.2 |
| 367 | 2 | 545.3 |
| 368 | 2 | 573.3 |
| 369 | 2 | 516.2 |
| 370 | 2 | 497.2 |
| 371 | 2 | 500.2 |
| 372 | 2 | 448.2 |
| 373 | 2 | 543.3 |
| 374 | 2 | 507.3 |
| 375 | 2 | 467.3 |
| 376 | 2 | 618.2 |
| 377 | 2 | 531.3 |
| 378 | 2 | 583.2 |
| 379 | 2 | 455.3 |
| 380 | 2 | 497.3 |
| 381 | 2 | 597.2 |
| 382 | 2 | 607.2 |
| 383 | 2 | 571.3 |
| 384 | 2 | 563.2 |
| 385 | 2 | 543.3 |

-continued

| Example | Method | Mass |
|---|---|---|
| 386 | 2 | 559.3 |
| 387 | 2 | 547.3 |
| 388 | 2 | 529.3 |
| 389 | 2 | 545.1 |
| 390 | 2 | 545.1 |
| 391 | 2 | 533.1 |
| 392 | 2 | 601.1 |
| 393 | 2 | 497.1 |
| 394 | 2 | 505 |
| 395 | 2 | 532.2 |
| 396 | 2 | 532.2 |
| 397 | 2 | 568.3 |
| 398 | 2 | 543.3 |
| 399 | 2 | 521.3 |
| 400 | 2 | 571.3 |
| 401 | 2 | 572.3 |
| 402 | 2 | 598.2 |
| 403 | 2 | 553.2 |
| 404 | 2 | 593.1 |
| 405 | 2 | 607.1 |
| 406 | 2 | 617.1 |
| 407 | 2 | 573.1 |
| 408 | 2 | 553.2 |
| 409 | 2 | 515.3 |
| 410 | 2 | 492.2 |
| 411 | 2 | 586.3 |
| 412 | 2 | 524.3 |
| 413 | 2 | 495.3 |
| 414 | 2 | 543.3 |
| 415 | 2 | 557.3 |
| 416 | 2 | 478.2 |
| 417 | 2 | 604.3 |
| 418 | 2 | 543.3 |
| 419 | 2 | 543.3 |
| 420 | 2 | 526.2 |
| 421 | 2 | 557.3 |
| 422 | 2 | 563.3 |
| 423 | 2 | 549.2 |
| 424 | 2 | 531.3 |
| 425 | 2 | 476.2 |
| 426 | 2 | 478.2 |
| 427 | 2 | 526.2 |
| 428 | 2 | 543.3 |
| 429 | 2 | 529.3 |
| 430 | 2 | 543.3 |
| 431 | 2 | 544.3 |
| 432 | 2 | 558.3 |
| 433 | 2 | 558.3 |
| 434 | 2 | 558.3 |
| 435 | 2 | 545.3 |
| 436 | 2 | 531.2 |
| 437 | 2 | 545.3 |
| 438 | 2 | 531.2 |
| 439 | 2 | 545.3 |
| 440 | 2 | 591.1 |
| 441 | 2 | 593.3 |
| 442 | 2 | 543.1 |
| 443 | 2 | 517.2 |
| 444 | 2 | 533.2 |
| 445 | 2 | 515.3 |
| 446 | 2 | 572.3 |
| 447 | 2 | 501.2 |
| 448 | 2 | 515.3 |
| 449 | 2 | 515.3 |
| 450 | 2 | 543.3 |
| 451 | 2 | 555.1 |
| 452 | 2 | 506.2 |
| 453 | 2 | 525.1 |
| 454 | 2 | 557.1 |
| 455 | 2 | 539.1 |
| 456 | 2 | 525.1 |
| 457 | 2 | 553.2 |
| 458 | 2 | 539.1 |
| 459 | 2 | 511.1 |
| 460 | 2 | 515.3 |
| 461 | 2 | 501.2 |
| 462 | 2 | 559.2 |
| 463 | 2 | 537.2 |

-continued

| Example | Method | Mass |
|---|---|---|
| 464 | 2 | 537.2 |
| 465 | 2 | 569.2 |
| 466 | 2 | 475.2 |
| 467 | 2 | 453.2 |
| 468 | 2 | 570.2 |
| 469 | 2 | 604.2 |
| 470 | 2 | 589.3 |
| 471 | 2 | 528.3 |
| 472 | 2 | 574.2 |
| 473 | 2 | 543.3 |
| 474 | 2 | 553.3 |
| 475 | 2 | 557.3 |
| 476 | 2 | 453.2 |
| 477 | 2 | 528.3 |
| 478 | 2 | 531.1 |
| 479 | 2 | 577.3 |
| 480 | 2 | 539.1 |
| 481 | 2 | 593.1 |
| 482 | 2 | 499.1 |
| 483 | 2 | 477.1 |
| 484 | 2 | 594.1 |
| 485 | 2 | 528.1 |
| 486 | 2 | 547.1 |
| 487 | 2 | 577.1 |
| 488 | 2 | 552.2 |
| 489 | 2 | 541.2 |
| 490 | 2 | 529.3 |
| 491 | 2 | 531.2 |
| 492 | 2 | 521.3 |
| 493 | 2 | 550.2 |
| 494 | 2 | 485.2 |
| 495 | 2 | 570.2 |
| 496 | 2 | 596.2 |
| 497 | 2 | 511.1 |
| 498 | 2 | 555.1 |
| 499 | 2 | 545.2 |
| 500 | 2 | 544.3 |
| 501 | 2 | 485.2 |
| 502 | 2 | 562.2 |
| 503 | 2 | 561.3 |
| 504 | 2 | 486.2 |
| 505 | 2 | 529.3 |
| 506 | 2 | 502.1 |
| 507 | 2 | 551.3 |
| 508 | 2 | 551.3 |
| 509 | 2 | 583.2 |
| 510 | 2 | 489.2 |
| 511 | 2 | 549.2 |
| 512 | 2 | 543.3 |
| 513 | 2 | 541.2 |
| 514 | 2 | 584.2 |
| 515 | 2 | 567.1 |
| 516 | 2 | 519.2 |
| 517 | 2 | 453.2 |
| 518 | 2 | 493.3 |
| 519 | 2 | 509.3 |
| 520 | 2 | 507.3 |
| 521 | 2 | 572.3 |
| 522 | 2 | 481.3 |
| 523 | 2 | 481.3 |
| 524 | 2 | 536.3 |
| 525 | 2 | 526.2 |
| 526 | 2 | 572.2 |
| 527 | 2 | 536.1 |
| 528 | 2 | 553.2 |
| 529 | 2 | 553.2 |
| 530 | 2 | 555.2 |
| 531 | 2 | 541.2 |
| 532 | 2 | 495.3 |
| 533 | 2 | 549.3 |
| 534 | 2 | 551.3 |
| 535 | 2 | 450.2 |
| 536 | 2 | 512.2 |
| 537 | 2 | 546.2 |
| 538 | 2 | 572.2 |
| 539 | 2 | 518.2 |
| 540 | 2 | 542.2 |
| 541 | 2 | 542.2 |

-continued

| Example | Method | Mass |
|---|---|---|
| 542 | 2 | 530.2 |
| 543 | 2 | 542.2 |
| 544 | 2 | 526.2 |
| 545 | 2 | 512.2 |
| 546 | 2 | 497.2 |
| 547 | 2 | 555.3 |
| 548 | 2 | 566.3 |
| 549 | 2 | 569.2 |
| 550 | 2 | 593.1 |
| 551 | 2 | 594 |
| 552 | 2 | 493.1 |
| 553 | 2 | 582.1 |
| 554 | 2 | 616.1 |
| 555 | 1 | 530.3 |
| 556 | 1 | 545.2 |
| 557 | 1 | 572.3 |
| 558 | 1 | 531.2 |
| 559 | 2 | 560.3 |
| 560 | 2 | 586.3 |
| 561 | 2 | 540.3 |
| 562 | 2 | 598.3 |
| 563 | 2 | 612.3 |
| 564 | 2 | 534.2 |
| 565 | 2 | 546.2 |
| 566 | 2 | 520.2 |
| 567 | 2 | 532.2 |
| 568 | 2 | 533.2 |
| 569 | 2 | 588.2 |
| 570 | 2 | 600.2 |
| 571 | 2 | 546.3 |
| 572 | 2 | 534.3 |
| 573 | 2 | 548.3 |
| 574 | 2 | 621.1 |
| 575 | 3 | 533.1 |
| 576 | 3 | 489.2 |
| 577 | 3 | 503.3 |
| 578 | 3 | 547.1 |
| 579 | 3 | 531.2 |
| 580 | 3 | 575.1 |
| 581 | 3 | 589.1 |

Example 8

2-[1-(4-methoxy-2,6-dimethyl-phenylsulfonyl)-piperidin-2-ylmethoxy]-1-[4-(1-methyl-piperidin-4-yl)-piperazin-1-yl]-ethanone

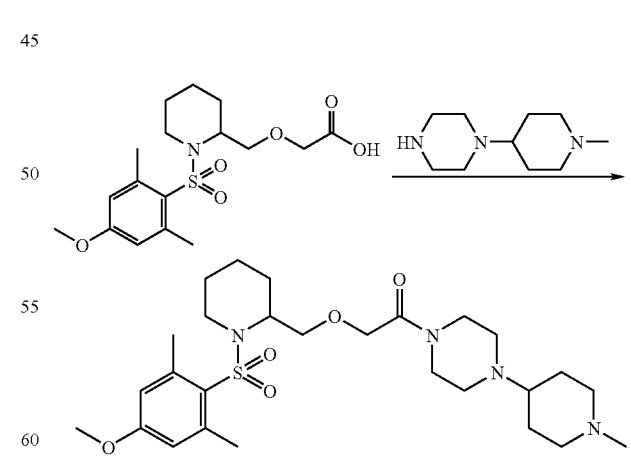

N,N'-Carbonyldiimidazole (114 mg, 0.706 mmol) was added to a solution of 2-((1-(4-methoxy-2,6-dimethylphenylsulfonyl)piperidin-2-yl)methoxy)acetic acid (250 mg, 0.673 mmol) in dichloromethane (15 ml), and the mixture was stirred for 1 h at room temperature. A solution of 1-(1-methylpiperidin-4-yl)piperazine (123 mg, 0.673 mmol) in dichloromethane (5 ml) was then added, and the reaction mixture was stirred for 15 h at room temperature. The reaction mixture was then extracted with water (20 ml) and saturated sodium chloride solution (20 ml), and the organic phase was dried over magnesium sulfate and concentrated in vacuo. The crude product was purified by flash chromatography using dichloromethane/methanol (97:3→90:10).

Yield: 296 mg (82%), brown resin $^1$H-NMR (600 MHz, DMSO-d$_6$): 1.27 (1H); 1.42 (1H); 1.55 (4H); 1.69 (2H); 1.79 (1H); 1.89 (2H); 2.18 (3H); 2.40 (4H); 2.53 (6H); 2.83 (2H); 2.95 (1H); 3.26 (4H); 3.38 (3H); 3.50 (1H); 3.66 (1H); 3.80 (4H); 4.05 (2H); 6.79 (2H).

Preparation of the Hydrochloride

Example 97

2-((1-(4-methoxy-2,6-dimethylphenylsulfonyl)piperidin-2-yl)methoxy)-1-(4-(1-methyl-piperidin-4-yl)piperazin-1-yl)ethanone dihydrochloride N,N'-Carbonyldiimidazole (272 mg, 1.696 mmol) was added to a solution of 2-((1-(4-methoxy-2,6-dimethylphenylsulfonyl)piperidin-2-yl)methoxy)acetic acid (600 mg, 1.615 mmol) in dichloromethane (15 ml), and the mixture was stirred for 1 h at room temperature. A solution of 1-(1-methylpiperidin-4-yl)piperazine (293 mg, 1.615 mmol) in dichloromethane (5 ml) was then added, and the reaction mixture was stirred for 15 h at room temperature. Saturated sodium hydrogen carbonate solution (20 ml) was then added to the reaction mixture, and then the aqueous phase was extracted with dichloromethane (2×20 ml). The combined organic phases were extracted with saturated sodium chloride solution (20 ml), dried over sodium sulfate and concentrated in vacuo. The crude product was purified by flash chromatography using dichloromethane/methanol (5:1). 2-((1-(4-methoxy-2,6-dimethylphenylsulfonyl)piperidin-2-yl)methoxy)-1-(4-(1-methylpiperidin-4-yl)piperazin-1-yl)ethanone (590 mg, 1.105 mmol) was dissolved in methyl ethyl ketone/ethanol (1:1) (20 ml) [plus a few drops of acetone], and chlorotrimethylsilane (168 µl, 1.326 mmol) was added slowly. Diethyl ether (20 ml) was then added, and the mixture was stirred for 1 h at 0° C. The resulting precipitate was filtered off, dried with the exclusion of air and washed with diethyl ether.

Yield: 430 mg (44%), white solid

HPLC-MS, m/z 537.2 (MH$^+$)

Example 92

3-((4-(2-((1-(4-methoxy-2,6-dimethylphenylsulfonyl)piperidin-2-yl)-methoxy)acetyl)piperazin-1-yl)methyl)benzonitrile hydrochloride

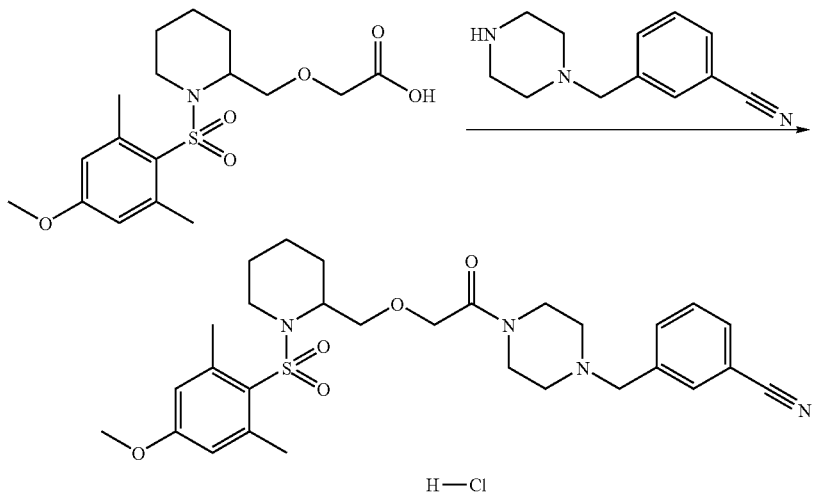

N,N'-Carbonyldiimidazole (68 mg, 0.424 mmol) was added to a solution of 2-((1-(4-methoxy-2,6-dimethylphenylsulfonyl)piperidin-2-yl)methoxy)acetic acid (150 mg, 0.404 mmol) in dichloromethane (4 ml), and the mixture was stirred for 1 h at room temperature. A solution of 3-(piperazin-1-ylmethyl)benzonitrile (81 mg, 0.404 mmol) in dichloromethane (1 ml) was then added, and the reaction mixture was stirred for 15 h at room temperature. Saturated sodium hydrogen carbonate solution (5 ml) was then added to the reaction mixture, and then the aqueous phase was extracted with dichloromethane (2×10 ml). The combined organic phases were extracted with saturated sodium chloride solution (10 ml), dried over sodium sulfate and concentrated in vacuo. The crude product was purified by flash chromatography using ethyl acetate/hexane (20:1). 3-((4-(2-((1-(4-methoxy-2,6-dimethylphenylsulfonyl)piperidin-2-yl)methoxy)acetyl)piperazin-1-yl)methyl)benzonitrile (100 mg, 0.180 mmol) was dissolved in methyl ethyl ketone (3 ml), and chlorotrimethylsilane (27 µl, 0.216 mmol) was added slowly. Diethyl ether (10 ml) was then added, and the mixture was stirred for 1 h at 0° C. The resulting precipitate was filtered off, dried with the exclusion of air and washed with diethyl ether.

Yield: 100 mg (42%), white solid $^1$H-NMR (400 MHz, DMSO-d$_6$): 1.24 (1H); 1.54 (4H); 1.79 (1H); 2.53 (6H); 2.79 (3H); 2.94 (2H); 3.10 (1H); 3.28 (3H); 3.36 (5H); 3.55 (1H); 3.69 (1H); 3.85 (1H); 4.12 (2H); 4.39 (2H); 6.79 (2H); 7.69 (1H); 7.95 (2H); 8.10 (1H); 11.65 (1H).

Example 93

3-((4-(2-((1-(4-methoxy-2,6-dimethylphenylsulfo-nyl)pyrrolidin-2-yl)-methoxy)acetyl)piperazin-1-yl)methyl)benzonitrile hydrochloride

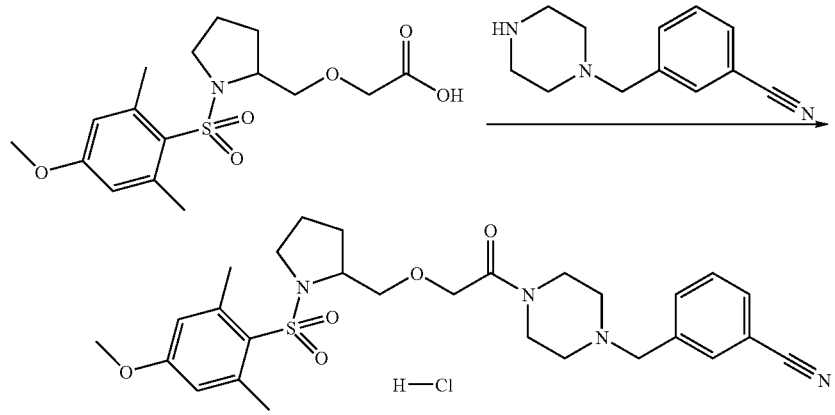

N,N'-Carbonyldiimidazole (71 mg, 0.441 mmol) was added to a solution of 2-((1-(4-methoxy-2,6-dimethylphenyl-sulfonyl)pyrrolidin-2-yl)methoxy)acetic acid (150 mg, 0.420 mmol) in dichloromethane (7 ml), and the mixture was stirred for 1 h at room temperature. A solution of 3-(piperazin-1-ylmethyl)benzonitrile (84 mg, 0.420 mmol) in dichloromethane (3 ml) was then added, and the reaction mixture was stirred for 15 h at room temperature. Saturated sodium hydrogen carbonate solution (10 ml) was then added to the reaction mixture, and then the aqueous phase was extracted with dichloromethane (2×10 ml). The combined organic phases were extracted with saturated sodium chloride solution (10 ml), dried over sodium sulfate and concentrated in vacuo. The crude product was purified by flash chromatography using ethyl acetate/hexane/ammonia solution (25% aq.) (100:10:1). 3-((4-(2-((1-(4-methoxy-2,6-dimethylphenylsul-fonyl)pyrrolidin-2-yl)methoxy)acetyl)piperazin-1-yl)me-thyl)benzonitrile (190 mg, 0.351 mmol) was dissolved in acetone/diethyl ether (1:1; 8 ml), and chlorotrimethylsilane (89 µl, 0.702 mmol) was added slowly. Diethyl ether (10 ml) was then added, and the mixture was stirred for 1 h at 0° C. The resulting precipitate was filtered off, dried with the exclusion of air and washed with diethyl ether.

Yield: 200 mg (83%), white solid
HPLC-MS, m/z 541.2 (MH$^+$)

Example 94

2-((1-(4-methoxy-2,6-dimethylphenylsulfonyl)pip-eridin-2-yl)methoxy)-1-(4-(2-(pyrrolidin-1-yl)ethyl)piperidin-1-yl)ethanone hydrochloride

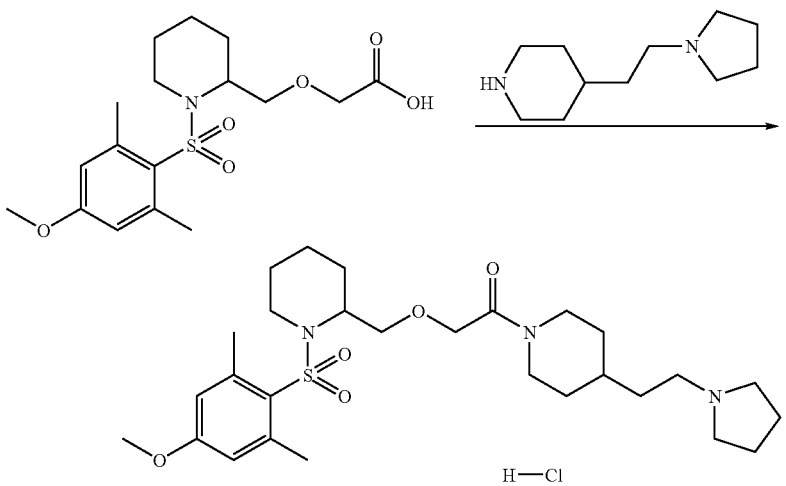

N,N'-Carbonyldiimidazole (68 mg, 0.424 mmol) was added to a solution of 2-((1-(4-methoxy-2,6-dimethylphenyl-sulfonyl)piperidin-2-yl)methoxy)acetic acid (150 mg, 0.404 mmol) in dichloromethane (4 ml), and the mixture was stirred for 1 h at room temperature. A solution of 4-(2-(pyrrolidin-1-yl)ethyl)piperidine (73 mg, 0.404 mmol) in dichloromethane (1 ml) was then added, and the reaction mixture was stirred for 15 h at room temperature. Saturated sodium hydrogen carbonate solution (5 ml) was then added to the reaction mixture, and then the aqueous phase was extracted with dichloromethane (2×10 ml). The combined organic phases were extracted with saturated sodium chloride solution (10 ml), dried over sodium sulfate and concentrated in vacuo. The crude product was purified by flash chromatography using ethyl acetate/methanol/ammonia solution (25 aq.) (400:100:5). 2-((1-(4-methoxy-2,6-dimethylphenylsulfonyl)piperidin-2-yl)methoxy)-1-(4-(2-(pyrrolidin-1-yl)ethyl)piperidin-1-yl)ethanone (160 mg, 0.299 mmol) was dissolved in methyl ethyl ketone (3 ml), and trimethylchlorosilane (75 μl, 0.358 mmol) was added slowly. Diethyl ether (10 ml) was then added, and the mixture was stirred for 1 h at 0° C. The resulting precipitate was filtered off, dried with the exclusion of air and washed with diethyl ether.

Yield: 100 mg (43%), white solid $^1$H-NMR (400 MHz, DMSO-d$_6$): 1.25 (1H); 1.60 (10H); 1.84 (4H); 1.97 (2H); 2.53 (6H); 2.92 (5H); 3.11 (2H); 3.30 (2H); 3.50 (1H); 3.66 (3H); 3.80 (5H); 4.03 (2H); 4.29 (1H); 6.80 (2H); 10.69 (1H).

Example 95

2-((1-(4-methoxy-2,6-dimethylphenylsulfonyl)pyrrolidin-2-yl)methoxy)-1-(4-(2-(pyrrolidin-1-yl)ethyl)piperidin-1-yl)ethanone

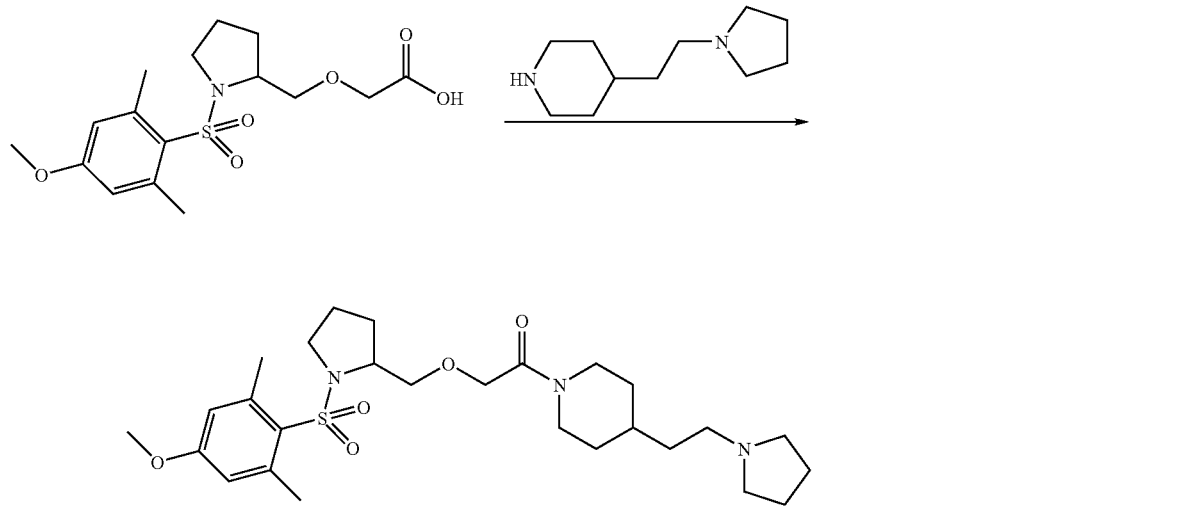

N,N'-Carbonyldiimidazole (71 mg, 0.441 mmol) was added to a solution of 2-((1-(4-methoxy-2,6-dimethylphenylsulfonyl)pyrrolidin-2-yl)methoxy)acetic acid (150 mg, 0.420 mmol) in dichloromethane (7 ml), and the mixture was stirred for 1 h at room temperature. A solution of 4-(2-(pyrrolidin-1-yl)ethyl)piperidine (76 mg, 0.420 mmol) in dichloromethane (3 ml) was then added, and the reaction mixture was stirred for 15 h at room temperature. Saturated sodium hydrogen carbonate solution (10 ml) was then added to the reaction mixture, and then the aqueous phase was extracted with dichloromethane (2×10 ml). The combined organic phases were extracted with saturated sodium chloride solution (10 ml), dried over sodium sulfate and concentrated in vacuo. The crude product was purified by flash chromatography using ethyl acetate/methanol/ammonia solution (25% aq.) (400:100:5).

Yield: 190 mg (87%), colorless oil

HPLC-MS, m/z 522.3 (MH$^+$)

Example 96

1-(3,4-dihydro-2,6-naphthyridin-2(1H)-yl)-2-((1-(4-methoxy-2,6-dimethylphenylsulfonyl)piperidin-2-yl)methoxy)ethanone hydrochloride

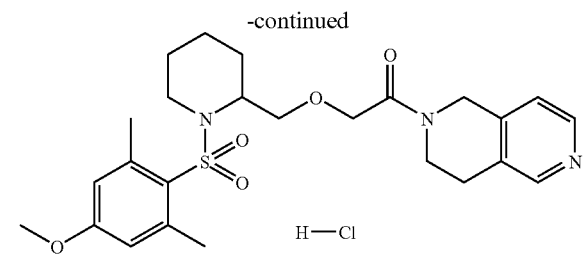

N,N'-Carbonyldiimidazole (68 mg, 0.424 mmol) was added to a solution of 2-((1-(4-methoxy-2,6-dimethylphenylsulfonyl)piperidin-2-yl)methoxy)acetic acid (150 mg, 0.404 mmol) in dichloromethane (4 ml), and the mixture was stirred for 1 h at room temperature. A solution of 1,2,3,4-tetrahydro- 2,6-naphthyridine (54 mg, 0.404 mmol) in dichloromethane (1 ml) was then added, and the reaction mixture was stirred for 15 h at room temperature. Saturated sodium hydrogen carbonate solution (5 ml) was then added to the reaction mixture, and then the aqueous phase was extracted with dichloromethane (2×10 ml). The combined organic phases were extracted with saturated sodium chloride solution (10 ml), dried over sodium sulfate and concentrated in vacuo. The crude product was purified by flash chromatography using ethyl acetate/methanol (20:1). 1-(3,4-dihydro-2,6-naphthyridin-2(1H)-yl)-2-((1-(4-methoxy-2,6-dimethylphenylsulfonyl)piperidin-2-yl)methoxy)ethanone (197 mg, 0.404 mmol) was dissolved in methyl ethyl ketone (5 ml), and trimethylchlorosilane (61 μl, 0.516 mmol) was added slowly. Diethyl ether (10 ml) was then added, and the mixture was stirred for 1 h at 0° C. The resulting precipitate was filtered off, dried with the exclusion of air and washed with diethyl ether.

Yield: 135 mg (64%), white solid $^1$H-NMR (400 MHz, DMSO-$d_6$): 1.25 (1H); 1.55 (4H); 1.80 (1H); 2.52 (6H); 2.96 (3H); 3.27 (2H); 3.58 (2H); 3.72 (2H); 3.77 (3H); 3.84 (1H); 4.20 (2H); 4.85 (2H); 6.77 (2H); 7.85 (1H); 8.69 (1H); 8.79 (1H); (OH masked).

Reaction of 2-((1-(4-methoxy-2,6-dimethylphenylsulfonyl)piperidin-2-yl)methoxy)acetic acid (acid structural unit S27) with amines (R$^5$R$^6$NH)

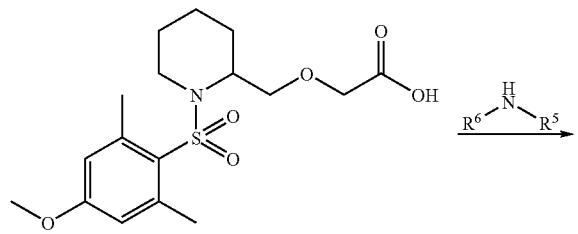

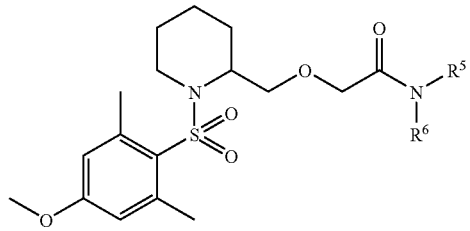

The example compounds listed in the following table were prepared from acid structural unit S27 by reaction with the corresponding amines (R$^5$R$^6$NH) closely following the processes described for Examples 8 and 92-96. The amines used are commercially available, can be prepared by methods known to the person skilled in the art, or were synthesized according to described processes. Instead of the solvent dichloromethane, the solvent N,N-dimethylformamide was used in the synthesis of the following example compounds: Example 113, 143 and 146. For the preparation of example compounds in which amines were used which were not in the form of the free base but in the form of the corresponding hydrochlorides (xHCl), a corresponding amount of triethylamine was added to the reaction (eq. Et$_3$N=xHCl). For Example 99, the formation of the hydrochloride was carried out analogously to the process described for Example 97. Examples 106 and 112 were converted into the corresponding hydrochlorides (xHCl) by the following general process: The free bases were in each case dissolved in a small amount of methyl ethyl ketone, and 2 M hydrogen chloride solution in diethyl ether (4-5 eq.) was added. Where appropriate, the mixture was cooled to 0° C. and/or diethyl ether was added before the hydrochloride (xHCl) was filtered out.

| Example No. | Amine (R$^5$R$^6$NH) | Yield (%) | MS, m/z (MH$^+$) |
| --- | --- | --- | --- |
| 98 | 2-(piperidin-4-yl)octahydro-1H-pyrido[1,2-a]pyrazine trihydrochloride | 94 | 577.3 |
| 99 | 2-(piperidin-4-yl)octahydro-1H-pyrido[1,2-a]pyrazine trihydrochloride | 30 | 577.3 |
| 100 | 2-(piperidin-4-yl)-1,2,3,4-tetrahydro-2,6-naphthyridine trihydrochloride | 82 | 571.3 |
| 101[1] | tert-butyl piperazine-1-carboxylate | 89 | 540.3 |
| 103 | 5-(piperidin-4-yl)-3-(pyridin-4-yl)-1,2,4-oxadiazole | 89 | 584.3 |
| 106 | 1-((1-methylpiperidin-4-yl)methyl)piperazine | 87 | 551.3 |
| 112 | 1-methyl-4-(piperidin-4-yl)piperazine | 69 | 537.3 |
| 113 | 4-(piperazin-1-yl)thieno[3,2-d]pyrimidine | 78 | 574.2 |
| 143 | 2-(1-(pyridin-4-yl)piperidin-4-yl)ethanamine dihydrochloride[2] | 55 | 559.2 |
| 146 | (4-methylpiperazin-1-yl)(piperidin-4-yl)methanone hydrochloride (xHCl) | 66 | 565.2 |
| 147 | 1-(pyridin-4-yl)piperazine | 62 | 517.2 |
| 165 | 3-(piperidin-4-yloxy)pyridine hydrochloride | 23 | 532.2 |
| 168 | 7-(piperazin-1-yl)-4-(pyrrolidin-1-yl)quinazoline dihydrochloride (C) | 63 | 637.3 |
| 188 | 4-(piperidin-4-ylmethoxy)pyridine dihydrochloride | 82 | 546.3 |

[1]This compound was additionally also obtained in a smaller yield of 80% by reaction in the presence of ECDI/HOBt in dichloromethane.
[2]The amine can be prepared analogously to the synthesis described in WO 2006/071775.

Preparation of the Amines

2-(piperidin-4-yl)-1,2,3,4-tetrahydro-2,6-naphthyridine trihydrochloride

Used in the Synthesis of Example Compound 100

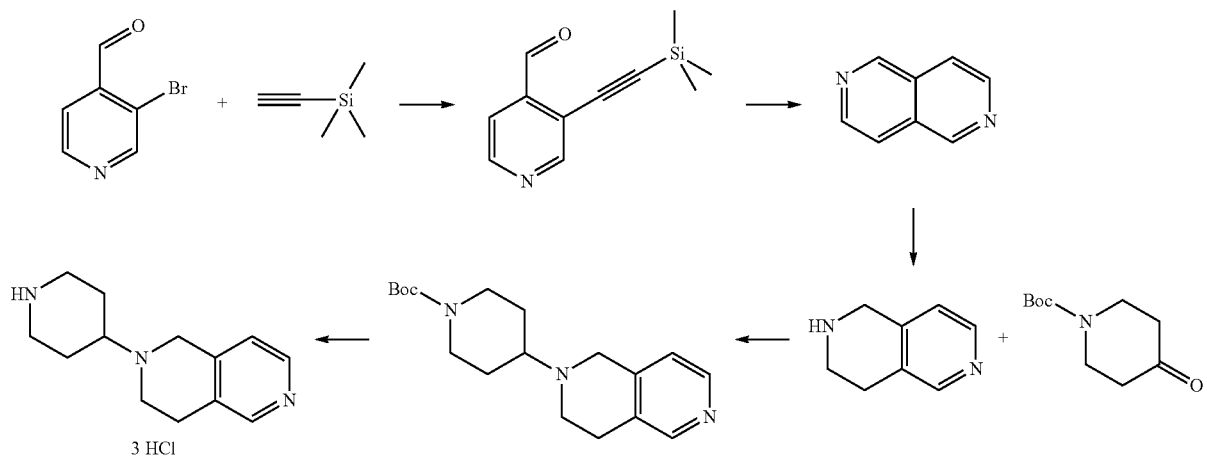

(i) Pd(PPh$_3$)$_2$Cl$_2$ (1.07 g, 1.52 mmol), trimethylsilylacetylene (18.9 ml, 133 mmol), 1,4-diazabicyclo[2.2.2]octane (DABCO) (17.1 g, 152 mmol) and copper(I) iodide (145 mg, 0.76 mmol) were added in succession, under nitrogen, to a solution of 3-bromo-4-pyridine carboxaldehyde (14.16 g, 76.1 mmol) in dry tetrahydrofuran (140 ml). The reaction mixture was stirred for 1 h, filtered off over Celite, washed with tetrahydrofuran and concentrated. The residue was purified by column chromatography (heptane/ethyl acetate, 9:1→9:2).

Yield: 14.62 g (94%)

(ii) A solution of 3-((trimethylsilyl)ethynyl)isonicotinaldehyde (13.22 g, 65.0 mmol) in ethanol (300 ml), under nitrogen, was refluxed for 7.5 h with the simultaneous continuous addition of ammonia. The mixture was then concentrated, and the residue was taken up in ethyl acetate and filtered over silica gel. The crude product was dissolved in hot hexane and decanted off twice. The filtrate was concentrated and crystallized from hexane/diisopropyl ether.

Yield: 3.29 g (39%)

(iii) Platinum(IV) oxide (223 mg, 0.984 mmol) was added to a suspension of calcium oxide (758 mg, 13.5 mmol) and 2,6-naphthyridine (1.60 g, 12.3 mmol) in 2-methoxyethanol (15 ml), under nitrogen. The reaction mixture was stirred overnight under a hydrogen atmosphere and then filtered over Celite, washed with ethanol, concentrated in vacuo and coevaporated with dichloromethane. The residue was taken up in ethyl acetate, filtered over a microfilter, washed with ethyl acetate and concentrated again. The residue was combined with a second batch, which was prepared analogously (from 1.66 g (12.8 mmol) of 2,6-naphthyridine), and coevaporated with toluene (2×) and dichloromethane (2×). The crude product was then dried overnight in vacuo. Purification was carried out by means of column chromatography (heptane/dichloromethane/7 M ammonia solution in methanol, 10:30:2). Coevaporation with dichloromethane was then carried out.

Yield: 2.83 g (84%)

(iv) 1,2,3,4-tetrahydro-2,6-naphthyridine (1.16 g, 8.65 mmol) and tert-butyl 4-oxopiperidine-1-carboxylate (1.72 g, 8.65 mmol) were dissolved in 1,2-dichloroethane (20.5 ml). Sodium triacetoxyborohydride (2.56 g, 12.10 mmol) and acetic acid (0.49 ml, 8.65 mmol) were added to this solution at room temperature. The reaction mixture was stirred for 15 h at room temperature, and then saturated sodium hydrogen carbonate solution (20 ml) was added and stirring was carried out for 30 min. The aqueous phase was extracted with diethyl ether (2×30 ml) and the organic phase was in turn washed with saturated sodium chloride solution (20 ml). The organic phase was dried (MgSO$_4$) and concentrated in vacuo. The crude product was purified by column chromatography (silica gel) using ethyl acetate/hexane/methanol/ammonia solution (25% aq.) (100:10:10:1).

Yield: 2.26 g (82%)

(v) Hydrogen chloride (28.48 ml, 35.60 mmol, 1.25 M solution in methanol) was added at room temperature to a solution of tert-butyl 4-(3,4-dihydro-2,6-naphthyridin-2(1H)-yl)-piperidine-1-carboxylate (2.26 g, 7.12 mmol) in methanol (10 ml). The reaction mixture was refluxed for 30 min. The solvent was removed in vacuo, the residue was taken up in a small amount of ethanol, and diethyl ether was added. The mixture was then cooled in an ice bath for 30 min., and the resulting solid was filtered off and dried.

Yield: 2.09 g (90%)

2-(piperidin-4-yl)octahydro-1H-pyrido[1,2-a]pyrazine trihydrochloride

Used in the Synthesis of Examples 98 and 99

The amine was prepared analogously to 2-(piperidin-4-yl)-1,2,3,4-tetrahydro-2,6-naphthyridine trihydrochloride from octahydro-1H-pyrido[1,2-a]pyrazine and tert-butyl 4-oxopiperidine-1-carboxylate (steps iv and v).

111

(4-methylpiperazin-1-yl)(piperidin-4-yl)methanone hydrochloride

Used in the Synthesis of Example Compound 146

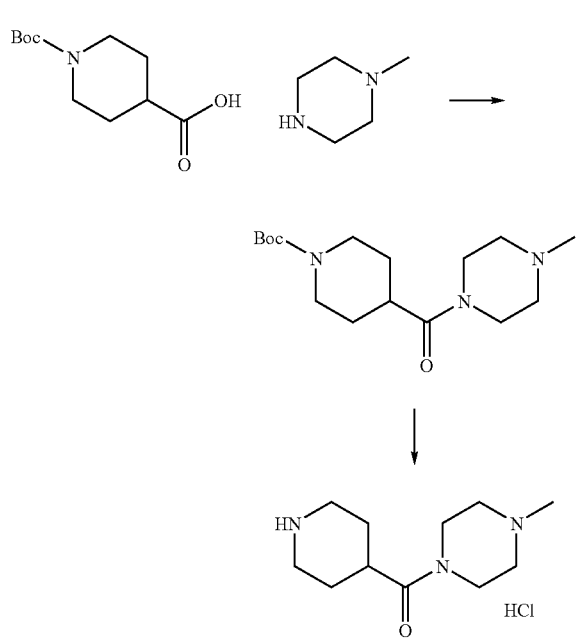

(i) 1-methylpiperazine (2.20 ml, 19.84 mmol) and 4-methylmorpholine (4.37 ml, 39.68 mmol) were added to a solution of 1-(tert-butoxycarbonyl)piperidine-4-carboxylic acid (5.0 g, 21.82 mmol) in N,N-dimethylformamide (76.3 ml). Benzotriazol-1-yloxytris-(dimethylamino)phosphonium hexafluorophosphate (11.44 g, 25.79 mmol) was then added to the mixture, and stirring was carried out for 15 h at room temperature. Concentration in vacuo was then carried out. The residue was taken up in ethyl acetate (100 ml) and saturated sodium hydrogen carbonate solution (100 ml), and the aqueous phase was extracted with ethyl acetate (2×30 ml). The combined organic phases were washed with saturated sodium chloride solution (30 ml), dried ($Na_2SO_4$) and concentrated in vacuo. The crude product was purified by column chromatography (silica gel) using ethyl acetate/methanol/ammonia solution (25% aq.) (40:10:0.5).

Yield: 5.61 g (83%)

(ii) Hydrogen chloride (49.46 ml, 61.83 mmol, 1.25 M solution in methanol) was added at room temperature to tert-butyl 4-(4-methylpiperazine-1-carbonyl)piperidine-1-carboxylate (4.81 g, 15.46 mmol), and the reaction mixture was refluxed for 1 h. The solvent was removed in vacuo, and the residue was taken up in a small amount of ethanol; methyl ethyl ketone and diethyl ether were added, and refluxing was carried out for 40 min. The mixture was then cooled slowly to room temperature and then cooled for 30 min. in an ice bath. The resulting solid was filtered off and dried.

Yield: 3.83 g (88%)

112

3-(piperidin-4-yloxy)pyridine hydrochloride

Used in the Synthesis of Example Compound 165

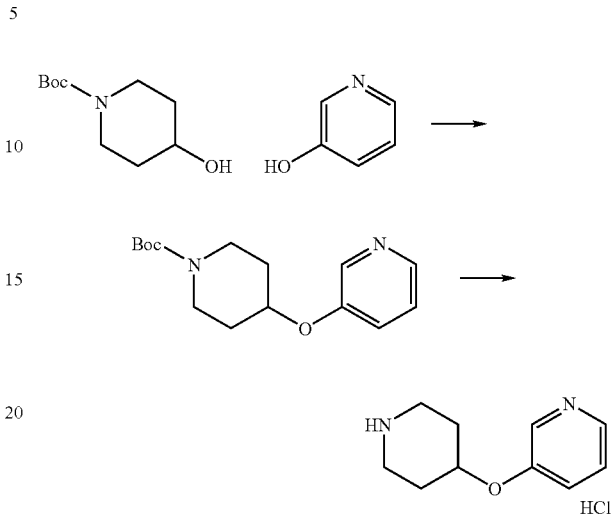

(i) tert-butyl-4-hydroxypiperidine-1-carboxylate (1.85 g, 9.20 mmol) and triphenylphosphine (2.41 g, 9.20 mmol) were added at room temperature to a solution of 3-pyrrolidinol (700 mg, 7.36 mmol) in tetrahydrofuran (10 ml). Diisopropyl-azodicarboxylate (1.79 ml, 125.1 mmol) was then added dropwise, and the mixture was then stirred for 15 h at 55° C. The solvent was removed in vacuo, and the residue was taken up in 1 M hydrochloric acid (20 ml) and extracted with dichloromethane (2×10 ml). The combined organic phases were extracted with 1 M hydrochloric acid (20 ml) and water (20 ml). The aqueous phases were combined, adjusted to pH 12 with 1 M sodium hydroxide solution and then extracted with dichloromethane (4×20 ml). The organic phase was then washed with saturated sodium chloride solution (20 ml), dried ($Na_2SO_4$) and concentrated in vacuo. The crude product was then purified by column chromatography (silica gel) using ethyl acetate/hexane (10:1).

Yield: 410 mg (20%)

[analogous process see: J. Chao et al., *Tetrahedron Lett.*, 2007, 48, 791]

(ii) Hydrogen chloride (4.71 ml, 5.89 mmol, 1.25 M solution in methanol) was added at room temperature to a solution of tert-butyl 4-(pyridin-3-yloxy)piperidine-1-carboxylate (410 mg, 1.473 mmol) in methanol (2-5 ml), and the reaction mixture was refluxed for 30 min. The solvent was removed in vacuo, the residue was taken up in a small amount of ethanol, and diethyl ether was added. Cooling in an ice bath was then carried out for 30 min., and the resulting solid was filtered off and dried.

Yield: 270 mg (85%)

4-(piperidin-4-ylmethoxy)pyridine dihydrochloride

Used in the Synthesis of Example Compound 188

The amine was prepared analogously to 3-(piperidin-4-yloxy)pyridine hydrochloride from tert-butyl 4-(hydroxymethyl)piperidine-1-carboxylate and 3-pyrrolidinol.

7-(piperazin-1-yl)-4-(pyrrolidin-1-yl)quinazoline dihydrochloride (C)

Used in the Synthesis of Example Compound 168

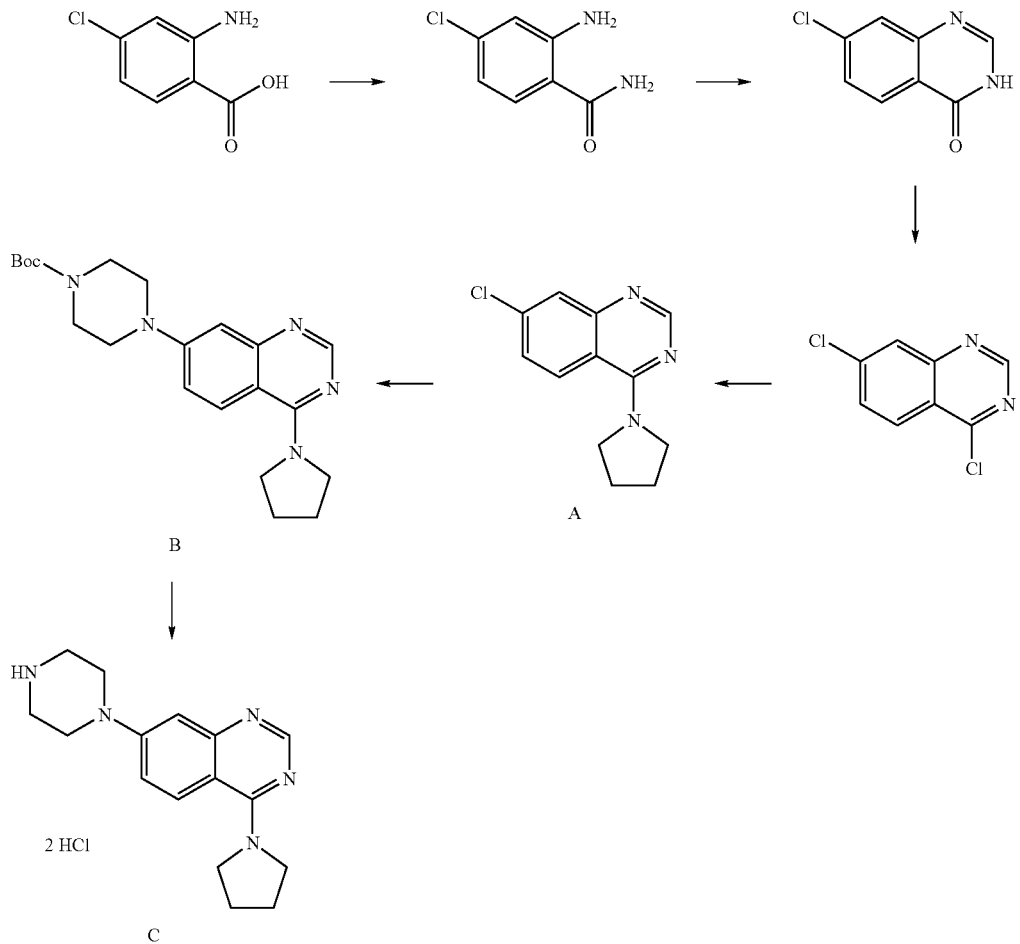

7-Chloro-4-(pyrrolidin-1-yl)quinazoline (A) was prepared from 2-amino-4-chlorobenzoic acid analogously to the following procedure, known from the literature, for the preparation of aminoquinazolines: H. Hayashi et al., *Bioorg. Med. Chem.*, 2003, 11, 383. [Review zur Synthese von Chinazolinen: P. J. Guiry et al., *Tetrahedron*, 2005, 61, 10153.]

tert-butyl 4-(4-(pyrrolidin-1-yl)quinazolin-7-yl)piperazine-1-carboxylate (B)

Potassium tert-butoxide (998 mg, 8.99 mmol), 2-dicyclohexylphosphino-2,4,6-triisopropyl-biphenyl (X-Phos) (79 mg, 0.18 mmol) and tris-(dibenzylideneacetone)-dipalladium [$Pd_2(dba)_3$] (36 mg, 0.036 mmol) were added, under nitrogen, to a mixture of 7-chloro-4-(pyrrolidin-1-yl)quinazoline (A) (840 mg, 3.59 mmol) and tert-butyl piperazine-1-carboxylate (1.0 g, 5.39 mmol) in toluene (49 ml). The reaction mixture was then heated for 15 h at 100° C. The reaction mixture was cooled to room temperature, and water (25 ml) and ethyl acetate (25 ml) were added. The aqueous phase was extracted with ethyl acetate (2×25 ml), and the combined organic phases were washed with saturated sodium chloride solution (20 ml). The organic phase was then dried ($MgSO_4$) and concentrated in vacuo. The crude product was purified by column chromatography (silica gel) using ethyl acetate/-dichloromethane/ammonia solution (25% aq.) (50:10:0.5) and ethyl acetate/dichloro-methane/methyl tert-butyl ether/ammonia solution (25% aq.) (50:10:10:0.7).

Yield: 700 mg (51%)

7-(piperazin-1-yl)-4-(pyrrolidin-1-yl)quinazoline dihydrochloride (C)

tert-butyl 4-(4-(pyrrolidin-1-yl)quinazolin-7-yl)piperazine-1-carboxylate (B) (130 mg, 0.339 mmol) was dissolved at room temperature in methanol (2 ml), and then hydrogen chloride (2.71 ml, 3.39 mmol, 1.25 M solution in methanol) was added. The reaction mixture was refluxed for 1 h and then stirred for 15 h at room temperature. Concentration in vacuo was carried out, and the residue was taken up in a small amount of ethanol and heated. Diethyl ether was then added, the mixture was cooled in an ice bath, and finally the resulting solid was filtered off.

Yield: 103 mg (85%)

115

Reaction of 2-((1-(benzo[b]thiophen-3-ylsulfonyl)piperidin-2-yl)methoxy)acetic acid (acid structural unit S32) with 1-(1-methylpiperidin-4-yl)piperazine Example 137

2-((1-(Benzo[b]thiophen-3-ylsulfonyl)piperidin-2-yl)methoxy)-1-(4-(1-methylpiperidin-4-yl)piperazin-1-yl)ethanone

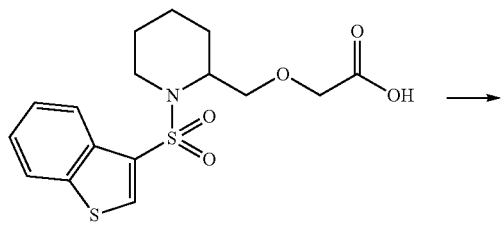

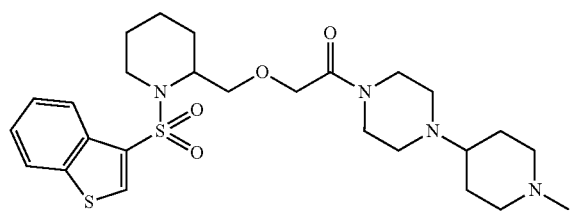

Example Compound 137 was prepared from acid structural unit S32 in a yield of 79% by reaction with 1-(1-methylpiperidin-4-yl)piperazine closely following the process described for Examples 8 and 92-96. MS, m/z 535.2 (MH+)

Reaction of 2-(2-(1-(4-methoxy-2,6-dimethylphenylsulfonyl)piperidin-2-yl)ethoxy)-acetic acid with 1-(1-methylpiperidin-4-yl)piperazine Example 164

2-(2-(1-(4-methoxy-2,6-dimethylphenylsulfonyl)piperidin-2-yl)ethoxy)-1-(4-(1-methyl-piperidin-4-yl)piperazin-1-yl)ethanone

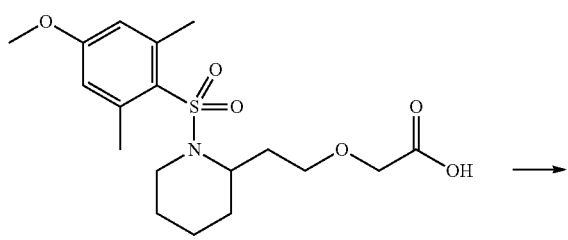

116

-continued

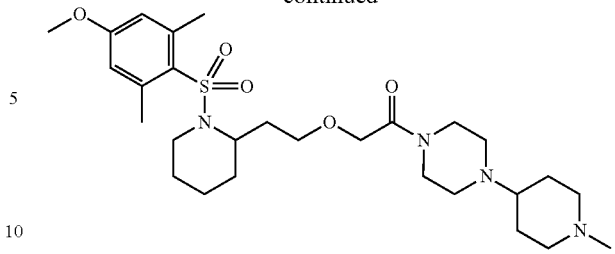

Example compound 164 was prepared from the corresponding acid structural unit in a yield of 80% by reaction with 1-(1-methylpiperidin-4-yl)piperazine closely following the process described for Examples 8 and 92-96. The acid structural unit was prepared analogously to the process described under Method 1 for the preparation of acid structural units for parallel synthesis.

MS, m/z 551.2 (MH+)

Reaction of 2-((2-(naphthalen-2-ylsulfonyl)-1,2,3,4-tetrahydroisoquinolin-3-yl)-methoxy)acetic acid with 1-(1-methylpiperidin-4-yl)piperazine:

Example 178

1-(4-(1-methylpiperidin-4-yl)piperazin-1-yl)-2-(2-(naphthalen-2-ylsulfonyl)-1,2,3,4-tetrahydroisoquinolin-3-yl)methoxy)ethanone dihydrochloride

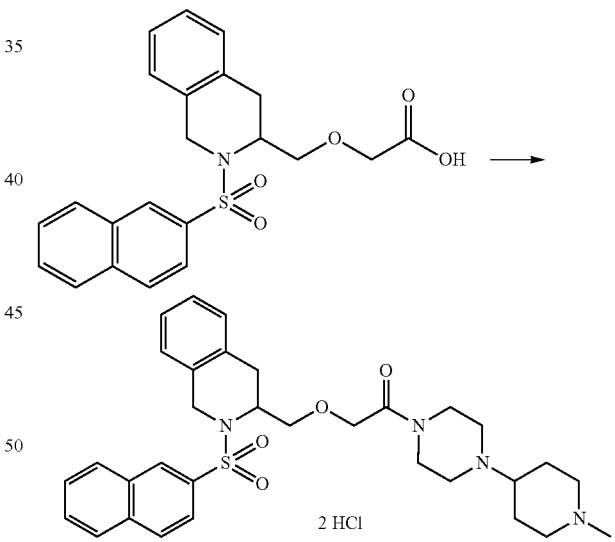

Example Compound 178 was prepared from the corresponding acid structural unit in a yield of 29% by reaction with 1-(1-methylpiperidin-4-yl)piperazine closely following the process described for Examples 8 and 92-96. The acid structural unit was prepared analogously to the process described under Method 1 for the preparation of acid structural units for parallel synthesis. The hydrochloride precipitation of the free base relating to Example 178 was carried out from a methyl ethyl ketone/diethyl ether solution of the base with addition of 2 M hydrogen chloride solution in diethyl ether.

MS, m/z 577.2 (MH+)

Reaction of 1-(4-(1-methylpiperidin-4-yl)piperazin-1-yl)-2-(piperidin-2-ylmethoxy)-ethanone trihydrochloride with sulfonyl chlorides

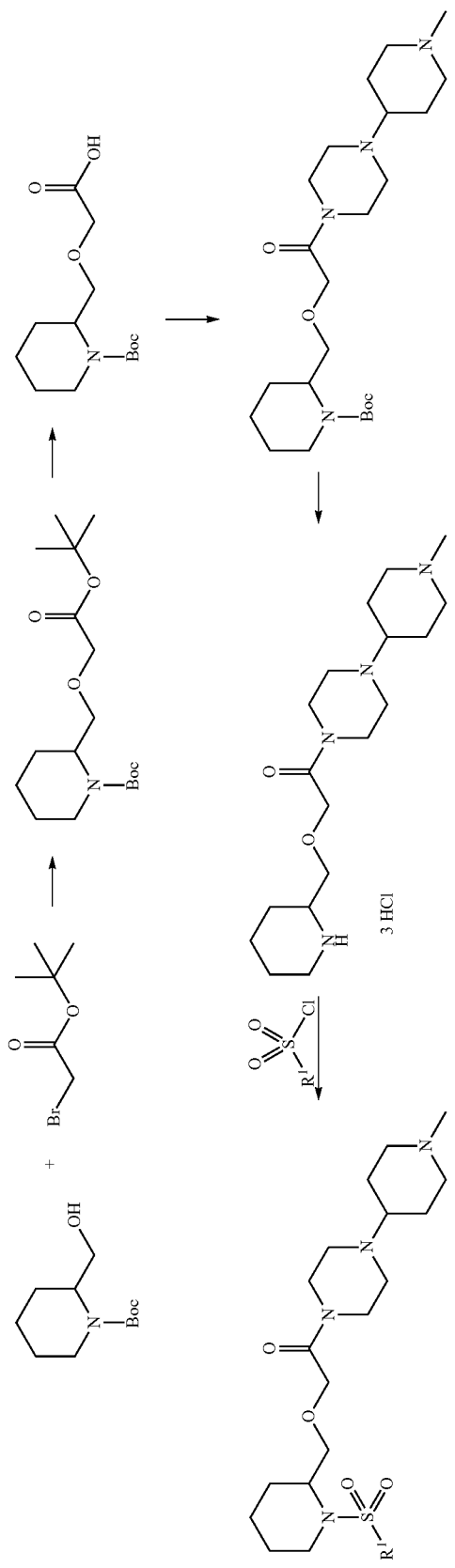

1-(4-(1-methylpiperidin-4-yl)piperazin-1-yl)-2-(piperidin-2-ylmethoxy)ethanone trihydrochloride Step (i): tert-butyl 2-bromoacetate (4.1 ml, 27.88 mmol) was added at room temperature to a mixture of tetra-n-butylammonium hydrogen sulfate (625 mg, 1.859 mmol), aqueous sodium hydroxide solution (18.58 g, 464.69 mmol in water (20 ml)) and toluene (15 ml), and then the mixture was cooled to 0° C. A solution of tert-butyl 2-(hydroxymethyl)piperidine-1-carboxylate (4.0 g, 18.587 mmol) in toluene (10 ml) was then added slowly. The reaction mixture was heated to room temperature and stirred for 1 h at that temperature. The phases were separated and the aqueous phase was extracted with diethyl ether (2×25 ml). The combined organic phases were washed with saturated sodium chloride solution (20 ml), dried ($Na_2SO_4$) and concentrated in vacuo. The crude product was purified by column chromatography (silica gel) using hexane/diethyl ether (3:1).

Yield: 3.53 g (58%)

Step (ii): tert-butyl 2-((2-tert-butoxy-2-oxoethoxy)methyl)piperidine-1-carboxylate (3.53 g, 10.717 mmol) was dissolved in tetrahydrofuran (20 ml), and sodium hydroxide solution (1.71 g, 42.87 mmol in water (2 ml)) was added. The reaction mixture was heated for 3 h at 90° C. and then cooled to room temperature again. The pH value of the mixture was adjusted to pH 2 with 2M hydrochloric acid, and extraction with ethyl acetate (3×30 ml) was then carried out. The combined organic phases were dried ($Na_2SO_4$) and concentrated in vacuo. The crude product was used in the next synthesis step without being purified further.

Yield: 3.28 g (>99%)

Step (iii): N,N'-Carbonyldiimidazole (2.02 g, 12.563 mmol) was added to a solution of 2-((1-(tert-butoxycarbonyl)piperidin-2-yl)methoxy)acetic acid (3.27 g, 11.965 mmol) in dichloromethane (15 ml), and stirring was carried out for 1.5 h at room temperature. A solution of 1-(1-methylpiperidin-4-yl)piperazine (2.19 g, 11.965 mmol) in dichloromethane (15 ml) was then added, and the reaction mixture was stirred for 3 d at room temperature. Saturated sodium hydrogen carbonate solution (30 ml) was added to the mixture, and then the aqueous phase was extracted with dichloromethane (2×30 ml). The combined organic phases were washed with saturated sodium chloride solution (30 ml), dried ($Na_2SO_4$) and concentrated in vacuo. The crude product was purified by column chromatography (silica gel) using ethyl acetate/methanol/dichloromethane/ammonia solution (25% aq.) (400:100:100:5).

Yield: 4.57 g (87%)

Step (iv): Hydrogen chloride (26.0 ml, 52.10 mmol, 2 M solution in diethyl ether) was added at room temperature to a solution of tert-butyl 2-((2-(4-(1-methylpiperidin-4-yl)piperazin-1-yl)-2-oxoethoxy)methyl)piperidine-1-carboxylate (4.57 g, 10.42 mmol) in a mixture of ethyl acetate (15 ml) and diethyl ether (50 ml). The reaction mixture was stirred for 2 h at 45° C. Then the resulting white solid was filtered off and dried.

Yield: 3.59 g (77%)

Example 107

2-((1-(mesitylsulfonyl)piperidin-2-yl)methoxy)-1-(4-(1-methylpiperidin-4-yl)piperazin-1-yl)ethanone Step (v): Triethylamine (0.221 ml, 1.608 mmol) and then 2,4,6-trimethylbenzenesulfonyl chloride (105 mg, 0.482 mmol) were added at 0° C. to a solution of 1-(4-(1-methylpiperidin-4-yl)piperazin-1-yl)-2-(piperidin-2-ylmethoxy)ethanone trihydrochloride (180 mg, 0.402 mmol) in tetrahydrofuran (10 ml). The reaction mixture was heated slowly to room temperature, stirred for 15 h at that temperature and then refluxed for 1 h. Saturated sodium hydrogen carbonate solution (5 ml) was then added to the mixture, and the aqueous phase was extracted with ethyl acetate (3×30 ml). The combined organic phases were dried ($Na_2SO_4$) and concentrated in vacuo, and the crude product was then purified by column chromatography (silica gel) using ethyl acetate/methanol/ammonia solution (25% aq.) (300:100:5). Yield: 90 mg (43%), yellow oil; MS, m/z 520.3 ($MH^+$)

Example 108

2-((1-(2,6-dichloro-4-(trifluormethyl)phenylsulfonyl)piperidin-2-yl)methoxy)-1-(4-(1-methylpiperidin-4-yl)piperazin-1-yl)ethanone Step (v): 1-(4-(1-methylpiperidin-4-yl)piperazin-1-yl)-2-(piperidin-2-ylmethoxy)ethanone trihydrochloride (150 mg, 0.335 mmol) was dissolved at room temperature in a mixture of dichloromethane (5 ml) and triethylamine (0.208 ml, 1.507 mmol), and 2,6-dichloro-4-(trifluoromethyl)benzenesulfonyl chloride (156 mg, 0.503 mmol) in dichlormethane (5 ml) was added. The reaction mixture was stirred for 3 d at that temperature, and then saturated sodium hydrogen carbonate solution (5 ml) was added thereto. The aqueous phase was extracted with dichloromethane (2×20 ml), and the combined organic phases were dried ($Na_2SO_4$) and concentrated in vacuo. The crude product was then purified by column chromatography (silica gel) using ethyl acetate/methanol/ammonia solution (25% aq.) (200:100:3). Yield: 120 mg (58%), yellow oil; MS, m/z 614.2 ($MH^+$)

The example compounds listed in the following table were prepared from 1-(4-(1-methylpiperidin-4-yl)piperazin-1-yl)-2-(piperidin-2-ylmethoxy)ethanone trihydrochloride by reaction with the corresponding sulfonyl chlorides ($R^1SO_2Cl$) closely following the process described for Example 108 (step (v)). The progress of the reaction was monitored by thin-layer chromatography; the reaction time was in most cases from 15 h to 3 d. The amounts of the reagents used varied as follows: sulfonyl chloride (from 0.9 to 1.5 eq.), triethylamine (3.5-4.5 eq.). The reactions were in some cases carried out in tetrahydrofuran as an alternative to dichloromethane. The sulfonyl chlorides used are commercially available, can be prepared by methods known to the person skilled in the art, or were synthesized according to described processes. Furthermore, for Examples 141, 155, 156, 158, 159, 169 and 170, the bases were converted into the corresponding dihydrochlorides (2×HCl) according to the following general process: The free bases were in each case dissolved in a small amount of dichloromethane or methyl ethyl ketone, and 2 M hydrogen chloride solution in diethyl ether (4-5 eq.) was added. In some cases, the mixture was cooled to 0° C. and/or diethyl ether was added thereto, before the dihydrochloride was filtered out.

| Example No. | Sulfonyl chloride ($R^1SO_2Cl$) | Yield (%) | MS, m/z ($MH^+$) |
|---|---|---|---|
| 109 | 2-Chloro-6-methylbenzene-1-sulfonyl chloride | 85 | 527.2 |
| 110 | Naphthalene-1-sulfonyl chloride | 79 | 529.3 |
| 111 | Naphthalene-2-sulfonyl chloride | 79 | 529.3 |
| 114 | 4-Chloro-2,5-dimethylbenzene-1-sulfonyl chloride | 24 | 541.2 |
| 115 | 4-Chloro-3-(trifluoromethyl)benzene-1-sulfonyl chloride | 51 | 581.2 |
| 118 | 2,4,6-Trichlorobenzene-1-sulfonyl chloride | 46 | 583.1 |
| 119 | 2,4,6-Triisopropylbenzene-1-sulfonyl chloride | 54 | 605.4 |
| 120 | 2,4-dichlorobenzene-1-sulfonyl chloride | 60 | 547.2 |
| 128 | 5-Chloro-1,3-dimethyl-1H-pyrazole-4-sulfonyl chloride | 39 | 531.3 |
| 129 | 6-Chloroimidazo[2,1-b]thiazole-5-sulfonyl chloride | 37 | 559.2 |
| 131 | 3-(o-Tolyloxy)benzene-1-sulfonyl chloride | 71 | 585.3 |
| 138 | 2-Chloro-4-(trifluoromethyl)benzene-1-sulfonyl chloride | 48 | 581.2 |
| 139 | 2-Chlorobenzene-1-sulfonyl chloride | 38 | 513.1 |
| 141 | 2,6-dichlorobenzene-1-sulfonyl chloride | 43 | 547.1 |
| 151 | 5-Chloro-3-methylbenzo[b]thiophene-2-sulfonyl chloride | 41 | 583.1 |
| 153 | 2,5-Bis(trifluoromethyl)benzene-1-sulfonyl chloride | 58 | 615.1 |
| 154 | 7-Chlorobenzo[c][1,2,5]oxadiazole-4-sulfonyl chloride | 27 | 555.1 |
| 155 | 4-methylnaphthalene-1-sulfonyl chloride | 44 | 543.2 |
| 156 | 2,4,5-Trichlorobenzene-1-sulfonyl chloride | 21 | 581.0 |
| 158 | 5-(Dimethylamino)naphthalene-1-sulfonyl chloride | 56 | 572.2 |
| 159 | 2-methylbenzene-1-sulfonyl chloride | 55 | 493.2 |
| 169 | 4-Fluoro-2,6-dimethylbenzene-1-sulfonyl chloride | 47 | 525.2 |
| 170 | 2,5-dichlorothiophene-3-sulfonyl chloride | 54 | 553.1 |
| 171 | Benzo[b]thiophene-2-sulfonyl chloride | 59 | 535.2 |
| 172 | 2,5-Dimethylthiophene-3-sulfonyl chloride | 57 | 513.2 |

Preparation of the Sulfonyl Chloride

4-Fluoro-2,6-dimethylbenzene-1-sulfonyl chloride

Used in the Synthesis of Example Compound 169

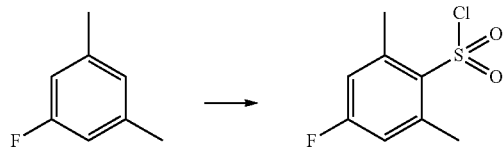

Chlorosulfonic acid (54.3 ml, 4 eq.) was added dropwise at 0° C., over a period of 45 min., to a solution of 1-fluoro-3,5-dimethylbenzene (25 g) in dichloromethane (250 ml). The reaction mixture was then stirred for 1 h at room temperature, and the progress of the reaction was monitored by thin-layer chromatography. The reaction mixture was poured onto ice, and the aqueous phase was extracted with dichloromethane (3×150 ml). The organic phase was dried ($Na_2SO_4$) and concentrated in vacuo. The crude product was then purified by column chromatography. Yield: 19.5 g (44%), white solid.

Reaction of 2-((1-(4-methoxy-2,6-dimethylphenyl-sulfonyl)piperidin-2-yl)methoxy)-1-(piperazin-1-yl) ethanone hydrochloride (Example 102) with ketones and aldehydes ($R^aR^bC=O$)

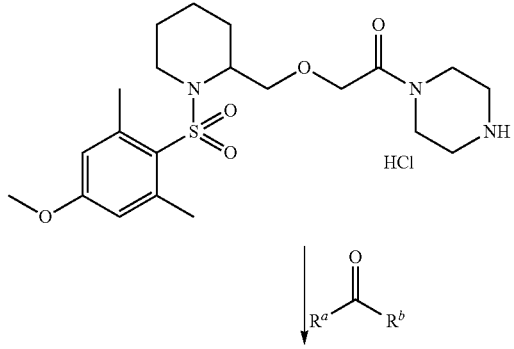

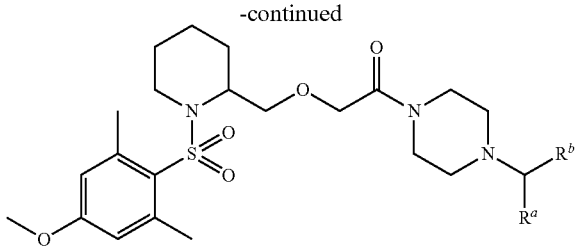

Example 102

2-((1-(4-methoxy-2,6-dimethylphenylsulfonyl)piperidin-2-yl)methoxy)-1-(piperazin-1-yl)ethanone hydrochloride Step (i): Hydrogen chloride (1.15 ml, 2.30 mmol, 2 M solution in diethyl ether) was added at room temperature to a solution of tert-butyl 4-(2-((1-(4-methoxy-2,6-dimethylphenylsulfonyl)piperidin-2-yl)methoxy)acetyl)piperazine-1-carboxylate (Example 101) (310 mg, 0.574 mmol) in diethyl ether (2-5 ml). The reaction mixture was stirred for 2 h at room temperature and then refluxed for 10 min. The resulting solid was filtered off and dried. Yield: 210 mg (77%), white solid

Reaction with Ketones

Example 104

2-((1-(4-methoxy-2,6-dimethylphenylsulfonyl)piperidin-2-yl)methoxy)-1-(4-(tetrahydro-2H-pyran-4-yl)piperazin-1-yl)ethanone Step (ii): 2-((1-(4-methoxy-2,6-dimethylphenylsulfonyl)piperidin-2-yl)methoxy)-1-(piperazin-1-yl)ethanone hydrochloride (Example 102) (90 mg, 0.189 mmol) and dihydro-2H-pyran-4(3H)-one (0.017 ml, 0.189 mmol) were dissolved in a mixture of 1,2-dichloroethane (4 ml) and triethylamine (0.026 ml, 0.189 mmol). Sodium triacetoxyborohydride (56 mg, 0.265 mmol) and acetic acid (0.011 ml, 0.189 mmol) were added at room temperature to that solution. The reaction mixture was stirred for 1 h at room temperature, and then saturated sodium hydrogen carbonate solution (5 ml) was added thereto. The aqueous phase was extracted with diethyl ether (2×20 ml), and the organic phase was in turn washed with saturated sodium chloride solution (10 ml). The organic phase was dried (MgSO$_4$) and concentrated in vacuo, and the crude product was purified by column chromatography (silica gel) using ethyl acetate/methanol (10:1). Yield: 90 mg (91%), yellow oil; MS, m/z 524.3 (MH$^+$)

The example compounds listed in the following table were prepared from 2-((1-(4-methoxy-2,6-dimethylphenylsulfonyl)piperidin-2-yl)methoxy)-1-(piperazin-1-yl)ethanone hydrochloride (Example 102) by reaction with the corresponding ketones (R$^a$R$^b$C=O) closely following the process described for Example 104 (step (ii)). The reactions were monitored by thin-layer chromatography and had reaction times of from 1 to 15 h. The ketones used are commercially available.

| Example No. | Ketone (R$^a$R$^b$C=O) | Yield (%) | MS, m/z (MH$^+$) |
|---|---|---|---|
| 105 | 4-methylcyclohexanone | 20 | 536.3 |
| 134 | 4-(trifluoromethyl)cyclohexanone | 19 | 590.3 |

Reaction with Aldehydes

Example 117

1-(4-((1H-benzo[d]imidazol-2-yl)methyl)piperazin-1-yl)-2-((1-(4-methoxy-2,6-dimethyl-phenylsulfonyl)piperidin-2-yl)methoxy)ethanone Step (ii): 2-((1-(4-methoxy-2,6-dimethylphenylsulfonyl)piperidin-2-yl)methoxy)-1-(piperazin-1-yl)ethanone hydrochloride (Example 102) (150 mg, 0.315 mmol) was suspended in a mixture of tetrahydrofuran (3 ml) and triethylamine (0.052 ml, 0.378 mmol). 1H-benzo[d]-imidazole-2-carbaldehyde (55 mg, 0.378 mmol) was added at room temperature to the suspension, and the resulting mixture was stirred for 10 min. at room temperature. Sodium triacetoxyborohydride (267 mg, 1.26 mmol) was then added, and stirring was carried out for a further 3 d at room temperature. Saturated sodium hydrogen carbonate solution (5 ml) was added to the reaction mixture, and extraction with ethyl acetate (4×10 ml) was carried out. The organic phase was dried (MgSO$_4$) and concentrated in vacuo, and the crude product was purified by column chromatography (silica gel) using ethyl acetate/methanol/ammonia solution (25% aq.) (100:1:1). Yield: 60 mg (33%), yellow solid; MS, m/z 570.3 (MH$^+$)

The example compound shown in the following table was prepared from 2-((1-(4-methoxy-2,6-dimethylphenylsulfonyl)piperidin-2-yl)methoxy)-1-(piperazin-1-yl)ethanone hydrochloride (Example 102) by reaction with the corresponding aldehyde (R$^a$R$^b$C=O) closely following the process described for Example 117 (step (ii)). The aldehyde used is commercially available.

| Example No. | Aldehyde (R$^a$R$^b$C=O) | Yield (%) | MS, m/z (MH$^+$) |
|---|---|---|---|
| 166 | Quinoxaline-6-carbaldehyde | 90 | 582.2 |

Reaction of 2-((1-(4-methoxy-2,6-dimethylphenylsulfonyl)piperidin-2-yl)methoxy)-1-(piperazin-1-yl)ethanone with aldehydes (R$^a$HC=O)

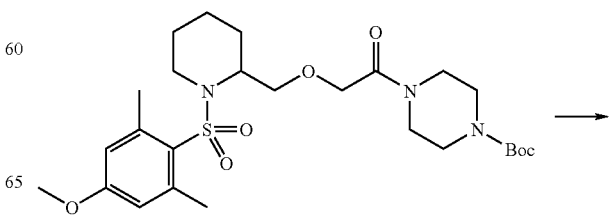

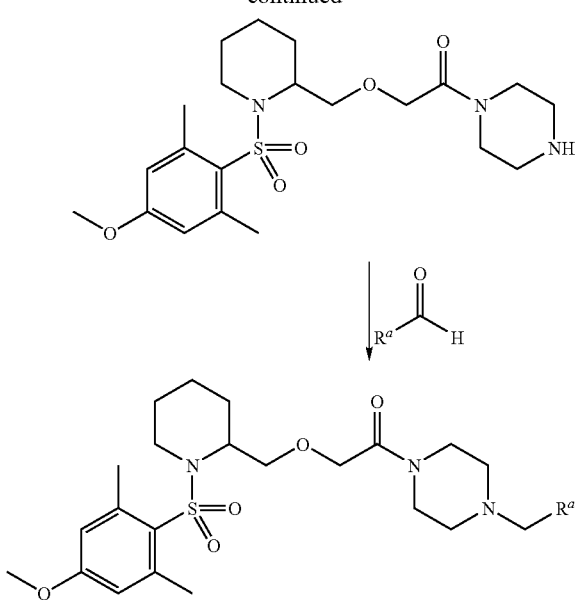

2-((1-(4-methoxy-2,6-dimethylphenylsulfonyl)pip-
eridin-2-yl)methoxy)-1-(piperazin-1-yl)ethanone Step (i): Trifluoroacetic acid (13 eq.) was added at 0° C. to a solution of tert-butyl 4-(2-((1-(4-methoxy-2,6-dimethylphenylsulfonyl)piperidin-2-yl)methoxy)acetyl)piperazine-1-carboxylate (Example 101) (1 eq.) in dichloromethane (10 ml/mmol). The reaction mixture was stirred for 2 h at room temperature and then concentrated in vacuo. The crude product was used in the next synthesis step without being purified further.

Example 197

1-(4-((5-Chloro-2-phenyl-1H-imidazol-4-yl)methyl)
piperazin-1-yl)-2-((1-(4-methoxy-2,6-dimethylphe-
nylsulfonyl)piperidin-2-yl)methoxy)ethanone Step (ii): 4-Chloro-2-phenyl-1H-imidazole-5-carbaldehyde (1.5 eq.) and acetic acid (cat.) were added to a solution of 2-((1-(4-methoxy-2,6-dimethylphenylsulfonyl)piperidin-2-yl)methoxy)-1-(piperazin-1-yl)ethanone (1 eq.) in dichloromethane (25 ml/mmol). The reaction mixture was stirred for 30 min. at 25° C., then sodium triacetoxyborohydride (4 eq.) was added and stirring was carried out for a further 16 h at 25° C. The mixture was diluted with dichloromethane and washed with saturated bicarbonate solution and saturated sodium chloride solution. The organic phase was dried ($Na_2SO_4$) and concentrated in vacuo. The crude product was purified by column chromatography using 3% methanol in ethyl acetate. Yield: 50%; MS, m/z 630.2 ($MH^+$)

The example compounds listed in the following table were prepared from 2-((1-(4-methoxy-2,6-dimethylphenylsulfonyl)piperidin-2-yl)methoxy)-1-(piperazin-1-yl)ethanone by reaction with the corresponding aldehydes ($R^aHC$=O) closely following the process described for Example 197 (step (ii)). The aldehydes used are commercially available, can be prepared by methods known to the person skilled in the art, or were synthesized according to described processes.

| Example No. | Aldehyde ($R^aHC$=O) | Yield (%) | MS, m/z ($MH^+$) |
|---|---|---|---|
| 198 | 1,5-Dimethyl-1H-pyrazole-4-carbaldehyde | 40 | 548.2 |
| 199 | 2-(Dimethylamino)pyrimidine-5-carbaldehyde | 30 | 575.2 |
| 212 | 2-(1-methylpiperidin-4-yl)acetaldehyde | 40 | 565.3 |
| 214 | 2-((4-Fluorophenyl)(methyl)amino)pyrimidine-5-carbaldehyde | 10 | 655.3 |

Preparation of the Aldehydes 2-((4-Fluorophenyl)(methyl)amino)pyrimidine-5-
carbaldehyde Used in the Synthesis of Example Compound 214

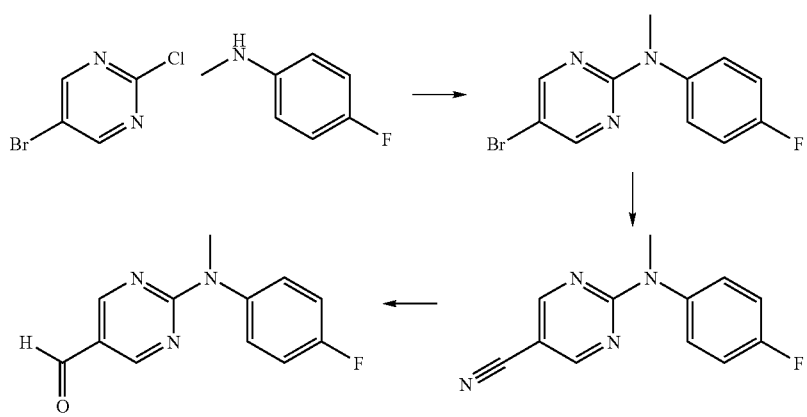

Step (i): To a solution of 5-bromo-2-chloropyrimidine (2.5 mmol) in dimethyl sulfoxide (6.5 ml) there was added 4-fluoro-N-methylaniline, followed by potassium carbonate (5 mmol). The resulting solution was heated for 2 h at 120° C., and the progress of the reaction was monitored by thin-layer chromatography. When the reaction was complete, the reaction mixture was extracted with ethyl acetate, and the organic phase was washed with water and saturated sodium chloride solution. The organic phase was dried ($Na_2SO_4$), filtered and concentrated in vacuo. The crude product was purified by column chromatography (5% ethyl acetate in hexane). Yield: 35%

Step (ii): Copper cyanide (2 eq.) was added to a solution of 5-bromo-N-(4-fluorophenyl)-N-methylpyrimidine-2-amine (1 mmol) in dimethylformamide (3 ml/mmol). The resulting solution was heated for 18 h at 100° C., and the progress of the reaction was monitored by thin-layer chromatography. When the reaction was complete, the reaction mixture was extracted with ethyl acetate, and the organic phase was washed with water and saturated sodium chloride solution. The organic phase was dried ($Na_2SO_4$), filtered and concentrated in vacuo. The crude product was purified by column chromatography (20% ethyl acetate in hexane). Yield: 25%

Step (iii): Diisobutylaluminium hydride (1 M solution, 0.75 mmol) was added to a cold solution of 2-((4-fluorophenyl)(methyl)amino)pyrimidine-5-carbonitrile (0.5 mmol) in benzene (8 ml). The resulting solution was stirred for 4 h at 25° C. The reaction mixture was then cooled to 0° C. again, and 10% hydrochloric acid (5 ml) was added dropwise. The mixture was then heated slowly to 25° C. and stirred for 2 h. The reaction mixture was neutralized with saturated bicarbonate solution and extracted with ethyl acetate. The organic phase was washed with saturated sodium chloride solution, dried ($Na_2SO_4$), filtered and concentrated in vacuo. The crude product was used directly in the next synthesis step.

2-(1-methylpiperidin-4-yl)acetaldehyde

Used in the Synthesis of Example Compound 212

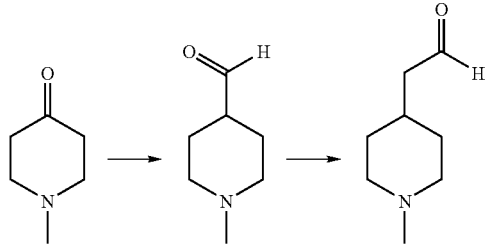

Step (i): A solution of potassium tert-butoxide (13.27 mmol) in tetrahydrofuran (2 ml/mmol) was added dropwise at 0° C., under argon, to a solution of methoxy-methyl-triphenylphosphine (8.84 mmol) in dry tetrahydrofuran (2 ml/mmol). The resulting solution was stirred for 30 min. at 25° C. The reaction mixture was then cooled to 0° C., and a solution of 1-methylpiperidin-4-one (4.42 mmol) in dry tetrahydrofuran (2 ml/mmol) was added dropwise. The mixture was stirred for 16 h at 25° C. until the reaction was complete. The mixture was then cooled to 0° C., 6 N hydrochloric acid (22 ml) was added dropwise, and stirring was carried out for 1 h. The aqueous phase was washed with diethyl ether (10 ml) and then rendered basic with 5 N sodium hydroxide solution and extracted with dichloromethane (4×75 ml). The organic phase was washed with saturated sodium chloride solution, dried ($Na_2SO_4$), filtered, and concentrated in vacuo. The crude product was used directly in the next synthesis step. Yield: 95%

Step (ii): A solution of potassium tert-butoxide (11.7 mmol) in dry tetrahydrofuran (2 ml/mmol) was added dropwise at 0° C., under argon, to a solution of methoxy-methyl-triphenylphosphine (7.8 mmol) in dry tetrahydrofuran (2 ml/mmol). The resulting solution was stirred for 30 min. at 25° C. The reaction mixture was then cooled to 0° C., and a solution of 1-methylpiperidine-4-carbaldehyde (3.9 mmol) in dry tetrahydrofuran (2 ml/mmol) was added dropwise. The mixture was stirred for 16 h at 25° C. until the reaction was complete. The mixture was then cooled to 0° C., 6 N hydrochloric acid (22 ml) was added dropwise, and stirring was carried out for 1 h. The aqueous phase was washed with diethyl ether (10 ml) and then rendered basic with 5 N sodium hydroxide solution and extracted with dichloromethane (4×75 ml). The organic phase was washed with saturated sodium chloride solution, dried ($Na_2SO_4$), filtered, and concentrated in vacuo. The crude product was used directly in the next synthesis step. Yield: 95%

Reaction of 1-(2-((1-(4-methoxy-2,6-dimethylphenylsulfonyl)piperidin-2-yl)methoxy)acetyl)piperidin-4-one (Example 116) with amines ($R^cR^dNH$)

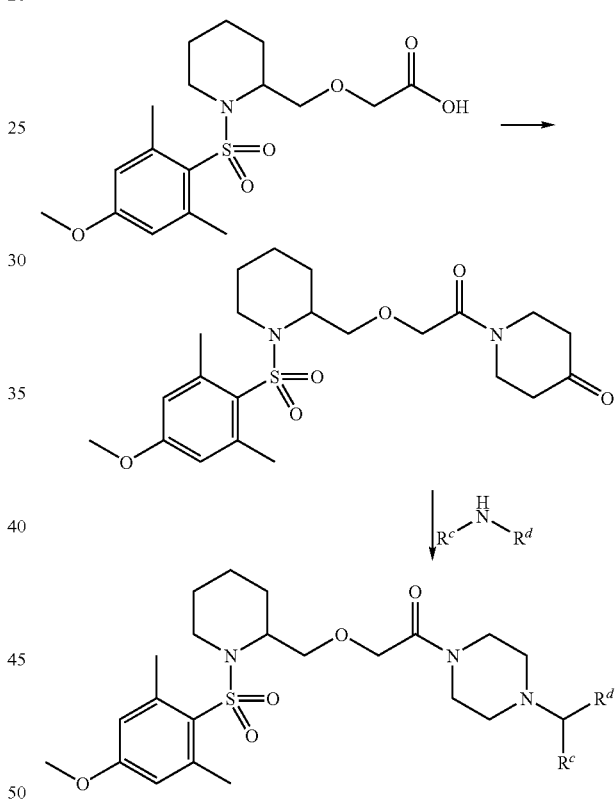

Example 116

1-(2-((1-(4-methoxy-2,6-dimethylphenylsulfonyl)piperidin-2-yl)methoxy)acetyl)piperidin-4-one Step (i): 4-piperidone monohydrate hydrochloride (260 mg, 2.692 mmol), triethylamine (0.560 ml, 4.038 mmol) and then 4-methylmorpholine (1.62 ml, 14.805 mmol) were added to a solution of 2-((1-(4-methoxy-2,6-dimethylphenylsulfonyl)pyrrolidin-2-yl)methoxy)acetic acid (acid structural unit S27) (1.0 g, 2.692 mmol) in N,N-dimethylformamide (20 ml). Benzotriazol-1-yloxytris(dimethylamino)phosphonium hexafluorophosphate (1.42 g, 3.230 mmol) was then added to the mixture, and stirring was carried out for 3 d at room temperature. The mixture was then concentrated in vacuo, and the residue was taken up in ethyl acetate (30 ml) and saturated sodium hydrogen carbonate solution (20 ml); the aqueous phase was extracted with ethyl acetate (4×10 ml). The combined organic phases were washed with saturated sodium hydrogen carbonate solution (20 ml) and saturated sodium chloride solution (20 ml), dried (MgSO$_4$), and concentrated in vacuo. The crude product was purified by column chromatography (silica gel) using diethyl ether/dichloromethane/ammonia solution (25% aq.) (100:100:2). Yield: 430 mg (35%); MS, m/z 540.3 (MH$^+$)

Example 130

1-(4-Fluoro-1,4'-bipiperidin-1'-yl)-2-((1-(4-methoxy-2,6-dimethylphenylsulfonyl)-piperidin-2-yl)methoxy)ethanone Step (ii): 1-(2-((1-(4-methoxy-2,6-dimethylphenylsulfonyl) piperidin-2-yl)methoxy)acetyl)-piperidin-4-one (Example 116) (100 mg, 0.221 mmol) and 4-fluoropiperidine hydrochloride (30 mg, 0.221 mmol) were dissolved in a mixture of 1,2-dichloroethane (4 ml) and triethylamine (0.036 ml, 0.265 mmol). Sodium triacetoxyborohydride (66 mg, 0.309 mmol) and acetic acid (0.013 ml, 0.221 mmol) were added at room temperature to the mixture. The reaction mixture was stirred for 15 h at room temperature, and then saturated sodium hydrogen carbonate solution (5 ml) was added thereto. The aqueous phase was extracted with diethyl ether (2×20 ml), and the organic phase was in turn washed with saturated sodium chloride solution (10 ml). The organic phase was dried (MgSO$_4$) and concentrated in vacuo, and the crude product was purified by column chromatography (silica gel) using ethyl acetate/methanol (20:1). Yield: 70 mg (59%); MS, m/z 540.3 (MH$^+$)

The example compounds listed in the following table were prepared from 1-(2-((1-(4-methoxy-2,6-dimethylphenylsulfonyl)piperidin-2-yl)methoxy)acetyl)piperidin-4-one (Example 116) by reaction with the corresponding amines (R$^c$R$^d$NH) closely following the process described for Example 130 (step (ii)). The reactions were monitored by thin-layer chromatography and had reaction times of about 15 h. In some cases, additional sodium triacetoxyborohydride was added subsequently. If the amine was not present in the form of the hydrochloride (xHCl), no triethylamine was added. The amines used are commercially available, can be prepared by methods known to the person skilled in the art, or were synthesized by described processes.

| Example No. | Amines (R$^c$R$^d$NH) | Yield (%) | MS, m/z (MH$^+$) |
|---|---|---|---|
| 136 | 2-Morpholino-2-(pyridin-3-yl)ethanamine | 79 | 644.4 |
| 144 | 5,6,7,8-tetrahydroimidazo[1,2-a]pyrazine | 70 | 560.2 |
| 145 | 5,6,7,8-tetrahydro-[1,2,4]triazolo[1,5-a]pyrazine | 75 | 561.2 |

Preparation of the Amines 5,6,7,8-tetrahydroimidazo[1,2-a]pyrazine

Used in the Synthesis of Example Compound 144

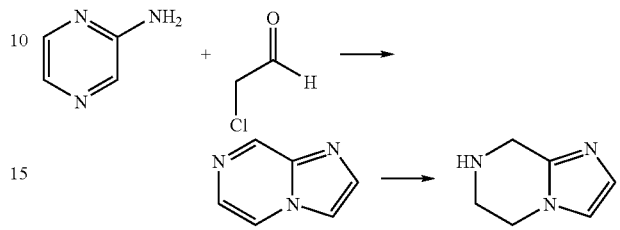

Step (i): A mixture of 2-aminopyrazine (25 g, 262.9 mmol) and chloroacetaldehyde (50% solution in water, 50 ml, 394 mmol) was heated for 2 d at 100° C. in the presence of sodium hydrogen carbonate (33.1 g, 394 mmol). The reaction mixture was cooled to room temperature, and saturated potassium carbonate solution (100 ml) was added thereto. Extraction with dichloromethane was then carried out, and the organic phase was dried (Na$_2$SO$_4$) and concentrated. Purification was carried out by column chromatography (dichloromethane/methanol 95:5+5% NH$_4$OH [35%]). Yield: 7.6 g (24%)

Step (ii): Imidazo[1,2-a]pyrazine (7.2 g, 60.44 mmol) was dissolved in 2-methoxyethanol (100 ml). Platinum(IV) oxide (1.2 g, 5.13 mmol) was added, and the mixture was stirred overnight at room temperature, under a hydrogen atmosphere of 4 bar, in an autoclave. The reaction mixture was flooded with nitrogen, filtered over Celite, concentrated and coevaporated with toluene. Purification was carried out by column chromatography dichloromethane/7 N ammonia in methanol 95:5). Yield: 5.7 g (76%)

5,6,7,8-tetrahydro-[1,2,4]-triazolo[1,5-a]pyrazine

Used in the Synthesis of Example Compound-145

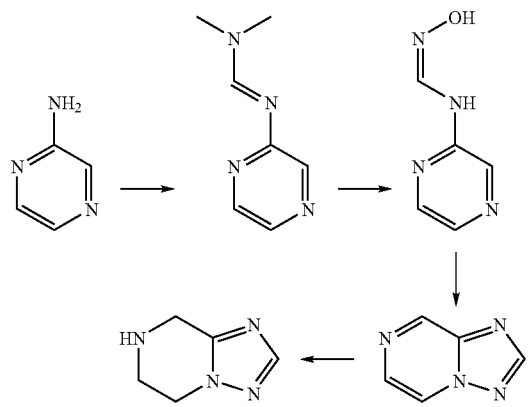

Step (i): N,N-Dimethylformamide dimethyl acetal (29.5 ml, 220 mmol) was added to a solution of pyrazine-2-amine (18.98 g, 200 mmol) in toluene (110 ml), and the mixture was refluxed for 2.25 h. The reaction mixture was cooled to room temperature, concentrated and coevaporated with toluene. Yield: 32.89 g (100%)

Step (ii): A solution of hydroxylamine hydrochloride (17.0 g, 245 mmol) in methanol (150 ml) was added dropwise, while cooling with ice, to a suspension of (E)-N,N-dimethyl-N'-(pyrazin-2-yl)formimide amide (38.27 g, 233 mmol) and sodium acetate (20.1 g, 245 mmol) in methanol (450 ml). The reaction mixture was stirred for 4 h at 0° C. and then heated to room temperature and concentrated. The residue was triturated with dichloromethane/7 M ammonia solution in methanol (~9:1), and the desired solid was filtered off and washed with dichloromethane/7 M ammonia solution in methanol (~9:1). The filtrate was concentrated, coevaporated with ethanol and then crystallized from ethanol. Further recrystallization of the resulting solids from ethanol finally yielded the purified product. Yield: 24.55 g (76%)

Step (iii): Polyphosphoric acid (250 g) was added to (Z)—N'-hydroxy-N-(pyrazin-2-yl)-formimide amide (25.07 g, 181 mmol), and the reaction mixture was then immediately heated to 90° C. The mixture was stirred for 4 h, and the hot reaction mixture was poured into ice-water and rendered basic with sodium hydrogen carbonate. The aqueous phase was extracted with dichloromethane (1 l, 3×0.5 l), and the combined organic phases were dried ($Na_2SO_4$) and concentrated. The crude product was crystallized from ethanol in several batches. Yield: 18.10 g (83%)

Step (iv): Platinum(IV) oxide (2.75 g, 12.1 mmol) was added, under nitrogen, to a suspension of calcium oxide (9.30 g, 166 mmol) and [1,2,4]triazolo[1,5-a]pyrazine (18.10 g, 151 mmol) in 2-methoxyethanol (150 ml). The reaction mixture was stirred for 21.5 h under a hydrogen atmosphere, filtered over Celite, and washed with dichloromethane/ethanol (9:1). The filtrate was concentrated, coevaporated with toluene and diisopropyl ether, and then dissolved in ethyl acetate, filtered over Celite, washed with ethyl acetate and concentrated again. The residue was dissolved in hot diisopropyl ether, filtered, washed with diisopropyl ether, and concentrated for 7 h in vacuo. Yield: 17.12 g (92%)

Preparation of (S)-2-((1-(4-methoxy-2,6-dimethylphenylsulfonyl)piperidin-2-yl)-methoxy)acetamide derivatives

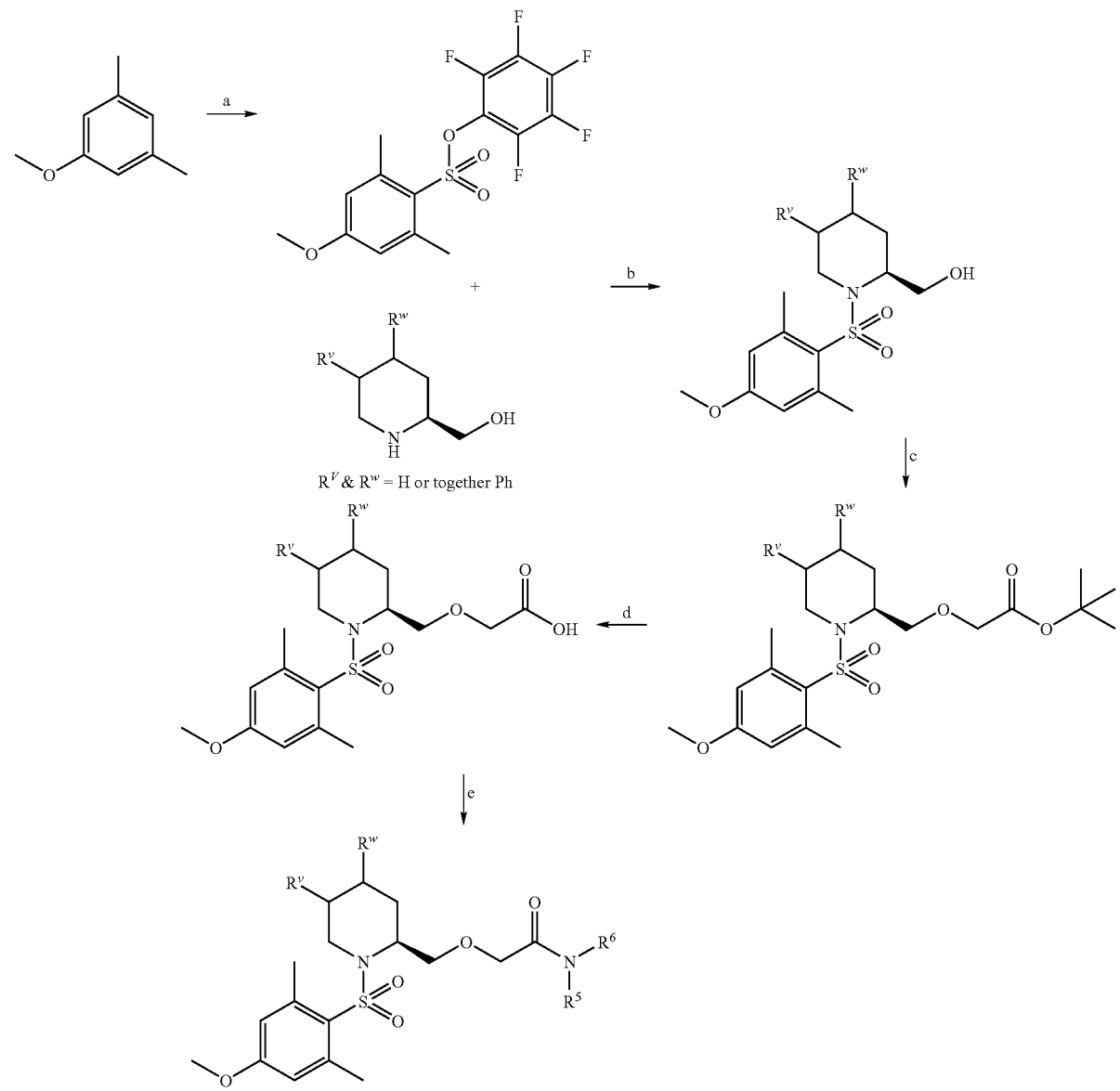

Example 127

(S)-2-((2-(4-methoxy-2,6-dimethylphenylsulfonyl)-1,2,3,4-tetrahydroisoquinolin-3-β-methoxy)-1-(4-(1-methylpiperidin-4-yl)piperazin-1-yl)ethanone Step (a): Chlorosulfonic acid (7.3 ml, 110.13 mmol) in dichloromethane (60 ml) was slowly added dropwise, over a period of 10 min., to a solution, cooled to 0° C., of 3,5-dimethylanisole (3.1 g, 22.03 mmol) in dichloromethane (50 ml). The reaction mixture was stirred for a further 10 min. and then slowly added dropwise to ice-water (300 ml) and stirred until the ice had melted. The phases were separated, and the aqueous phase was extracted with dichloromethane (50 ml). The combined organic phases were washed with saturated sodium chloride solution (50 ml), dried ($Na_2SO_4$) and concentrated in vacuo. A solution of pentafluorophenol (4.1 g, 22.03 mmol) and triethylamine (6.1 ml, 44.05 mmol) in dichloromethane (50 ml) was stirred for 30 min. at room temperature. A solution of the sulfonyl chloride that had been prepared in dichloromethane (50 ml) was then slowly added dropwise. The reaction mixture was stirred for 1 h at room temperature. Saturated sodium hydrogen carbonate solution (50 ml) was added to the mixture, and the organic phase was washed with saturated sodium chloride solution (50 ml), dried ($Na_2SO_4$) and concentrated in vacuo. The crude product was purified by column chromatography (silica gel) using hexane/diethyl ether/dichloromethane (20:1:2). Yield: 6.1 g (72%). [The undesired regioisomer was isolated in a yield of 14%.]

Step (b): Perfluorophenyl 4-methoxy-2,6-dimethylbenzenesulfonate (1.5 g, 3.92 mmol) and tetra-n-butylammonium chloride (2.18 g, 7.85 mmol) were added to a solution of the amino alcohol (S)-(1,2,3,4-tetrahydroisoquinolin-3-yl)methanol (960 mg, 5.89 mmol) in N,N-dimethylformamide (15 ml). The reaction mixture was heated for 1 h at 120° C. It was then concentrated in vacuo, and the residue was taken up in ethyl acetate (50 ml) and washed with 10% aqueous ammonium chloride solution (20 ml). The organic phase was dried ($Na_2SO_4$) and concentrated in vacuo. The crude product was purified by column chromatography (silica gel) using hexane/diethyl ether/dichloromethane (3:2:2). Yield: 1.2 g (85%)

Step (c): tert-butyl 2-bromoacetate (1.02 ml, 6.07 mmol) was added at room temperature to a mixture of tetra-n-butylammonium hydrogen sulfate (113 mg, 0.332 mmol), aqueous sodium hydroxide solution (6.64 g, 165.98 mmol in water (7 ml)) and toluene (5 ml), and the mixture was then cooled to 0° C. A solution of (S)-(2-(4-methoxy-2,6-dimethylphenylsulfonyl)-1,2,3,4-tetrahydroisoquinolin-3-yl)methanol (1.2 g, 3.32 mmol) in toluene (5 ml) was then added slowly. The reaction mixture was heated to room temperature and then stirred for 1 h at that temperature. The phases were separated, and the aqueous phase was extracted with diethyl ether (2×20 ml). The combined organic phases were washed with saturated sodium chloride solution (20 ml), dried ($Na_2SO_4$) and concentrated in vacuo. The crude product was used in the next step without being purified further. Yield: 1.79 g (>99%)

Step (d): (S)-tert-butyl 2-((2-(4-methoxy-2,6-dimethylphenylsulfonyl)-1,2,3,4-tetrahydroiso-quinolin-3-yl)methoxy)acetate (1.58 g, 3.32 mmol) was dissolved in tetrahydrofuran (10 ml), and sodium hydroxide solution (531 mg, 13.28 mmol in water (0.5 ml)) was added. The reaction mixture was refluxed for 2 h and then cooled to room temperature again, and water (20 ml) was added. The pH value of the aqueous phase was adjusted to pH 2 with 2 M hydrochloric acid, and extraction with ethyl acetate (3×20 ml) was carried out. The combined organic phases were dried ($Na_2SO_4$) and concentrated in vacuo. The crude product was used in the next step without being purified further. Yield: 580 mg (42%)

Step (e): 1-(1-methylpiperidin-4-yl)piperazine (65 mg, 0.358 mmol) and 4-methylmorpholine (0.117 ml, 1.073 mmol) were added to a solution of (S)-2-((2-(4-methoxy-2,6-dimethylphenylsulfonyl)-1,2,3,4-tetrahydroisoquinolin-3-yl)methoxy)acetic acid (150 mg, 0.358 mmol) in N,N-dimethylformamide (5 ml). Benzotriazol-1-yloxytris(dimethylamino)phosphonium hexafluorophosphate (188 mg, 0.429 mmol) was added to the mixture, and stirring was carried out for 15 h at room temperature. The mixture was then concentrated in vacuo, the residue was taken up in ethyl acetate (20 ml) and saturated sodium hydrogen carbonate solution (10 ml), and the aqueous phase was extracted with ethyl acetate (20 ml). The combined organic phases were dried ($Na_2SO_4$) and concentrated in vacuo. The crude product was purified by column chromatography (silica gel) using diethyl ether/dichloromethane/methanol/ammonia solution (25% aq.) (20:10:10:0.4). Yield: 90 mg (43%), orange oil; MS, m/z 595.2 ($MH^+$).

Example 185

(S)-2-((2-(4-methoxy-2,6-dimethylphenylsulfonyl)-1,2,3,4-tetrahydroisoquinolin-3-yl)-methoxy)-1-(4-((1-methylpiperidin-4-yl)methyl)piperazin-1-yl)ethanone Step (e): N,N'-Carbonyldiimidazole (131 mg, 0.813 mmol) was added to a solution of (S)-2-((2-(4-methoxy-2,6-dimethylphenylsulfonyl)-1,2,3,4-tetrahydroisoquinolin-3-yl)methoxy)-acetic acid (step d, Example 127) (325 mg, 0.775 mmol) in dichloromethane (5 ml), and stirring was carried out for 2 h at 30° C. A solution of 1-((1-methylpiperidin-4-yl)methyl)piperazine (152 mg, 0.775 mmol) in dichloromethane (5 ml) was then added at room temperature, and the reaction mixture was stirred for 15 h at that temperature. Saturated sodium hydrogen carbonate solution (10 ml) was added to the mixture, and the aqueous phase was extracted with dichloromethane (20 ml). The combined organic phases were dried ($Na_2SO_4$) and concentrated in vacuo. The crude product was purified by column chromatography (silica gel) using ethyl acetate/methanol/ammonia solution (25% aq.) (40:10:0.5). Yield: 263 mg (57%); MS, m/z 599.3 (MW).

The example compounds listed in the following table were prepared from the corresponding starting materials closely following the process described for Example 185. The progress of the reaction was monitored in each case by thin-layer chromatography and, on the basis thereof, the reaction times for analogous reactions were adapted accordingly. The reaction temperatures and the equivalent amounts of the reagents used can differ slightly in analogous reactions. The starting materials used are commercially available or were prepared in the manner described.

| Example No. | Amino alcohol | Amine ($R^5R^6NH$) | Yield (%) (over 5 steps) | MS, m/z ($MH^+$) |
|---|---|---|---|---|
| 186[3] | (S)-piperidin-2-ylmethanol[4] | 4-(piperidin-4-yloxy)pyridine dihydrochloride[5] | 14 | 532.2 |
| 187 | (S)-(1,2,3,4-tetrahydroisoquinolin-3-yl)methanol | 4-(2-(pyrrolidin-1-yl)ethyl)-piperidine | 18 | 584.3 |

[3] The hydrochloride precipitation was carried out from a methyl ethyl ketone solution of the free base, with addition of 2M hydrogen chloride solution in diethyl ether (5 eq.).
[4] The (S)-amino alcohol used was prepared as follows: Hydrogen bromide-tetrahydrofuran complex (3 eq., 1M solution in tetrahydrofuran) was added dropwise to a suspension, cooled to 0° C., of the carboxylic acid (1 eq.) in tetrahydrofuran (4 ml/mmol), and the mixture was then stirred for 1 h at room temperature. The reaction mixture was then refluxed for 4 h and stirred for a further 15 h at room temperature. The mixture was cooled to 0° C., and 3M sodium hydroxide solution was added, and then refluxing was carried out for 6 h. The mixture was extracted with dichloromethane (4x), and the combined organic phases were dried ($Na_2SO_4$) and concentrated in vacuo. The crude product was used in the next synthesis step without being purified.
[5] The amine $R^5R^6NH$ was prepared analogously to 3-(piperidin-4-yloxy)pyridine hydrochloride (used in the synthesis of Example compound 165) [analogous process see also: J. Chao et al., *Tetrahedron Lett.*, 2007, 48, 791]

Reaction of substituted (S)-2-((2-(phenylsulfonyl)-1,2,3,4-tetrahydroisoquinolin-3-yl)-methoxy)acetic acid derivatives with amines ($R^5R^6NH$)

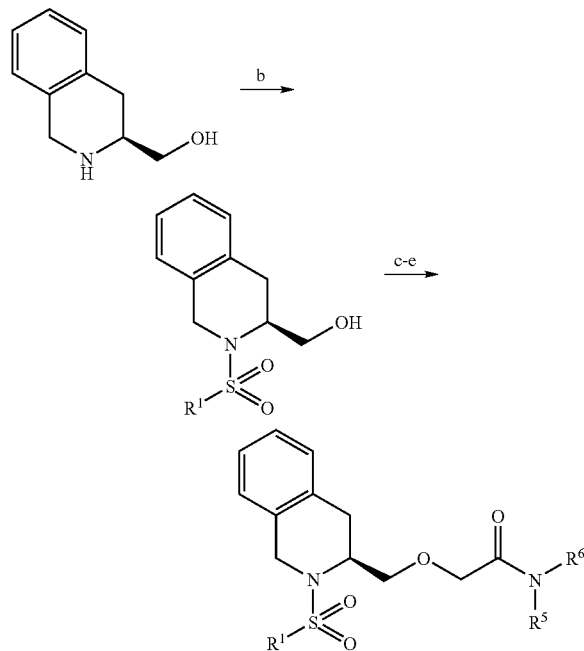

Example 133

(S)-2-((2-(2,4-dichlorophenylsulfonyl)-1,2,3,4-tetrahydroisoquinolin-3-yl)methoxy)-1-(4-(1-methylpiperidin-4-yl)piperazin-1-yl)ethanone The synthesis of this compound was for the most part carried out analogously to the synthesis described for Example 185. However, synthesis step (a) was omitted and synthesis step (b) was carried out as follows:
Step (b): Triethylamine (1.27 ml, 9.19 mmol) was added to a solution of (S)-(1,2,3,4-tetrahydroisoquinolin-3-yl)methanol (1.0 g, 6.13 mmol) in dichloromethane (10 ml), and the mixture was stirred for 5 min. at room temperature. A solution of 2,4-dichlorobenzene-1-sulfonyl chloride (1.35 g, 5.51 mmol) in dichloromethane (10 ml) was then added dropwise at 0° C. The reaction mixture was heated to room temperature and stirred for 1 h at that temperature. Saturated sodium hydrogen carbonate solution (20 ml) was then added to the mixture, and the aqueous phase was extracted with dichloromethane (30 ml). The combined organic phases were dried ($Na_2SO_4$) and concentrated in vacuo, and the crude product was then purified by column chromatography (silica gel) using hexane/diethyl ether/dichloromethane (1:1:1). Yield: 1.59 g (70%).

Synthesis steps (c) to (e) were carried out analogously to the processes described for Example 185. Example 133 (clear oil) was obtained in this manner in a yield of 85% over 3 steps. MS, m/z 585.3 ($MH^+$)

The example compounds listed in the following table were prepared analogously to Example 133 from (S)-(1,2,3,4-tetrahydroisoquinolin-3-yl)methanol, the corresponding sulfonyl chloride ($R^1SO_2Cl$) and the corresponding amine ($R^5R^6NH$).

| Example No. | Sulfonyl chloride ($R^1SO_2Cl$) | Amine ($R^5R^6NH$) | Yield (%) (over 4 steps) | MS, m/z ($MH^+$) |
|---|---|---|---|---|
| 142 | 4-methoxybenzene-1-sulfonyl chloride | 1-(1-methyl-piperidin-4-yl)-piperazine | 62 | 557.2 |
| 182 | 4-methoxybenzene-1-sulfonyl chloride | 4-(2-(pyrrolidin-1-yl)ethyl)piperidine | 56 | 556.2 |
| 183 | 2,4-dichlorobenzene-1-sulfonyl chloride | 4-(2-(pyrrolidin-1-yl)ethyl)piperidine | 20 | 594.1 |
| 184 | 2,4-dichlorobenzene-1-sulfonyl chloride | 1-((1-methyl-piperidin-4-yl)-methyl)piperazine | 28 | 609.2 |

| Example No. | Sulfonyl chloride (R¹SO₂Cl) | Amine (R⁵R⁶NH) | Yield (%) (over 4 steps) | MS, m/z (MH⁺) |
|---|---|---|---|---|
| 189[6] | 4-methoxybenzene-1-sulfonyl chloride | 1-((1-methyl-piperidin-4-yl)-methyl)piperazine | 14 | 571.3 |

[6] The corresponding base was converted into the corresponding dihydrochloride (2 × HCl) as follows: The free base was dissolved in a small amount of dichloromethane/diethyl ether (1:5); 2M hydrogen chloride solution in diethyl ether (3 eq.) was added, and the resulting dihydrochloride was filtered off.

Example 135

(S)-2-((1-(4-methoxy-2,6-dimethylphenylsulfonyl)azetidin-2-yl)methoxy)-1-(4-(1-methylpiperidin-4-yl)piperazin-1-yl)ethanone

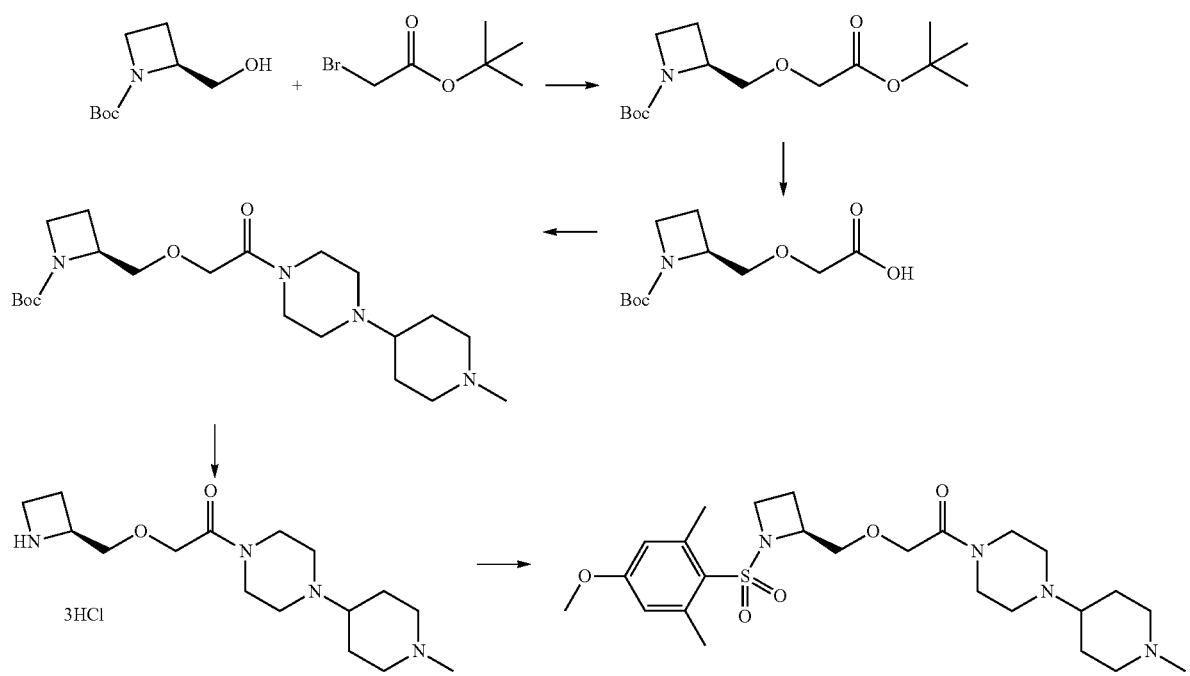

Step (i): tert-butyl 2-bromoacetate (0.799 ml, 5.45 mmol) was added at room temperature to a mixture of tetra-n-butylammonium hydrogen sulfate (122 mg, 0.363 mmol), aqueous sodium hydroxide solution (7.27 g, 181.7 mmol in water (7 ml)) and toluene (5 ml), and the mixture was then cooled to 0° C. A solution of (S)-tert-butyl 2-(hydroxymethyl)azetidine-1-carboxylate (680 mg, 3.63 mmol) in toluene (5 ml) was then added slowly. The reaction mixture was heated to room temperature and stirred for 1 h at that temperature. The phases were separated, and the aqueous phase was extracted with diethyl ether (2×20 ml). The combined organic phases were washed with saturated sodium chloride solution (20 ml), dried (Na₂SO₄) and concentrated in vacuo. The crude product was purified by column chromatography (silica gel) using hexane/diethyl ether/dichloromethane (2:1:1).

Yield: 910 mg (83%)

Step (ii): (S)-tert-butyl 2-((2-tert-butoxy-2-oxoethoxy)methyl)azetidine-1-carboxylate (890 mg, 2.95 mmol) was dissolved in tetrahydrofuran (10 ml), and sodium hydroxide (708 mg, 17.72 mmol in water (1 ml)) was added. The reaction mixture was refluxed for 2 h and then cooled to room temperature again, and water (20 ml) was added. The pH value of the aqueous phase was adjusted to pH 2 with 2 M hydrochloric acid, and extraction with ethyl acetate (3×20 ml) was carried out. The combined organic phases were dried (Na₂SO₄) and concentrated in vacuo. The crude product was used in the next synthesis step without being purified further. Yield: 700 mg (97%)

Step (iii): 1-(1-methylpiperidin-4-yl)piperazine (433 mg, 2.39 mmol) and 4-methylmorpholine (0.798 ml, 7.95 mmol) were added to a solution of (S)-2-((1-(tert-butoxycarbonyl)azetidin-2-yl)methoxy)acetic acid (650 mg, 2.65 mmol) in N,N-dimethylformamide (20 ml). Benzotriazol-1-yloxytris(dimethylamino)phosphonium hexafluorophosphate (1.39 mg, 3.18 mmol) was added to the mixture, and stirring was carried out for 15 h at room temperature. The mixture was then concentrated in vacuo, the residue was taken up in ethyl acetate (20 ml) and saturated sodium hydrogen carbonate solution (10 ml), and the aqueous phase was extracted with ethyl acetate (2×20 ml). The combined organic phases were dried (Na₂SO₄) and concentrated in vacuo. The crude product was purified by column chromatography (silica gel) using diethyl ether/dichloromethane/methanol/ammonia solution (25% aq.) (20:10:10:0.4). Yield: 580 mg (53%).

Step (iv): Hydrogen chloride (3.47 ml, 6.94 mmol, 2 M solution in diethyl ether) was added at room temperature to a solution of (S)-tert-butyl 2-((2-(4-(1-methylpiperidin-4-yl)piperazin-1-yl)-2-oxoethoxy)methyl)azetidine-1-carboxylate (570 mg, 1.39 mmol) in ethyl acetate/diethyl ether (2 ml; 2:5). The reaction mixture was stirred for 2 h at 40° C., and the resulting solid was filtered off and dried. Yield: 520 mg (89%)

Step (v): 1,8-diazabicyclo[5.4.0]-undec-7-ene (DBU) (0.15 ml, 0.993 mmol) and perfluoro-phenyl 4-methoxy-2,6-dimethylbenzenesulfonate (123 mg, 0.298 mmol) [for synthesis see Example 127] were added to a solution of (S)-2-(azetidin-2-ylmethoxy)-1-(4-(1-methyl-piperidin-4-yl)piperazin-1-yl)ethanone trihydrochloride (100 mg, 0.238 mmol) in tetrahydrofuran (10 ml). The reaction mixture was refluxed for 1 h and stirred for 3 d at room temperature. Then saturated sodium hydrogen carbonate solution (20 ml) and ethyl acetate (30 ml) were added to the mixture. The aqueous phase was extracted with ethyl acetate (2×15 ml), and the combined organic phases were washed with saturated sodium chloride solution (20 ml). The organic phase was then dried (Na$_2$SO$_4$) and concentrated in vacuo, and the crude product was then purified by column chromatography (silica gel) using diethyl ether/dichloromethane/methanol/ammonia solution (25% aq.) (20:10:10:0.4).

Yield: 40 mg (33%), yellow resin; MS, m/z 509.3 (MH$^+$).

Reaction of pyrrolidin-2-ylmethanol to substituted 2-((1-(phenylsulfonyl)pyrrolidin-2-yl)methoxy)acetamides sodium hydroxide solution (9.93 g, 248.43 mmol in water (10 ml)) and toluene (7.5 ml), and then the mixture was cooled to 0° C. A solution of the amino alcohol (R)-tert-butyl 2-(hydroxymethyl)pyrrolidine-1-carboxylate (2.0 g, 9.94 mmol) in toluene (7.55 ml) was then added slowly. The reaction mixture was heated to room temperature and then stirred for 2 h at that temperature. The phases were separated, and the aqueous phase was extracted with diethyl ether (2×30 ml). The combined organic phases were washed with saturated sodium chloride solution (30 ml), dried (Na$_2$SO$_4$) and concentrated in vacuo. The crude product was filtered over silica gel using ethyl acetate and was used in the next step.

Yield: 3.2 g (>99%).

Step (ii): (R)-tert-butyl 2-((2-tert-butoxy-2-oxoethoxy)methyl)pyrrolidine-1-carboxylate (3.2 g, 10.15 mmol) was dissolved in tetrahydrofuran (25 ml), and sodium hydroxide solution (2.44 g, 60.88 mmol in water (2.5 ml)) was added. The reaction mixture was refluxed for 2 h and then cooled to room temperature again, and water (20 ml) was added. The pH value of the aqueous phase was adjusted to pH 2 with 2 M hydrochloric acid, and extraction with ethyl acetate (3×30 ml) was carried out. The combined organic phases were dried (Na$_2$SO$_4$) and concentrated in vacuo. The crude product was used in the next synthesis step without being purified further. Yield: 2.0 g (76%)

Step (iii): N,N'-Carbonyldiimidazole (328 mg, 1.93 mmol) was added to a solution of (R)-2-((1-(tert-butoxycarbonyl)pyrrolidin-2-yl)methoxy)acetic acid (500 mg, 1.93 mmol) in dichloromethane (5 ml), and stirring was carried out for 30 min. at room temperature. A solution of 1-(1-methylpiperidin-4-yl)piperazine (353 mg, 1.93 mmol) in dichloromethane

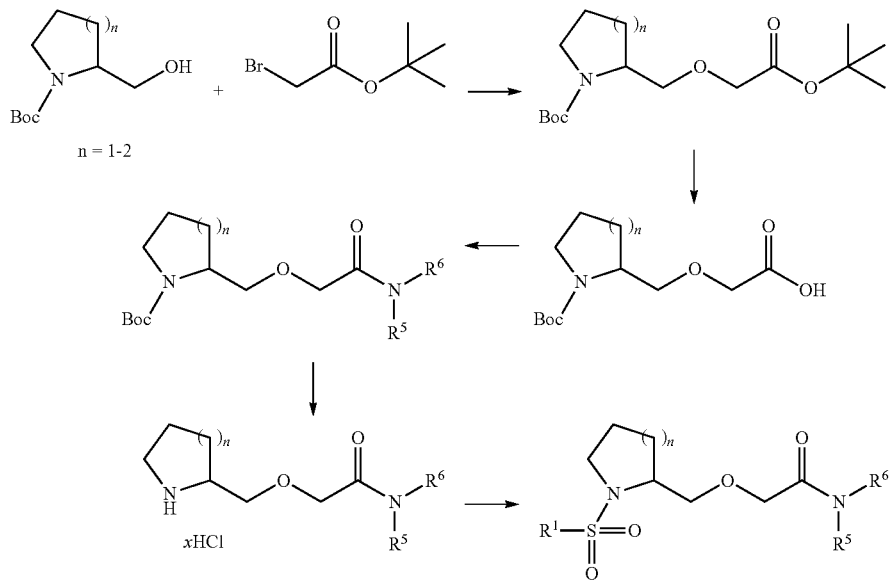

Example 140

(R)-2-((1-(4-methoxy-2,3,6-trimethylphenylsulfonyl)pyrrolidin-2-yl)methoxy)-1-(4-(1-methylpiperidin-4-yl)piperazin-1-yl)ethanone dihydrochloride Step (i): tert-butyl 2-bromoacetate (2.19 ml, 14.91 mmol) was added at room temperature to a mixture of tetra-n-butylammonium hydrogen sulfate (334 mg, 0.994 mmol), aqueous (5 ml) was then added at room temperature, and the reaction mixture was stirred for 15 h at that temperature. Saturated sodium hydrogen carbonate solution (10 ml) was then added to the mixture, and the aqueous phase was then extracted with dichloromethane (20 ml). The combined organic phases were dried (Na$_2$SO$_4$) and concentrated in vacuo. The crude product was purified by column chromatography (silica gel) using diethyl ether/dichloromethane/methanol/ammonia solution (25% aq.) (20:10:10:0.4). Yield: 540 mg (66%)

Step (iv): Hydrogen chloride (6.24 ml, 12.48 mmol, 2 M solution in diethyl ether) was added at room temperature to a solution of (R)-tert-butyl 2-((2-(4-(1-methylpiperidin-4-yl)piperazin-1-yl)-2-oxoethoxy)methyl)pyrrolidine-1-carboxylate (530 mg, 1.25 mmol) in ethyl acetate/-diethyl ether (30 ml; 1:2). The reaction mixture was stirred for 2 h at 40° C., and the resulting solid was filtered off and dried. Yield: 440 mg (81%)

Step (v): Triethylamine (0.172 ml, 1.25 mmol) was added to a solution of (R)-1-(4-(1-methylpiperidin-4-yl)piperazin-1-yl)-2-(pyrrolidin-2-ylmethoxy)ethanone trihydrochloride (120 mg, 0.277 mmol) in dichloromethane (5 ml). A solution of 4-methoxy-2,3,6-trimethylbenzene-1-sulfonyl chloride[10] (58 mg, 0.249 mmol) in dichloromethane (5 ml) was then added dropwise at 0° C. The reaction mixture was heated to room temperature and stirred for 3 d at that temperature. Saturated sodium hydrogen carbonate solution (5 ml) was added to the mixture, and the aqueous phase was extracted with dichloromethane (20 ml). The combined organic phases were dried (Na$_2$SO$_4$) and concentrated in vacuo, and the crude product was then purified by column chromatography (silica gel) using diethyl ether/dichloromethane/methanol/ammonia solution (25% aq.) (20:10:10:0.4). The crude product was dissolved in a small amount of dichloromethane/diethyl ether, and chlorotrimethylsilane (2.5 eq.) was added slowly. The resulting precipitate was filtered off and dried. Yield: 80 mg (47%), white solid; MS, m/z 537.2 (MH$^+$).

The example compounds listed in the following table were prepared from the corresponding starting materials closely following the process described for Example 140. The progress of the reaction was in each case monitored by thin-layer chromatography and, on the basis thereof, the reaction times in analogous reactions were adapted accordingly. The reaction temperatures and equivalent amounts of the reagents used can differ in analogous reactions. The amount of triethylamine used in step (v) in each case was adapted according to the stoichiometry of the amine hydrochloride (x HCl) used. The starting materials used are commercially available or were prepared in the manner described.

| Example No. | Amino alcohol | Amine (R$^5$R$^6$NH) | Sulfonyl chloride (R$^1$SO$_2$Cl) | Yield (%) (over 5 steps) | MS, m/z (MH$^+$) |
|---|---|---|---|---|---|
| 152[7] | (R)-tert-butyl 2-(hydroxymethyl)pyrrolidine-1-carboxylate | 1-(1-methylpiperidin-4-yl)piperazine | 2-Chloro-6-methylbenz-1-sulfonyl chloride | 34 | 513.1 |
| 161[8] | (S)-tert-butyl 2-(hydroxymethyl)pyrrolidine-1-carboxylate | 4-(2-(pyrrolidin-1-yl)ethyl)piperidine | 2-Chloro-6-methylbenz-1-sulfonyl chlorid | 27 | 512.1 |
| 162[8] | (S)-tert-butyl 2-(hydroxymethyl)pyrrolidine-1-carboxylate | 1-(1-methylpiperidin-4-yl)piperazine | 2-Chloro-6-methylbenz-1-sulfonyl chloride | 20 | 513.1 |
| 163[8] | (S)-tert-butyl 2-(hydroxymethyl)pyrrolidine-1-carboxylate | 1-((1-methylpiperidin-4-yl)methyl)-piperazine | 2-Chloro-6-methylbenz-1-sulfonyl chloride | 11 | 527.1 |
| 167 | (S)-tert-butyl 2-(hydroxymethyl)piperidine-1-carboxylate[9] | 1-(1-methylpiperidin-4-yl)piperazine | 4-methoxy-2,6-dimethylbenzene-1-sulfonyl chloride[10] | 53 | 537.3 |
| 177[8] | (R)-tert-butyl 2-(hydroxymethyl)piperidine-1-carboxylate[9] | 1-(1-methylpiperidin-4-yl)piperazine | 4-methoxy-2,6-dimethylbenzene-1-sulfonyl chloride[10] | 16 | 537.3 |
| 180 | (S)-tert-butyl 2-(hydroxymethyl)pyrrolidine-1-carboxylate | 1-(1-methylpiperidin-4-yl)piperazine | 4-methoxy-2,6-dimethylbenzene-1-sulfonyl chloride[10] | 10 | 523.2 |
| 181 | (S)-tert-butyl 2-(hydroxymethyl)pyrrolidine-1-carboxylate | 4-(2-(pyrrolidin-1-yl)ethyl)piperidine | 4-methoxy-2,6-dimethylbenzene-1-sulfonyl chloride[10] | 8 | 537.3 |
| 190[8] | (S)-tert-butyl 2-(hydroxymethyl)pyrrolidine-1-carboxylate | 1-((1-methylpiperidin-4-yl)methyl)-piperazine | 4-methoxy-2,6-dimethylbenzene-1-sulfonyl chloride[10] | 20 | 522.3 |

[7]The hydrochloride precipitation was carried out from a dichloromethane solution of the free base with addition of 2M hydrogen chloride solution in diethyl ether (10 eq.).
[8]The hydrochloride precipitation was carried out from a methyl ethyl ketone/(optional) diethyl ether solution of the free base with addition of 2M hydrogen chloride solution in diethyl ether (3-5 eq.).
[9]The Boc-protected (R)- or (S)-amino alcohol used was prepared as follows: Hydrogen bromide-tetrahydrofuran complex (1.5 eq., 1M solution in tetrahydrofuran) was added dropwise to a solution, cooled to 0° C., of the Boc-protected carboxylic acid (1 eq.) in tetrahydrofuran (50 ml/mmol), and the mixture was then stirred for 3 h at room temperature. Water and potassium carbonate were added to the mixture, cooled to 0° C., and stirring was carried out for 30 min. The aqueous phase was then extracted with diethyl ether (3x), and the combined organic phases were washed with saturated sodium chloride solution (1x) and then dried (Na$_2$SO$_4$) and concentrated in vacuo. The crude product was purified by column chromatography (silica gel). [see also Timothy J. Wilkinson et al.; Org. Lett.; 2000; 155-158]
[10]4-methoxy-2,6-dimethylbenzene-1-sulfonyl chloride was prepared as follows: Chlorosulfonic acid (5 eq.) in dichloromethane (25 ml/mmol) was slowly added dropwise over a period of 10 min. to a solution, cooled to 0° C., of 3,5-dimethylanisole (1 eq.) in dichloromethane (26 ml/mmol). The reaction mixture was stirred for a further 10 min. and then slowly added dropwise to ice-water and stirred until the ice had melted. The phases were separated, and the aqueous phase was extracted with dichloromethane. The combined organic phases were washed with saturated sodium chloride solution, dried (Na$_2$SO$_4$) and concentrated in vacuo. The crude product was used in the next synthesis step without being purified further.

Reaction of 2((1-(4-methoxy-2,6-dimethylphenylsulfonyl)piperidin-2-yl)methoxy)-acetic acid (acid structural unit S27) with amines (R$^5$R$^6$NH)

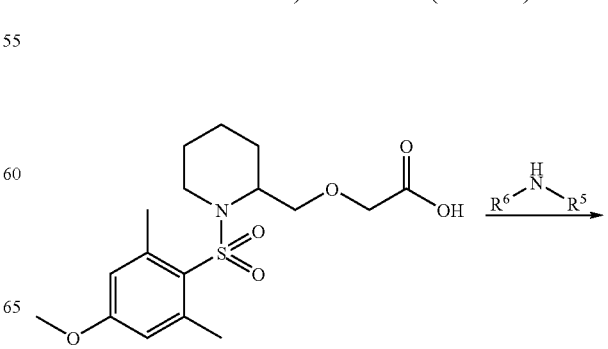

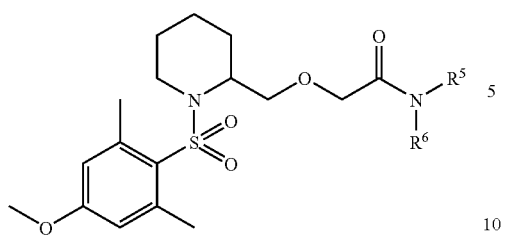

Example 201

2-((1-(4-methoxy-2,6-dimethylphenylsulfonyl)piperidin-2-yl)methoxy)-1-(4-(pyridin-4-yl)piperidin-1-yl)ethanone Diisopropylethylamine (2.5 eq.), followed by N-hydroxybenzotriazole (HOBt) (1 eq.) and N-ethyl-N'-(3-dimethylaminopropyl)carbodiimide hydrochloride (EDCI) (1.5 eq.) were added to a solution of the acid structural unit S27 (1 eq.) in dichloromethane (5 ml/mmol). The resulting reaction mixture was stirred for 15 min. at 25° C. Cooling to 0° C. was then carried out, and 4-(piperidin-4-yl)pyridine (1.2 eq.) was added. The mixture was stirred for 16 h at 25° C. until the reaction was complete. It was diluted with dichloromethane (30 ml) and extracted with saturated ammonium chloride solution, saturated sodium chloride solution, saturated sodium hydrogen carbonate solution and again with saturated sodium chloride solution. The organic phase was dried (Na$_2$SO$_4$) and concentrated in vacuo. The crude product was purified by column chromatography (2% methanol in dichloromethane). Yield: 40%; MS, m/z 516.2 (MH$^+$).

The example compounds listed in the following table were prepared from the corresponding starting materials closely following the process described for Example 201. 2-((1-(4-methoxy-2,6-dimethylphenylsulfonyl)piperidin-2-yl)methoxy)acetic acid (acid structural unit S27) was synthesized analogously to the process described for Examples 202 and 210 for the preparation of the corresponding carboxylic acid from the corresponding amino alcohol, 4-methoxy-2,6-dimethylbenzene-1-sulfonyl chloride being prepared analogously to the process described for Example 167 (except that 2 eq. of chlorosulfonic acid were used).

| Example No. | Amine (R$^5$R$^6$NH) | Yield (%) | MS, m/z (MH$^+$) |
|---|---|---|---|
| 200 | 6-Fluoro-2-(piperidin-4-yl)-1,2,3,4-tetrahydroisoquinoline | 50 | 588.2 |
| 211* | 2-(piperidin-4-yl)-1,2,3,4-tetrahydropyrrolo[1,2-a]pyrazine | 11 | 559.3 |
| 217 | 3-(piperidin-4-yl)pyridine | 50 | 516.2 |

*The reaction was carried out in N,N-dimethylformamide instead of dichloromethane.

Preparation of the Amines

6-Fluoro-2-(piperidin-4-yl)-1,2,3,4-tetrahydroisoquinoline

Used in the Synthesis of Example Compound 200

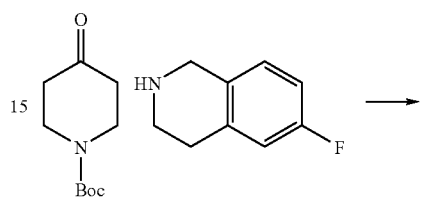

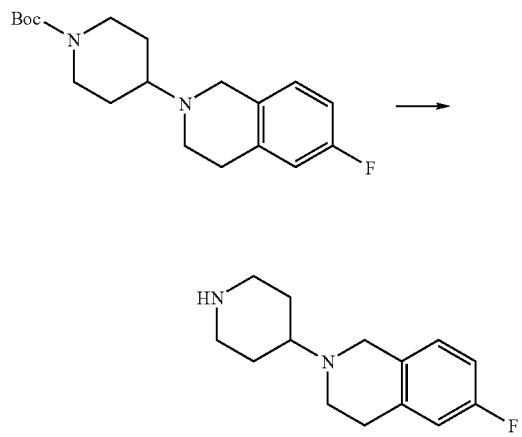

Step (i): To a solution of tent-butyl 4-oxopiperidine-1-carboxylate (3.12 mmol) and 6-fluoro-1,2,3,4-tetrahydroisoquinoline (2.6 mmol) in methanol (15 ml) there was added, under nitrogen, at 25° C., a catalytic amount of acetic acid followed by sodium cyanoborohydride (2.5 eq.). The resulting solution was stirred for 16 h at that temperature until the reaction was complete (TLC monitoring). Ice was added to the reaction mixture, and concentration in vacuo was then carried out. The residue was taken up in dichloromethane (100 ml) and washed with saturated sodium bicarbonate solution and with saturated sodium chloride solution. The organic phase was dried (Na$_2$SO$_4$), filtered, and concentrated in vacuo. The crude product so obtained was used directly in the following synthesis step. Yield: 50%.

Step (ii): Trifluoroacetic acid (13 eq.) was added at 0° C. to a solution of tert-butyl 4-(6-fluoro-3,4-dihydroisoquinolin-2 (1H)-yl)piperidine-1-carboxylate (1 eq.) in dichloromethane (10 ml/mmol), and the reaction mixture was then stirred for 2 h at 25° C. The solvent was removed, and the crude product was dried in vacuo. The amine so obtained was reacted further without being purified.

2-(piperidin-4-yl)-1,2,3,4-tetrahydropyrrolo[1,2-a]
pyrazine

Used in the Synthesis of Example Compound 211

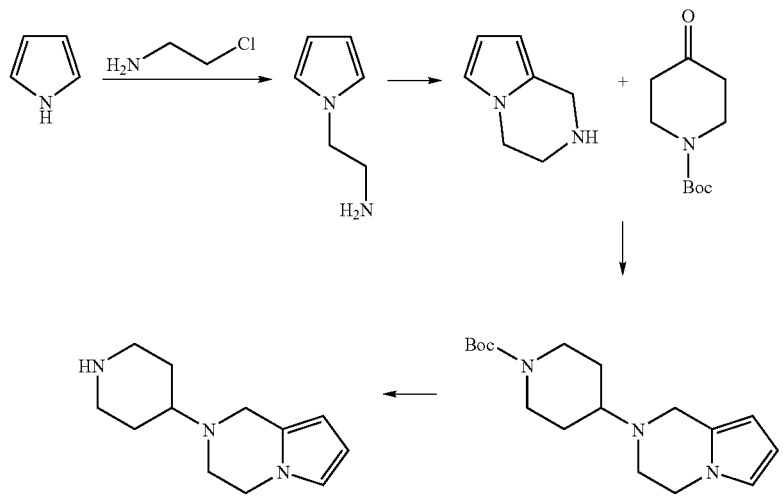

Step (i): Sodium hydroxide (9.4 g, 0.23 mol; powder) and tetrabutylammonium hydrogen sulfate (0.8 g, 2.36 mmol) were added to a solution of 1H-pyrrole (4 g, 0.06 mol) in acetonitrile (33 ml). The mixture was stirred for 30 min. at 25° C., and then 2-chloroethylamine hydrochloride (8.2 g, 0.07 mol) was added. The reaction mixture was refluxed for 24 h, the solid was filtered off, and the filtrate was concentrated in vacuo. The crude product was purified by distillation in vacuo. Yield: 30%

Step (ii): Trifluoroacetic acid (0.5 ml) was added to a solution of 1-(2-aminoethyl)pyrrole (9 mmol) and 37% aqueous formaldehyde solution (9 mmol) in ethanol (20 ml), and the resulting reaction mixture was stirred for 15 min. at 50° C. It was then cooled to 25° C. and stirred for a further 4 h at that temperature. The solvent was removed in vacuo, and the residue was taken up in ethyl acetate, rendered basic with aqueous sodium carbonate solution. The organic phase was dried ($Na_2SO_4$) and concentrated. The crude product was used in the next synthesis step without being purified further. Yield: 40%.

Step (iii): To a solution of 4-oxo-piperidine-1-carboxylic acid tert-butyl ester (4.68 mmol) and 1,2,3,4-tetrahydro-pyrrolo[1,2-a]pyrazine (3.9 mmol) in methanol (15 ml) there was added, under nitrogen, at 25° C., a catalytic amount of acetic acid, followed by sodium cyanoborohydride (2.5 eq.). The resulting solution was stirred for 16 h at that temperature until the reaction was complete (TLC monitoring). Ice was added to the reaction mixture, and then concentration in vacuo was carried out. The residue was taken up in dichloromethane (100 ml) and washed with saturated sodium bicarbonate solution and with saturated sodium chloride solution. The organic phase was dried ($Na_2SO_4$), filtered, and concentrated in vacuo. The crude product so obtained was used directly in the following synthesis step. Yield: 40%.

Step (iv): A solution of tert-butyl 4-(6-fluoro-3,4-dihydroisoquinolin-2(1H)-yl)piperidine-1-carboxylate (1.8 mmol) and hydrogen chloride in ethyl acetate (30 ml, saturated solution) was stirred for 2 h at room temperature until the reaction was complete (TLC monitoring). The solvent was removed, and the crude product was dried in vacuo. The amine so obtained was used in the next synthesis step without being purified further.

3-(piperidin-4-yl)pyridine

Used in the Synthesis of Example Compound 217

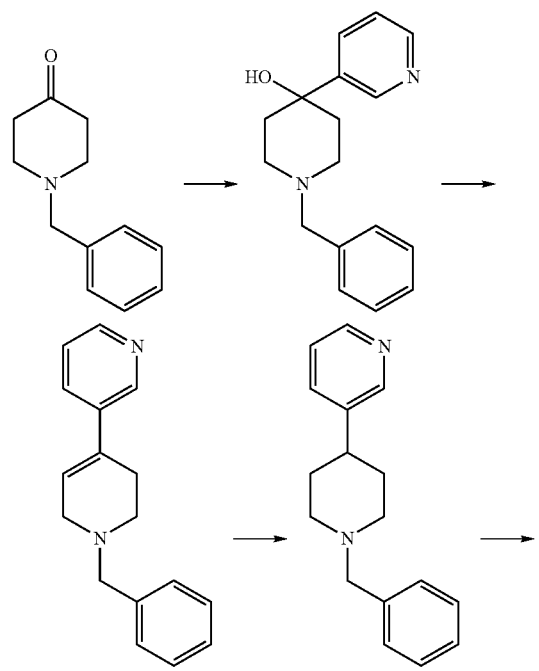

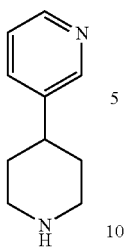

Step (i): n-butyllithium (2 eq.) was added dropwise over a period of 2 hours at −78° C. to a solution of 3-bromopyridine (1 eq.) in dry tetrahydrofuran (250 ml). The reaction mixture was then stirred for 1 h at −78° C. N-benzyl-piperidone (3 g, in 50 ml of tetrahydrofuran) was slowly added dropwise to the solution over a period of 30 min. at −78° C. The reaction mixture was stirred for 1 h at −78° C., and the progress of the reaction was monitored by thin-layer chromatography. When the reaction was complete, water was added and extraction with ethyl acetate (3×100 ml) was carried out. The combined organic phases were dried (Na$_2$SO$_4$), filtered, and concentrated in vacuo. The crude product was purified by column chromatography (4% methanol in dichloromethane). Yield: 20%.

Step (ii): 80% sulfuric acid was added dropwise at 0° C. to a solution of 1-benzyl-4-(pyridin-3-yl)piperidin-4-ol (1 g) in methanol (10 ml). The reaction mixture was maintained for 4 d at 90° C., and the progress of the reaction was monitored by thin-layer chromatography. When the reaction was complete, excess methanol was removed and the mixture was then adjusted to pH 14 by addition of sodium hydroxide solution and extracted with dichloro-methane (4×100 ml). The organic phase was dried (Na$_2$SO$_4$), filtered, and concentrated in vacuo. The crude product so obtained was used directly in the next synthesis step. Yield: quantitative.

Step (iii): 10% Pd/C (600 mg) was added, under argon, to a solution of 3-(1-benzyl-1,2,3,6-tetrahydropyridin-4-yl)pyridine (950 mg) in methanol (10 ml), and the resulting mixture was stirred for 16 h at 23° C. under a hydrogen atmosphere. The progress of the reaction was monitored by LC-MS analysis and, when the reaction was complete, the mixture was filtered over Celite and washed with methanol. The filtrate was concentrated in vacuo, and the crude product was used directly in the next synthesis step. Yield: quantitative Step (iv): To a solution of 3-(1-benzylpiperidin-4-yl)pyridine (650 mg) in methanol (10 ml) there was added, under argon, Pd(OH)$_2$ (600 mg), followed by a catalytic amount of acetic acid. The resulting mixture was stirred for 16 h at 23° C. under a hydrogen atmosphere. The progress of the reaction was monitored by LC-MS analysis and, when the reaction was complete, the mixture was filtered over Celite and washed with methanol. The filtrate was concentrated in vacuo, and the crude product was used directly in the following synthesis step. Yield: quantitative Example 215

2-((1-(4-methoxy-2,6-dimethylphenylsulfonyl)piperidin-2-yl)methoxy)-1-(6-(4-methyl-piperazin-1-yl)-3,4-dihydroisoquinolin-2(1H)-yl)ethanone

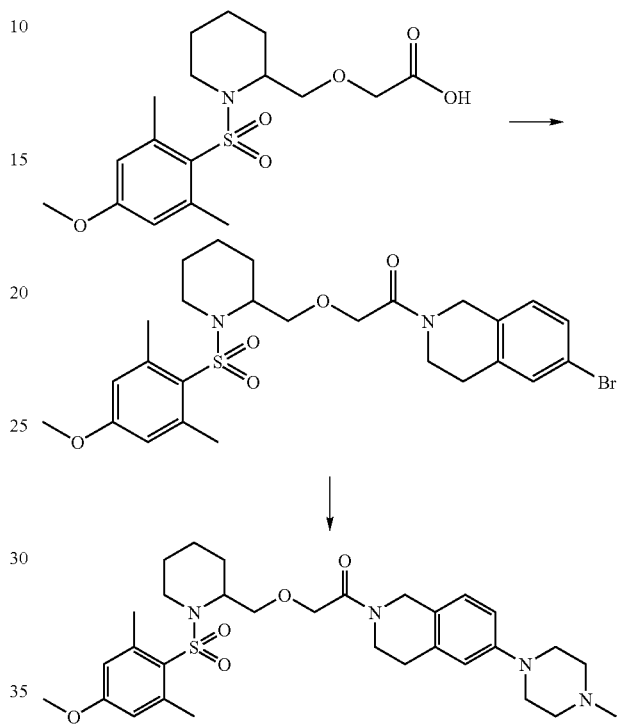

Step (i): To a solution of the acid structural unit S27 (1.5 g) in dichloromethane (5 ml/mmol) there was added at 0° C. diisopropylethylamine (2.5 eq.), followed by N-hydroxybenzotriazole (HOBt) (1 eq.) and N-ethyl-N'-(3-dimethylaminopropyl)carbodiimide hydrochloride (EDCI) (1.5 eq.). The resulting reaction mixture was stirred for 15 min. at 23° C. It was then cooled to 0° C., and 6-bromo-1,2,3,4-tetrahydroisoquinoline (1.2 eq., dissolved in dichloromethane) was added dropwise. The reaction mixture was stirred for 16 h at 25° C. until the reaction was complete. The mixture was diluted with dichloromethane (100 ml) and extracted with saturated ammonium chloride solution, saturated sodium chloride solution, saturated sodium hydrogen carbonate solution and again with saturated sodium chloride solution. The organic phase was dried (Na$_2$SO$_4$) and concentrated in vacuo. The crude product was purified by column chromatography (5% ethyl acetate in dichloromethane). Yield: 80%

Step (ii): Cesium carbonate (2.5 eq.) was added to a solution of N-methylpiperazine (3.6 mmol) and 1-(6-bromo-3,4-dihydroisoquinolin-2(1H)-yl)-2-((1-(4-methoxy-2,6-dimethylphenylsulfonyl)piperidin-2-yl)methoxy)ethanone (3 mmol) in dioxane (20 ml), and the resulting solution was degassed for 30 min. with argon. Xanthphos (2 mmol), followed by palladium tris(dibenzylideneacetone)dipalladium (0.15 mmol) were then added, under argon, and the mixture was heated for 16 h at 120° C. The progress of the reaction was monitored by thin-layer chromatography. The reaction mixture was filtered and washed with ethyl acetate, and the filtrate was concentrated in vacuo. The crude product was taken up in dichloromethane and washed with water and saturated sodium chloride solution. The organic phase was dried (Na$_2$SO$_4$), filtered, and concentrated in vacuo. The product was purified by column chromatography (4% methanol in dichloromethane). Yield: 10%; MS, m/z 585.3 (MH$^+$).

Preparation of substituted 2-((1-(4-methoxy-2,6-dimethylphenylsulfonyl)-1,2,3,4-tetrahydroquinolin-2-yl)methoxy)acetic acid derivatives Step (iii): Tetrabutylammonium chloride (0.33 eq.) and 35% sodium hydroxide solution (3 ml) were added at 0° C. to a cold solution of (1-(4-methoxy-2,6-dimethylphenylsulfonyl)-1,2,3,4-tetrahydroquinolin-2-yl)methanol (0.47 mmol) in toluene (3 ml). tert-butyl bromoacetate (1.5 eq.) was added dropwise at 0° C. to this cold reaction mixture. The mixture was then stirred for 90 min. at 25° C. until the reaction was complete (TLC monitoring). The mixture was extracted with ethyl acetate (50 ml), and the organic phase was washed with water until the pH value was neutral. Extraction with saturated sodium chloride solution was then carried out, and the organic phase was dried (Na$_2$SO$_4$) and concentrated in vacuo.

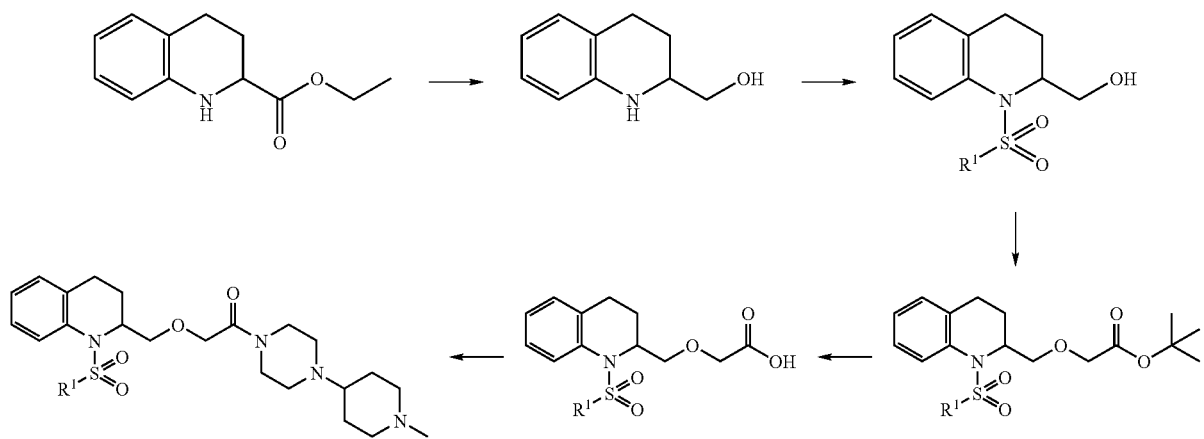

Example 202

2-((1-(4-methoxy-2,6-dimethylphenylsulfonyl)-1,2,3,4-tetrahydroquinolin-2-yl)methoxy)-1-(4-(1-methylpiperidin-4-yl)piperazin-1-yl)ethanone Step (i): 1,2,3,4-tetrahydroquinoline-2-carboxylic acid ethyl ester (25 mmol) in tetrahydrofuran (5 ml/mol) was added dropwise at 0° C. to a suspension of lithium aluminium hydride (2 eq.) in tetrahydrofuran (50 ml). The reaction mixture was stirred for 1 h at 25° C. and then refluxed for 4 h. The progress of the reaction was monitored by thin-layer chromatography. Saturated sodium sulfate solution was added to the reaction mixture, and the mixture was then filtered over Celite and washed with ethyl acetate. The filtrate was concentrated in vacuo and the crude product was purified by column chromatography (3:7 ethyl acetate/hexane). Yield: 50%

Step (ii): To a solution of (1,2,3,4-tetrahydro-quinolin-2-yl)-methanol (0.67 mmol) in dichloromethane (5 ml) there was added at 0° C. pyridine (5 eq.) followed by a catalytic amount of dimethylaminopyridine (0.01 eq.). 4-methoxy-2,6-dimethyl-benzenesulfonyl chloride (1.2 eq.) in dichloromethane (2 ml) was then added dropwise. The reaction mixture was stirred for 1 h at 25° C. until the reaction was complete (TLC monitoring) and then diluted with dichloromethane (50 ml) and washed with saturated copper sulfate solution (4×15 ml) and saturated sodium chloride solution. The organic phase was dried (Na$_2$SO$_4$), filtered, and concentrated in vacuo. The crude product was purified by column chromatography (5% ethyl acetate in dichloromethane).
[4-methoxy-2,6-dimethylbenzene-1-sulfonyl chloride was prepared analogously to the process described for Example 167 (except that 2 eq. of chlorosulfonic acid were used).]
Yield: 75%

The crude product was purified by column chromatography (20% ethyl acetate in hexane). Yield: 66%

Step (iv): Trifluoroacetic acid (13 eq.) was added at 0° C. to a solution of tert-butyl 2-((1-(4-methoxy-2,6-dimethylphenylsulfonyl)-1,2,3,4-tetrahydroquinolin-2-yl)methoxy)acetate (1 eq.) in dichloormethane (10 ml/mmol), and the mixture was stirred for 2 h at 25° C. The reaction mixture was then concentrated in vacuo, and the crude product was used in the next synthesis step without being purified further.

Step (v): To a solution of 2-((1-(4-methoxy-2,6-dimethylphenylsulfonyl)-1,2,3,4-tetrahydro-quinolin-2-yl)methoxy)acetic acid (1 eq.) in dichloromethane (5 ml/mmol) there was added at 0° C. diisopropylethylamine (2.5 eq.), followed by N-hydroxybenzotriazole (HOBt) (1 eq.) and N-ethyl-N'-(3-dimethylaminopropyl)carbodiimide hydrochloride (EDCI) (1.5 eq.). The resulting reaction mixture was stirred for 15 min. at 25° C. It was then cooled to 0° C., and 1-(1-methylpiperidin-4-yl)piperazine (1.2 eq.) was added. The reaction mixture was stirred for 16 h at 25° C. until the reaction was complete. It was diluted with dichloromethane (30 ml) and extracted with saturated ammonium chloride solution, saturated sodium chloride solution, saturated sodium hydrogen carbonate solution and again with saturated sodium chloride solution. The organic phase was dried (Na$_2$SO$_4$) and concentrated in vacuo. The crude product was purified by column chromatography (2% methanol in dichloromethane). Yield: 60%; MS, m/z 585.3 (MH$^+$)

The example compounds listed in the following table were prepared from the corresponding sulfonyl chlorides closely following the process described for Example 202 (step (v)).

| Example No. | Sulfonyl chloride (R¹SO₂Cl) | Yield (%) (over 5 steps) | MS, m/z (MH⁺) |
|---|---|---|---|
| 203 | Naphthalene-2-sulfonyl chloride | 18 | 577.2 |
| 204 | 4-methoxybenzene-1-sulfonyl chloride | 10 | 557.2 |

Example 210

2-((1-(6-methoxynaphthalen-2-ylsulfonyl)piperidin-2-yl)methoxy)-1-(4-(1-methyl-piperidin-4-yl)piperazin-1-yl)ethanone

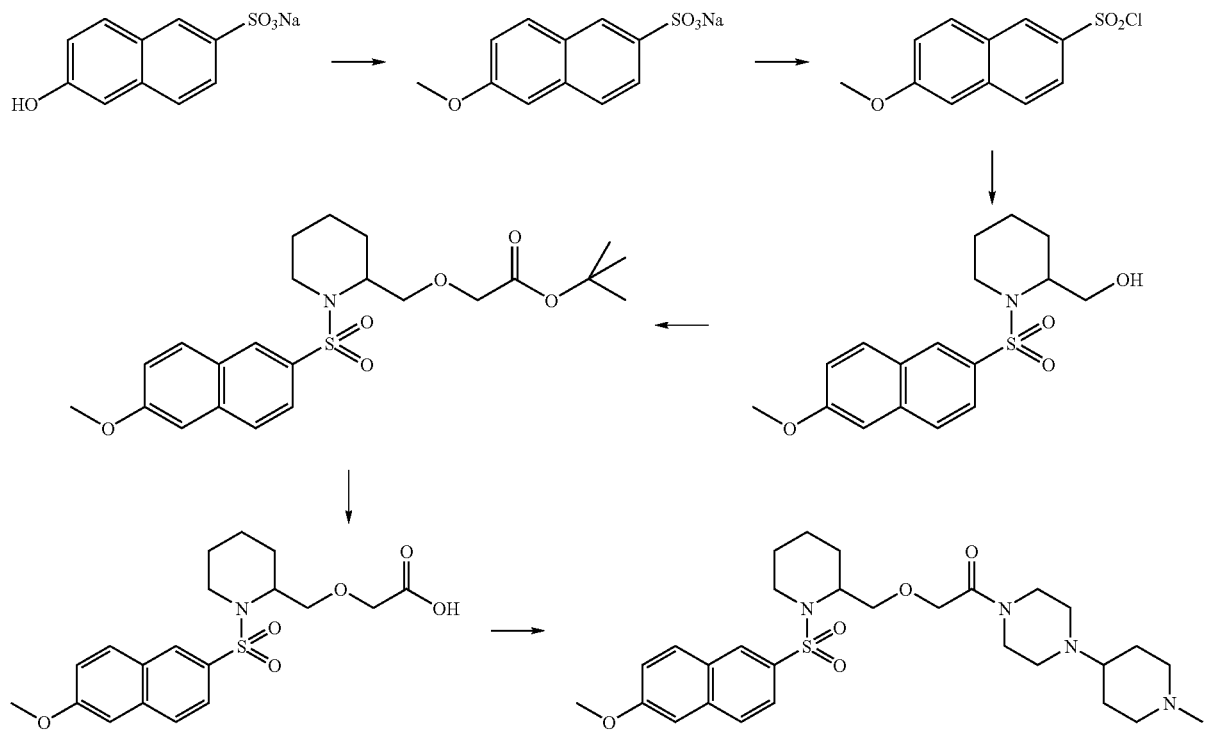

Step (i): Sodium hydroxide (0.7 g) was added to a solution of sodium 6-hydroxynaphthalene-2-sulfonate (9 mmol) in water (20 ml). To this solution there was added over a period of 1 h at 50-55° C. dimethyl sulfate (1.1 eq.), followed by sodium chloride (3.3 g). The solid was filtered off and washed with saturated sodium chloride solution and toluene. The crude product was then dried. Yield: 75%.

Step (ii): Thionyl chloride (0.25 ml) was added at 0° C., under nitrogen, to a solution of sodium 6-methoxynaphthalene-2-sulfonate (2 mmol) in dry N,N-dimethylformamide (1 ml). The reaction mixture was stirred for 3 h at 0° C., and then ice-water (20 ml) was added thereto. The solid was filtered off and washed with cold water. The solid was then taken up in dichloromethane (25 ml), dried (Na₂SO₄) and concentrated in vacuo. Yield: 75%

Step (iii): Triethylamine (2.5 eq.) was added to a cold solution of piperidin-2-ylmethanol (1.5 mmol) in dichloromethane (10 ml). A solution of 6-methoxynaphthalene-2-sulfonyl chloride (1.5 mmol) in dichloromethane (5 ml) was then added dropwise, and the mixture was stirred for 90 min. at 25° C. until the reaction was complete (TLC monitoring). Dichloromethane (100 ml) was added to the reaction mixture, and extraction with water was carried out. The organic phase was dried (Na₂SO₄) and concentrated in vacuo. The crude product was purified by column chromatography (5% methanol in dichloromethane). Yield: 50%

Step (iv): Tetrabutylammonium chloride (0.33 eq.) and 35% sodium hydroxide solution (4.5 ml) were added at 0° C. to a cold solution of (1-(6-methoxynaphthalen-2-ylsulfonyl)-piperidin-2-yl)methanol (0.75 mmol) in toluene (4.5 ml). tert-butyl bromoacetate (1.5 eq.) was added dropwise at 0° C. to this cold reaction mixture. The mixture was then stirred for 90 min. at 25° C. until the reaction was complete (TLC monitoring). The mixture was extracted with ethyl acetate (100 ml), and the organic phase was washed with water until the pH value was neutral. Extraction with saturated sodium chloride solution was then carried out, and the organic phase was dried (Na₂SO₄) and concentrated in vacuo. The crude product was purified by column chromatography (50% ethyl acetate in hexane). Yield: 90%.

Step (v): Trifluoroacetic acid (13 eq.) was added at 0° C. to a solution of tert-butyl 2-((1-(6-methoxynaphthalen-2-ylsulfonyl)piperidin-2-yl)methoxy)acetate (1 eq.) in dichloromethane (10 ml/mmol), and the mixture was stirred for 2 h at 25° C. The reaction mixture was then concentrated in vacuo, and the crude product was used in the following synthesis step without being purified further.

Step (vi): To a solution of 2-((1-(6-methoxynaphthalen-2-ylsulfonyl)piperidin-2-yl)methoxy)-acetic acid (1 eq.) in dichloromethane (5 ml/mmol) there was added at 0° C. diisopropylethylamine (2.5 eq.), followed by N-hydroxybenzotriazole (HOBt) (1 eq.) and N-ethyl-N'-(3-dimethylaminopropyl)carbodiimide hydrochloride (EDCI) (1.5 eq.). The resulting reaction mixture was stirred for 15 min. at 25° C. It was then cooled to 0° C., and 1-(1-methylpiperidin-4-yl)

piperazine (1.2 eq.) was added. The reaction mixture was stirred for 16 h at 25° C. until the reaction was complete. It was diluted with dichloromethane (100 ml) and extracted with saturated ammonium chloride solution, saturated sodium chloride solution, saturated sodium hydrogen carbonate solution and again with saturated sodium chloride solution. The organic phase was dried ($Na_2SO_4$) and concentrated in vacuo. The crude product was purified by column chromatography (2% methanol in dichloromethane). Yield: 50%; MS, m/z 559.3 ($MH^+$)

Examples 121-126 and 148-150

Reaction Scheme (about 3.25 ml/mmol) is added at room temperature. The reaction mixture is stirred at room temperature until the tert-butyl ester has reacted completely (TLC monitoring) and is then concentrated to dryness in vacuo. Finally, toluene is added 3 times to the residue, and concentration to dryness is carried out.

AAV 4: Amine Coupling

The corresponding carboxylic acid (1 equivalent) is dissolved in dichloromethane (about 8 ml/mmol); 1,1'-carbonyldiimidazole (about 1.05 equivalents) is added, and stirring is carried out for 1 hour at room temperature. The corresponding amine (1 equivalent), dissolved in dichloromethane (about 8 ml/mmol), is then added, and the reaction mixture is

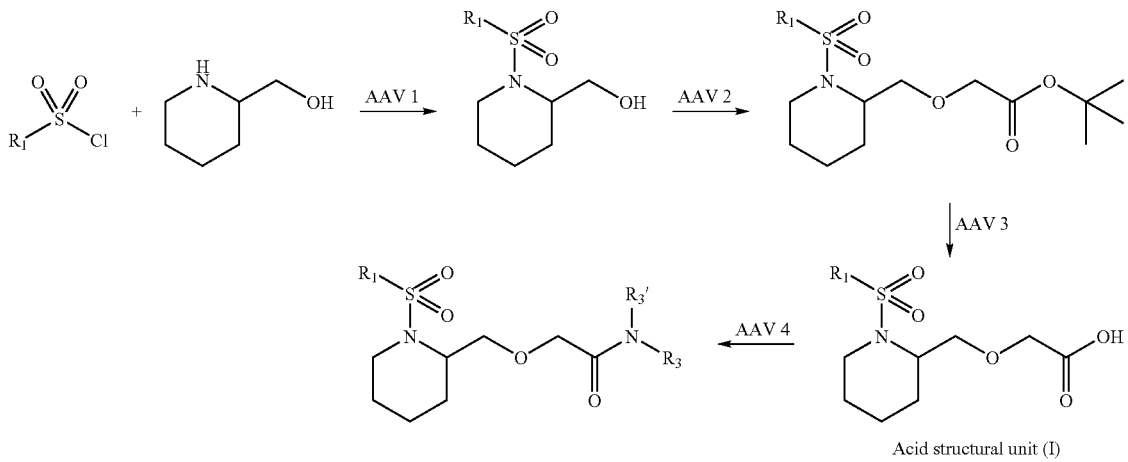

Acid structural unit (I)

AAV 1: Sulfonylation

Five equivalents of the corresponding amino alcohol are dissolved in dichloromethane (about 1.5 ml/mmol), and the corresponding sulfonyl chloride (1 equivalent) dissolved in dichloromethane (about 1.5 ml/mmol) is added at room temperature. When the sulfonyl chloride has dissolved completely (TLC monitoring), the batch is washed 3 times with 5% HCl. The organic phase is dried over sodium sulfate and concentrated to dryness in vacuo.

AAV 2: Etherification

The corresponding alcohol (1 equivalent) is dissolved in THF (about 5.5 ml/mmol) and cooled to 0° C., and sodium hydride (1.2 equivalents) is added in portions. The reaction mixture is stirred for 15 min. at 0° C. before tert-butyl bromoacetate (2.5 equivalents) is added. The reaction mixture is stirred for 16 hours at room temperature. For working up, the batch is quenched with saturated ammonium chloride solution, the aqueous phase is extracted twice with ethyl acetate, and the combined organic phases are washed with saturated sodium hydrogen carbonate solution and saturated sodium chloride solution. The organic phase is dried over sodium sulfate and concentrated to dryness in vacuo, and the residue is purified by column chromatography.

AAV 3: Tert-Butyl Ester Cleavage

The corresponding tert-butyl ester is dissolved in dichloromethane (about 15 ml/mmol), and trifluoroacetic acid stirred for 16 hours at room temperature. For working up, the batch is washed 3 times with saturated ammonium chloride solution and 3× with saturated sodium hydrogen carbonate solution, the organic phase is dried over sodium sulfate, and finally concentration to dryness in vacuo is carried out.

Acid Structural Units (I)

AAV 1-AAV 3

(Ia) 2-((1-(4-bromophenylsulfonyl)piperidin-2-yl)methoxy)acetic acid

According to AAV 1, 4-bromobenzene-1-sulfonyl chloride (58.7 mmol) was reacted with 2-(hydroxymethyl)-piperidine in 77% yield to form (1-(4-bromophenylsulfonyl)piperidin-2-yl)-methanol. This was reacted further according to AAV2, yielding tert-butyl 2-((1-(4-bromo-phenylsulfonyl)piperidin-2-yl)methoxy)acetate in a yield of 38% (17.3 mmol). Finally, tert-butyl ester cleavage according to AAV 3 yielded 2-((1-(4-bromophenylsulfonyl)piperidin-2-yl)methoxy)acetic acid without losses.

(Ib) 2-((1-(3-bromophenylsulfonyl)piperidin-2-yl)methoxy)acetic acid

According to AAV 1, 3-bromobenzene-1-sulfonyl chloride (58.7 mmol) was reacted with 2-(hydroxymethyl)-piperidine in 80% yield to form (1-(4-bromophenylsulfonyl)piperidin-2-yl)-methanol. This was reacted further according to AAV2, yielding tert-butyl 2-((1-(3-bromo-phenylsulfonyl)piperidin- 2-yl)methoxy)acetate in a yield of 31% (14.9 mmol). Finally, tert-butyl ester cleavage according to AAV 3 yielded 2-((1-(3-bromophenylsulfonyl)piperidin-2-yl)methoxy)acetic acid without losses.

(Ic) (1-(4-bromo-2,6-dimethylphenylsulfonyl)piperidin-2-yl)methanol 4-bromo-2,6-dimethylbenzene-1-sulfonyl chloride: A solution of 42 g of sodium nitrite in 150 ml of water is added to a mixture, cooled to −5° C., of 200 ml of 48% HBr and 50 g of 3,5-dimethylaniline. The reaction mixture is stirred for 1 hour at from −5° C. to 0° C. Finally, this reaction mixture is slowly added to a mixture, heated to 80° C., of 88.3 g of copper(I) bromide and 150 ml of 48% HBr. The reaction mixture is stirred for 2 hours at 80° C. and observed by TLC monitoring (silica; hexane). When the reaction is complete, the product is obtained by water-vapour distillation and is purified by column chromatography (silica; hexane). In this manner, 1-bromo-3,5-dimethylbenzene was obtained in a yield of 60% (30 g).

The bromide obtained above, dissolved in 150 ml of dichloromethane, was added dropwise at 0° C., in the course of 20 minutes, to 90 ml of chlorosulfonic acid. When the addition is complete, stirring is carried out for 1 hour at room temperature. The progress of the reaction is monitored by means of TLC (hexane). When the reaction is complete, the reaction mixture is agitated on ice and extracted 3× with dichloromethane (200 ml each time). The combined organic phases are dried over $Na_2SO_4$, concentrated in vacuo and purified by column chromatography (silica; hexane). The desired 4-bromo-2,6-dimethylbenzene-1-sulfonyl chloride was obtained in a yield of 65% (29.8 g).

(1-(4-bromo-2,6-dimethylphenylsulfonyl)piperidin-2-yl) methanol: Potassium carbonate is added to a solution of (1-(4-bromo-2,6-dimethylphenylsulfonyl)piperidin-2-yl) methanol (22.5 g) in dichloromethane (290 ml), and the mixture is cooled to 0° C. A suspension of the hydrochloride of piperidin-2-ylmethanol (39 g, commercially available, CAS No.: 3433372) in dichloromethane (300 ml) was added to the sulfonyl chloride suspension in the course of 45 minutes at 0° C. When the addition was complete, the reaction mixture was stirred for 12 hours at room temperature. The progress of the reaction was monitored by thin-layer chromatography (silica; 10% EtOAc/heptane). When the reaction was complete, filtration was carried out, followed by washing with water and drying over $Na_2SO_4$. The solvent was removed in vacuo, and the crude product was purified by column chromatography (silica; 10% EtOAc/hexane). (1-(4-bromo-2,6-dimethylphenylsulfonyl)piperidin-2-yl)methanol was obtained in a yield of 61.2% (30 g).

tert-butyl 2-((1-(4-bromo-2,6-dimethylphenylsulfonyl)piperidin-2-yl)methoxy)acetate 180 ml of 50% sodium hydroxy solution and 180 ml of tert-butyl bromoacetate were added to a solution of 18 g of (1-(4-bromo-2,6-dimethylphenylsulfonyl)piperidin-2-yl) methanol, and stirring was carried for 10 minutes. 1.815 g of tetra-n-butylammonium hydrogen sulfate were then added, and stirring was carried out for a further 45 minutes at room temperature. The progress of the reaction was monitored by thin-layer chromatography (20% EtOAc/hexane). When the reaction was complete, 400 ml of ethyl acetate were added, and the phases were separated. The organic phase was washed with saturated sodium chloride solution, dried over sodium sulfate and concentrated in vacuo. The crude product was purified by column chromatography (silica; 5% EtOAc/hexane). tert-butyl 2-((1-(4-bromo-2,6-dimethylphenylsulfonyl) piperidin-2-yl)methoxy)acetate was obtained in a yield of 78.2% (18 g).

The tert-butyl ester cleavage of 40 g of 2-((1-(4-bromo-2, 6-dimethylphenylsulfonyl)-piperidin-2-yl)methoxy)acetate according to AAV 3 resulted in 2-((1-(4-bromo-2,6-dimethylphenylsulfonyl)piperidin-2-yl)methoxy)acetic acid in a yield of 76%.

Example No. 121

2-((1-(3-bromophenylsulfonyl)piperidin-2-yl)methoxy)-1-(4-(1-methylpiperidin-4-yl)-piperazin-1-yl) ethanone Acid structural unit (Ib) (6.4 mmol) was reacted according to AAV4 with 1-(1-methyl-4-piperidinyl)piperazine. The desired product was obtained in a yield of 57%. HPLC-MS, m/z 557.2 ($MH^+$)

Example No. 122

2-((1-(3-bromophenylsulfonyl)piperidin-2-yl)methoxy)-1-(4-(pyridin-4-yl)piperazin-1-yl)ethanone Acid structural unit (Ib) (4 mmol) was reacted according to AAV4 with 1-(4-pyridyl)piperazine. The desired product was obtained in a yield of 97%. HPLC-MS, m/z 537.1 ($MH^+$)

Example No. 123

2-((1-(4-bromophenylsulfonyl)piperidin-2-yl)methoxy)-1-(4-(1-methylpiperidin-4-yl)-piperazin-1-yl) ethanone Acid structural unit (Ia) (7.6 mmol) was reacted according to AAV4 with 1-(1-methyl-4-piperidinyl)piperazine. The desired product was obtained in a yield of 73%. HPLC-MS, m/z 557.2 ($MH^+$)

Example No. 124

2-((1-(3-bromophenylsulfonyl)piperidin-2-yl)methoxy)-1-(4-(2-(pyrrolidin-1-Methyl)-piperidin-1-yl) ethanone Acid structural unit (Ib) (5 mmol) was reacted according to AAV4 with 4-(2-pyrrolidinoethyl)piperidine. The desired product was obtained in a yield of 69%. HPLC-MS, m/z 556.2 ($MH^+$)

Example No. 125

2-((1-(4-bromophenylsulfonyl)piperidin-2-yl)methoxy)-1-(4-(2-(pyrrolidin-1-yl)ethyl)-piperidin-1-yl) ethanone Acid structural unit (Ia) (7.6 mmol) was reacted according to AAV4 with 4-(2-pyrrolidinoethyl)piperidine. The desired product was obtained in a yield of 71%. HPLC-MS, m/z 556.2 ($MH^+$)

Example No. 126

2-((1-(4-bromophenylsulfonyl)piperidin-2-yl)methoxy)-1-(4-(pyridin-4-yl)piperazin-1-yl)ethanone Acid structural unit (Ia) (5 mmol) was reacted according to AAV4 with 1-(4-pyridyl)piperazine. The desired product was obtained in a yield of 70%. HPLC-MS, m/z 537.1 (MH⁺)

Example No. 148

2-((1-(4-bromo-2,6-dimethylphenylsulfonyl)piperidin-2-yl)methoxy)-1-(4-(1-methyl-piperidin-4-yl)piperazin-1-yl)ethanone Acid structural unit (Ic) (7.1 mmol) was reacted according to AAV4 with 1-(1-methyl-4-piperidinyl)piperazine. The desired product was obtained in a yield of 70%. HPLC-MS, m/z 585.1 (MH⁺)

Example No. 149

2-((1-(4-bromo-2,6-dimethylphenylsulfonyl)piperidin-2-yl)methoxy)-1-(4-(2-(pyrrolidin-1-yl)ethyl)piperidin-1-yl)ethanone Acid structural unit (Ic) (7.1 mmol) was reacted according to AAV4 with 4-(2-pyrrolidionoethyl)-piperidine. The desired product was obtained in a yield of 70%. HPLC-MS, m/z 584.0 (MH⁺)

Example No. 150

2-((1-(4-bromo-2,6-dimethylphenylsulfonyl)piperidin-2-yl)methoxy)-1-(4-(pyridin-4-yl)-piperazin-1-yl)ethanone Acid structural unit (Ic) (7.1 mmol) was reacted according to AAV4 with 1-(4-pyridyl)piperazine. The desired product was obtained in a yield of 79%. HPLC-MS, m/z 565.0 (MH⁺)

Preparation of the Sulfonyl Chlorides

Preparation of 2-methylnaphthalene-1-sulfonyl chloride

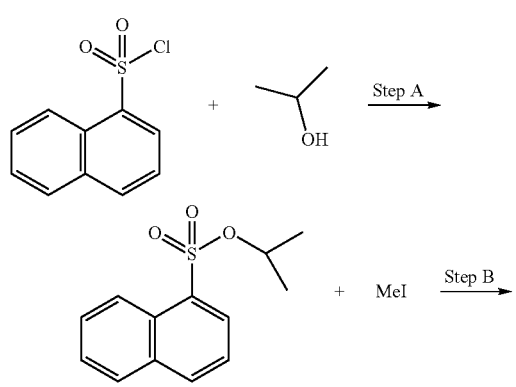

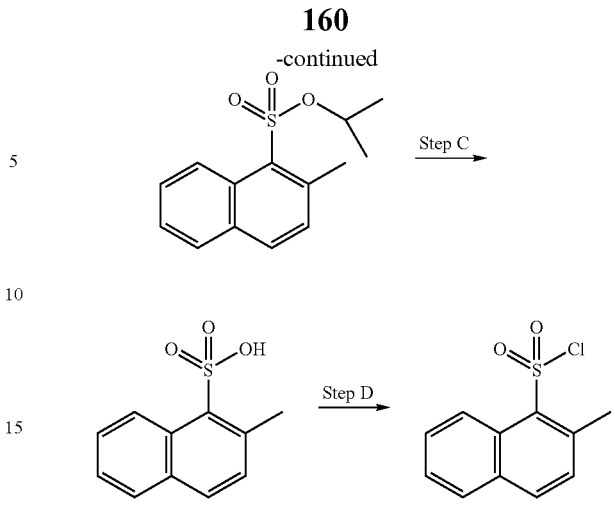

Step A:

Commercially available 1-naphthylsulfonyl chloride (21.5 g) was added in portions at −5° C. to a mixture of 2-propanol (7.3 ml) and pyridine (25 ml). The reaction mixture was stirred for 15 h at 0° C. For working up, DCM (75 ml) and 1 M HCl (75 ml) were added at that temperature, and the organic phase was separated off. The aqueous phase was extracted with DCM (3×75 ml), and the combined organic phases were washed with 1 M HCl (2×50 ml) and sat. NaCl solution (50 ml). After drying over MgSO₄, complete concentration was carried out and the desired product was obtained in the required purity. 22.8 g, 96%.

Step B:

The title compound from step A (18.6 g) was dissolved in THF (190 ml), and the mixture was cooled to −78° C. under a protecting gas atmosphere. Then 1.6 M n-BuLi in n-hexane (51 ml) was added sufficiently slowly that the temperature did not rise above −70° C. The reaction mixture was stirred for 2 h at −70° C., and then MeI (9.7 ml) was added. The reaction mixture was allowed to warm to 0° C. and was stirred for 3 h at that temperature. For working up, sat. NH₄Cl (80 ml) was added at that temperature, and then the mixture was diluted with EtOAc (500 ml). The organic phase was separated off and the aqueous phase was extracted with EtOAc (2×120 ml), and the combined organic phases were washed with water (50 ml) and sat. NaCl solution (50 ml). After drying over MgSO₄, complete concentration was carried out, and the residue was purified by column chromatography on silica gel (hexane/EtOAc). The desired product was obtained. 12.4 g, 63%.

Step C:

The title compound from step B (0.8 g) was suspended in 4 M HCl (31 ml), and the mixture was heated for 1-2 h at 110° C. It was then cooled to room temperature over a period of 15 h and concentrated completely; the residue obtained after coevaporation twice with DCM (2×30 ml) was dried under a high vacuum. The product so obtained was used in the next step without being purified further. 0.47 g, 70%.

Step D:

The title compound from step C (0.46 g) was suspended in toluene (2.2 ml), and SOCl₂ (0.75 ml) and DMF (0.010 ml) were added to the resulting mixture. Heating was then carried out for 1 h at 90° C. until a solution was present. The solution was concentrated completely, and the residue was dried under a high vacuum. The product so obtained was used in the next step without being purified further.

Preparation of 2-chloronaphthalene-1-sulfonic acid

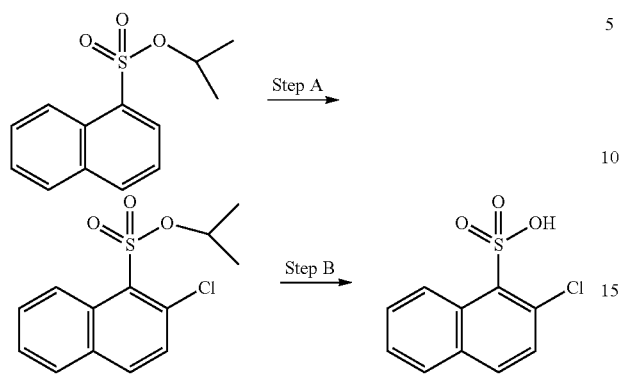

Step A:
The title compound from the preparation of 2-methylnaphthalene-1-sulfonyl chloride, step A (20 g) was dissolved in THF (213 ml), and the mixture was cooled to −78° C. under a protecting gas atmosphere. Then 1.6 M n-BuLi in n-hexane (55 ml) was added sufficiently slowly that the temperature did not rise above −70° C. The reaction mixture was stirred for 2 h at −70° C., and then hexachloroethane (21 g) was added. The reaction mixture was allowed to warm to 0° C. and was stirred for 15 h at that temperature. For working up, sat. NH$_4$Cl (100 ml) was added at that temperature, and then the mixture was diluted with EtOAc (350 ml). The organic phase was separated off and the aqueous phase was extracted with EtOAc (2×120 ml), and the combined organic phases were washed with water (50 ml) and sat. NaCl solution (50 ml). After drying over MgSO$_4$, complete concentration was carried out, and the residue was purified by column chromatography on silica gel (hexane/EtOAc). The desired product was obtained. 19.8 g, 87%.

Step B:
The title compound from step A (3 g) was dissolved in EtOH (15.4 ml), and TFA (0.04 ml) was added. The resulting solution was refluxed for 5 h. After cooling, the mixture was concentrated and the residue was dissolved in DCM (20 ml) and washed with water (10 ml). After drying over MgSO$_4$, complete concentration was carried out. The resulting product was used in the next step without being purified further. 2.2 g, 87%.

Preparation of 4-methoxynaphthalene-1-sulfonic acid

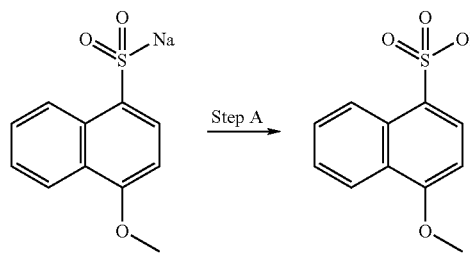

Step A:
Commercially available sodium 4-methoxynaphthyl-1-sulfonate (2.5 g) was added at RT to a mixture of water (5.2 ml) and conc. HCl (22 ml). The mixture was extracted several times with MeOH/EtOAc 1:15 (a total of 400 ml), and the combined organic phases were washed with sat. NaCl solution (50 ml). After drying over MgSO$_4$, complete concentration was carried out. The resulting product was used in the next step without being purified further. 1.2 g, 52%.

The preparation of the following examples was carried out closely following the process described for 2-methylnaphthalene-1-sulfonyl chloride, except that the sulfonic acids mentioned in the following table were used.

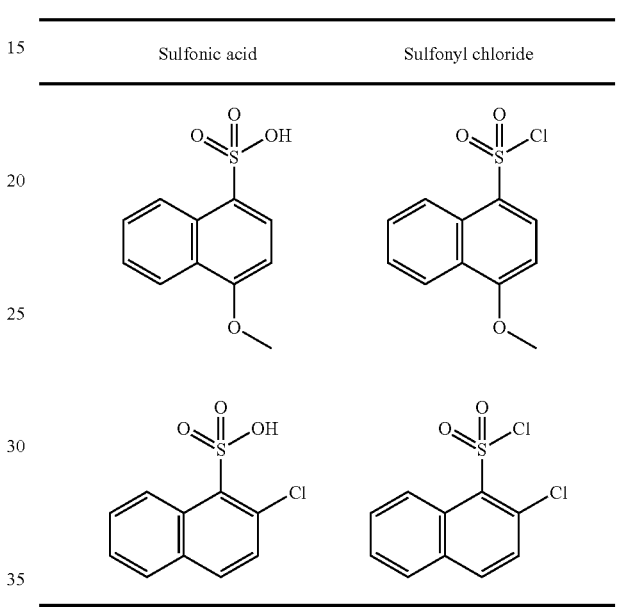

| Sulfonic acid | Sulfonyl chloride |
| --- | --- |

Example 179

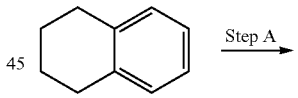

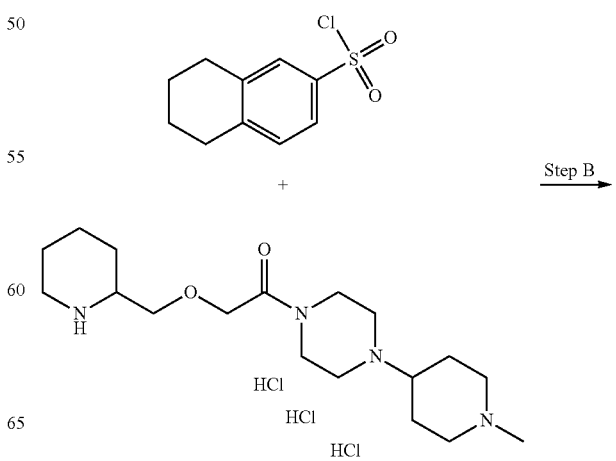

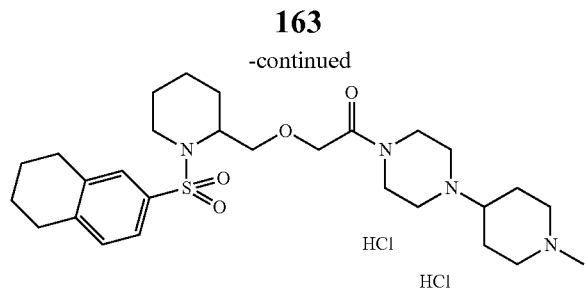

Step A:
Commercially available 1,2,3,4-tetrahydronaphthalene (50 ml) was placed in chloroform (110 ml). At from −5 to −10° C., chlorosulfonic acid (73 ml) was added dropwise, with stirring, in the course of 30 min. The cooling was removed, and the solution was heated to RT in the course of 1 h. The reaction solution was poured onto ice, and the organic phase was separated off. The aqueous phase is extracted with DCM/MeOH 9:1 (3×150 ml), and the combined organic phases are washed with ice-water (2×50 ml). After drying over MgSO$_4$, complete concentration was carried out, and the residue was purified by column chromatography on silica gel (hexane/EtOAc). The desired product is obtained. 8.4 g, 10%.

Step B:
The title compound from Example 107, step 4 (1.0 g) was placed in DCM (19 ml); cooling to 0° C. was carried out, and Et$_3$N (1.8 ml) was added. The title compound from step A (0.5 g) was then added rapidly at that temperature. Stirring was carried out at RT until TLC monitoring indicated that the reaction was complete. For working up, NH$_4$Cl solution (10 ml) and water (10 ml) were added, and the organic phase was separated off. The aqueous phase was extracted with DCM (3×15 ml), and the combined organic phases were washed with water (10 ml) and sat. NaCl solution (10 ml). After drying over MgSO$_4$, complete concentration was carried out, and the residue was purified by column chromatography on silica gel (DCM/MeOH/NH$_3$). 638 mg of the base were obtained, which was precipitated from acetone (10 ml)/ether (10 ml) by addition of H$_2$O (21 µl) and TMSCI (302 µl). 598 mg, 46%, 533 (MH$^+$).

Examples 157, 160, 173-176 and 191 were prepared closely following the process described for Example 179, except that the sulfonyl chlorides and amines mentioned in the following table were used. The preparation of sulfonyl chlorides that are not commercially available was carried out as described above.

| No. | Sulfonyl chloride | Amine | Yield (%) | MS (MH+) |
|---|---|---|---|---|
| 157 | | | 8 | 543 |
| 191 | | | 27 | 563 |
| 174 | | | 30 | 559 |

-continued

| No. | Sulfonyl chloride | Amine | Yield (%) | MS (MH+) |
|---|---|---|---|---|
| 176 | | · HCl · HCl · HCl | 57 | 530 |
| 175 | | · HCl · HCl · HCl | 3 | 530 |
| 173 | | · HCl · HCl · HCl | 61 | 547 |
| 160 | | · HCl · HCl · HCl | 69 | 627 |

Example 192

Preparation of 2-((1-(4-methoxy-2,6-dimethylphenylsulfonyl)pyrrolidin-2-yl)methoxy)-1-(4-(1-methylpiperidin-4-yl)piperazin-1-yl)ethanone

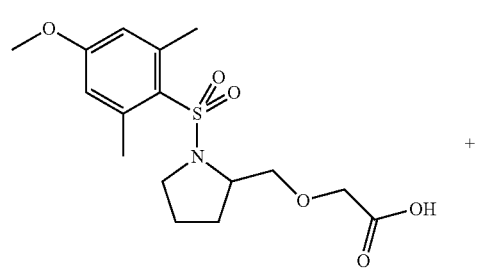

+

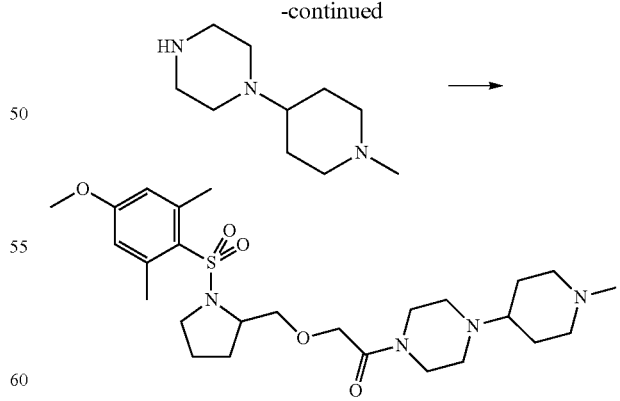

A suspension of the acid (500 mg, 1.4 mmol), amine (256 mg, 1.4 mmol) and HOAt (19 mg, 0.14 mmol) in $CH_2Cl_2$ (10 ml) was cooled to 0° C. After addition of EDCI (296 mg, 1.54 mmol), the reaction mixture was stirred for 30 min. at 0° C. and overnight at RT under a nitrogen atmosphere. After addition of CH$_2$Cl$_2$ (20 ml), the organic phase was extracted with aqueous saturated NaHCO$_3$ solution (30 ml), and then the aqueous phase was separated off and extracted with CH$_2$Cl$_2$ (15 ml). The combined organic phases were dried over Na$_2$SO$_4$. After filtration and removal of the solvent in vacuo, the product was purified by column chromatography (silica, CH$_2$Cl$_2$/(7 M NH$_3$ in methanol) 4/6-93/7). Yield: 331 mg, 45%.

Example 208

Preparation of 2-((1-(4-methoxy-2,6-dimethylphenylsulfonyl)piperidin-2-yl)methoxy)-1-(3-(pyridin-3-ylmethyl)pyrrolidin-1-yl)ethanone

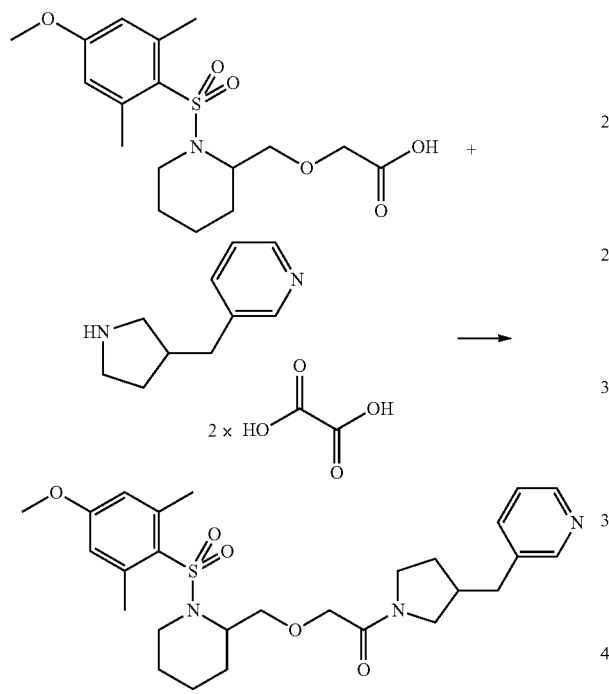

EDCI (402 mg, 2.1 mmol) was added to a solution of the acid (520 mg, 1.4 mmol), 3-(pyrrolidin-3-ylmethyl)pyridine dioxalate (527 mg, 1.54 mmol), HOAt (28.6 mg, 0.21 mmol) and DIPEA (0.98 ml, 5.6 mmol) in CH$_2$Cl$_2$ (10 ml), and the mixture was stirred overnight at RT. After removal of the solvent in vacuo, the product was purified by column chromatography (silica, CH$_2$Cl$_2$/(7 M NH$_3$ in methanol), 99/1-96/4). Yield: 378 mg, 52%

Example 206

Preparation of 2-((1-(4-methoxy-2,6-dimethylphenylsulfonyl)piperidin-2-yl)methoxy)-1-(1H-pyrrolo[3,4-c]pyridin-2(3H)-yl)ethanone

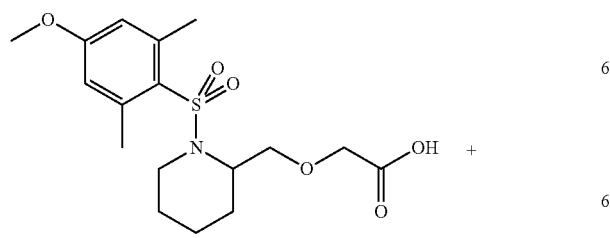

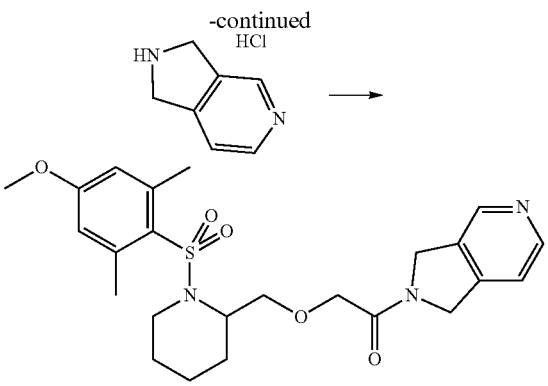

EDCI (486 mg, 2.53 mmol) was added to a solution of the acid (627 mg, 1.69 mmol), 2,3-dihydro-1H-pyrrolo[3,4-c]pyridine hydrochloride (291 mg, 1.86 mmol), HOAt (34.5 mg, 0.25 mmol) and DIPEA (0.89 ml, 5.07 mmol) in CH$_2$Cl$_2$ (10 ml), and the mixture was stirred overnight at RT. After removal of the solvent in vacuo, the product was purified by column chromatography (silica, CH$_2$Cl$_2$/(7 M NH$_3$ in methanol), 99/1-97/3). Yield: 481 mg, 60%

Example 207

Preparation of 2-((1-(4-methoxy-2,6-dimethylphenylsulfonyl)piperidin-2-yl)methoxy)-1-(2-(pyridin-3-yl)morpholino)ethanone

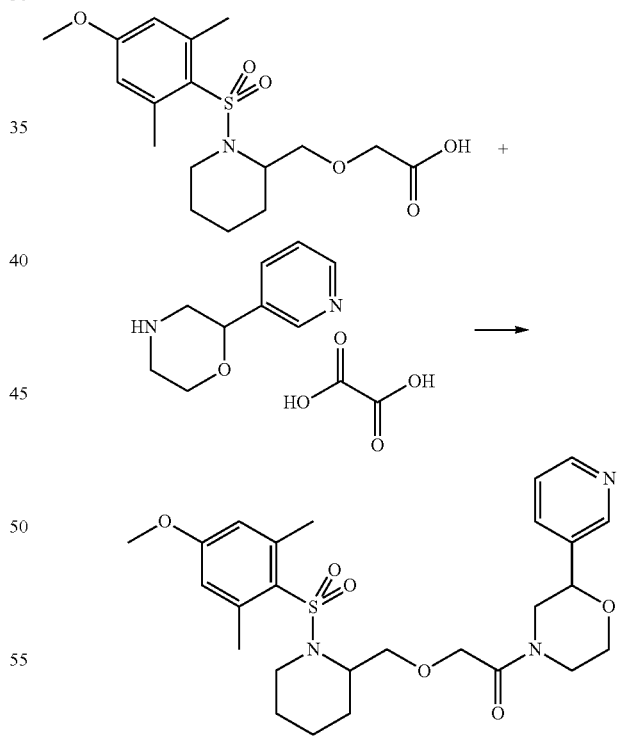

EDCI (497 mg, 2.59 mmol) was added to a solution of the acid (642 mg, 1.73 mmol), 2-(pyridin-3-yl)morpholine oxalate (483 mg, 1.90 mmol), HOAt (35.3 mg, 0.26 mmol) and DIPEA (0.91 ml, 5.18 mmol) in CH$_2$Cl$_2$ (10 ml), and the mixture was stirred overnight at RT. After removal of the solvent in vacuo, the product was purified by column chromatography (silica, CH$_2$Cl$_2$/(7 M NH$_3$ in methanol), 99/1-96/4). Yield: 453 mg, 51%

Example 205

Preparation of 2-((1-(4-methoxy-2,6-dimethylphenylsulfonyl)piperidin-2-yl)methoxy)-N-(2-(pyrazin-2-yloxy)benzyl)acetamide

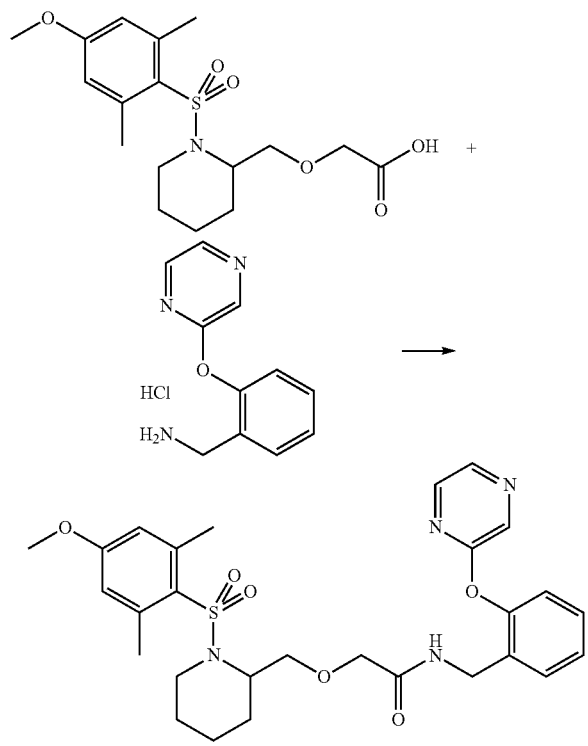

EDCI (580 mg, 3.02 mmol) was added to a solution of the acid (749 mg, 2.02 mmol), (2-(pyrazin-2-yloxy)phenyl)methanamine hydrochloride (527 mg, 2.22 mmol), HOAt (41.2 mg, 0.30 mmol) and DIPEA (1.06 ml, 6.05 mmol) in CH$_2$Cl$_2$ (10 ml), and the mixture was stirred overnight at RT. After removal of the solvent in vacuo, the product was purified by column chromatography (silica, CH$_2$Cl$_2$/(7 M NH$_3$ in methanol), 99/1-97/3). Yield: 977 mg, 87%

Example 196

Preparation of 2-((1-(4-methoxy-2,6-dimethylphenylsulfonyl)piperidin-2-yl)methoxy)-N-(4-(pyrazin-2-yloxy)benzyl)acetamide Preparation of 2-((1-(4-methoxy-2,6-dimethylphenylsulfonyl)piperidin-2-yl)methoxy)acetyl chloride

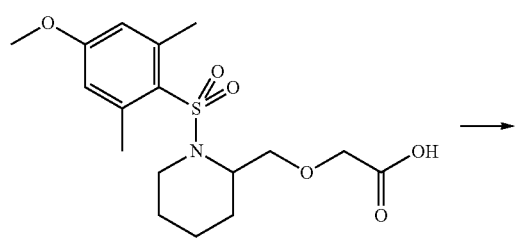

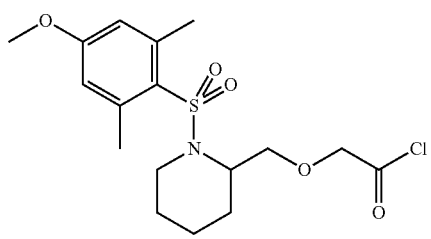

Oxalyl chloride (3.68 ml, 42.8 mmol) and a catalytic amount of DMF were added to a solution of the acid (5.3 g, 14.3 mmol) in CH$_2$Cl$_2$ (100 ml), and the mixture was stirred overnight at RT. After removal of the solvent in vacuo, the residue was coevaporated with CH$_2$Cl$_2$ (3×50 ml). Yield: 5.38 g, 96%

Preparation of 2-((1-(4-methoxy-2,6-dimethylphenylsulfonyl)piperidin-2-yl)methoxy)-N-(4-(pyrazin-2-yloxy)benzyl)acetamide

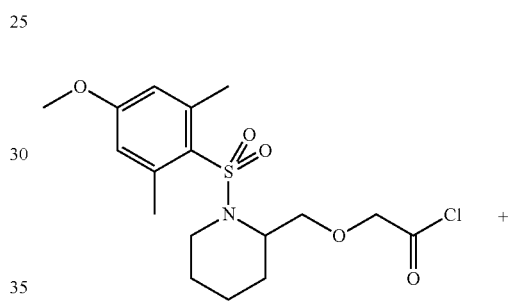

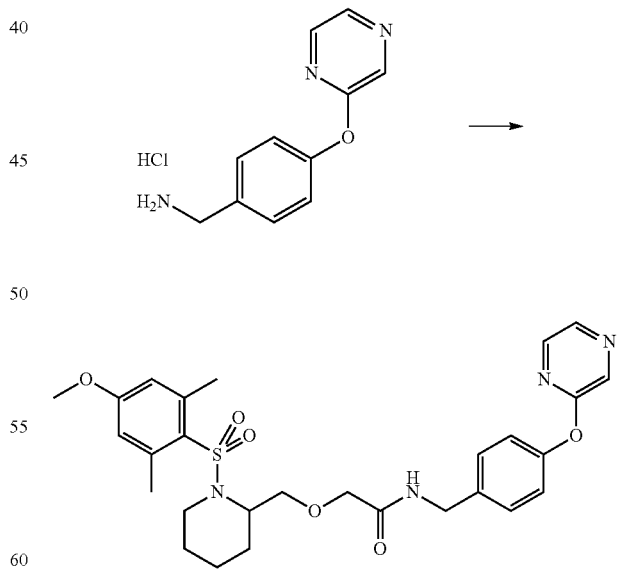

4-(pyrazin-2-yloxy)-benzylamine hydrochloride (439 mg, 1.85 mmol) was added to a solution of the acid chloride (600 mg, 1.54 mmol) and Et$_3$N (535 µl, 3.85 mmol) in CH$_2$Cl$_2$ (10 ml). The reaction mixture was stirred for 4 h at RT. The solvent was then removed in vacuo. The product was purified by column chromatography (silica, CH$_2$Cl$_2$/(7 M NH$_3$ in methanol), 95/5). Yield: 468 mg, 55%

Example 195

Preparation of 2-((1-(4-methoxy-2,6-dimethylphenylsulfonyl)piperidin-2-yl)methoxy)-N-(3-(pyrazin-2-yloxy)benzyl)acetamide

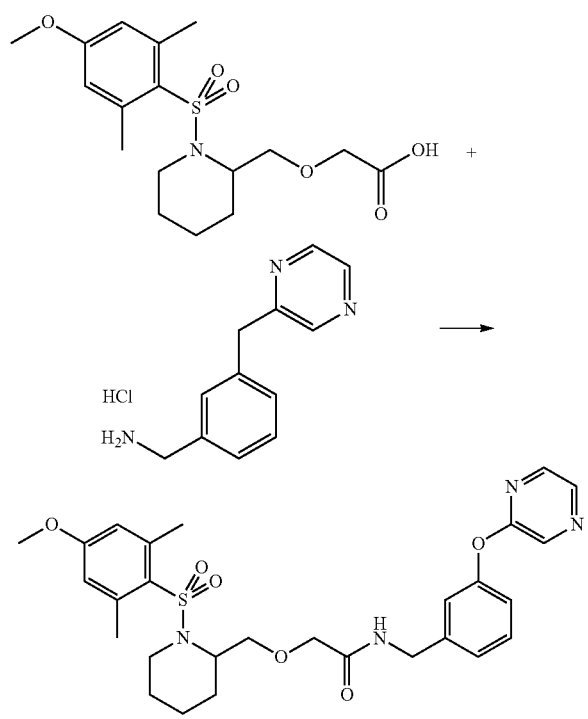

EDCI (387 mg, 2.0 mmol) was added at 0° C. to a solution of the acid (500 mg, 1.35 mmol), (3-(pyrazin-2-yloxy)phenyl)methanamine hydrochloride (320 mg, 1.35 mmol), HOAt (27.5 mg, 0.20 mmol) and DIPEA (705 μl, 4.1 mmol) in CH$_2$Cl$_2$ (10 ml), and the mixture was stirred for 30 min. at 0° C. and overnight at RT. After removal of the solvent in vacuo, the product was purified by column chromatography (silica, CH$_2$Cl$_2$/(7 M NH$_3$ in methanol), 99/1-95/5). Yield: 412 mg, 55%

Example 193

Preparation of N-(4-(4,5-dihydro-1H-imidazol-2-yl)benzyl)-2-((1-(4-methoxy-2,6-dimethylphenylsulfonyl)piperidin-2-yl)methoxy)-N-methylacetamide hydrochloride

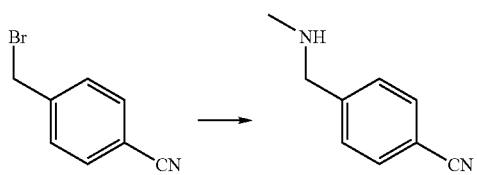

Methylamine (350 ml of a 40% aqueous solution, 4.06 mol) was added to a solution of 4-(bromomethyl)benzonitrile (51.3 g, 262 mmol) in EtOH (500 ml). After 2 h, the solvent was removed in vacuo and CH$_2$Cl$_2$ (500 ml) and aqueous saturated NaHCO$_3$ solution (400 ml) were added. The organic phase was separated off and extracted with aqueous saturated NaCl solution (250 ml), over Na$_2$SO$_4$, and the solvent was removed after filtration in vacuo. The residue was taken up in 1 M HCl in Et$_2$O (300 ml) and stirred for 30 min., then filtered off and washed with Et$_2$O. The residue was taken up in H$_2$O (500 ml), rendered basic with aqueous 6 M NaOH and extracted with CH$_2$Cl$_2$ (500 ml). The organic phase was dried over Na$_2$SO$_4$ and filtered off, and the solvent was removed in vacuo. Yield: 31.17 g, 81%

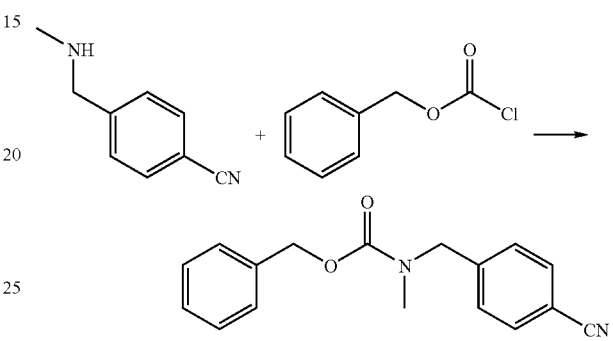

Et$_3$N (35.96 ml, 256 mmol) was added to a solution of the amine (31.17 g, 213 mmol) in CH$_2$Cl$_2$ (150 ml). Benzyl chloroformate (36.37 ml, 256 mmol) in CH$_2$Cl$_2$ (50 ml) was then added dropwise at a temperature of 0° C. The reaction mixture was stirred overnight at RT and washed with aqueous 0.1 M HCl (150 ml) and H$_2$O (150 ml), dried over Na$_2$SO$_4$ and filtered out, and the solvent was removed in vacuo.

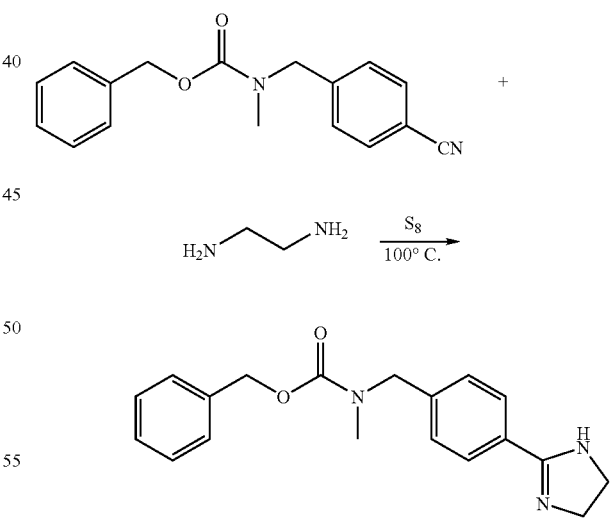

Sulfur (3.41 g, 107 mmol) was added to a reaction mixture of the carbamate (62.1 g, max. 213 mmol) and ethylenediamine (192 ml, 2.87 mol), and stirring was carried out for 2 h at 100° C. After cooling to RT, H$_2$O (250 ml) was added, and extraction with ethyl acetate (2×250 ml) was carried out. The combined organic phases were extracted with H$_2$O (250 ml) and dried over Na$_2$SO$_4$, and the solvent was removed after filtration in vacuo. Yield: 67.6 g, 98%

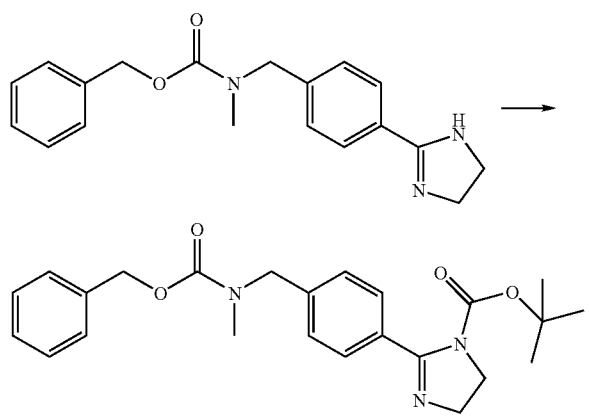

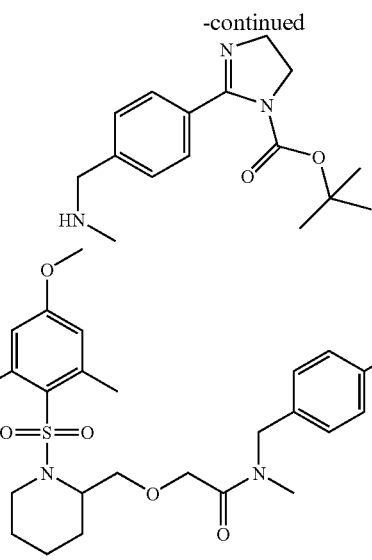

A solution of (Boc)₂O (50.2 g, 230 mmol) in CH₂Cl₂ (500 ml) was added dropwise to a solution of the imidazoline (67.6 g, 209 mmol) and DMAP (28.1 g, 230 mmol) in CH₂Cl₂ (500 ml), and stirring was carried out overnight at RT. 0.5 M HCl (300 ml) and H₂O (300 ml) were then added. The organic phase was separated off and dried over Na₂SO₄. After filtration, the solvent was removed in vacuo and product was purified by column chromatography (silica, CH₂Cl₂/MeOH, 98:2). Yield: 50.7 g, 57%

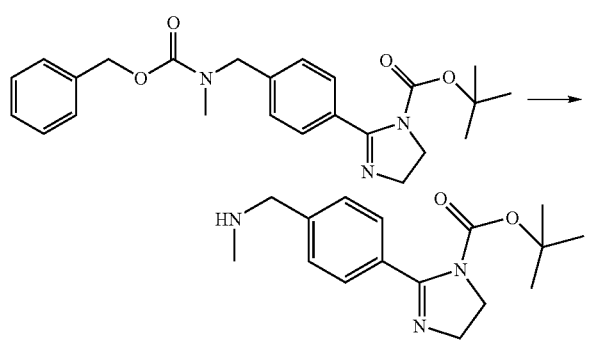

The Boc-protected imidazoline (3.03 g, 7.15 mmol) was dissolved in absolute EtOH (60 ml) and hydrogenated under nitrogen for 10 min. with Pd/C (10%, 381 mg, 0.36 mmol) and hydrogen. After stirring for 2 h at RT, filtration over kieselguhr was carried out, followed by washing with EtOH. After removal of the solvent in vacuo, the product was used in the next step without being worked up further.

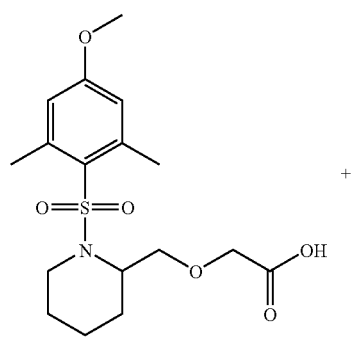

+

A reaction mixture of the carboxylic acid (683 mg, 1.84 mmol), amine (2.10 g, 1.93 mmol), DIPEA (608 μl, 3.68 mmol) and HOAt (38 mg, 0.28 mmol) in CH₂Cl₂ (100 ml) was cooled to 0° C. EDCI (388 mg, 2.02 mmol) was then added, and stirring was carried out overnight at RT. After addition of aqueous saturated NaCl solution (25 ml), the aqueous phase was separated off and extracted with CH₂Cl₂ (25 ml). The combined organic phases were dried over Na₂SO₄ and, after filtration, the solvent was removed in vacuo. Purification was carried out by column chromatography (silica, CH₂Cl₂/MeOH, 95:5). Yield: 750 mg, 63%

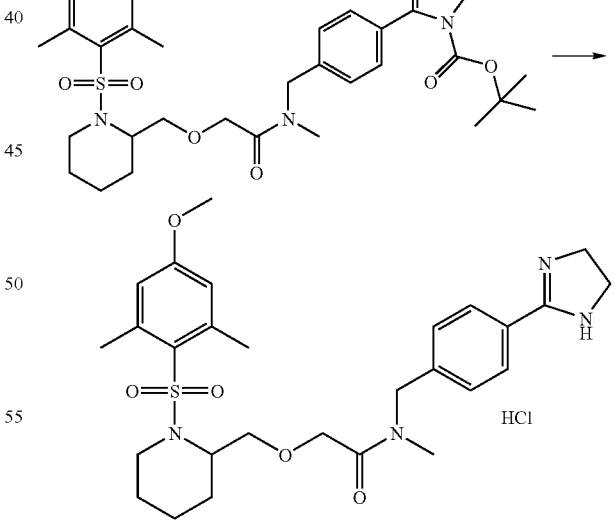

TFA (4.3 ml, 58 mmol) was added to a solution of the Boc-protected derivative (750 mg, 1.16 mmol) in CH₂Cl₂ (10 ml), and stirring was carried out for 4 h at RT. The solvent was removed in vacuo, and the residue was dissolved in CH₂Cl₂ (20 ml) and washed with aqueous saturated NaHCO₃ solution (25 ml). The organic phase was separated off, dried over Na₂SO₄ and filtered off, and the solvent was removed in vacuo. The product was purified by column chromatography (silica, $CH_2Cl_2$/MeOH/$Et_3N$, 95:5:2). The free amine was stirred for 1 h in 1 M HCl in $Et_2O$ (10 ml), and the solvent was removed in vacuo. The product was obtained in the form of the hydrochloride in a yield of 641 mg, 95%.

Pharmacological Studies

Functional Study on the Bradykinin Receptor 1 (B1R)

The agonistic or antagonistic action of substances can be determined on the bradykinin receptor 1 (B1R) of the species human and rat using the following assay. According to this assay, the $Ca^{2+}$ influx through the channel is quantified with the aid of a $Ca^{2+}$-sensitive dye (type Fluo-4, Molecular Probes Europe BV, Leiden, Netherlands) using a Fluorescent Imaging Plate Reader (FLIPR, Molecular Devices, Sunnyvale, USA).

Method:

Chinese hamster ovary cells (CHO K1 cells) which have been stably transfected with the human B1R gene (hB1R cells, Euroscreen s.a., Gosselies, Belgium) or with the B1R gene of the rat (rB1R cells, Axxam, Milan, Italy) are used. For functional studies, the cells are plated out on black 96-well plates having a clear base (BD Biosciences, Heidelberg, Germany) in a density of 20,000-25,000 cells/well. The cells are incubated overnight at 37° C. and with 5% $CO_2$ in culture medium (hB1R cells: Nutrient Mixture Ham's F12, Gibco Invitrogen GmbH, Karlsruhe, Germany; rB1R cells: D-MEM/F12, Gibco Invitrogen GmbH, Karlsruhe, Germany), with 10 vol. % FBS (fetal bovine serum, Gibco Invitrogen GmbH, Karlsruhe, Germany). On the following day, the cells are loaded for 60 minutes at 37° C. with 2.13 µM Fluo-4 (Molecular Probes Europe BV, Leiden, Netherlands) in HBSS buffer (Hank's buffered saline solution, Gibco Invitrogen GmbH, Karlsruhe, Germany) with 2.5 M probenecid (Sigma-Aldrich, Taufkirchen, Germany) and 10 mM HEPES (Sigma-Aldrich, Taufkirchen, Germany). The plates are then washed twice with HBSS buffer, and HBSS buffer additionally containing 0.1% BSA (bovine serum albumin; Sigma-Aldrich, Taufkirchen, Germany), 5.6 mM glucose and 0.05% gelatin (Merck KGaA, Darmstadt, Germany) is added to the plates. After incubation for a further 20 minutes at room temperature, the plates are inserted into the FLIPR for $Ca^{2+}$ measurement. The $Ca^{2+}$-dependent fluorescence is measured before and after the addition of substances ($\lambda_{ex}$=488 nm, $\lambda_{em}$=540 nm). Quantification is carried out by measuring the highest fluorescence intensity (FC, fluorescence counts) over time.

FLIPR Assay:

The FLIPR protocol consists of 2 substance additions. Test substances (10 µM) are first pipetted onto the cells and the $Ca^{2+}$ influx is compared with the control (hB1R: Lys-Des-$Arg^9$-bradykinin 0.5 nM; rB1R: Des-$Arg^9$-bradykinin 100 nM). This gives the activation in %, based on the $Ca^{2+}$ signal after addition of Lys-Des-$Arg^9$-bradykinin (0.5 nM) or Des-$Arg^9$-bradykinin (100 nM).

After 10 minutes' incubation, 0.5 nM Lys-Des-$Arg^9$-bradykinin (hB1R) or 100 nM Des-$Arg^9$-bradykinin (rB1R) are applied, and the influx of $Ca^{2+}$ is likewise determined. Antagonists lead to suppression of the $Ca^{2+}$ influx. The % inhibition compared with the maximum achievable inhibition is calculated. The compounds exhibit good activity on the human and the rat receptor.

| Example | B1R Antagonism, human [10 µM] % Inhibition | B1R Antagonism, rat [10 µM] % Inhibition |
|---|---|---|
| 1 | 104.68 | 106.8 |
| 2 | 104.12 | 87.41 |
| 3 | 103.84 | 108.97 |
| 4 | 103.63 | 106.31 |
| 5 | 102.96 | 102.66 |
| 6 | 102.21 | 94.88 |
| 7 | 101.85 | 99.28 |
| 8 | 101.66 | 106.6 |
| 9 | 101.53 | 85.33 |
| 10 | 100 | 91.84 |
| 11 | 99.62 | 105.97 |
| 12 | 99.1 | 74.91 |
| 13 | 97.67 | 112.52 |
| 14 | 96.97 | 104.22 |
| 15 | 96 | 92.47 |
| 16 | 95.89 | 25.53 |
| 17 | 95.53 | 96.94 |
| 18 | 95.33 | 109.83 |
| 19 | 95.03 | 98.89 |
| 20 | 94.86 | 86.42 |
| 21 | 93.47 | 107.92 |
| 22 | 92.64 | 21.4 |
| 23 | 92.35 | 85.35 |
| 24 | 92.25 | 106.89 |
| 25 | 91.03 | 80.59 |
| 26 | 86.78 | 4.56 |
| 27 | 85.41 | 97.69 |
| 28 | 84.73 | 0 |
| 29 | 84.37 | 109.8 |
| 30 | 83.97 | 108.46 |
| 31 | 83.75 | 94.69 |
| 32 | 83.26 | 63.28 |
| 33 | 82.71 | 47.69 |
| 34 | 79.9 | 39.48 |
| 35 | 79.7 | 99 |
| 36 | 79.43 | 45.71 |
| 37 | 78.23 | 102.66 |
| 38 | 74.95 | 65.36 |
| 39 | 73.21 | 0 |
| 40 | 72.7 | 88.65 |
| 41 | 72.61 | 16.38 |
| 42 | 70.57 | 57.85 |
| 43 | 69.88 | 24.16 |
| 44 | 69.62 | 0 |
| 45 | 69.07 | 92.41 |
| 46 | 68.25 | 0 |
| 47 | 68.07 | 48.84 |
| 48 | 66.59 | 30.49 |
| 49 | 65.88 | 92.34 |
| 50 | 65.71 | 50.31 |
| 51 | 65.06 | 87.91 |
| 52 | 65.01 | 92.83 |
| 53 | 64.83 | 0 |
| 54 | 63.8 | 0 |
| 55 | 63.23 | 88.78 |
| 56 | 62.66 | 0 |
| 57 | 62.39 | 0 |
| 58 | 62.23 | 10.18 |
| 59 | 61.48 | 0 |
| 60 | 59.89 | 108.64 |
| 61 | 59.7 | 30.54 |
| 62 | 59.58 | 33.97 |
| 63 | 58.57 | 26.41 |
| 64 | 57.92 | 25.48 |
| 65 | 55.41 | 93.17 |
| 66 | 55.38 | 38.64 |
| 67 | 55.03 | 80.49 |
| 68 | 54.11 | 0 |
| 69 | 53.64 | 82.89 |
| 70 | 53.27 | 42.16 |
| 71 | 53.19 | 95.22 |
| 72 | 52.58 | 13.25 |
| 73 | 51.02 | 105.54 |
| 74 | 50.42 | 102.6 |
| 75 | 50.14 | 9.11 |
| 76 | 48.94 | 40.3 |

-continued

| Example | B1R Antagonism, human [10 μM] % Inhibition | B1R Antagonism, rat [10 μM] % Inhibition |
| --- | --- | --- |
| 77 | 47.95 | 104.71 |
| 78 | 45.73 | 35.22 |
| 79 | 45.47 | 54.49 |
| 80 | 45.26 | 22.47 |
| 81 | 44.9 | 34.14 |
| 82 | 44.86 | 4.42 |
| 83 | 43.94 | 30.77 |
| 84 | 43.73 | 0 |
| 85 | 43.69 | 40.84 |
| 86 | 43.22 | 0 |
| 87 | 42.69 | 44.38 |
| 88 | 42.06 | 7.33 |
| 89 | 41.34 | 0 |
| 90 | 49.96 | 99.55 |
| 91 | 48.78 | |
| 92 | 103.49 | 101.34 |
| 93 | 105.57 | 99.12 |
| 94 | 105.3 | 103.1 |
| 95 | 106.86 | 100.63 |
| 96 | 104.91 | 91.35 |
| 97 | 98.05 | 98.2 |
| 98 | 104.09 | 101.37 |
| 99 | 103.76 | 100.08 |
| 100 | 103.71 | 101.69 |
| 101 | 100.27 | 100.47 |
| 102 | 103.94 | 99.95 |
| 103 | 105.15 | 100.39 |
| 104 | 105.3 | 100.57 |
| 105 | 105.66 | 100.37 |
| 106 | 102.6 | 102.64 |
| 107 | 102.05 | 102.39 |
| 108 | 102.41 | 102.31 |
| 109 | 102.82 | 101.69 |
| 110 | 102.5 | 101.77 |
| 111 | 91.86 | 101.4 |
| 112 | 102.43 | 101.88 |
| 113 | 99.23 | 97.07 |
| 114 | 102.24 | 102.56 |
| 115 | 102.47 | 58.09 |
| 116 | 74.25 | 100.94 |
| 117 | 100.65 | 100.53 |
| 118 | 103.54 | 102.07 |
| 119 | 95.94 | 61.85 |
| 120 | 103.28 | 102.56 |
| 121 | 70.47 | 52.72 |
| 122 | 12.11 | 13.04 |
| 123 | 43.88 | 79.94 |
| 124 | 76.28 | 63.16 |
| 125 | 50.56 | 95.36 |
| 126 | 46.36 | 81.06 |
| 127 | 102.31 | 93.69 |
| 128 | 90.8 | 94.47 |
| 129 | 0.03 | 31.23 |
| 130 | 103.2 | 96.3 |
| 131 | 82.09 | 95.37 |
| 133 | 103.01 | 98.08 |
| 134 | 102.44 | 98.25 |
| 135 | 102.68 | 98.31 |
| 136 | 103.97 | 98.94 |
| 137 | 102.25 | 98.75 |
| 138 | 103.55 | 98.45 |
| 139 | 99.91 | 98.83 |
| 140 | 100.08 | 80.7 |
| 141 | 100.51 | 100.7 |
| 142 | 89.91 | 62.99 |
| 143 | 99.91 | 99.3 |
| 144 | 100.57 | 98.16 |
| 145 | 99.4 | 98.64 |
| 146 | 97.26 | 99.64 |
| 147 | 99.95 | 99.96 |
| 148 | 100.09 | 99.97 |
| 149 | 99.41 | 100.05 |
| 150 | 98.31 | 99.06 |
| 151 | 106.94 | 103.01 |
| 152 | 100.06 | 90.83 |
| 153 | 81.64 | 40.58 |
| 154 | 83.21 | 84.36 |
| 155 | 107.43 | 89.64 |
| 156 | 108.3 | 102.71 |
| 157 | 98.2 | 99.97 |
| 158 | 98.49 | 99.3 |
| 159 | 99.17 | 100.6 |
| 160 | 98.97 | 99.04 |
| 161 | 98.53 | 99.25 |
| 162 | 99.53 | 99.51 |
| 163 | 95.05 | 100.8 |
| 164 | 99.63 | 100.63 |
| 165 | 97.13 | 96.78 |
| 166 | 99.44 | 99.28 |
| 167 | 101.53 | 100.86 |
| 168 | 93.83 | 98.38 |
| 169 | 100.44 | 101.1 |
| 170 | 101.02 | 97.85 |
| 171 | 101.89 | 82.78 |
| 172 | 101.45 | 85.19 |
| 173 | 100.61 | 100.68 |
| 174 | 101.35 | 97.95 |
| 175 | 103.24 | 86.31 |
| 176 | −24.81 | 36.52 |
| 177 | 103.86 | 100.43 |
| 178 | 101.6 | 99.82 |
| 179 | 104.26 | 100.13 |
| 180 | 104 | 98.6 |
| 181 | 105.03 | 98.54 |
| 182 | 91.1 | 99.72 |
| 183 | 100.16 | 96.92 |
| 184 | 104.83 | 99 |
| 185 | 105.43 | 97.93 |
| 186 | 105.87 | 97.13 |
| 187 | 100.41 | 101.8 |
| 188 | 101.92 | 102.25 |
| 189 | 70.72 | 86.37 |
| 190 | 101.56 | 101.94 |
| 191 | — | — |
| 192 | 105.69 | 100.29 |
| 193 | 103.95 | 98.28 |
| 194 | 103.08 | 100.27 |
| 195 | 85.11 | 98.81 |
| 196 | 100.47 | 98.8 |
| 197 | 103.6 | 100 |
| 198 | 105.4 | 99.75 |
| 199 | 104.01 | 100.83 |
| 200 | 102.44 | 98.73 |
| 201 | 103.19 | 98.19 |
| 202 | 103.84 | 99.79 |
| 203 | 103.19 | 98.78 |
| 204 | 104.58 | 98.98 |
| 205 | 49.98 | 99.71 |
| 206 | 53.94 | 99.49 |
| 207 | 101.93 | 100.16 |
| 208 | 104.84 | 100.76 |
| 209 | 103.97 | 99.93 |
| 210 | 106.17 | 96.03 |
| 211 | 106.08 | 100.06 |
| 212 | 106.74 | 100.18 |
| 213 | 59.72 | 94.53 |
| 214 | 101.16 | 101.91 |
| 215 | 99.94 | 100.96 |
| 216 | −10.12 | 4.48 |
| 217 | — | — |
| 218 | 100.43 | — |
| 219 | 5.04 | 96.23 |
| 220 | 15.27 | 86.34 |
| 221 | 38.04 | 89.58 |
| 222 | 7.55 | 113.93 |
| 223 | 26.23 | 86.37 |
| 224 | 72.06 | 52.77 |
| 225 | 104.47 | 84.08 |
| 226 | 76.38 | 96.87 |
| 227 | 26.87 | 94.52 |
| 228 | 88.56 | 99.82 |
| 229 | 101.09 | 100.53 |

-continued

| Example | B1R Antagonism, human [10 μM] % Inhibition | B1R Antagonism, rat [10 μM] % Inhibition |
|---|---|---|
| 230 | 95.42 | 62.33 |
| 231 | 102.03 | 83.34 |
| 232 | 102.37 | 90.03 |
| 233 | 101.96 | 86.74 |
| 234 | 51.96 | 103.02 |
| 235 | 102.3 | 83.46 |
| 236 | 95.86 | 99.58 |
| 237 | 99.72 | 99.45 |
| 238 | 99.93 | 99.35 |
| 239 | 94.7 | 99.7 |
| 240 | 78.48 | 97.3 |
| 241 | 103.76 | 99.26 |
| 242 | 102.04 | 87.99 |
| 243 | 24.76 | 80.63 |
| 244 | 70.16 | 97.28 |
| 245 | 69.86 | 80.5 |
| 246 | 56.38 | 72.1 |
| 247 | 70.78 | 96.75 |
| 248 | 95.6 | 89.86 |
| 249 | 59.22 | 92.36 |
| 250 | 96.85 | 90.55 |
| 251 | 45.81 | 98.51 |
| 252 | 101.72 | 97.94 |
| 253 | 59.31 | 101.11 |
| 254 | 105.08 | 97.8 |
| 255 | 104.91 | 100.81 |
| 256 | 50.23 | 91.02 |
| 257 | 34.31 | 99.94 |
| 258 | 75.25 | 99.75 |
| 259 | 66.06 | 99.3 |
| 260 | 101.6 | 60.62 |
| 261 | 78.92 | 98.87 |
| 262 | 81.81 | 99.65 |
| 263 | 100.01 | 97.85 |
| 264 | 103.07 | 31.71 |
| 265 | 99.95 | 51.3 |
| 266 | 102.46 | 2.12 |
| 267 | 103.79 | 95.16 |
| 268 | 103.88 | 101.64 |
| 269 | 103.6 | 99 |
| 270 | 103.77 | 93.42 |
| 271 | 59.08 | 85.9 |
| 272 | 97.14 | 84.61 |
| 273 | 96.05 | 84.87 |
| 274 | 103.75 | 98.08 |
| 275 | 101.73 | 93.06 |
| 276 | 98.92 | 94.16 |
| 277 | 85.55 | 81.59 |
| 278 | 103.71 | 96.94 |
| 279 | 103.74 | 95.39 |
| 280 | 103.9 | 92.04 |
| 281 | 103.69 | 92.37 |
| 282 | 102.79 | 85.95 |
| 283 | 103.46 | 92.9 |
| 284 | 102.93 | 93.55 |
| 285 | 103.77 | 90.97 |
| 286 | 103.72 | 97.93 |
| 287 | 101.02 | 89.25 |
| 288 | 101.83 | 93.34 |
| 289 | 102.52 | 95.5 |
| 290 | 104.09 | 92.91 |
| 291 | 104.28 | 92.99 |
| 292 | 105.83 | 99.22 |
| 293 | 90.51 | −6.96 |
| 294 | 105.91 | 100 |
| 295 | 96.67 | 103.18 |
| 296 | 105.85 | 99.28 |
| 297 | 105.76 | 102.53 |
| 298 | 105.09 | 103.58 |
| 299 | 106.32 | 102.79 |
| 300 | 105.73 | 103.1 |
| 301 | 106.36 | 100.99 |
| 302 | 100.69 | 102.41 |
| 303 | 106.27 | 100.4 |
| 304 | 71.12 | 101.52 |
| 305 | 76.41 | 95.47 |

-continued

| Example | B1R Antagonism, human [10 μM] % Inhibition | B1R Antagonism, rat [10 μM] % Inhibition |
|---|---|---|
| 306 | 103.75 | 99.16 |
| 307 | 105.47 | 98.38 |
| 308 | 104.85 | 100.95 |
| 309 | 52.02 | 101.11 |
| 310 | 106.11 | 102.07 |
| 311 | 94.88 | 103.15 |
| 312 | 98.52 | 98.68 |
| 313 | 103.46 | 102.58 |
| 314 | 105.18 | 103.91 |
| 315 | 105.13 | 100.59 |
| 316 | 82.66 | 98.17 |
| 317 | 92.19 | 100.22 |
| 318 | 101.58 | 101.55 |
| 319 | 104.47 | 100.08 |
| 320 | 105.66 | 101.93 |
| 321 | 41.19 | 100.13 |
| 322 | 101.81 | 98.72 |
| 323 | 104.72 | 88.06 |
| 324 | 83.97 | 98.44 |
| 325 | 101.91 | 100.88 |
| 326 | 103.59 | 101.04 |
| 327 | 104.27 | 100.52 |
| 328 | 103.86 | 101.85 |
| 329 | 104.89 | 98.16 |
| 330 | 104.39 | 100.44 |
| 331 | 105.94 | 100.52 |
| 332 | 105.29 | 100.79 |
| 333 | 107.07 | 100.76 |
| 334 | 106.56 | 100.58 |
| 335 | 106.11 | 99.82 |
| 336 | 103.22 | 104.8 |
| 337 | 103.65 | 104.4 |
| 338 | 92.57 | 92.22 |
| 339 | 77.54 | 41.63 |
| 340 | 104.92 | 100.73 |
| 341 | 104.72 | 102.33 |
| 342 | 104.5 | 100.29 |
| 343 | 79.97 | 100.23 |
| 344 | 48.77 | 88.4 |
| 345 | 22.26 | 95.94 |
| 346 | 95.54 | 100.91 |
| 347 | 56.56 | 102.91 |
| 348 | 87.09 | 102.94 |
| 349 | 100.78 | 102.8 |
| 350 | 103.91 | 103.72 |
| 351 | 44.01 | 103.99 |
| 352 | 103.57 | 103.63 |
| 353 | 102.72 | 102.17 |
| 354 | 62.46 | 102.22 |
| 355 | 83.39 | 101.52 |
| 356 | 43.04 | 103.33 |
| 357 | 79.38 | 104.35 |
| 358 | 101.48 | 102.53 |
| 359 | 98.56 | 102.84 |
| 360 | 96.66 | 103.03 |
| 361 | 93.42 | 100.74 |
| 362 | 103.34 | 101.91 |
| 363 | 90.7 | 101.09 |
| 364 | 104.69 | 101.44 |
| 365 | 55.61 | 99.85 |
| 366 | 14.76 | 99.03 |
| 367 | 20.1 | 102.67 |
| 368 | 62.06 | 100.94 |
| 369 | 82.34 | 100.93 |
| 370 | 18.72 | 98.83 |
| 371 | 0.38 | 100.72 |
| 372 | −2.76 | 83.81 |
| 373 | 104.41 | 98.85 |
| 374 | 80.78 | 101.66 |
| 375 | 98.74 | 99.85 |
| 376 | 67.07 | 99.02 |
| 377 | 87.21 | 99.56 |
| 378 | 63.42 | 98.75 |
| 379 | 67.92 | 101.75 |
| 380 | 91.51 | 100.9 |
| 381 | 77.88 | 100.15 |

| Example | B1R Antagonism, human [10 μM] % Inhibition | B1R Antagonism, rat [10 μM] % Inhibition |
|---|---|---|
| 382 | 103.44 | 101.03 |
| 383 | 40.17 | 101.54 |
| 384 | 104.56 | 98.56 |
| 385 | 101.05 | 99.45 |
| 386 | 100.74 | 97.86 |
| 387 | 90.98 | 100.56 |
| 388 | 22.88 | 100.66 |
| 389 | 100.51 | 100.49 |
| 390 | 102.87 | 99.78 |
| 391 | 97.78 | 101.54 |
| 392 | 100.93 | 99.09 |
| 393 | 103.77 | 101.49 |
| 394 | 31.48 | 99.08 |
| 395 | 12.63 | 100.41 |
| 396 | 24.69 | 80.61 |
| 397 | 97.25 | 101.46 |
| 398 | 59.84 | 98 |
| 399 | 93.05 | 102.16 |
| 400 | 62.01 | 102.17 |
| 401 | 90.84 | 95.62 |
| 402 | 47.09 | 101.25 |
| 403 | 100.68 | 100.41 |
| 404 | 55.06 | 98.55 |
| 405 | 98.59 | 100.41 |
| 406 | 102.96 | 100.21 |
| 407 | 102.44 | 99.02 |
| 408 | 102.22 | 99.79 |
| 409 | 28.09 | 81.39 |
| 410 | 102.43 | 102.85 |
| 411 | 101.07 | 100.19 |
| 412 | 101.44 | 102.89 |
| 413 | 99.93 | 102.79 |
| 414 | 100.97 | 100.12 |
| 415 | 99.23 | 97.52 |
| 416 | 50.22 | 100.96 |
| 417 | 96.16 | 103.38 |
| 418 | 101.28 | 103.53 |
| 419 | 99.98 | 101.17 |
| 420 | 100.33 | 92.05 |
| 421 | 97.3 | 93.36 |
| 422 | 48.04 | 98.61 |
| 423 | 58.71 | 80.13 |
| 424 | 35.11 | 97.61 |
| 425 | −0.97 | 98.84 |
| 426 | −4.95 | 94.38 |
| 427 | 101.54 | 98.83 |
| 428 | 23.84 | 101.75 |
| 429 | 14.33 | 99.48 |
| 430 | 38.56 | 100.57 |
| 431 | 28.42 | 96.18 |
| 432 | 94.03 | 100.3 |
| 433 | 103.47 | 99.97 |
| 434 | 103.69 | 101.47 |
| 435 | 6.23 | 99.56 |
| 436 | 39.2 | 101.6 |
| 437 | 36.08 | 101.67 |
| 438 | 22.12 | 99.98 |
| 439 | 48.25 | 100.94 |
| 440 | 98.07 | 95.62 |
| 441 | 103.96 | 98.36 |
| 442 | 101.8 | 98.56 |
| 443 | 103.85 | 99.33 |
| 444 | 92.79 | 98.58 |
| 445 | 102.23 | 98.61 |
| 446 | 95.03 | 99.75 |
| 447 | 66.5 | 94.21 |
| 448 | 85.75 | 99.78 |
| 449 | 90.75 | 99.72 |
| 450 | 87.36 | 99.66 |
| 451 | 80.68 | 99.23 |
| 452 | 104.82 | 95.19 |
| 453 | 40.51 | 74.44 |
| 454 | 101.91 | 100.32 |
| 455 | 102.81 | 99.34 |
| 456 | 100.44 | 100.76 |
| 457 | 102 | 99.65 |
| 458 | 102.65 | 100.43 |
| 459 | 57.14 | 102.04 |
| 460 | 96.59 | 100.78 |
| 461 | 100.64 | 99.1 |
| 462 | 101.3 | 98.25 |
| 463 | 97.39 | 100.72 |
| 464 | 56.56 | 101.94 |
| 465 | 101.95 | 98.82 |
| 466 | 92.52 | 99.72 |
| 467 | 101.34 | 100.88 |
| 468 | 84.49 | 101.4 |
| 469 | 92.34 | 101.61 |
| 470 | 92.67 | 98.07 |
| 471 | 102.93 | 98.79 |
| 472 | 92.06 | 101.17 |
| 473 | 94.59 | 99.49 |
| 474 | 96.7 | 96.3 |
| 475 | 90.42 | 101.75 |
| 476 | 90.06 | 100.14 |
| 477 | 94.46 | 98.77 |
| 478 | 36.16 | 90.24 |
| 479 | 32.3 | 99.07 |
| 480 | 100.76 | 102.62 |
| 481 | 72.64 | 103.71 |
| 482 | 97.92 | 102.46 |
| 483 | 102.72 | 104.43 |
| 484 | 75.57 | 100.57 |
| 485 | 65.25 | 103.41 |
| 486 | 70.44 | 101.22 |
| 487 | 100.93 | 99.13 |
| 488 | 100.99 | 101.64 |
| 489 | 99.28 | 99.96 |
| 490 | 93.52 | 103.22 |
| 491 | 96.35 | 97.94 |
| 492 | 102.54 | 103.95 |
| 493 | 40.64 | 99.47 |
| 494 | 26.16 | 73.41 |
| 495 | 30.7 | 95.72 |
| 496 | 68.19 | 103.02 |
| 497 | 66.04 | 101.25 |
| 498 | 94.25 | 96.7 |
| 499 | 103.35 | 100.58 |
| 500 | 41.81 | 93.22 |
| 501 | 65.06 | 89.7 |
| 502 | 96.74 | 103.44 |
| 503 | 103.07 | 97.92 |
| 504 | 24.18 | 90.61 |
| 505 | 74.02 | 100.82 |
| 506 | 98.27 | 98.91 |
| 507 | −10.08 | 102.4 |
| 508 | 31.93 | 102.55 |
| 509 | 92.72 | 102.13 |
| 510 | 51.42 | 101.9 |
| 511 | 86.96 | 102.91 |
| 512 | 93.03 | 102.26 |
| 513 | 73.53 | 101.16 |
| 514 | 85.25 | 99.02 |
| 515 | 30.9 | 100.15 |
| 516 | 101.34 | 99.39 |
| 517 | 98.85 | 101.92 |
| 518 | 102.58 | 99.69 |
| 519 | 81.88 | 102.71 |
| 520 | 102.91 | 102.07 |
| 521 | 85.17 | 99.34 |
| 522 | 54.17 | 98.7 |
| 523 | 66.38 | 101.41 |
| 524 | 101.62 | 100.66 |
| 525 | 15.41 | 102.31 |
| 526 | 73.35 | 101.65 |
| 527 | 97.16 | 97.33 |
| 528 | 88.22 | 101.57 |
| 529 | 105.85 | 101.47 |
| 530 | 93.08 | 101.41 |
| 531 | 92.59 | 96.17 |
| 532 | 96.4 | 107.74 |
| 533 | 105.76 | 107.71 |

-continued

| Example | B1R Antagonism, human [10 μM] % Inhibition | B1R Antagonism, rat [10 μM] % Inhibition |
|---|---|---|
| 534 | 104.14 | 107.17 |
| 535 | 48.36 | 107.33 |
| 536 | 63.12 | 107.33 |
| 537 | 12.53 | 98.72 |
| 538 | −11.76 | 105.77 |
| 539 | 38.81 | 107.39 |
| 540 | 7.17 | 100.18 |
| 541 | 103.13 | 107.61 |
| 542 | 49.24 | 107.2 |
| 543 | 21.14 | 104.54 |
| 544 | 11.72 | 106.99 |
| 545 | 39.81 | 106.41 |
| 546 | 7.44 | 104.05 |
| 547 | 77.44 | 99.97 |
| 548 | 24.68 | 95.44 |
| 549 | 75.84 | 99.05 |
| 550 | 57.78 | 101.12 |
| 551 | 52.7 | 101.87 |
| 552 | 46.78 | 101.41 |
| 553 | 54.09 | 100.52 |
| 554 | 25.2 | 101.97 |
| 555 | 62.48 | 102.09 |
| 556 | 12.13 | 85.58 |
| 557 | 29.73 | 87.56 |
| 558 | −3.53 | 102.69 |
| 559 | 99.91 | 100.17 |
| 560 | 101.72 | 99.35 |
| 561 | 102.13 | 101.17 |
| 562 | 102.46 | 100.03 |
| 563 | 101.86 | 100.42 |
| 564 | 104.58 | 102.33 |
| 565 | 104.82 | 102.52 |
| 566 | 103.44 | 102.51 |
| 567 | 104.25 | 102.19 |
| 568 | 38.49 | 81.34 |
| 569 | 90.04 | 92.89 |
| 570 | 97.65 | 98.06 |
| 571 | 103.97 | 100.34 |
| 572 | — | 98.98 |
| 573 | — | 101.21 |
| 574 | 89.99 | — |
| 575 | 23.44 | 96.83 |
| 576 | 1.85 | 107.17 |
| 577 | 17.34 | 107.05 |
| 578 | 8.96 | 87.13 |
| 579 | 39.4 | 107.07 |
| 580 | 39.09 | 88.5 |
| 581 | 27.54 | 76.31 |

Inhibition of the Bradykinin Receptor 1 (B1R)-Mediated Formation of IL-6 in Fibroblasts by Substances According to the Invention as B1R Antagonists The pro-inflammatory cytokines TNFα (or IL-1) lead in various cell types, such as, for example, fibroblasts, to an activation, which brings about inter alia enhanced expression of B1R. Subsequent stimulation of these cells with a B1R agonist results in the formation of further pro-inflammatory cytokines, such as, for example, IL-6. The chronification of inflammations is thereby promoted. Treatment with a B1R antagonist should lead to inhibition of the B1R agonist-induced IL-6 formation. By way of example, a B1R antagonist identified in the FLIPR assay was tested in this respect.

Methods:

The human fibroblast cell line IMR-90 (ATCC, CCL-186) was passaged in culture medium (Ham's F12 nutrient mixture, Gibco Invitrogen GmbH, Karlsruhe Germany with 10% FBS, fetal bovine serum, Gibco, Invitrogen GmbH, Karlsruhe Germany; 0.1 mM non-essential amino acids, Gibco, 11140-035, 1 mM sodium pyruvate, Euro Clone, ECM0542D; 1.5 g/l sodium bicarbonate, Euro Clone, ECM0980D) on 80 cm² bottles (Nunc; 178905) (ratio:1:2 to 1:6; medium replaced every 3-4 days) and plated out for experiments on 96-well plates (Greiner bio-one; No. 655180) with $1×10^5$ cells per well. The cells are incubated overnight at 37° C. and 5% $CO_2$.

For activation with TNFα (human, recombinant, expressed in *E. coli*, SIGMA-ALDRICH T6674, 10 ng/ml) alone or TNFα combined with the human B1R agonist Lys-Des-Arg$^9$-bradykinin (Lys-Des-Arg$^9$-BK), the IMR-90 fibroblasts were incubated overnight at 37° C. and 5% $CO_2$ in culture medium. The final concentrations of Lys-Des-Arg$^9$-BK were 1000 nM or 10 nM. Some IMR-90 stimulation batches additionally contained the B1R antagonist of Example 8 in a final concentration of 10 μM. 24 hours after activation, in each case 150 μl of culture medium were removed from all the different stimulation batches and were transferred to a new plate and frozen. After thawing of the supernatants, the IL-6 content was determined by means of a commercially available IL-6 Elisa.

ELISA Assay (Procedure, Modified According the Manufacturer's Specifications):

Elisa kit: from: BIOSOURCE; CytoSets™, Art. No.: CHC 1264

Material: 96-well microplates: NUNC Brand Systems, Art. No.: 442404A

Procedure:

Coating: application of primary antibody solution: 50 μl/well

Incubation: covered plate overnight at RT, then tap the plate

Blocking: application of blocking buffer: 300 μl/well; incubate plate for 2 hours at RT Washing: 3× with 300 μl of washing solution/well Standard; samples; secondary antibody: application standard, samples per 50 μl/well immediate addition of the secondary antibody solution: application: 25 μl/well Incubation: shake covered plate for 2 h at RT Washing: 3× with 300 μl of washing solution/well Streptavidin: application of streptavidin solution: 100 μl/well Incubation: covered plate 30 min. at RT Washing: 3× with 300 μl of washing solution/well Substrate: application of substrate solution: 100 μl/well Incubation: incubate plate for about 20 min. at RT in the dark, with shaking (dependent on the colour reaction)

Termination: addition of 1.8 N $H_2SO_4$: 50 μl/well

Measurement (within 30 min.):

ELISA reader: from Mikrotek; MPP 4008

Evaluation software: from Mikrotek; MikroWin 3.0

Measuring filter: 450 nm

Reference filter: 620 nm

The above-described processes were carried out with Example compound 8. The results are shown in the following table:

| | Production of IL-6 (pg/ml) by IMR-90 fibroblasts | | |
|---|---|---|---|
| | TNFα alone | TNFα + Lys-Des-Arg$^9$-BK (1000 nM) | TNFα + Lys-Des-Arg$^9$-BK (10 nM) |
| without antagonist | 149 pg/ml | 2155 pg/ml | 2462 pg/ml |
| Example 8 | 136 pg/ml | 483 pg/ml | 119 pg/ml |

IMR-90 fibroblasts stimulated with TNFα or Lys-Des-Arg$^9$-BK alone produce only small amounts of IL-6 (149 pg/ml and 34 pg/ml, respectively). Stimulation with TNFα in combination with Lys-Des-Arg$^9$-BK results in an about 10- to 20-fold increase in IL-6 synthesis. This activation of IL-6 formation is inhibited by the B1R antagonist of Example 8 in a dose-dependent manner. The action of the relatively low dose of the agonist Lys-Des-Arg$^9$-BK (10 nM) is eliminated almost completely, whereas a relatively high dose of Lys-Des-Arg⁹-BK (1000 nM) is still partially inhibited. The inhibitory action of Example 8 is B1R-specific, because the activating effect of TNFα alone is not taken into account.

Formalin Test in the Mouse

The formalin test (Dubuisson, D. and Dennis, S. G., 1977, Pain, 4, 161-174) represents a model for both acute and chronic pain. By means of a single formalin injection into the dorsal side of a rear paw, a biphasic nociceptive reaction is induced in freely mobile test animals; the reaction is detected by observing three behaviour patterns which are clearly distinguishable from one another. The reaction is two-phase: phase 1=immediate reaction (duration up to 10 min., shaking of the paw, licking), phase 2=late reaction (after a rest phase; likewise shaking of the paw, licking; duration up to 60 min.). The 1st phase reflects a direct stimulation of the peripheral nocisensors with high spinal nociceptive input (acute pain phase); the 2nd phase reflects a spinal and peripheral hypersensitization (chronic pain phase). In the studies described here, the chronic pain component (phase 2) has been evaluated.

Formalin in a volume of 20 μl and a concentration of 1% is administered subcutaneously into the dorsal side of the right rear paw of each animal. The specific changes in behavior, such as lifting, shaking or licking of the paw (score 3, Dubuisson & Dennis, 1977), are observed and recorded in the observation period of 21 to 24 minutes following the formalin injection. The behaviour of the animals after administration of the substance (n=10 per dose of substance) was compared with a control group which received vehicle (n=10).

Based on the quantification of the pain behavior, the action of the substance in the formalin test was determined as the change in percent compared with the control. The $ED_{50}$ calculations ($ED_{50}$=mean effective dose) were carried out by regression analysis according to the method of Litchfield and Wilcoxon (Litchfield, J. T., Wilcoxon, J. J., 1949, J. Pharmacol. Exp. Ther. 96, 99-113). The time of administration before the formalin injection was chosen in dependence on the mode of administration of the compounds according to the invention (intravenous: 5 min.).

The $ED_{50}$ values of some examples are given in the following table:

| Example | Type of administration | $ED_{50}$ value [mg/kg] |
|---------|------------------------|-------------------------|
| 8       | i.v.                   | 12.8                    |
| 97      | i.v.                   | 13.3                    |
| 98      | i.v.                   | 13.6                    |
| 193     | i.v.                   | 2.59                    |

Parenteral Solution of a Substituted Sulfonamide Derivative According to the Invention 38 g of one of the substituted sulfonamide derivatives according to the invention, in this case Example 1, are dissolved in 1 litre of water for injection purposes at room temperature and then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claim and equivalents thereof.

What is claimed is:

1. A substituted sulfonamide compound corresponding to formula I

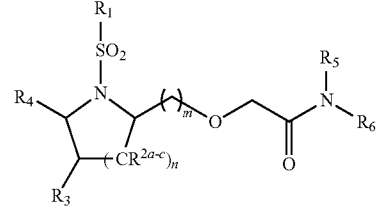

wherein m represents 1 or 2;

n represents 2;

$R_1$ represents 2,6-dimethyl-4-methoxyphenyl, 2,6-dichloro-4-trifluoromethylphenyl, 2,6-dimethyl-4-bromophenyl, 2,6-dichloro-4-bromophenyl, 2,4,6-trichlorophenyl, 2,4-dichlorophenyl, 2,6-dichlorophenyl, 2,3-dichlorophenyl, benzothiophenyl, or naphthyl optionally mono- or poly-substituted with one or more substituents independently selected from the group consisting of $C_{1-3}$-alkoxy, $C_{1-6}$-alkyl, Br, Cl, F and $CF_3$;

$R^{2a-c}$, $R_3$ and $R_4$ represent H or, with an adjacent radical $R^{2a-c}$, $R_3$ or $R_4$, form a five- or six-membered aromatic ring which optionally can be mono- or poly-substituted and which optionally can contain 1 or 2 hetero atoms selected from the group consisting of N and O, $NR_5R_6$ forms a cyclic group

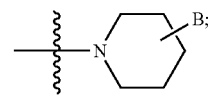

wherein

B is selected from the group consisting of

—$NR^8R^9$, wherein $R^8$ and $R^9$ indedendently of one another represent H or $C_{1-6}$-alkyl;

a radical corresponding to formula aa1

 (aa1)

wherein a, b and c, independently of one another, can be 0 or 1, with the proviso that when b is equal to 0, a and c are not simultaneously 1;

the bridging $C_{1-3}$-alkyl optionally can be monosubstituted by =O; and $R^{10}$ is a heterocyclic group selected from the group consisting of:

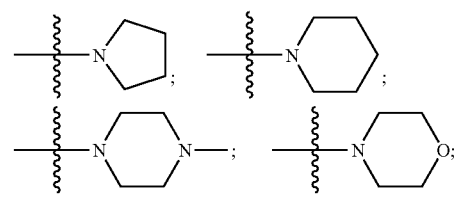

-continued

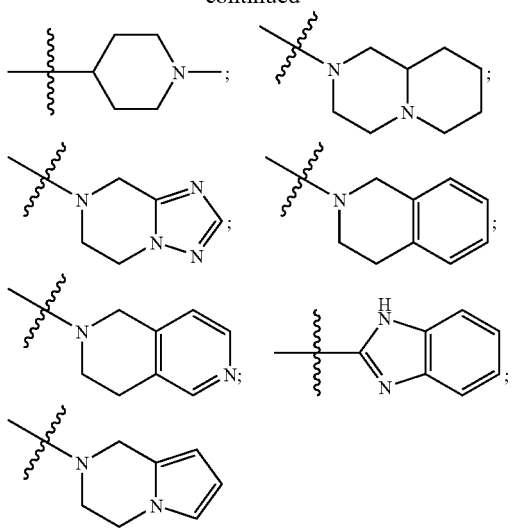

wherein the heterocyclic group can be unsubstituted or monosubstituted on one or more ring members by $C_{1-6}$-alkyl, F, Cl or Br; or
$R^{10}$ represents

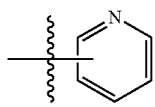

which can be unsubstituted or mono- or poly-substituted by $C_{1-6}$-alkyl, F, Cl, Br, $C_{1-6}$-alkoxy, or phenyl; or
$R^{10}$ represents phenyl substituted by $-N(C_{1-3}\text{-alkyl})_2$; or
$R^{10}$ represents a group corresponding to formula (aa2):

$$-N\!-\!(CHR^{14})_d\!-\!R^{15}, \quad \text{(aa2)}$$
$$\phantom{-}R^{13}$$

wherein
d is 1 or 2,
$R^{13}$ represents H or methyl,
$R^{14}$ represents phenyl or pyridinyl, and
$R^{15}$ represents morpholinyl or 4-methylpiperazinyl;
or $NR_5R_6$ forms a group

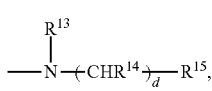

wherein
$R^{16}$ represents H or a group corresponding to formula bb1:

$$-(O)_a\!-\!(CH_2)_b\!-\!(O)_c\!-\!R^{18} \quad \text{(bb1)}$$

wherein
a and c, independently of one another, are 0 or 1,
b=0, 1, 2 or 3, with the proviso that when b=0, a and c are not simultaneously 1, and wherein in the alkyl chain defined by b, a $CH_2$ chain member optionally can be replaced by $C(=O)$,
$R^{18}$ is a cyclic substituent selected from the group consisting of

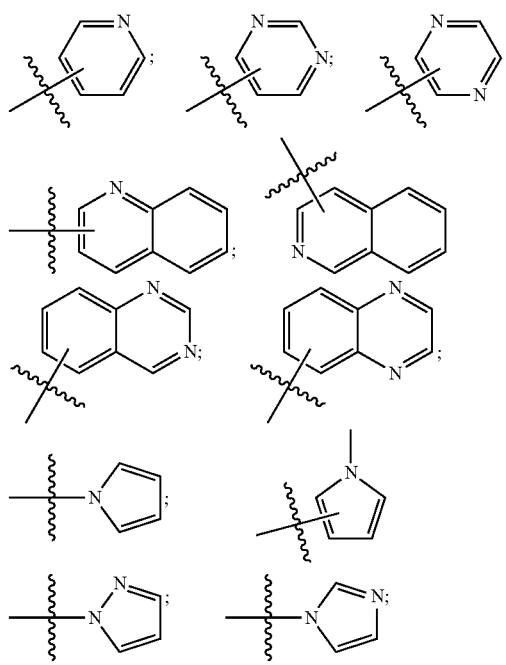

wherein the cyclic substituent can be unsubstituted or mono- or poly-substituted by $C_{1-3}$-alkyl, $C_{1-3}$-alkoxy, F, Cl, Br, I; $-CN$; $CF_3$; $N(C_{1-3}\text{-alkyl})_2$, $NH(C_{1-3}\text{-alkyl})$, $N(C_{1-3}\text{-alkyl})(\text{aryl})$, wherein the aryl or alkylaryl substituent can be mono- or poly-substituted; benzyl; or

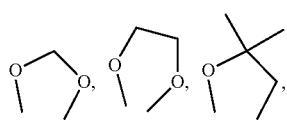

wherein all those substituents optionally can likewise be mono- or poly-substituted by F, Cl, Br, $-CN$, $-CF_3$, $C_{1-3}$-alkyl; pyrrolidinyl, piperidinyl, 4-methylpiperidinyl or morpholinyl; or
$R^{18}$ represents a heterocyclyl group selected from the group consisting of:

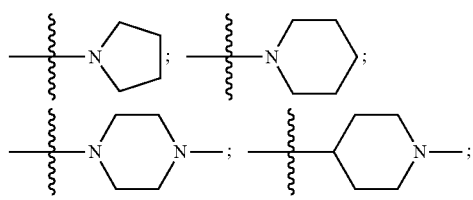

-continued

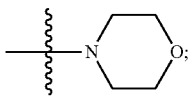

wherein the heterocyclyl group optionally can be monosubstituted on one or more ring members by substituents selected from the group consisting of F, Cl, Br, I, —CN, $NH_2$, $NH-C_{1-6}$-alkyl, $NH-C_{1-6}$-alkyl-OH, $C_{1-6}$-alkyl, $N(C_{1-6}$-alkyl$)_2$, $N(C_{1-6}$-alkyl-OH$)_2$, pyrrolidinyl, piperazinyl, morpholinyl, $NO_2$, SH, $S-C_{1-6}$-alkyl, S-benzyl, $O-C_{1-6}$-alkyl, OH, $O-C_{1-6}$-alkyl-OH, O-benzyl, $C(=O)C_{1-6}$-alkyl, $CO_2H$, $CO_2-C_{1-6}$-alkyl and benzyl;

wherein, unless otherwise indicated,
the $C_{1-6}$-alkyl radicals can be unsubstituted or mono- or poly-substituted by F, Cl, Br, I, —CN, $NH_2$, $NH-C_{1-6}$-alkyl, $NH-C_{1-6}$-alkyl-OH, $C_{1-6}$-alkyl, $N(C_{1-6}$-alkyl$)_2$, $N(C_{1-6}$-alkyl-OH$)_2$, $NO_2$, SH, $S-C_{1-6}$-alkyl, S-benzyl, $O-C_{1-6}$-alkyl, OH, $O-C_{1-6}$-alkyl-OH, =O, O-benzyl, $C(=O)C_{1-6}$-alkyl, $CO_2H$, $CO_2-C_{1-6}$-alkyl or benzyl;

the aryl or heteroaryl radicals can be unsubstituted or mono- or poly-substituted by F, Cl, Br, I, CN, $NH_2$, $NH-C_{1-6}$-alkyl, $NH-C_{1-6}$-alkyl-OH, $N(C_{1-6}$-alkyl$)_2$, $N(C_{1-6}$-alkyl-OH$)_2$, NHaryl; $N(aryl)_2$, $N(C_{1-6}$-alkyl)aryl, $NO_2$, SH, $S-C_{1-6}$-alkyl, OH, $O-C_{1-6}$-alkyl, $O-C_{1-6}$-alkyl-OH, $C(=O)C_{1-6}$-alkyl, $CO_2H$, $CH_2SO_2$-phenyl, $CO_2-C_{1-6}$-alkyl, $OCF_3$, $CF_3$,

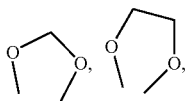

$C_{1-6}$-alkyl, pyrrolidinyl, imidazolyl, piperidinyl, morpholinyl, benzyloxy, phenoxy, phenyl, pyridyl, alkylaryl, thienyl or furyl; and the $C_{3-8}$-cycloalkyl radicals can be unsubstituted or monosubstituted on one or more ring members by F, Cl, Br, I, —CN, $NH_2$, $NH-C_{1-6}$-alkyl, $NH-C_{1-6}$-alkyl-OH, $C_{1-6}$-alkyl, $N(C_{1-6}$-alkyl$)_2$, $N(C_{1-6}$-alkyl-OH$)_2$, $NO_2$, SH, $S-C_{1-6}$-alkyl, S-benzyl, $O-C_{1-6}$-alkyl, OH, $O-C_{1-6}$-alkyl-OH, =O, O-benzyl, $C(=O)C_{1-6}$-alkyl, $CO_2H$, $CO_2-C_{1-6}$-alkyl or benzyl;

in the form of a pure stereoisomer or a mixture of stereoisomers in any mixing ratio;
or a salt thereof with a physiologically acceptable acid.

2. A compound according to claim 1, wherein the compound is in the form of a pure enantiomer or diastereoisomer.

3. A compound according to claim 1, wherein the compound is in the form of a racemic mixture.

4. A compound according to claim 1, wherein $R_1$ represents phenyl or naphthyl, optionally mono- or poly-substituted with one or more substituents selected from the group consisting of methyl, methoxy, —$CF_3$, Cl, Br and F.

5. A compound according to claim 1, wherein one of $R^{2a-c}$, $R_3$ and $R_4$ forms with an adjacent radical $R^{2a-c}$, $R_3$ or $R_4$ a benzene group optionally mono- or poly-substituted by at least one substituent selected from the group consisting of methyl, methoxy, $CF_3$, Cl, Br and F.

6. A compound according to claim 1, wherein m is 1, and n is 2.

7. A compound according to claim 1, wherein
a) $NR_5R_6$ forms a cyclic group corresponding to the formula

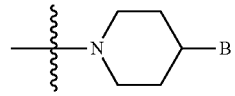

wherein B represents
a group corresponding to formula (aa1); wherein
i) a=b=c=0,
ii) a=c=0 and b=1,
iii) a=b=0 and c=1 or
iv) a=b=1 and c=0; or
a group corresponding to formula (aa2) wherein
d=1 or 2,
$R^{14}$ is pyridinyl, and
$R^{15}$ is morpholinyl; or b) $NR_5R_6$ forms a cyclic group corresponding to the formula

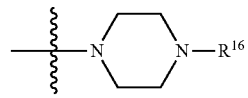

wherein $R^{16}$ represents a group of the formula bb1 wherein a=c=0 and b=0, 1 or 2 and $R^{18}$ is selected from

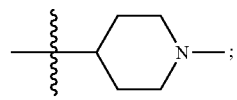

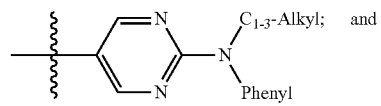

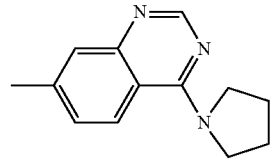

wherein the phenyl group is optionally substituted by F, Cl or Br.

8. A compound according to claim 7, wherein B represents a group corresponding to formula aa2 wherein d=2 and $R^{14}$ is 3-pyridinyl.

9. A compound according to claim 7, wherein the phenyl group is monosubstituted by F in the 4-position.

10. A compound according to claim 1, wherein the group

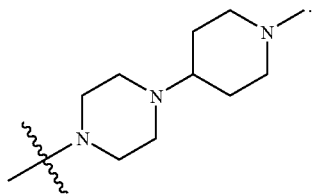 [SMILES: *N1CCN(C2CCN(C)CC2)CC1]

represents

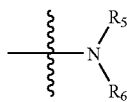

11. A compound according to claim 1, wherein said compound is selected from the group consisting of:
- 8   2-[1-(4-methoxy-2,6-dimethyl-phenylsulfonyl)-piperidin-2-ylmethoxy]-1-[4-(1-methyl-piperidin-4-yl)-piperazin-1-yl]-ethanone
- 9   1-(1,4'-bipiperidin-1-yl)-2-((2-(2,4-dichlorophenylsulfonyl)-1,2,3,4-tetrahydro-isoquinolin-3-yl)methoxy)ethanone
- 17   2-((2-(2,4-dichlorophenylsulfonyl)-1,2,3,4-tetrahydroisoquinolin-3-yl)methoxy)-1-(4-pyrrolidin-1-yl)piperidin-1-yl)ethanone
- 94   2-((1-(4-methoxy-2,6-dimethylphenylsulfonyl)piperidin-2-yl)methoxy)-1-(4-(2-(pyrrolidin-1-yl)ethyl)piperidin-1-yl)ethanone hydrochloride
- 97   2-((1-(4-methoxy-2,6-dimethylphenylsulfonyl)piperidin-2-yl)methoxy)-1-(4-(1-methylpiperidin-4-yl)piperazin-1-yl)ethanone dihydrochloride
- 98   1-(4-(dihydro-1H-pyrido[1,2-a]pyrazin-2(6H,7H,8H,9H,9aH)-yl)piperidin-1-yl)-2-((1-(4-methoxy-2,6-dimethylphenylsulfonyl)piperidin-2-yl)methoxy)ethanone
- 99   1-(4-dihydro-1H-pyrido[1,2-a]pyrazin-2(6H,7H,8H,9H,9aH)-yl)piperidin-1-yl)-2-((1-(4-methoxy-2,6-dimethylphenylsulfonyl)piperidin-2-yl)methoxy)ethanone dihydrochloride
- 100   1-(4-(3,4-dihydro-2,6-naphthyridin-2(1H)-yl)piperidin-1-yl)-2-(1-(4-methoxy-2,6-dimethylphenylsulfonyl)piperidin-2-yl)methoxy)ethanone
- 106   2-((1-(4-methoxy-2,6-dimethylphenylsulfonyl)piperidin-2-yl)methoxy)-1-(4-((1-methylpiperidin-4-yl)methyl)piperazin-1-yl)ethanone dihydrochloride
- 108   2-((1-(2,6-dichloro-4-(trifluoromethyl)phenylsulfonyl)piperidin-2-yl)methoxy)-1-(4-(1-methylpiperidin-4-yl)piperazin-1-yl)ethanone
- 110   1-((1-methylpiperidin-4-yl)piperazin-1-yl)-2-((1-(naphthalen-1-ylsulfonyl)piperidin-2-yl)methoxy)ethanone
- 111   1-((1-methylpiperidin-4-yl)piperazin-1-yl)-2-((1-(naphthalen-2-ylsulfonyl)piperidin-2-yl)methoxy)ethanone
- 112   2-((1-(4-methoxy-2,6-dimethylphenylsulfonyl)piperidin-2-yl)methoxy)-1-(4-(4-methylpiperazin-1-yl)piperidin-1-yl)ethanone hydrochloride
- 118   1-(4-(1-methylpiperidin-4-yl)piperazin-1-yl)-2-((1-(2,4,6-trichlorophenylsulfonyl)piperidin-2-yl)methoxy)ethanone
- 120   2-((1-(2,4-dichlorophenylsulfonyl)piperidin-2-yl)methoxy)-1-(4-(1-methylpiperidin-4-yl)piperazin-1-yl)ethanone
- 127   (S)-2-((2-(4-methoxy-2,6-dimethylphenylsulfonyl)-1,2,3,4-tetrahydroisoquinolin-3-yl)methoxy)-1-(4-(1-methylpiperidin-4-yl)piperazin-1-yl)ethanone
- 130   1-(4-fluoro-1,4'-bipiperidin-1'-yl)-2-((1-(4-methoxy-2,6-dimethylphenylsulfonyl)piperidin-2-yl)methoxy)ethanone
- 133   (S)-2-((2-(2,4-dichlorophenylsulfonyl)-1,2,3,4-tetrahydroisoquinolin-3-yl)methoxy)-1-(4-(1-methylpiperidin-4-yl)piperazin-1-yl)ethanone
- 136   2-((1-(4-methoxy-2,6-dimethylphenylsulfonyl)piperidin-2-yl)methoxy)-1-(4-(2-morpholin-2-(pyridin-3-yl)ethylamino)piperidin-1-yl)ethanone
- 137   24(1-(benzo[b]thiophen-3-ylsulfonyl)piperidin-2-yl)methoxy)-1-(4-(1-methylpiperidin-4-yl)piperazin-1-yl)ethanone
- 141   2-((1-(2,6-dichlorophenylsulfonyl)piperidin-2-yl)methoxy)-1-(4-(1-methylpiperidin-4-yl)piperazin-1-yl)ethanone dihydrochloride
- 144   1-(4-(5,6-dihydroimidazo[1,2-a]pyrazin-7(8H)-yl)piperidin-1-yl)-2-((1-(4-methoxy-2,6-dimethylphenylsulfonyl)piperidin-2-yl)methoxy)ethanone
- 145   1-(4-(5,6-dihydro-[1,2,4]triazolo[1,5-a]pyrazin-7(8H)-yl)piperidin-1-yl)-2-((1-(4-methoxy-2,6-dimethylphenylsulfonyl)piperidin-2-yl)methoxy)ethanone
- 146   2-((1-(4-methoxy-2,6-dimethylphenylsulfonyl)piperidin-2-yl)methoxy)-1-(4-(4-methylpiperazin-1-carbonyl)piperidin-1-yl)ethanone
- 147   2-((1-(4-methoxy-2,6-dimethylphenylsulfonyl)piperidin-2-yl)methoxy)-1-(4-(pyridin-4-yl)piperazin-1-yl)ethanone
- 148   2-((1-(4-bromo-2,6-dimethylphenylsulfonyl)piperidin-2-yl)methoxy)-1-(4-(1-methylpiperidin-4-yl)piperazin-1-yl)ethanone
- 155   2-((1-(4-methylnaphthalen-1-ylsulfonyl)piperidin-2-yl)methoxy)-1-(4-(1-methylpiperidin-4-yl)piperazin-1-yl)ethanone dihydrochloride
- 157   2-((1-(2-methylnaphthalen-1-ylsulfonyl)piperidin-2-yl)methoxy)-1-(4-(1-methylpiperidin-4-yl)piperazin-1-yl)ethanone dihydrochloride
- 160   2-((1-(4-bromo-2,6-dichlorophenylsulfonyl)piperidin-2-yl)methoxy)-1-(4-(1-methylpiperidin-4-yl)piperazin-1-yl)ethanone dihydrochloride
- 164   2-(2-(1-(4-methoxy-2,6-dimethylphenylsulfonyl)piperidin-2-yl)ethoxy)-1-(4-(1-methylpiperidin-4-yl)piperazin-1-yl)ethanone
- 165   2-((1-(4-methoxy-2,6-dimethylphenylsulfonyl)piperidin-2-yl)methoxy)-1-(4-(pyridin-3-yloxy)piperidin-1-yl)ethanone
- 166   2-((1-(4-methoxy-2,6-dimethylphenylsulfonyl)piperidin-2-yl)methoxy)-1-(4-(quinoxalin-6-ylmethyl)piperazin-1-yl)ethanone
- 167   (S)-2-((1-(4-methoxy-2,6-dimethylphenylsulfonyl)piperidin-2-yl)methoxy)-1-(4-(1-methylpiperidin-4-yl)piperazin-1-yl)ethanone
- 168   2-((1-(4-methoxy-2,6-dimethylphenylsulfonyl)piperidin-2-yl)methoxy)-1-(4-(4-(pyrrolidin-1-yl)quinazolin-7-yl)piperazin-1-yl)ethanone
- 173   2-((1-(2,3-dichlorophenylsulfonyl)piperidin-2-yl)methoxy)-1-(4-(1-methylpiperidin-4-yl)piperazin-1-yl)ethanone dihydrochloride
- 174   2-((1-(4-methoxynaphthalen-1-ylsulfonyl)piperidin-2-yl)methoxy)-1-(4-(1-methylpiperidin-4-yl)piperazin-1-yl)ethanone dihydrochloride 177 (R)-2-((1-(4-methoxy-2,6-dimethylphenylsulfonyl)piperidin-2-yl)methoxy)-1-(4-(1-methylpiperidin-4-yl)piperazin-1-yl)ethanone dihydrochloride
178 1-(4-(1-methylpiperidin-4-yl)piperazin-1-yl)-2-((2-(naphthalen-2-ylsulfonyl)-1,2,3,4-tetrahydroisoquinolin-3-yl)methoxy)ethanone dihydrochloride
183 (S)-2-((2-(2,4-dichlorophenylsulfonyl)-1,2,3,4-tetrahydroisoquinolin-3-yl)methoxy)-1-(4-(2-(pyrrolidin-1-yl)ethyl)piperidin-1-yl)ethanone
184 (S)-2-((2-(2,4-dichlorophenylsulfonyl)-1,2,3,4-tetrahydroisoquinolin-3-yl)methoxy)-1-(4-((1-methylpiperidin-4-yl)methyl)piperazin-1-yl)ethanone
185 (S)-2-((2-(4-methoxy-2,6-dimethylphenylsulfonyl)-1,2,3,4-tetrahydroisoquinolin-3-yl)methoxy)-1-(4-((1-methylpiperidin-4-yl)methyl)piperazin-1-yl)ethanone
186 (S)-2-((1-(4-methoxy-2,6-dimethylphenylsulfonyl)piperidin-2-yl)methoxy)-1-(4-(pyridin-4-yloxy)piperidin-1-yl)ethanone hydrochloride
187 (S)-2-((2-(4-methoxy-2,6-dimethylphenylsulfonyl)-1,2,3,4-tetrahydroisoquinolin-3-yl)methoxy)-1-(4-(2-(pyrrolidin-1-yl)ethyl)piperidin-1-yl)ethanone
188 2-((1-(4-methoxy-2,6-dimethylphenylsulfonyl)piperidin-2-yl)methoxy)-1-(4-((pyridin-4-yloxy)methyl)piperidin-1-yl)ethanone
191 2-((1-(2-chloronaphthalen-1-ylsulfonyl)piperidin-2-yl)methoxy)-1-(4-(1-methylpiperidin-4-yl)piperazin-1-yl)ethanone dihydrochloride
199 1-(4-((2-(dimethylamino)pyrimidin-5-yl)methyl)piperazin-1-yl)-2-((1-(4-methoxy-2,6-dimethylphenylsulfonyl)piperidin-2-yl)methoxy)ethanone
200 1-(4-(6-fluoro-3,4-dihydroisoquinolin-2(1H)-yl)piperidin-1-yl)-2-((1-(4-methoxy-2,6-dimethylphenylsulfonyl)piperidin-2-yl)methoxy)ethanone
201 2-((1-(4-methoxy-2,6-dimethylphenylsulfonyl)piperidin-2-yl)methoxy)-1-(4-(pyridin-4-yl)piperidin-1-yl)ethanone
202 2-((1-(4-methoxy-2,6-dimethylphenylsulfonyl)-1,2,3,4-tetrahydroquinolin-2-yl)methoxy)-1-(4-(1-methylpiperidin-4-yl)piperazin-1-yl)ethanone
203 1-(4-(1-methylpiperidin-4-yl)piperazin-1-yl)-2-((1-(naphthalen-2-ylsulfonyl)-1,2,3,4-tetrahydroquinolin-2-yl)methoxy)ethanone
210 2-((1-(6-methoxynaphthalen-2-ylsulfonyl)piperidin-2-yl)methoxy)-1-(4-(1-methylpiperidin-4-yl)piperazin-1-yl)ethanone
211 1-(4-(3,4-dihydropyrrolo[1,2-a]pyrazin-2(1H)-yl)piperidin-1-yl)-2-((1-(4-methoxy-2,6-dimethylphenylsulfonyl)piperidin-2-yl)methoxy)ethanone
212 2-((1-(4-methoxy-2,6-dimethylphenylsulfonyl)piperidin-2-yl)methoxy)-1-(4-(2-(1-methylpiperidin-4-yl)ethyl)piperazin-1-yl)ethanone
214 1-(4-((2-((4-fluorophenyl)(methyl)amino)pyrimidin-5-yl)methyl)piperazin-1-yl)-2-((1-(4-methoxy-2,6-dimethylphenylsulfonyl)piperidin-2-yl)methoxy)ethanone
217 2-((1-(4-methoxy-2,6-dimethylphenylsulfonyl)piperidin-2-yl)methoxy)-1-(4-(pyridin-3-yl)piperidin-1-yl)ethanone
233 2-((2-(2,4-dichlorophenylsulfonyl)-1,2,3,4-tetrahydroisoquinolin-3-yl)methoxy)-1-(4-(4-methylpiperazin-1-yl)piperidin-1-yl)ethanone
235 1-(1,4'-bipiperidin-1'-yl)-2-((1-(naphthen-1-ylsulfonyl)piperidin-2-yl)methoxy)ethanone
278 2-((1-(2,6-dichlorophenylsulfonyl)piperidin-2-yl)methoxy)-1-(4-(4-methylpiperazin-1-yl)piperidin-1-yl)ethanone
279 2-((1-(2,6-dichlorophenylsulfonyl)piperidin-2-yl)methoxy)-1-(4-(2-(piperidin-1-yl)ethyl)piperidin-1-yl)ethanone
280 2-((1-(2,6-dichlorophenylsulfonyl)piperidin-2-yl)methoxy)-1-(4-(2-(2,5-dimethyl-1H-pyrrol-1-yl)ethyl)piperazin-1-yl)ethanone
283 2-((1-(2,6-dichlorophenylsulfonyl)piperidin-2-yl)methoxy)-1-(4-(pyridin-4-yl)piperazin-1-yl)ethanone
336 141,4'-bipiperidin-1'-yl)-2-((1-(2,6-dichlorophenylsulfonyl)piperidin-2-yl)methoxy)ethanone
397 2-((1-(4-methoxy-2,6-dimethylphenylsulfonyl)piperidin-2-yl)methoxy)-1-(4-(5-methyl-1H-benzo[d]imidazol-2-yl)piperidin-1-yl)ethanone
443 2-((1-(2,6-dichlorophenylsulfonyl)piperidin-2-yl)methoxy)-1-(4-(pyrrolidin-1-yl)piperidin-1-yl)ethanone
487 24(1-(2,6-dichlorophenylsulfonyl)piperidin-2-yl)methoxy)-1-(4-(5-methyl-1H-benzo[d]imidazol-2-yl)piperidin-1-yl)ethanone
524 2-((1-(4-methoxy-2,6-dimethylphenylsulfonyl)piperidin-2-yl)methoxy)-1-(4-(4-methylpiperazin-1-yl)piperidin-1-yl)ethanone
533 2-((1-(4-methoxy-2,6-dimethylphenylsulfonyl)piperidin-2-yl)methoxy)-1-(4-(2-(piperidin-1-yl)ethyl)piperidin-1-yl)ethanone
534 2-((1-(4-methoxy-2,6-dimethylphenylsulfonyl)piperidin-2-yl)methoxy)-1-(2-(2-morpholinoethyl)piperidin-1-yl)ethanone
559 1-(4-(2-(2,5-dimethyl-1H-pyrrol-1-yl)ethyl)piperazin-1-yl)-2-((1-(4-methoxy-2,6-dimethylphenylsulfonyl)piperidin-2-yl)methoxy)ethanone
565 2-((1-(2,6-dichlorophenylsulfonyl)piperidin-2-yl)methoxy)-1-(4-(1-methylpiperidin-4-yl)piperazin-1-yl)ethanone
572 24(1-(benzo[b]thiophen-3-ylsulfonyl)piperidin-2-yl)methoxy)-1-(4-(4-methylpiperazin-1-yl)piperidin-1-yl)ethanone
and
573 2-((1-(benzo[b]thiophen-3-ylsulfonyl)piperidin-2-yl)methoxy)-1-(4-((1-methylpiperidin-4-yl)methyl)piperazin-1-yl)ethanone
in the form of a pure stereoisomer or a mixture of stereoisomers in any mixing ratio,
and salts thereof with a physiologically acceptable acid.

12. A pharmaceutical composition comprising a compound according to claim 1 and at least one pharmaceutically acceptable carrier or auxiliary substance.

* * * * *